(12) United States Patent
Davidson et al.

(10) Patent No.: US 11,332,544 B2
(45) Date of Patent: May 17, 2022

(54) GLYCAN-BASED ANTIBODY-DRUG CONJUGATES

(71) Applicant: Merck Sharp & Dohme Corp., Rahway, NJ (US)

(72) Inventors: Robert Davidson, Enfield, NH (US); Bing Gong, North Reading, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 811 days.

(21) Appl. No.: 15/493,720

(22) Filed: Apr. 21, 2017

(65) Prior Publication Data
US 2017/0362338 A1 Dec. 21, 2017

Related U.S. Application Data

(60) Provisional application No. 62/325,497, filed on Apr. 21, 2016.

(51) Int. Cl.
| | |
|---|---|
| *C07K 16/32* | (2006.01) |
| *C12P 21/00* | (2006.01) |
| *A61K 47/68* | (2017.01) |
| *C07K 16/00* | (2006.01) |
| *A61K 39/00* | (2006.01) |

(52) U.S. Cl.
CPC .......... *C07K 16/32* (2013.01); *A61K 47/6803* (2017.08); *A61K 47/6811* (2017.08); *A61K 47/6851* (2017.08); *A61K 47/6889* (2017.08); *C07K 16/00* (2013.01); *C12P 21/005* (2013.01); *A61K 2039/505* (2013.01); *C07K 2317/14* (2013.01); *C07K 2317/21* (2013.01); *C07K 2317/24* (2013.01); *C07K 2317/41* (2013.01); *C07K 2317/52* (2013.01)

(58) Field of Classification Search
None
See application file for complete search history.

(56) References Cited

U.S. PATENT DOCUMENTS

2007/0148165 A1* 6/2007 Shitara ............... C07K 16/2887
424/133.1

FOREIGN PATENT DOCUMENTS

WO  WO-2015057064 A1 * 4/2015

OTHER PUBLICATIONS

Alley et al., Antibody-drug conjugates: targeted drug delivery for cancer, Curr. Opin. Chem. Biol., 2010, Issue 4, pp. 529-537, vol. 14.
Axup et al., Synthesis of site-specific antibody-drug conjugates using unnatural amino acids, Proc. Natl. Acad. Sci. USA, 2012, Issue 40, pp. 16101-16106, vol. 109.
Barnard et al., High-throughput screening and selection of yeast cell lines expressing monoclonal antibodies, J. Ind. Microbiol. Biotechnol., 2010, Issue 9, pp. 961-971, vol. 37.
Burnina et al., A cost-effective plate-based sample preparation for antibody N-glycan analysis, J. Chromatogr. A., 2013, Issue: 1307, pp. 201-206, vol. 3.
Burris et al., Developments in the Use of Antibody-Drug Conjugates, Antibody-Drug Conjugate Developments, 2013, pp. e99-e102, vol. 33.
Butler et al., Recent advances in technology supporting biopharmaceutical production from mammalian cells, Appl Microbiol. Biotechnol., 2012, Issue 4, pp. 885-894, vol. 96.
Choi et al., Recombinant human lactoferrin expressed in glycoengineered Pichia pastoris: effect of terminal N-acetylneuraminic acid on in vitro secondary humoral immune response, Glycoconj. J., 2008, Issue 6, pp. 581-593, vol. 25.
Choi,Byung-Kwon et al., Use of combinatorial genetic libraries to humanize N-linked glycosylation in the yeast *Pichia pastoris*, Proc Natl Acad Sci USA, 2003, 5022-5027, vol. 100(9).
Cooper et al., Galactose Oxidase from Polyporus Circinatus, Fr, Fr. J. Biol. Chem., 1959, pp. 445-448, vol. 234.
Costa et al., Guidelines to cell engineering for monoclonal antibody production, Eur. J. Pharm. Biopharm., 2010, Issue 2, pp. 127-138, vol. 74.
Cregg et al., Recombinant Protein Expression in Pichia pastoris, Mol. Biotechnol., 2000, Issue 1, pp. 23-52, vol. 16.
Crisalli et al., Water-Soluble Organocatalysts for Hydrazone and Oxime Formation, J. Org. Chem., 2013, Issue 3, pp. 1184-1189, vol. 78.
Flygare et al., Antibody-Drug Conjugates for the Treatment of Cancer, Chem. Biol. Drug Des., 2013, Issue 1, pp. 113-121, vol. 81.
Gomathinayagam et al., High-Throughput Multimodal Strong Anion Exchange Puri fi cation and N-Glycan Characterization of Endogenous Glycoprotein Expressed in Glycoengineered Pichia pastoris, Methods Mol. Biol., 2012, pp. 315-323, vol. 899.
Hamilton et al., Science, Science, 2006, pp. 1441-1443, vol. 313.
Hopkins et al., Elimination of Beta-mannose Glycan Structures in Pichia Pastoris, Glycobiology, 2011, No. 12 pp. 1616-1626, vol. 21.
Hossler, Optimal and Consistent Protein Glycosylation in Mammalian Cell Culture, Glycobiology, 2009, pp. 936-949, vol. 19.
Jackson et al., In Vitro and In Vivo Evaluation of Cysteine and SiteSpecific Conjugated Herceptin Antibody-Drug Conjugates, PLoS One, PubMed Central PMCID: PMC3891645, 2014, Issue 1, p. e83865, vol. 9.
Jayasekara et al., Rapid Synthesis of Alkoxyamine Hydrochloride Derivatives From Alkyl Bromide and N,N-Di-Tert Butoxycarbonylhydroxylamine, Synth. Commun., 2014, Issue 16, pp. 2344-2347, vol. 44.
Jiang et al., Purification process development of a recombinant monoclonal antibodyexpressed in glycoengineered Pichia pastoris, Protein Expr. Purif., 2011, Issue 1, pp. 7-14, vol. 76.

(Continued)

*Primary Examiner* — Brad Duffy
(74) *Attorney, Agent, or Firm* — John David Reilly; Anna Cocuzzo

(57) ABSTRACT

Genetically engineered antibodies containing non-native N-glycosylated sites, preparation of the antibodies in yeast and fungi, site-specific conjugation of drugs to these antibodies, and methods of treatment utilizing these antibodies are described herein.

4 Claims, 51 Drawing Sheets

Specification includes a Sequence Listing.

(56) References Cited

OTHER PUBLICATIONS

Junutula et al., Engineered Thio-Trastuzumab-DM1 Conjugate with an Improved Therapeutic Index to Target Human Epidermal Growth Factor Receptor 2—Positive Breast Cancer, Clin. Cancer Research, 2010, Issue 19, pp. 4769-4778, vol. 16.

Junutula et al., Site-specific conjugation of a cytotoxic drug to an antibody improves the therapeutic index, Nat. Biotechnol., 2008, Issue 8, pp. 925-932, vol. 26.

Kaneko et al., Science, Science, 2006, pp. 670-673, vol. 313.

Liu et al., Recovery and purification process development for monoclonal antibody production, MAbs, 2010, Issue 5, pp. 480-499, vol. 2.

Lynaugh et al., Rapid Fc glycosylation analysis of Fc fusions with IdeS and liquid chromatography mass spectrometry, MAbs, 2013, Issue 5, pp. 641-645, vol. 5.

Mullard et al., Maturing antibody-drug conjugate pipeline hits 30, Nat. Rev. Drug Discov., 2013, Issue 5, pp. 329-332, vol. 12.

Nett et al., Optimization of erythropoietin production with controlled glycosylation-PEGylated erythropoietin produced in glycoengineered Pichia pastoris, J. Biotechnol., 2012, Issue 1, pp. 198-206, vol. 157.

Nitschke et al., CD22 and Siglec-G: B-cell inhibitory receptors with distinct functions, Immunol. Rev., 2009, Issue 1, pp. 128-143, vol. 230.

Omasa et al., Cell Engineering and Cultivation of Chinese Hamster Ovary (CHO) Cells, Curr. Pharm. Biotechnol., 2010, Issue 3, pp. 233-240, vol. 11.

Panowski et al., Site-specific antibody drug conjugates for cancer therapy, MAbs, 2014, Issue 1, pp. 34-45, vol. 6.

Potgieter et al., Production of monoclonal antibodies by glycoengineered Pichia pastoris, J. Biotechnol., 2009, Issue 4, pp. 318-325, vol. 139.

Prime et al., Oligosaccharide sequencing based on exo- and endoglycosidase digestion and liquid chromatographic analysis of the products, J. Chromatogr. A., 1996, Issues 1-2, pp. 263-274, vol. 720.

Ramya et al., Glycoproteomics enabled by tagging sialic acid-orgalactose-terminated glycans, Glycobiology, 2013, Issue 2, pp. 211-221, vol. 23.

Restelli et al., The Effect of Dissolved Oxygen on the Production and the Glycosylation Profile of Recombinant Human Erythropoietin Produced From CHO Cells, Biotechnol. Bioeng., 2006, Issue 3, pp. 481-494, vol. 94.

Ricart et al., Technology Insight: cytotoxic drug immunoconjugates for cancer therapy, Nat. Clin. Pract. Oncol., 2007, Issue 4, pp. 245-255, vol. 4.

Schirrmann et al., Production systems for recombinant antibodies, Front Biosci., 2008, pp. 4576-4594, vol. 13.

Schrama et al., Antibody targeted drugs as cancer therapeutics, Nat. Rev. Drug Discov., 2006, Issue 2, pp. 147-159, vol. 5.

Sethuraman et al., Challenges in Therapeutic Glycoprotein Production, Current Opinion. Biotech, 2006, 341-346, vol. 17.

Sethuraman et al., Challenges in therapeutic glycoprotein production, Nat. Biotechnol., 2006, Issue 2, pp. 210-215, vol. 24.

Singh et al., Preparation of a Multitopic Glycopeptide-Oligonucleotide Conjugate, Org. Lett., 2005, Issue 7, pp. 1359-1362, vol. 7.

Su et al., Convergent Synthesis of a Complex Oxime Library Using Chemical Domain Shuffling, Org. Lett., 2005, Issue 13, pp. 2751-2754, vol. 7.

Tian et al., A general approach to site-specific antibody drug conjugates, Proc.Natl. Acad. Sci. USA, 2014, Issue 5, pp. 1766-1771, vol. 111.

Trimalille et al., Peptide ligation from alkoxyamine based radical addition, Chem. Commun. (Camb), 2014, Issue 21, pp. 2744-2777, vol. 50.

Tsubata et al., Role of Inhibitory BCR Co-Receptors in Immunity, Infect. Disord. Drug Targets, 2012, Issue 3, pp. 181-190, vol. 12.

Verma et al., Trastuzumab Emtansine for HER2-Positive Advanced Breast Cancer, N. Engl. J.Med., 2012, Issue 19, pp. 1783-1791, vol. 367.

Walsh et al., Biopharmaceutical benchmarks 2014, Nat. Biotechnol., 2014, Issue 10, pp. 992-1000, vol. 32.

Wang et al., An Immunosuppressive Antibody-Drug Conjugate, JACS, 2015, pp. 3229-3232, vol. 137.

Zha, D., Glycoengineered Pichia-Based Expression of Monoclonal Antibodies, Methods Mol. Biol., 2013, pp. 31-43, vol. 988.

Zhang et al., Glycoengineered Pichia produced anti-HER2 is comparable to trastuzumab in preclinical study, MAbs, 2011, Issue 3, pp. 289-298, vol. 3.

Zhou et al., Generation of stable cell lines by site-specific integration of transgenes into engineered Chinese hamster ovary strains using an FLP-FRT system, J. Biotechnol., 2010, Issue 2, pp. 122-129, vol. 147.

Zimmerman et al., Production of Site-Specific Antibody-Drug Conjugates Using Optimized Non-Natural Amino Acids in a Cell-Free Expression System, Bioconjug. Chem., 2014, Issue 2, pp. 351-361, vol. 25.

* cited by examiner

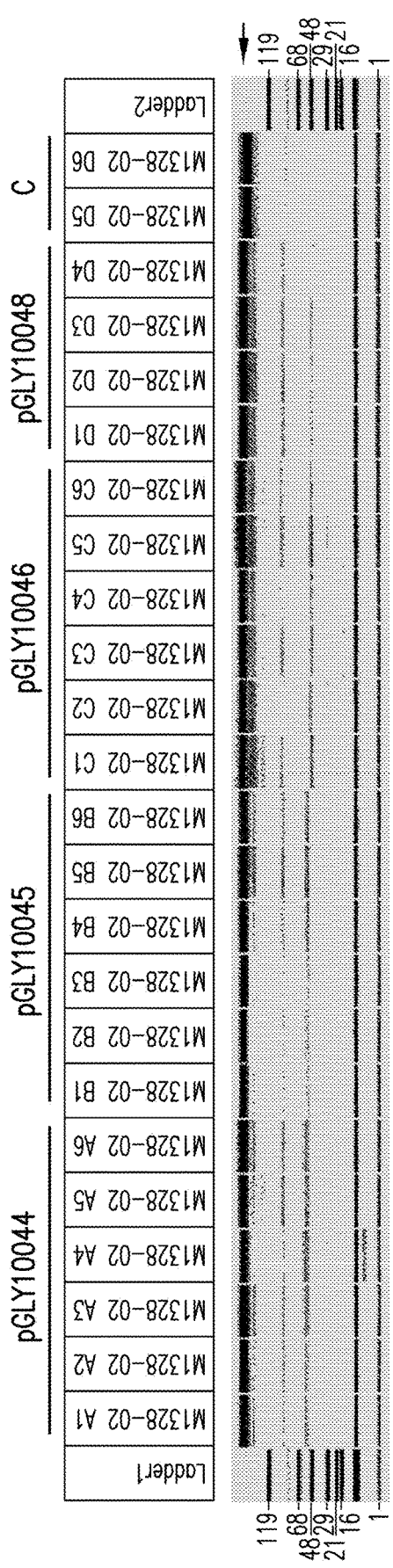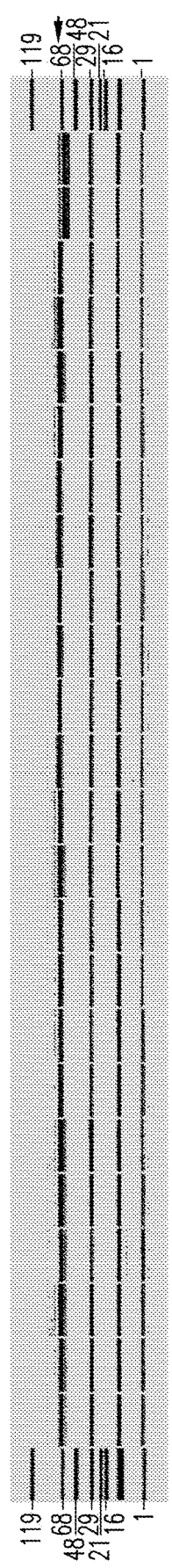
FIG.5C
FIG.5D

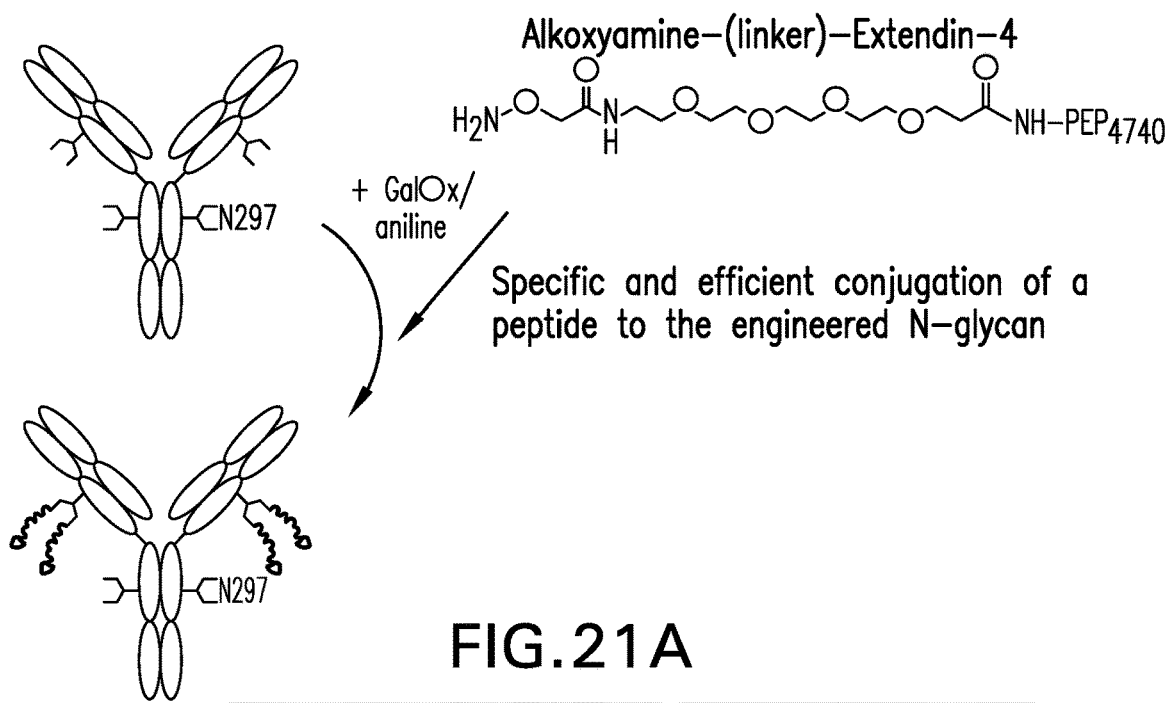
FIG.21A
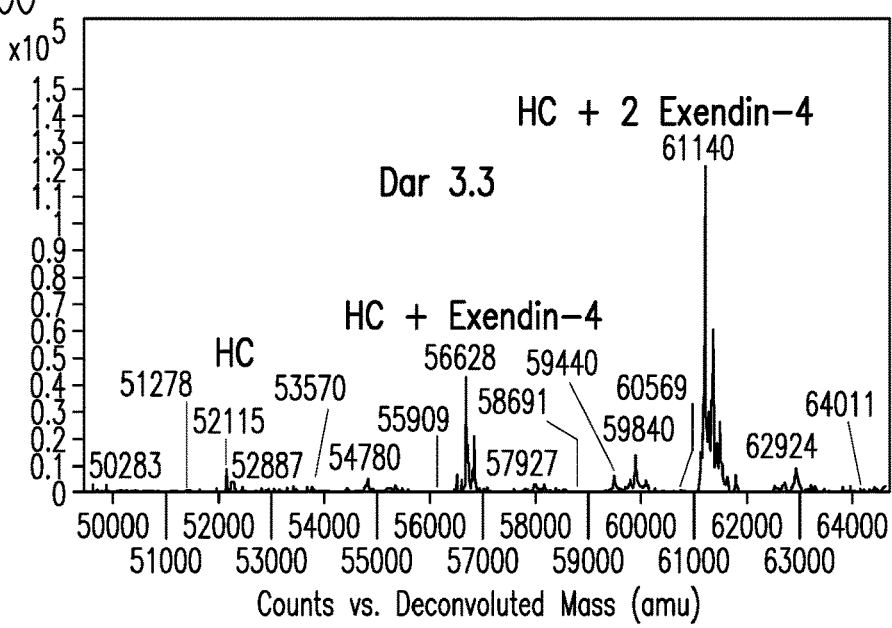
FIG.21B
| Reagent | Mouse GLP1R | Human GLP1R |
|---|---|---|
| Glyco-mAb exendin-4 | 10 nM | 7 nM |
| GLP-1 peptide | 5 nM | 2 nM |
FIG.21C

"Glyco-mAb"

Single position glyco-mAb conjugate (DAR: 2-4)

Conjugation (drug, peptide, etc.)

Add 1,2,3 etc. more positions

Cont. On FIG.26D and FIG.26E

Conjugate

Multi-position glyco-mAb DAR: 8, 12, 20, 40, etc.

US 11,332,544 B2

GLYCAN-BASED ANTIBODY-DRUG CONJUGATES

This application claims the benefit of U.S. Provisional Patent Application No. 62/325,497, filed Apr. 21, 2016; which is herein incorporated by referenced in its entirety.

FIELD OF THE INVENTION

The present invention relates to engineered immunoglobulin comprising mutations in the constant domains useful in antibody-drug conjugates (ADCs), methods of treatment utilizing the ADCs and methods of preparing the ADCs.

BACKGROUND

Monoclonal antibodies (mAbs) represent one of the fastest growing and most important sectors of the pharmaceutical market (Walsh, 2014). Antibodies (Abs) are unique molecules that provide the ability to target cell-associated and soluble antigens in a highly specific manner. This targeting can be used to block activities such as receptor-ligand interactions, influence or induce target-specific biological processes such as complement activities and immune cell-mediated cytotoxic activities, or modulate inflammation. However, efficient target cell killing, especially in the context of a solid tumor remains a limitation for many conventional mAbs (Schrama et al, 2006; Ricart, 2007). Increasing the versatility and effectiveness of these molecules will be a crucial focus as the next generation of antibody-based therapeutics is developed. One of the primary advancements in recent years is the resurgence of ADCs, particularly in the area of oncology (Flygare, 2013; Mullard, 2013). ADCs are comprised of a targeting vehicle and a linker that provides a stable support for the drug to prevent off-target release but allow effective release at the target location (Alley et al, 2010). Using the same strategy, Abs can also be conjugated to radioisotopes, peptides, or other macromolecules such as RNA (Ricart, 2011). However, to date, ADCs have been most often used for the delivery of drug payloads to improve cytotoxicity of a mAb to a known target (e.g. trastuzumab in the case of Her2; also known as Herceptin), which concomitantly increases the therapeutic index of an otherwise intolerable cytotoxic therapy (Burris, 2013).

While important technical challenges such as an optimal drug:antibody ratio (DAR) and methods of linker attachment (cleavable vs. non-cleavable) have been addressed to improve the characteristics of the current generation of ADCs, important limitations still exist (Panowski, 2013; Boylan, 2013). These hurdles include more efficient manufacture of ADCs, increased product homogeneity, and improving the sophistication of the chemistry available to allow broadening the scope of ADCs to include combining Abs with peptides and hormones.

It has been shown that site-specific targeting of a cytotoxic agent to an Ab not only improves the homogeneity of the drug product but also the therapeutic index and efficacy of the ADC (Junutula, 2008; Junutula, 2012). However, all current site-specific targeting technologies have significant limitations. Using engineered Cysteine (Cys) residues allows for a large degree of site specificity but does not prevent targeting to native Cys residues within the Ab protein, thus resulting in residual heterogeneity while likely decreasing the stability of the molecule through the disruption of native disulfide bonds, as well as complicating manufacture of an Ab that now contains free thiol residues (native Abs typically only contain paired Cys residues that are engaged in disulfide bonds). Recent technologies that rely on the incorporation of non-native amino acids are a step forward from engineered Cys residues because they allow for unique chemistry that is not present in the 20 amino acid code (Axup, 2012; Zimmerman, 2014). Incorporation of non-native amino acids also allows for more discrete control of the number of sites of conjugation. However scale-up and the subsequent manufacture of mAbs in mammalian cell lines, e.g., CHO cells, expressing non-native amino acids and efficient incorporation of these non-native amino acids introduces new challenges. Several other new technologies have emerged, but each with its own limitations, including introducing site specific tags in the mAb, which could promote immunogenicity, or modifying the N-297 glycan, which limits or abolishes immune effector function (Panowski, 2013). Also, in each case, scalability is either challenging or an unknown. Thus, an opportunity remains for a practical and scalable site-specific modification technology that would permit linking Abs to a range of different payloads.

SUMMARY OF THE INVENTION

The present invention relates to engineered Abs or fragments thereof, and in particular IgG Abs possessing one to ten mutations within the heavy chain constant domains, e.g., $C_H1$, hinge, $C_H2$, $C_H3$, and Fc. These mutations create non-native N-glycosylation sites in the heavy chain constant domain. In one embodiment, the engineered Abs of the invention are expressed in yeast or filamentous fungal host cells, for example *Pichia pastoris* host cells. When the engineered Abs are expressed in yeast and filamentous fungi host cells genetically engineered to produce human N-glycans, N-glycans are efficiently incorporated into the non-native N-glycosylation site(s) of the heavy chain constant domain. The engineered Abs expressed in genetically engineered yeast and filamentous fungal host cells possess a high degree of N-glycan occupancy without disrupting the normal folding or function of the Ab, and allow conjugation of a suitable amount of payload/drug to the Ab to form an ADC. In particular, the engineered Abs of the invention comprise galactose-terminated N-glycans, which can be oxidized by an oxidizing reagent to produce aldehyde groups. The reactive aldehyde groups, in the presence of a derivatized drug containing a reactive amine form a bond (e.g., the reactive amine, alkoxyamine, reacts with aldehyde groups to form an oxime bond), thereby conjugating the drug to the Ab. In one embodiment, the engineered IgG Ab or fragment thereof comprises a human IgG1 constant domain.

In one embodiment, the present invention provides an engineered IgG Ab or fragment thereof comprising one to ten mutations (or pairs of mutations) in the heavy chain constant domain which generate one to ten non-native N-glycosylation sites, the mutations being selected from the group consisting of S134N, G161T, G161S, N203T, N203S, V363T, V363S, Q438N, S176N, A118N, S132N, K133N, A162N, T195N, K210T, Y391T, F423T, F423S, Y436T, Y436S, L193N, K392T, K392S, F423T, S176N/G178T, S176N/G178S, Q419N/N421T, Q419N/N421S, S191N/L193T, S191N/L193S, G194N/Q196T, and G194N/Q196S, according to EU numbering. In one embodiment, the engineered IgG Ab or fragment thereof comprises a human IgG1 constant domain.

In one embodiment, the engineered IgG Ab or fragment thereof comprises at least one or two amino acid mutations (or a pair of mutations) in the heavy chain constant domain selected from S134N, G161T and S134N/G161T. In one embodiment, the engineered IgG Ab or fragment thereof comprises a human IgG1 constant domain.

In another embodiment, the engineered IgG Ab or fragment thereof comprises at least two amino acid mutations in the heavy chain constant domain selected from G161T/S134T and G161S/S134T. In one embodiment, the engineered Ab comprises a human IgG1 constant domain.

In another embodiment, the N-glycosylated non-native site of the engineered IgG Ab or fragment thereof is conjugated to a drug selected from the group consisting of a polymer, cytotoxic agent, a radionuclide, fluorescent or chemiluminescent labels, steroid, steroid receptor agonist, signal transduction inhibitor, a peptide and scFv.

The present invention also relates to engineered IgG Abs or fragments thereof, and in particular Abs possessing one to two mutations in the heavy chain variable framework domain which generate one to two non-native N-glycosylation sites, the mutations being selected from the group consisting of Q105N and S113N, according to Kabat numbering.

In an embodiment, the engineered IgG Ab or fragment comprising one to two mutations in the heavy chain variable framework domain is conjugated to a drug and is selected from the group consisting of a polymer, cytotoxic agent, a radionuclide, fluorescent or chemiluminescent labels, steroid, signal transduction inhibitor, a peptide and scFv.

In another embodiment, a method of treating a disease or cancer in a patient suffering from the disease or cancer is provided, the method comprising administering to the patient a therapeutically effective amount of any of the aforementioned engineered IgG Abs or fragments thereof which are conjugated to a drug.

In another embodiment, a method of preparing a conjugated N-glycosylated IgG Ab or fragment thereof containing one to ten non-native N-glycosylation sites (or pairing of mutations) in the heavy chain constant domain is provided, the method comprising:
(a) transforming a yeast or filamentous fungus host cell genetically engineered to produce N-glycans comprising terminal galactose residues of the structure $Gal_{(1-4)}GlcNAc_{(1-4)}Man_3GlcNAc_2$ or the structure $Gal_{(1-2)}GlcNAc_{(1-2)}Man_5GlcNAc_2$ with a nucleic acid encoding an IgG heavy chain constant domain or fragment thereof, wherein the IgG heavy chain constant domain comprises one to ten amino acid mutations, and wherein the one to ten amino acid mutations generate at least one N-glycosylation site in the IgG heavy chain constant domain;
(b) culturing the transformed host cell under conditions that allow the expression of the IgG heavy chain constant domain comprising terminal galactose residues,
(c) contacting the expressed IgG heavy chain constant domain with a reagent that oxidizes the terminal galactose residues; and
(d) conjugating a drug to the oxidized moiety of the terminal galactose residues.

In one embodiment, the yeast host cell used in the method of preparing a conjugated N-glycosylated IgG Ab or fragment thereof containing one to ten non-native N-glycosylation sites in the heavy chain constant domain is selected from the group consisting of *Pichia pastoris* (*Komagataella pastoris*), *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia minuta* (*Ogataea minuta*, *Pichia lindneri*), *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa* and *Yarrowia lipolytica*. In another embodiment, the yeast host cell is *Pichia pastoris*.

In another embodiment, the IgG Ab or fragment thereof prepared by the aforementioned method comprises one to ten mutations (or pairs of mutations) in the heavy chain constant domain polypeptide selected from the group consisting of S134N, G161T, G161S, N203T, N203S, V363T, V363S, Q438N, S176N, A118N, S132N, K133N, A162N, T195N, K210T, Y391T, F423T, F423S, Y436T, Y436S, L193N, K392T, K392S, F423T, S176N/G178T, S176N/G178S, Q419N/N421T, Q419N/N421S, S191N/L193T, S191N/L193S, G194N/Q196T, and G194N/Q196S, according to EU numbering. In one embodiment, the IgG heavy chain is a human IgG1 constant domain.

In another embodiment, methods of preparing a conjugated N-glycosylated IgG Ab or fragment thereof containing one to two non-native N-glycosylation sites in the heavy chain variable framework domain are also provided.

In another embodiment, a method of preparing a conjugated N-glycosylated IgG Ab or fragment thereof containing one to ten non-native N-glycosylation sites in the heavy chain constant domain is provided, the method comprising:
(a) transforming a yeast or filamentous fungus host cell genetically engineered to produce N-glycans comprising terminal sialic acid residues of the structure $NANA_{(1-4)}Gal_{(1-4)}GlcNAc_{(1-4)}Man_3GlcNAc_2$ with a nucleic acid encoding an IgG heavy chain contain domain, wherein the IgG heavy chain comprises one to ten amino acid mutations (or pairs of mutations), and wherein the one to ten amino acid mutation generates at least one non-native N-glycosylation site in the IgG heavy chain constant domain;
(b) culturing the transformed host cell under conditions that allow the expression of the IgG heavy chain constant domain comprising terminal sialic acid residues,
(c) contacting the expressed IgG heavy chain constant domain with neuraminidase to remove the terminal sialic acid residues to form N-glycosylated heavy chain constant domain comprising terminal galactose residues;
(d) contacting the expressed glycosylated heavy chain constant domain comprising terminal galactose residues of step (c), with a reagent that oxidizes the terminal galactose residues; and
(e) conjugating a drug to the oxidized moiety of the terminal galactose residues.

In one embodiment, the IgG heavy chain is a human IgG1 constant domain.

BRIEF DESCRIPTION OF THE FIGURES

FIG. 21 (A-C): Conjugation of exendin-4 peptide to a glycan-engineered antibody. A, Illustration of the site-specific conjugation of alkoxyamine activated exendin-4 peptide to the Fab glycan of the GS5.0 *Pichia* produced glycan-engineered antibody. B, A deconvoluted Q-ToF mass spectrum of reduced antibody (H chain) after conjugation with exendin-4 peptide, which was used as the basis calculating the peptide:mAb ratio (DAR). C, GLP1-receptor agonist activity assay demonstrating the activity of the mAb/exendin-4 conjugate compared to native GLP-1 peptide, calculated as the EC50 of intracellular cAMP change in GLP-1R recombinant CHO cells.

DESCRIPTION OF THE INVENTION

Figure 1:
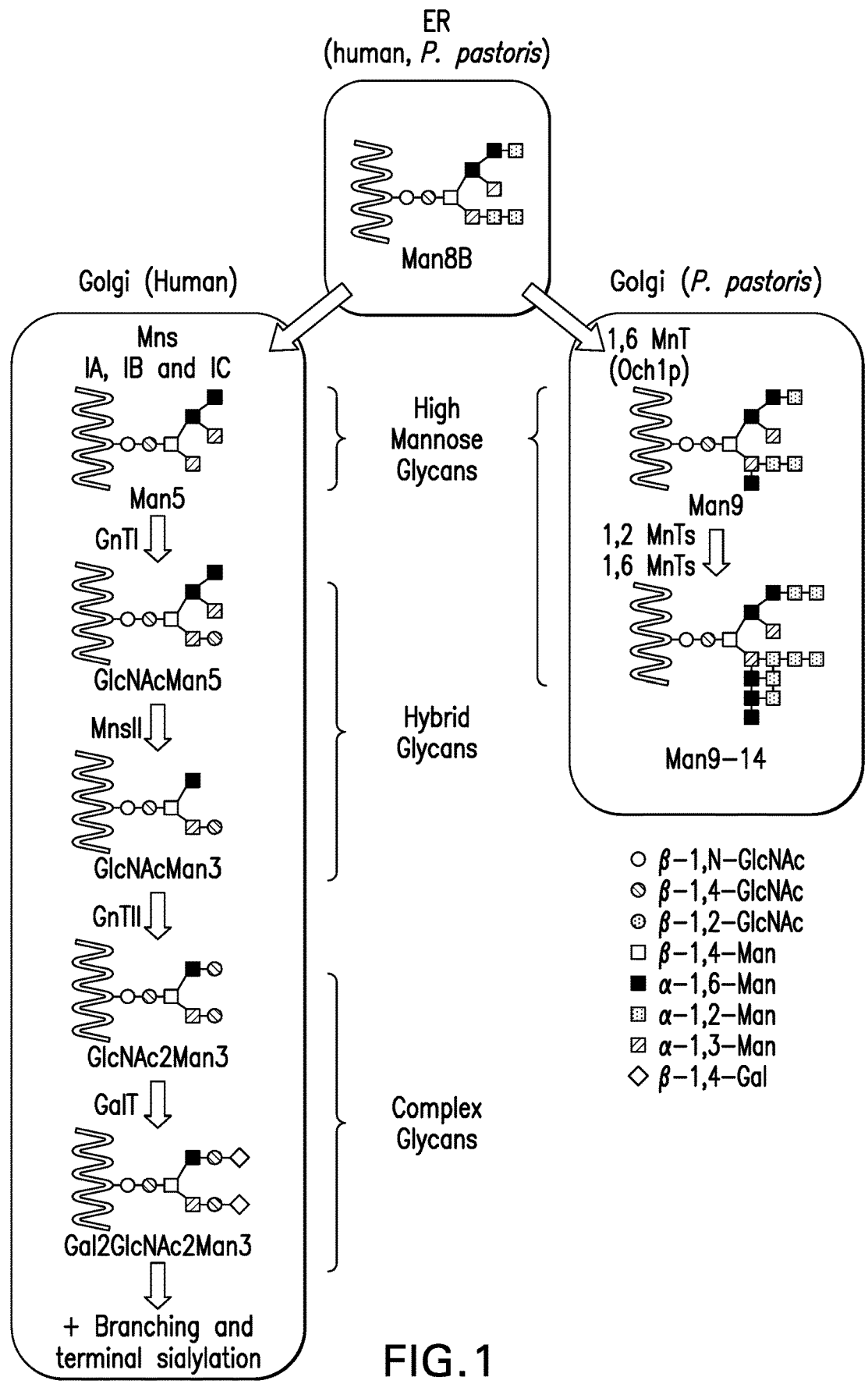
FIG. 1. A comparison of the N-glycosylation machinery between yeast and mammals. Yeast and mammals initiate glycosylation similarly via the secretory pathway, both resulting in a $Man_8GlcNAc_2$ N-glycan following protein folding and ER maturation. N-glycosylation pathways differ in the Golgi with mammals trimming mannose residues and adding GlcNAc to produce hybrid and complex N-glycans in bi-, tri-, or tetra-antennary form, which are then terminated with varying amounts of galactose and sialic acid. In contrast, fungi, such as *P. pastoris*, add additional mannose with various linkages, including an outer chain initiated by the Och1p α-1,6-mannosyltransferase, resulting in glycans that in total can be comprised of dozens of mannose residues. Man, mannose; GlcNAc, N-acetyl glucosamine; Gal, galactose; MnT, mannosyltransferase; MNS, mannosidase; GnT, GlcNAc transferase; GalT, galactosyl transferase.

Patents, patent applications, publications, product descriptions, and protocols are cited throughout this application, the disclosures of which are incorporated herein by reference in their entireties for all purposes. All references cited herein are incorporated by reference to the same extent as if each individual publication, database entry (e.g. GenBank sequences or GeneID entries), patent application, or patent, was specifically and individually indicated to be incorporated by reference. Citation of the references herein is not intended as an admission that the reference is pertinent prior art, nor does it constitute any admission as to the contents or date of these publications or documents.

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

By "position" as used herein is meant a location in the sequence of a protein. Positions may be numbered sequentially, or according to an established format, for example the EU index for antibody numbering or the Kabat numbering.

Amino acid positions in a heavy chain constant domain include amino acid positions in the $C_H1$, hinge, $C_H2$, $C_H3$, Fc, and are numbered according to the EU index numbering system (also referred as the "EU index of Kabat" or the "EU index for antibody numbering" or "EU numbering). See Kabat et al., "Sequence of proteins of Immunological interest", 5$^{th}$ edition, U.S. Dept Health and Human Services, U.S. Gov. Printing Office, 1991.

Amino acid positions in a variable domain (for example, in framework 4 of the heavy chain) are numbered according to the Kabat numbering system (Kabat 1991).

Kabat numbering is based on the seminal work of Kabat et al. (1991) Sequences of Proteins of Immunological Interest, Publication No. 91-3242, published as a three volume set by the National Institutes of Health, National Technical Information Service (hereinafter "Kabat"). Kabat provides multiple sequence alignments of immunoglobulin chains from numerous species antibody isotypes. The aligned sequences are numbered according to a single numbering system, the Kabat numbering system. The Kabat sequences have been updated since the 1991 publication and are available as an electronic sequence database (latest downloadable version 1997). Any immunoglobulin sequence can be numbered according to Kabat by performing an alignment with the Kabat reference sequence. Herein the heavy chain variable sequences are numbered according to the Kabat reference sequence.

The term "$C_H1$" domain as used herein refers to the first constant domain of an IgG heavy chain that extends from about amino acid position 118-215 of the EU numbering system.

The term "hinge region" as used herein refers to the portion of a heavy chain that attaches the $C_H1$ domain to the $C_H2$ domain and comprises about 25 amino acid residues.

The term "$C_H2$ domain" as used herein refers to the portion of a heavy chain IgG constant domain that extends from about amino acid positions 231-340 of the EU numbering system.

The term "$C_H3$ domain" as used herein refers to the heavy chain IgG constant domain that extends from the N-terminus of the $C_H2$ domain from about amino acid positions 341-445 of the EU numbering system.

The term "cytotoxic agent" as used herein refers to the effect of an agent that has a cytotoxic effect on a cell (i.e., an agent that can cause cell death).

The term "drug" as used herein refers to a compound including a compound, a pharmaceutically active compound, element, agent, pharmaceutically active peptide or protein, or molecular entity.

In general, the basic Ab structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function.

As used herein "fragment" with respect to "antibody" or "IgG" or "monoclonal antibody" refers to those fragments produced by digestion with various proteases, those produced by chemical cleavage and/or chemical dissociation and those produced by recombination or recombinant DNA technology so long as the fragment remains capable of specific binding to a target molecule. Examples of fragments include, but are not limited to, Fc, Fab, Fab', F(ab')$_2$, Fv, and scFv fragments.

In an embodiment, the Ab or fragment thereof comprises a heavy chain constant region, e.g. a human constant region, such as γ1, γ2, γ3, or γ4 human heavy chain constant region or a variant thereof. In another embodiment, the Ab or antigen binding fragment comprises a light chain constant region, e.g. a human light chain constant region, such as lambda or kappa human light chain region or variant thereof. By way of example, and not limitation the human heavy chain constant region can be γ1 and the human light chain constant region can be kappa.

A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an Ab.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains. An "$F(ab')_2$ fragment" can be the product of pepsin cleavage of an Ab.

The term "Fc domain" as used herein refers to the portion of a heavy chain constant domain contains the hinge region (i.e., residue 216 in IgG, taking the first amino acid residue of the heavy chain constant domain to be 114), and $C_H2$, and $C_H3$ domains and ending at the C-terminus of the Ab.

The "Fv region" comprises the variable regions from both the heavy and light chains, but lacks the constant regions.

As used herein, a "chimeric Ab" is an Ab having the variable domain from a first Ab and the constant domain from a second Ab, where the first and second Abs are from different species. (U.S. Pat. No. 4,816,567; and Morrison et al., (1984) *Proc. Natl. Acad. Sci. USA* 81: 6851-6855). Typically the variable domains are obtained from an antibody from an experimental animal (the "parental Ab"), such as a rodent, and the constant domain sequences are obtained from human Ab, so that the resulting chimeric Ab will be less likely to elicit an adverse immune response in a human subject than the parental (e.g. rodent) antibody.

Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the Ab binding site. Thus, in general, an intact Ab has two binding sites. Except in bifunctional or bispecific Abs, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "IgG" refers to IgG1, IgG2, IgG3 and IgG4. In an embodiment, IgG is IgG1. In one embodiment, the IgG1 is human IgG1.

As used herein, the term "hypervariable region" refers to the amino acid residues of an Ab that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991); see also Chothia and Lesk (1987) *J. Mol. Biol.* 196: 901-917 (defining the CDR regions of an Ab by structure).

As used herein, the term "framework" or "FR" residues refers to those variable domain residues other than the hypervariable region residues defined herein as CDR residues.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

"Treat" or "treating" means to administer a therapeutic agent, such as a composition containing any of the genetically engineered Abs of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The term further includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the term "therapeutically effective amount" or "effective amount" refers to an amount of an engineered Ab drug conjugate or engineered Ab fragment thereof, that when administered alone or in combination with an additional therapeutic agent to a cell, tissue, or subject is effective to prevent or ameliorate the disease or condition to be treated. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

As used herein, the terms "N-glycan" refers to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins.

Typically, N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the $Man._3GlcNAc_2$ ("Man3") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3mannose arm and at least one GlcNAc attached to the 1,6mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising bisecting GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3mannose arm of the trimannose core and zero or more mannoses on the 1,6mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as $Man_3GlcNAc_2$; the term "G-1" refers to an N-glycan structure that can be characterized as $GlcNAcMan_3GlcNAc_2$; the term "G0" refers to an N-glycan structure that can be characterized as $GlcNAc_2Man_3GlcNAc_2$; the term "G1" refers to an N-glycan structure that can be characterized as $GalGlcNAc_2Man_3GlcNAc_2$; the term "G2" refers to an N-glycan structure that can be characterized as $Gal_2GlcNAc_2Man_3GlcNAc_2$; the term "A1" refers to an N-glycan structure that can be characterized as $NANAGal_2Gal_2GlcNAc_2Man_3GlcNAc_2$; and, the term "A2" refers to an N-glycan structure that can be characterized as $NANA_2Gal_2GlcNAc_2Man_3GlcNAc_2$. Unless otherwise indicated, the terms G-2", "G-1", "G0", "G1", "G2", "A1", and "A2" refer to N-glycan species that lack fucose attached to the GlcNAc residue at the reducing end of the N-glycan.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas $GlcNAc_{(2-4)}Man_3GlcNAc_2$, $Gal_{(1-4)}GlcNAc(2-4)Man_3GlcNAc_2$, or $NANA_{(1-4)}Gal(1-4)GlcNAc_{(2-4)}Man_3GlcNAc_2$. The term "1-4" refers to 1, 2, 3, or 4 residues.

The term "GS3.5", when used herein refers to the N-glycosylation structure $GalGlcNAcMan_5GlcNAc_2$.

The term "GS4.0", when used herein refers to the N-glycosylation structure $GlcNAc_2Man_3GlcNAc_2$.

The term "GS5.0", when used herein refers to the N-glycosylation structure $Gal_2GlcNAc_2Man_3GlcNAc_2$.

The term "GS6.0", when used herein refers to the N-glycosylation structure $NANA_2Gal_2GlcNAc_2Man_3GlcNAc_2$.

The term "non-native N-glycosylation site" as used herein refers to any consensus (N—X—S/T, wherein X is any amino acid except proline) N-glycosylation site incorporated by mutation into an IgG that is not observed on naturally occurring IgG molecules (e.g. N-297). Moreover, while Asn-297 is the N-glycosylation site typically found in murine and human IgG molecules (Kabat et al, Sequences of Proteins of Immunological Interest, 1991), this site doesn't necessarily have to be maintained for function. Using known methods for mutagenesis, the skilled artisan can alter a DNA molecule encoding an Ig of the present invention so that the N-glycosylation site at Asn-297 is deleted.

As used herein, the term "predominantly" or variations such as "the predominant" or "which is predominant" will be understood to mean the glycan species or collective species that has the highest mole percent (%) of total N-glycans after the glycoprotein has been analyzed by mass spectrometry (e.g. Q-ToF) or enzymatically released N-glycans analyzed by mass spectroscopy (e.g. MALDI-TOF MS) or HPLC. For example, if a composition consists of species A in 40 mole percent, species B in 35 mole percent and species C in 25 mole percent, the composition comprises predominantly species A, and species B would be the next most predominant species. Furthermore, if a composition contains a mixture of species where 60% contain terminal galactose and 40% contain terminal sialic acid the composition will be defined has having predominantly terminal galactose.

As used herein, a glycoprotein composition "lacks" or "is lacking" a particular sugar residue, such as fucose or galactose, when no detectable amount of such sugar residue is present on the N-glycan structures at any time. For example, in preferred embodiments of the present invention, the glycoprotein compositions are produced by lower eukaryotic organisms, as defined above, including yeast and fungi [e.g., *Pichia* sp.; *Saccharomyces* sp.; *Kluyveromyces* sp.; *Aspergillus* sp.], and will "lack fucose," because the cells of these organisms do not have the enzymes needed to produce fucosylated N-glycan structures. Thus, the term "essentially free of fucose" encompasses the term "lacking fucose."

However, a composition may be "essentially free of fucose" even if the composition at one time contained fucosylated N-glycan structures or contains limited, but detectable amounts of fucosylated N-glycan structures.

The term "mole percent" of a glycan present in a preparation of a N-glycosylated Ab refers to the molar percent of a particular glycan present in the pool of N-linked oligosaccharides released when the N-glycosylated Ab preparation is treated with PNGase and then quantified by a method that is not affected by glycoform composition, for instance, labeling a PNGase released glycan pool with a fluorescent tag such as 2-aminobenzamide and then separating by high performance liquid chromatography or capillary electrophoresis and then quantifying glycans by fluorescence intensity, or MALDI-TOF mass spectrometry. For example, 50 mole percent $NANA_2Gal_2GlcNAc_2Man_3GlcNAc_2$ means that 50 percent of the released glycans are $NANA_2Gal_2GlcNAc_2Man_3GlcNAc_2$ and the remaining 50 percent are comprised of other N-linked oligosaccharides. In embodiments, the mole percent of a particular glycan in a preparation of glycoprotein will be between 20% and 100%, preferably above 25%, 30%, 35%, 40% or 45%, more preferably above 50%, 55%, 60%, 65% or 70% and most preferably above 75%, 80% 85%, 90% or 95%.

Overview

The present invention provides engineered Abs, in particular IgG Abs or fragments thereof comprising one to ten mutations (or pairs of mutations) in the heavy chain constant domain which generate one to ten non-native N-glycosylation sites. As shown in the Examples (see Example 1 and Example 14), the non-native N-glycosylation sites provide specific targeting sites for drug conjugates. In one embodiment, the engineered Abs, or fragments thereof of the invention are expressed in yeast and filamentous fungi host cells that have been engineered to produce human like N-glycans of the structure: $Gal_{(1-4)}GlcNAc_{(1-4)}Man_3GlcNAc_2$, $Gal_{1-2}GlcNAc_{(1-2)}Man_5GlcNAc_2$ or $NANA_{(1-4)}Gal_{(1-4)}GlcNAc_{(1-4)}Man_3GlcNAc_2$. In some embodiments, engineered Abs or fragments thereof expressed in these engineered yeast and filamentous fungi host cells comprise N-glycans where the predominant glycoform comprise the following structures: $Gal_{(1-4)}GlcNAc_{(1-4)}Man_3GlcNAc_2$ or $Gal_{(1-2)}GlcNAc_{(1-2)}Man_5GlcNAc_2$. In some embodiments, engineered Abs or fragments thereof expressed in glycoengineered yeast and filamentous fungi host cells comprise N-glycans in the non-native N-glycosylation sites comprising predominantly terminal sialylated residues ($NANA_{(1-4)}Gal_{(1-4)}GlcNAc_{(1-4)}Man_3GlcNAc_2$), which in turn, can be converted into terminal galactose residues by an enzymatic reaction.

In some embodiments, the engineered Abs comprise N-glycans at the non-native N-glycosylation sites which do not disrupt the normal folding or function of the mAb, and allow the efficient, uniform conjugation of drugs such as toxins, peptides or bioactive sugar moieties. The DAR of the conjugated Ab can be modulated through the number of non-native N-glycosylation sites engineered into the Ab at specific sites as specified by the invention examples and the number of terminal galactose residues, which is driven by the N-glycan machinery of the recombinant host strain.

As background, the N-glycans are important molecules in biology that participate in a wide-range of different activities, from protein folding and trafficking to immune cell and host-pathogen interactions, owing in large part to the heterogeneity available from the modular, non-template nature of this protein modification, leading to an impressive breadth of potential forms that can be produced from a single core structure. N-glycans are also a key factor in biotherapeutic discovery and manufacture and limit the choice of expression system in many cases (Hossler, 2009; Schirrmann, 2008; Sethuraman, 2006). Examples of the differences in N-glycan pathways between humans and yeast can be found in FIG. 1. A unique biotherapeutic platform has been developed in yeast, in particular, in the species *Pichia pastoris*, in which the N-glycosylation pathway has been modified to generate human-like N-glycans (See, e.g., Bobrowicz et al., 2004; Sethuraman, 2006; Hamilton, 2006; Li et al., 2006; Nett et al., 2010; Choi et al., 2009; U.S. Pat. Nos. 7,029,872 and 7,449,308). Glycoengineered *Pichia* allows for unprecedented uniformity, specificity and control of N-glycans on recombinantly produced proteins, including Abs. A summary of glycoengineered *Pichia* can be found in FIG. 2. The unique nature of this genetically engineered system and process versatility allows for a tremendous level of freedom over what sugars can be attached and in what arrangements, ultimately allowing for modifications both prior to and after addition to the growing N-glycan chain.

Directed and specific control of N-glycosylation can provide unique control over biology (e.g. modulation of inflammation, tissue and cell type targeting) but can also provide an opportunity for creating unique macromolecule chemistry, particularly in the case of the terminal sugars galactose and sialic acid (Ramya et al, 2013). Galactose oxidase (GO) is an enzyme that can specifically modify terminal galactose sugars present on an N-glycan, thus allowing for highly versatile and specific aldehyde-based chemistry that is not otherwise available in the 20 amino acid repetoire. However, the glycan heterogeneity that is confronted with conventional expression systems such as mammalian cells could complicate such an approach. For example, as demonstrated for human Erythropoietin (Nett et al, 2010; Restelli et al, 2006), proteins with exposed N-glycans can have huge variability in numbers of antennae (bi-, tri-, and tetra-) and amount of terminal sialic acid, whereas antibodies can contain differing amounts of fucose and galactose in addition to trace amounts of sialic acid (Li et al, 2006), all of which contributes to the considerable heterogeneity of mammalian N-glycans.

In one embodiment, the present invention provides an engineered IgG Ab or fragment thereof comprising one to ten mutations (or pairs of mutations) in the heavy chain constant domain, which generate one to ten non-native N-glycosylation sites, the mutations being selected from the group consisting of S134N, G161T, G161S, N203T, N203S, V363T, V363S, Q438N, S176N, A118N, S132N, K133N, A162N, T195N, K210T, Y391T, F423T, F423S, Y436T, Y436S, L193N, K392T, K392S, F423T, S176N/G178T, S176N/G178S, Q419N/N421T, Q419N/N421S, S191N/L193T, S191N/L193S, G194N/Q196T, and G194N/Q196S, according to EU numbering.

In one embodiment, the engineered IgG Ab or fragment thereof comprises at least one or two amino acid mutations in the heavy chain constant polypeptide selected from S134N, G161T and S134N/G161T.

In another embodiment, the engineered IgG Ab or fragment thereof comprises at least two amino acid mutations in the heavy chain constant domain selected from G161T/S134T and G161S/S134T.

In one embodiment, the engineered heavy chain constant domains comprise, at the non-native N-glycosylated sites, predominantly complex N-glycans having the structure $Gal_{(1-4)}GlcNAc_{(1-4)}Man_3GlcNAc_2$. In one embodiment, engineered heavy chain constant domains comprise, at the non-native N-glycosylation sites, predominantly complex N-glycans having the structure Gal$_2$GlcNAc$_2$Man$_3$GlcNAc$_2$ (also referred to as GS5.0 N-glycans in FIG. 2 and Example 3)

In another embodiment, the engineered heavy chain constant domains comprise, at the non-native N-glycosylated sites, predominantly hybrid N-glycans having the structure Gal$_{(1-2)}$GlcNAc$_{(1-2)}$Man$_5$GlcNAc$_2$.

In another embodiment, the engineered heavy chain constant domains comprise, at the non-native N-glycosylated sites, predominantly N-glycans having the structure NANA$_{(1-4)}$Gal$_{(1-4)}$GlcNAc$_{(1-4)}$Man$_3$GlcNAc$_2$.

In another embodiment, the engineered IgG Abs or fragments thereof having non-native N-glycosylation sites comprise N-glycans wherein about 50 to about 100 mole % of the N-glycans comprise the structure: Gal$_2$GlcNAc$_2$Man$_3$GlcNAc$_2$, Gal$_{(1-2)}$GlcNAc$_{(1-2)}$Man$_5$GlcNAc$_2$ or NANA$_{(1-4)}$Gal$_{(1-4)}$GlcNAc$_{(1-4)}$Man$_3$GlcNAc$_2$. In another embodiment, the engineered IgG Abs or fragments thereof having non-native N-glycosylation sites comprise N-glycans where about 80 to about 100 mole % of the N-glycans comprise the structure: Gal$_2$GlcNAc$_2$Man$_3$GlcNAc$_2$, Gal$_{(1-2)}$GlcNAc$_{(1-2)}$Man$_5$GlcNAc$_2$ or NANA$_{(1-4)}$Gal$_{(1-4)}$GlcNAc$_{(1-4)}$Man$_3$GlcNAc$_2$.

In one embodiment, the engineered Abs or fragments thereof are expressed in host cells capable of producing a composition of Abs or fragments thereof comprising N-glycans where the predominant glycoform comprise a Gal$_2$GlcNAc$_2$Man$_3$GlcNAc$_2$ N-glycan structure lacking fucose, wherein said structure is present at a level that is at least about 5 mole percent more than the next predominant N-glycan structure in the composition. In one embodiment, the engineered IgG Ab or fragments thereof comprise a predominant Gal$_2$GlcNAc$_2$Man$_3$GlcNAc$_2$ N-glycan structure lacking fucose, wherein said structure is present at a level of at least about 10 mole percent to about 25 mole percent more than the next predominant N-glycan structure in the composition. In one embodiment, the engineered IgG Abs or fragments thereof comprise a predominant Gal$_2$GlcNAc$_2$Man$_3$GlcNAc$_2$ N-glycan structure lacking fucose, wherein said structure is present at a level that is at least about 25 mole percent to about 50 mole percent more than the next predominant N-glycan structure in the composition. In one embodiment, the engineered IgG Abs or fragments thereof comprise a predominant Gal$_2$GlcNAc$_2$Man$_3$GlcNAc$_2$ glycan structure lacking fucose, wherein said structure is present at a level that is greater than about 50 mole percent more than the next predominant glycan structure in the composition. In one embodiment, the engineered IgG Abs or fragments thereof comprise a predominant Gal$_2$GlcNAc$_2$Man$_3$GlcNAc$_2$ N-glycan structure lacking fucose, wherein said structure is present at a level that is greater than about 75 mole percent more than the next predominant glycan structure in the composition. In still another embodiment, the engineered IgG Abs or fragments thereof comprise a predominant Gal$_2$GlcNAc$_2$Man$_3$GlcNAc$_2$ N-glycan structure lacking fucose wherein said structure is present at a level that is greater than about 90 mole percent more than the next predominant glycan structure in the composition. MALDI-TOF analysis of N-glycans of an IgG having a predominant (greater than 95 mole %) Gal2GlcNAc2Man3GlcNAc2 lacking fucose is shown in FIG. 26.

In another embodiment, the aforementioned IgG Ab or fragment thereof used for genetic engineering in its heavy chain constant domain is selected from the group consisting of anti-Her2, anti-Her2/neu (Herceptin), anti-glycoprotein IIb/IIIa (Abciximab), anti-TNF-α (Adalimumab, Certolizumab pegol, Golimumab, Infliximab), anti-CD52 (Alemtuzumab), anti-IL-2Rα (CD25) (Basiliximab), anti-BAFF (Belimumab), anti-Vascular endothelial growth factor (VEGF) (Bevacizumab), anti-CD30 (Brentuximab vedotin), anti-IL-1β (Canakinumab), anti-epidermal growth factor receptor (EGFR) (Cetuximab), anti-IL-2Rα receptor (CD25) (Daclizumab), anti-RANK Ligand (Denosumab), anti-Complement C5 (Eculizumab), anti-CD11a (Efalizumab), anti-CD33 (Gemtuzumab), anti-CD20 (Ibritumomab tiuxetan), anti-CTLA-4 (Ipilimumab (MDX-101)), anti-T cell CD3 Receptor (Muromonab-CD3), anti-alpha-4 (α4) integrin, anti-(Natalizumab), anti-CD20 (Ofatumumab), anti-Immunoglobulin E (IgE) (Omalizumab), anti-RSV F protein (Palivizumab), anti-epidermal growth factor receptor (Panitumumab), anti-VEGF-A (Ranibizumab), anti-CD20 (Rituximab), anti-Anti-IL-6R (Tocilizumab, Atlizumab), anti-CD20 (Tositumomab), anti-ErbB2 (Trastuzumab), anti-IL-12/IL-23 (Ustekinumab), anti-integrin α4β7 (Vedolizumab), anti-CD274, anti-3-amyloid, anti-4-1BB, anti-SAC, anti-5T4, anti-ACVR2B, anti-adenocarcinomaantigen, anti-AGS-22M6, anti-alpha-fetoprotein, anti-angiopoietin 2, anti-angiopoietin 3, anti-anthrax toxin, anti-AOC3 (VAP-1), anti-, anti-B7-H3, anti-*Bacillus anthracia*, anti-BAFF, anti-beta amyloid, anti-B-lymphoma cell, anti-C242 antigen, anti-05, anti-CA-125, anti-carbonic anhydrase 9 (CA-IX), anti-cardiac myosin, anti-CCL11 (eotaxin-1), anti-CCR4, anti-CCR5, anti-CD11/CD18, anti-CD125, anti-CD140a, anti-CD147 (basigin), anti-CD15, anti-CD152, anti-CD154 (CD40L), anti-CD19, anti-CD2, anti-CD20, anti-CD200, anti-CD22, anti-CD221, anti-CD23, anti-CD25, anti-CD27, anti-CD28, anti-CD28, anti-CD3, anti-CD3 epsilon, anti-CD30 (TNFRSF8), anti-CD33, anti-CD37, anti-CD38, anti-CD4, anti-CD40, anti-CD41, anti-CD44, anti-CD5, anti-CD51, anti-CD52, anti-CD56, anti-CD6, anti-CD70, anti-CD74, anti-CD79B, anti-CD80, anti-CEA, anti-CFD, anti-ch4D5, anti-CLDN18.2, anti-*C. difficile*, anti-clumping factor A, anti-CSF2, anti-CTLA-4, anti-cytomegalovirus, anti-CMV gp B, anti-DLL4, anti-DR5, anti-*E. coli* shiga toxin type-1 or 2, anti-EGFL7, anti-EGFR, anti-endotoxin, anti-EpCAM, anti-EpCAM/CD3, anti-episialin, anti-ERBB3, anti-*Escherichia coli*, anti-F protein RSV, anti-FAP, anti-fibrin II, beta chain, anti-fibronectin extra domain-B, anti-folate receptor 1, anti-Frizzled receptor, anti-ganglioside GD2, anti-GD2, anti-GD3 ganglioside, anti-GD3 ganglioside, anti-GMCSF receptor α-chain, anti-GPNMB, anti-Influenza, anti-Influenza hemagglutinin, anti-hepatitis B, anti-hepatitis B, anti-surface antigen, HER1, anti-HER2/neu, anti-HER2, CD3, anti-HER3, anti-HGF, anti-HGF, anti-HHGFR, anti-HIV-1, anti-HLA-DR, anti-HNGF, anti-Hsp90, anti-human scatter factor receptor kinase, anti-human TNF, anti-human beta-amyloid, anti-ICAM-1 (CD54), anti-IFN-α, anti-IFN-γ, anti-IgE, anti-IgE Fc region, anti-IGF-1 receptor, anti-IGF-I, anti-IgG4, anti-IGHE, anti-IL 20, anti-IL-1beta, anti-IL-12/IL-23, anti-IL-13, anti-IL-17, anti-IL-17A, anti-IL-10, anti-IL-22, anti-IL-23, anti-IL-4, anti-IL-S, anti-IL-6, anti-IL-6 receptor, anti-IL9, anti-ILGF2, anti-insulin-like growth factor I receptor (IGF-1R), anti-integrin α4β7, anti-integrin α4, anti-integrin α4β7, anti-integrin α5β1, anti-integrin α7 β7, anti-integrin αIIbβ3, anti-integrin αvβ3, anti-interferon receptor, anti-interferon α/β receptor, anti-interferon gamma-induced protein, anti-ITGA2, anti-ITGB2 (CD18), anti-KIR2D, anti-Lewis-Y antigen, anti-LFA-1 (CD11a), anti-lipoteichoic acid, anti-LOXL2, anti-L-selectin (CD62L), anti-LTA, anti-MCP-1, anti-mesothelin, anti-MS4A1, anti-MUC1, anti-mucin CanAg, anti-myostatin, anti-NARP-1, anti-NCA-90, anti-NGF, anti-N-glycolyl-neuraminic acid (NGNA), anti-NOGO-A, anti-Notch receptor, anti-NRP1, anti-*Oryctolagus cuniculus*, anti-OX-40, anti-oxLDL, anti-PCSK9, anti-PD-1, anti-PDCD1, anti-PDCD1, anti-PDGF-R α, anti-phosphate-sodium co-transporter, anti-phosphatidylserine, anti-prostatic carcinoma cells, anti-*Pseudomonas aeruginosa*, anti-rabies virus, anti-rabies virus glycoprotein, anti-RANKL, anti-respiratory syncytial virus, anti-RHD, anti-Rhesus factor, anti-RON, anti-RTN4, anti-sclerostin, anti-SDC1, anti-selectin P, anti-SLAMF7, anti-SOST, anti-sphingosine-1-phosphate, anti-TAG-72, anti-T-cell receptor, anti-TEM1, anti-tenascin C, anti-TFPI, anti-TGF beta 1, anti-TGF beta 2, anti-TGF-β, anti-TNF-α, anti-TRAIL-R1, anti-TRAIL-R2, anti-tumor antigen CTAA16.88, anti-MUC1 (tumor-specific glycan), anti-TWEAK receptor, anti-TYRP1 (glycoprotein 75), anti-VEGF-A, anti-VEGFR-1, anti-VEGFR2, anti-vimentin, anti-VWF, anti-IL-1, anti-IL-2, anti-IL-4, anti-IL-5, anti-IL-6, anti-IL-8, anti-IL-9, anti-IL-10, anti-IL-12, anti-IL-15, anti-IL-17, anti-IL-18, anti-IL-20, anti-IL-21, anti-IL-22, anti-IL-23, anti-IL-23R, anti-IL-25, anti-IL-27, anti-IL-33, anti-CD2, anti-CD4, anti-CD11A, anti-CD14, anti-CD18, anti-CD19, anti-CD23, anti-CD25, anti-CD40, anti-CD40L, anti-CD20, anti-CD52, anti-CD64, anti-CD80, anti-CD147, anti-CD200, anti-CD200R, anti-TSLP, anti-TSLPR, anti-PD-1, anti-PDL1, anti-CTLA4, anti-VLA-4, anti-VEGF, anti-PCSK9, anti-α4β7-integrin, anti-E-selectin, anti-Fact II, anti-ICAM-3, anti-beta2-integrin, anti-IFNγ, anti-O5, anti-CBL, anti-LCAT, anti-CR3, anti-MDL-1, anti-GITR, anti-CGRP, anti-TRKA, anti-IGF1R, anti-GTC.

In one embodiment, the engineered IgG Ab or fragment thereof is human anti-Her2 Ab or a fragment thereof. In another embodiment, the engineered IgG Ab is human anti-PD-1 Ab or a fragment thereof.

In another embodiment, the engineered IgG Ab or fragment thereof is an anti-Her2 Ab comprising a heavy chain mutant polypeptide comprising an amino acid sequence selected from SEQ ID NOs: 4-29, 31, 32, 33, 34, 35, 36, 37, 38, 39 and 40.

In another embodiment, the engineered IgG Ab or fragment thereof is an anti-mouse-PD-1 Ab comprising a heavy chain mutant polypeptide comprising an amino acid sequence selected from SEQ ID NOs: 41-45.

In another embodiment, the engineered IgG Ab or fragment thereof is an anti-CS1 Ab comprising a heavy chain mutant polypeptide comprising an amino acid sequence selected from SEQ ID NOs: 46-50.

In another embodiment, the engineered IgG Ab or fragment thereof is an anti-CD70 Ab comprising a heavy chain mutant polypeptide comprising an amino acid sequence selected from SEQ ID NOs: 51-55.

In another embodiment, the present invention provides an engineered IgG Ab or fragment thereof comprising one to two mutations in the heavy chain framework domain which generate one to two non-native N-glycosylation sites, the mutations being selected from the group consisting of Q105N and S113N, according to Kabat numbering.

In one embodiment, the engineered heavy chain constant domain comprises, at the non-native N-glycosylated sites, predominantly complex N-glycans having the structure $Gal_{(1-4)}GlcNAc_{(1-4)}Man_3GlcNAc_2$. In one embodiment, engineered heavy chain constant domain comprise, at the non-native N-glycosylation sites, predominantly complex N-glycans having the structure $Gal_2GlcNAc_2Man_3GlcNAc_2$ (also referred to as GS5.0 N-glycans in FIG. 2 and Example 3)

In another embodiment, the engineered heavy chain constant domain comprises, at the non-native N-glycosylated sites, predominantly hybrid N-glycans having the structure $Gal_{(1-2)}GlcNAc_{(1-2)}Man_5GlcNAc_2$.

In another embodiment, the engineered heavy chain constant domain comprises, at the non-native N-glycosylated sites, predominantly N-glycans having the structure $NANA_{(1-4)}Gal_{(1-4)}GlcNAc_{(1-4)}Man_3GlcNAc_2$ In another embodiment, the engineered IgG Ab having non-native N-glycosylation sites comprises N-glycans wherein about 50 to about 100 mole % of the N-glycans comprise the structure: $Gal_2GlcNAc_2Man_3GlcNAc_2$, $Gal_{(1-2)}GlcNAc_{(1-2)}Man_5GlcNAc_2$ or $NANA_{(1-4)}Gal_{(1-4)}GlcNAc_{(1-4)}Man_3GlcNAc_2$. In another embodiment, the engineered Ab having non-native N-glycosylation sites comprises N-glycans where about 80 to about 100 mole % of the N-glycans comprise the structure: $Gal_2GlcNAc_2Man_3GlcNAc_2$, $Gal_{(1-2)}GlcNAc_{(1-2)}Man_5GlcNAc_2$ or $NANA_{(1-4)}Gal_{(1-4)}GlcNAc_{(1-4)}Man_3GlcNAc_2$.

In one embodiment, the aforementioned IgG Ab or fragment thereof used for genetic engineering in its heavy chain framework domain is selected from the Abs as described above.

Ab-Drug Conjugates

In another embodiment, the engineered IgG Ab or fragment thereof is conjugated to a drug via the Ab's non-native N-glycosylated site. The drug is selected from the group consisting of a polymer, cytotoxic agent, a radionuclide, fluorescent or chemiluminescent labels, steroid, steroid receptor agonist, signal transduction inhibitor, a peptide and scFv.

In one embodiment, the drug is a polymer which increases the half-life of the engineered Ab or fragment thereof in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Methods for pegylating proteins are known in the art and can be applied to the Abs of the invention. See, e.g., EP 0 154 316 and EP 0 401 384. Lee, et al., (1999) (*Bioconj. Chem.* 10:973-981) discloses PEG conjugated single-chain Abs. Wen, et al., (2001) (*Bioconj. Chem.* 12:545-553) disclose conjugating antibodies with PEG which is attached to a radiometal chelator (diethylenetri-aminpentaacetic acid (DTPA)). For example, to pegylate an Ab, the Ab, or fragment thereof, typically is reacted with a reactive form of polyethylene glycol (PEG), such as a reactive ester or aldehyde derivative of PEG, under conditions in which one or more PEG groups become attached to the antibody or antibody fragment. In particular embodiments, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide.

The engineered IgG Ab or fragments thereof may also be conjugated to a cytotoxic agent such as diphtheria toxin, *Pseudomonas aeruginosa* exotoxin A chain, ricin A chain, abrin A chain, modeccin A chain, alpha-sarcin, *Aleurites fordii* proteins and compounds (e.g., fatty acids), dianthin proteins, *Phytoiacca americana* proteins PAPI, PAPII, and PAP-S, *Momordica charantia* inhibitor, curcin, crotin, *Saponaria officinalis* inhibitor, mitogellin, restrictocin, phenomycin, and enomycin.

The engineered IgG Ab and fragments thereof may also be conjugated with labels such as $^{99}$Tc, $^{90}$Y, $^{111}$In, $^{32}$P, $^{14}$C, $^{125}$I, $^{3}$H, $^{131}$I, $^{11}$C, $^{15}$O, $^{13}$N, $^{18}$F, $^{35}$S, $^{51}$Cr, $^{57}$To, $^{226}$Ra, $^{60}$Co, $^{59}$Fe, $^{57}$Se, $^{152}$Eu, $^{67}$CU, $^{217}$Ci, $^{211}$At, $^{212}$Pb, $^{47}$Sc, $^{109}$Pd, $^{234}$Th, and $^{40}$K, $^{157}$Gd, $^{55}$Mn, $^{52}$Tr, and $^{56}$Fe.

The engineered IgG Ab or fragment thereof may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthalaldehyde, fluorescamine, $^{152}$Eu, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

The engineered IgG Ab or fragment thereof may also be conjugated to a steroid such as glucocorticoid.

The engineered IgG Ab or fragment thereof may also be conjugated to a steroid receptor agonist such as a glucocorticoid receptor agonist (e.g., mapracorat).

The engineered IgG Ab or fragment thereof may also be conjugated to a signal transduction inhibitor such as dasatinib (see Wang et al., 2015).

The engineered IgG Ab or fragment thereof may also be conjugated to a peptide, e.g., activated GLP-1 receptor agonistic peptide (see Example 9)

The engineered IgG Ab or fragment thereof may also be conjugated to a scFv.

Any method known in the art for conjugating the Ab molecules to the various moieties may be employed (see e.g., Axup, 2012; Tian, 2014; Jackson, 2014, WO2005047334, WO2005047336, WO200547337 and WO2006107124 (the disclosures of which are incorporated herein by reference) disclose chemically conjugating peptides or drug molecules to Fc fragment. Methods for conjugating Abs are conventional and very well known in the art.

ADC delivery of a drug moiety to its intracellular target occurs via a multistep sequence of events: binding to the cell surface, endocytosis, trafficking (within an endosome) to a lysosome, proteolytic degradation of the conjugate, and diffusion of the released drug moiety across the lysosomal or endosomal membrane toward its intracellular target and its interaction with the target. Therefore, the linker should be sufficiently stable while in circulation to allow delivery of the intact ADC to the target cell but, on the other hand, sufficiently labile to allow release of the drug moiety from the ADC once inside the targeted cell.

In an embodiment as described below in the method of preparing an engineered Ab-drug conjugate, the linker is comprised of an oxime linkage. In this regard, the terminal galactose residues of the human complex N-glycan or human hybrid N-glycan are specifically oxidized to produce chemically-reactive aldehyde groups utilizing an enzyme known as galactose oxidase (GO) as described e.g., in Cooper et al., 1959. The chemically reactive aldehyde group is receptive to direct conjugation with an alkoxyamine substrate forming a stable oxime bond as described e.g., in Ramya et al. 2013, and as described below and in Example 5.

Uses of Ab-Drug Conjugates
Immunoimaging

In another embodiment, the engineered IgG Ab-drug conjugates of the present invention can be used for in vivo immunoimaging. For this purpose, the Ab or fragment thereof is labeled by means which permit external visualization of its position or location within a subject or part thereof, such as an organ. Typically, an immunoimaging agent will be an Ab labeled directly (as with Technetium) or indirectly (as with chelated Indium) with a suitable radioisotope. After injection into the patient, the location of the conjugate may be tracked by a detector sensitive to particles emitted by the radiolabel, e.g., a gamma-scintillation camera in the case of a gamma emitter.

Immunotherapy

In another embodiment, the engineered IgG Ab-drug conjugate of the present invention can be used to treat cancer or a disease, such as an autoimmune disease or an infectious disease, in a patient, such as a human or an animal (e.g., a dog or a cat) suffering from the cancer or the disease. Accordingly, methods of treating a disease or cancer in a patient suffering from the cancer or disease are provided, the methods comprising administering to the patient a therapeutically effective amount of the engineered IgG Ab or fragment thereof, which is conjugated to a drug.

With respect to cancer, the engineered Ab-drug conjugates can be used for inhibiting the multiplication of a tumor cell or cancer cell, causing apoptosis in a tumor or cancer cell, or for treating cancer in a patient by delivering a drug to a tumor cell or cancer cell.

The specificity of the Ab for a particular tumor cell or cancer cell can be important for determining those tumors or cancers that are most effectively treated. For example, the anti-HER2 mAb trastuzumab is known to be useful in treating HER+ tumors such as breast cancer and brain cancer.

Examples of cancers that can be treated with the engineered Ab-drug conjugates include, but are not limited to, solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, blood-borne cancers (including but not limited to: acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma), acute and chronic leukemias (e.g., lymphoblastic, myelogenous, lymphocytic, and myelocytic leukemias), and Lymphomas (e.g., Hodgkin's disease, non-Hodgkin's Lymphoma, Multiple myeloma, Waldenstrom's macroglobulinemia, Heavy chain disease, and Polycythemia vera).

In another embodiment, the engineered Ab-drug conjugate can be administered concurrently with another anticancer agent such as a chemotherapeutic agent or with radiation therapy. In another embodiment, the chemotherapeutic agent or radiation therapy is administered prior or subsequent to administration of the engineered Ab-drug conjugate. Any one or a combination of the chemotherapeutic agents listed below can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Examples of chemotherapeutic agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel. drugs such as an alkylating agents such as a nitrogen mustard (e.g., cyclophosphamide, ifosfamide, trofosfamide, chlorambucil, melphalan), nitrosoureas (e.g., carmustine (BCNU), lomustine (CCNU)), alkyl sulphonates (e.g., busulfan, treosulfan), triazenes (e.g., decarbazine), Platinum containing compounds (e.g., cisplatin, carboplatin); plant alkaloids, such as *vinca* alkaloids (e.g., vincristine, vinblastine, vindesine, vinorelbine), taxoids (e.g., paclitaxel, docetaxol); DNA topoisomerase inhibitors such as epipodophyllins (e.g., etoposide, teniposide, topotecan, 9-aminocamptothecin, camptothecin, crisnatol, mitomycins (e.g., mitomycin C); anti-metabolites such as anti-folates such as DHFR inhibitors (e.g., methotrexate, trimetrexate), IMP dehydrogenase inhibitors (mycophenolic acid, tiazofurin, ribavirin, EICAR) and ribonucleotide reductase inhibitors (e.g., hydroxyurea, deferoxamine), pyrimidine analogs such as uracil analogs (5-fluorouracil, floxuridine, doxifluridine, ratitrexed), cytosine analogs (e.g., cytarabine (ara C), cytosine arabinoside, fludarabine), and purine analogs (e.g., mercaptopurine, thioguanine); hormonal therapies, such as receptor antagonists, such as anti-estrogens (e.g., tamoxifen, raloxifene, megestrol), LHRH agonists (e.g., goscrclin, leuprolide acetate), and anti-androgens (e.g., flutamide, bicalutamide; retinoids/deltoids such as vitamin D3 analogs (e.g., EB 1089, CB 1093, KH 1060), photodynamic therapies (e.g., vertoporfin (BPD-MA), phthalocyanine, photosensitizer Pc4, demethoxy-hypocrellin A (2BA-2-DMHA)), cytokines (e.g., interferon-.alpha., interferon-.gamma., tumor necrosis factor), as well as other drugs, such as gemcitabine, velcade, revamid, thalamid, isoprenylation inhibitors (e.g., lovastatin), dopaminergic neurotoxins (e.g., 1-methyl-4-phenylpyridinium ion), cell cycle inhibitors (e.g., staurosporine), actinomycins (e.g., actinomycin D, dactinomycin), bleomycins, bleomycin A2, bleomycin B2, peplomycin), anthracyclines (daunorubicin, Doxorubicin (adriamycin), idarubicin, epirubicin, pirarubicin, zorubicin, mtoxantrone), MDR inhibitors (e.g., verapamil), and $Ca^{2+}$ ATPase inhibitors (e.g., thapsigargin)

The engineered Ab-drug conjugates can also be used for killing or inhibiting the replication of a cell that produces an autoimmune disease or for treating an autoimmune disease. Accordingly, the engineered Ab-drug conjugates can be used accordingly in a variety of settings for treating an autoimmune disease in a patient suffering from the autoimmune disease. For example, the conjugates can be used to deliver a drug to a target cell. Without being bound by theory, in one embodiment, the engineered Ab-drug conjugates associate with an antigen on the surface of a target cell, and the conjugate is then taken up inside a target-cell through receptor-mediated endocytosis. Once inside the cell, one or more specific peptide sequences (e.g., within a linker) are enzymatically or hydrolytically cleaved, resulting in release of a drug. The released drug is then free to migrate in the cytosol and induce cytotoxic or cytostatic activities. In another embodiment, the drug is cleaved from the engineered Ab-conjugate outside the target cell, and the drug subsequently penetrates the cell.

In another embodiment, the engineered Ab-drug conjugates bind to an autoimmune antigen which is on the surface of a cell. For example, the engineered Ab can bind to activated lymphocytes that are associated with the autoimmune disease state. In a further embodiment, the engineered Ab-drug conjugates kill or inhibit the multiplication of cells that produce an autoimmune antibody associated with a particular autoimmune disease.

Examples of autoimmune diseases that can be treated with the engineered Ab-drug conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis and tuberculosis); and activated B lymphocyte related disorders (e.g., systemic lupus erythematosus, Goodpasture's syndrome, rheumatoid arthritis and type I diabetes). Other autoimmune diseases include, but are not limited to, active chronic hepatitis, Addison's disease, allergic alveolitis, allergic reaction, allergic rhinitis, Alport's Syndrome, anaphylaxis, ankylosing spondylitis, anti-phospholipid syndrome, arthritis, ascariasis, aspergillosis, atopic allergy, atropic dermatitis, atropic rhinitis, Behcet's disease, Bird-Fancier's Lung, bronchial asthma, Caplan's syndrome, cardiomyopathy, Celiac disease, Chagas' disease, chronic glomerulonephritis, Cogan's Syndrome, cold agglutinin disease, congenital rubella infection, CREST syndrome, Crohn's disease, cryoglobulinemia, Cushing's syndrome, dermatomyositis, discoid lupus, Dressler's syndrome, Eaton-Lambert syndrome, echovirus infection, encephalomyelitis, endocrine opthalmopathy, Epstein-Barr virus infection, equine heaves, erythematosis, Evan's syndrome, Felty's syndrome, fibromyalgia, Fuch's cyclitis, gastric atrophy, gastrointestinal allergy, giant cell arteritis, glomerulonephritis, goodpasture's syndrome, graft v. host disease, Graves' disease, Guillain-Barre disease, Hashimoto's thyroiditis, hemolytic anemia, Henoch-Schonlein Purpura, idiopathic adrenal atrophy, idiopathic pulmonary fibritis, IgA nephropathy, inflammatory bowel disease, insulin-dependent diabetes mellitus, juvenile arthritis, juvenile diabetes mellitus (Type I), Lambert-Eaton syndrome, laminitis, lichen planus, lupoid hepatitis, lupus, lymphopenia, Meniere's disease, mixed connective tissue disease, multiple sclerosis, myasthenia gravis, pernicious anemia, polyglandular syndromes, presenile dementia, primary agammaglobulinemia, primary biliary cirrhosis, psoriasis, psoriatic arthritis, Raynauds phenomenon, recurrent abortion, Reiter's syndrome, rheumatic fever, rheumatoid arthritis, Sampter's syndrome, schistosomiasis, Schmidt's syndrome, scleroderma, Shulman's syndrome, Sjorgen's syndrome, stiff-man syndrome, sympathetic ophthalmia, systemic lupus erythematosis, Takayasu's arteritis, temporal arteritis, thyroiditis, thrombocytopenia, thyrotoxicosis, toxic epidermal necrolysis, Type B insulin resistance, Type I diabetes mellitus, ulcerative colitis, uveitis, vitiligo, Waldenstrom's macroglobulemia, and Wegener's granulomatosis.

In another embodiment, methods for treating an autoimmune disease are also provided that comprise administering to a patient in need thereof an effective amount of an engineered IgG Ab-drug conjugate alone or in combination another therapeutic agent known for the treatment of an autoimmune disease. Examples of anti-autoimmune disease agent include, but are not limited to, the following: cyclosporine, cyclosporine A, mycophenylate mofetil, sirolimus, tacrolimus, etanercept, prednisone, azathioprine, methotrexate, cyclophosphamide, aminocaproic acid, chloroquine, hydroxychloroquine, hydrocortisone, dexamethasone, chlorambucil, DHEA, danazol, bromocriptine, meloxicam and infliximab.

In another embodiment, methods for treating an infectious disease are provided which comprise administering to the patient suffering from the infectious disease a therapeutically effective amount of an engineered IgG Ab or fragment thereof conjugated to a drug. The engineered Ab-drug conjugates can be used accordingly in a variety of settings for the treatment of an infectious disease in a patient. The ADCs can be used to deliver a drug to a target cell. In one embodiment, the Ab binds to the infectious disease cell. In another embodiment, the engineered Ab-drug conjugate kills or inhibit the multiplication of cells that produce a particular infectious disease. Examples of infectious diseases that can be treated with the engineered Ab-drug conjugates include, but are not limited to, the following: bacterial diseases, such as diphtheria, pertussis, occult bacteremia, urinary tract infection, gastroenteritis, cellulites, epiglottitis, tracheitis, adenoid hypertrophy, retropharyngeal abcess, impetigo, ecthyma, pneumonia, endocarditis, septic arthritis, pneumococcal, peritonitis, bactermia, meningitis, acute purulent meningitis, urethritis, cervicitis, proctitis, pharyngitis, salpingitis, epididymitis, gonorrhea, syphilis, listeriosis, anthrax, nocardiosis, *Salmonella*, typhoid fever, dysentery, conjunctivitis, sinusitis, brucellosis, tularemia, cholera, bubonic plague, tetanus, necrotizing enteritis, and actinomycosis; mixed anaerobic infections, such as syphilis, relapsing fever, leptospirosis, Lyme disease, rat bite fever, tuberculosis, lymphadenitis, leprosy, *Chlamydia*, chlamydial pneumonia, trachoma, and inclusion conjunctivitis; systemic fungal diseases such as histoplamosis, coccidiodomycosis, blastomycosis, sporotrichosis, cryptococcsis, systemic candidiasis, aspergillosis, mucormycosis, mycetoma, and chromomycosis; rickettsial diseases such as typhus, Rocky Mountain Spotted Fever, ehrlichiosis, Eastern Tick-Borne Rickettsioses, rickettsialpox, Q fever and bartonellosis; parasitic diseases such as malaria, babesiosis, African sleeping sickness, Chagas' disease, leishmaniasis, Dum-Dum fever, toxoplasmosis, meningoencephalitis, keratitis, entamebiasis, giardiasis, cryptosporidiosis, isosporiasis, cyclosporiasis, microsporidiosis, ascariasis, whipworm infection, hookworm infection, threadworm infection, ocular larva migrans, trichinosis, Guinea worm disease, lymphatic Filariasis, loiasis, River Blindness, canine heartworm infection, schistosomiasis, swimmer's itch, Oriental lung fluke, Oriental liver fluke, fascioliasis, fasciolopsiasis, opisthorchiasis, tapeworm infections, hydatid disease, and alveolar hydatid disease; viral diseases such as measles, subacute sclerosing panencephalitis, common cold, mumps, rubella, roseola, Fifth Disease, chickenpox, respiratory syncytial virus infection, croup, bronchiolitis, infectious mononucleosis, poliomyelitis, herpangina, hand-foot-and-mouth disease, Bornholm disease, genital herpes, genital warts, aseptic meningitis, myocarditis, pericarditis, gastroenteritis, acquired immunodeficiency syndrome (AIDS), human immunodeficiency virus (HIV), Reye's syndrome, Kawasaki syndrome, influenza, bronchitis, viral "Walking" pneumonia, acute febrile respiratory disease, acute pharyngoconjunctival fever, epidemic keratoconjunctivitis, Herpes Simplex Virus 1 (HSV-1), Herpes Simplex Virus 2 (HSV-2), shingles, cytomegalic inclusion disease, rabies, progressive multifocal leukoencephalopathy, kuru, fatal familial insomnia, Creutzfeldt-Jakob disease, Gerstmann-Straussler-Scheinker disease, tropical spastic paraparesis, western equine encephalitis, California encephalitis, St. Louis encephalitis, Yellow Fever, Dengue, lymphocytic choriomeningitis, Lassa fever, hemorrhagic fever, Hantvirus pulmonary syndrome, Marburg virus infections, Ebola virus infections and smallpox.

In yet another embodiment, methods for treating an infectious disease are provided which comprise administering to a patient suffering from the infectious disease an engineered IgG Ab-drug conjugate alone or in combination with another therapeutic agent that is an anti-infectious disease agent. Examples of anti-infectious disease agents include, but not limited to, beta.-lactam antibiotics, such as penicillin G, penicillin V, cloxacillin, dicloxacillin, methicillin, nafcillin, oxacillin, ampicillin, amoxicillin, bacampicillin, azlocillin, carbenicillin, mezlocillin, piperacillin and ticarcillin; aminoglycosides such as amikacin, gentamicin, kanamycin, neomycin, netilmicin, streptomycin and tobramycin; macrolides such as azithromycin, clarithromycin, erythromycin, lincomycin and clindamycin; tetracyclines such as demeclocycline, doxycycline, minocycline, oxytetracycline and tetracycline; quinolones such as cinoxacin, and nalidixic acid; fluoroquinolones such as ciprofloxacin, enoxacin, grepafloxacin, levofloxacin, lomefloxacin, norfloxacin, ofloxacin, sparfloxacin and trovafloxicin; polypeptides such as bacitracin, colistin and polymyxin B; sulfonamides such as sulfisoxazole, sulfamethoxazole, sulfadiazine, sulfamethizole and sulfacetamide; and other antibacterial agents, such as trimethoprim, sulfamethazole, chloramphenicol, vancomycin, metronidazole, quinupristin, dalfopristin, rifampin, spectinomycin and nitrofurantoin; and antiviral agents, such as general antiviral agents such as idoxuradine, vidarabine, trifluridine, acyclovir, famcicyclovir, pencicyclovir, valacyclovir, gancicyclovir, foscarnet, ribavirin, amantadine, rimantadine, cidofovir; antisense oligonucleotides, immunoglobulins and interferons; drugs for HIV infection such as tenofovir, emtricitabine, zidovudine, didanosine, zalcitabine, stavudine, lamivudine, nevirapine, delavirdine, saquinavir, ritonavir, indinavir, and drugs for treatment of metabolic disease such as nelfinavir.

Pharmaceutical Compositions Containing the Ab-Drug Conjugates

In another embodiment, pharmaceutical compositions are provided comprising an effective amount of the engineered IgG Ab-drug conjugate and a pharmaceutical acceptable carrier. The pharmaceutical compositions can be in various forms for administration to a patient. For example, the composition can be in the form of a solid, liquid or gas (aerosol). Typical routes of administration include, without limitation, oral, topical, parenteral, sublingual, rectal, vaginal, ocular, intra-tumor, and intranasal. Parenteral administration includes subcutaneous injections, intravenous, intramuscular, intrasternal injection or infusion techniques. In one embodiment, the compositions are administered parenterally. In another embodiment, the conjugate or compositions are administered intravenously. Such compositions are suitable for veterinary or human administration.

Pharmaceutical compositions can be formulated so as to allow a conjugate to be bioavailable upon administration of the composition to a patient. Compositions can take the form of one or more dosage units, where for example, a tablet can be a single dosage unit, and a container of a conjugate in injectable form can hold a plurality of dosage units.

Materials used in preparing the pharmaceutical compositions can be non-toxic in the amounts used. As evident to those of ordinary skill in the art that the optimal dosage of the active ingredient(s) in the pharmaceutical composition will depend on a variety of factors. Relevant factors include, without limitation, the type of patient, e.g., human or animal, the particular form of the engineered-Ab conjugate, the manner of administration, and the composition employed.

The pharmaceutically acceptable carrier or vehicle can be particulate, so that the compositions are, for example, in tablet or powder form. The carrier(s) can be liquid, with the compositions being, for example, an oral syrup or injectable liquid. In addition, the carrier(s) can be gaseous or particulate, so as to provide an aerosol composition useful in, e.g., inhalatory administration.

When intended for oral administration, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins; disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent. When the composition is in the form of a capsule, e.g., a gelatin capsule, it can contain, in addition to materials of the above type, a liquid carrier such as polyethylene glycol, cyclodextrin or a fatty oil.

The composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavor enhancer. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The effective amount of the engineered Ab-drug conjugate for treatment of a particular cancer or disease will depend on the nature of the cancer or disease and can be determined by standard clinical techniques. The dosage ranges for the administration of the disclosed engineered Ab-drug conjugates are those large enough to produce the desired effect in which the symptoms of the condition or disorder are ameliorated. The dosage should not be so large as to cause adverse side effects, such as unwanted cross-reactions, anaphylactic reactions, and the like. In addition, in vitro or in vivo assays can optionally be employed to help identify optimal dosage ranges.

The precise dose to be employed in the pharmaceutical compositions will also depend on the age, condition, sex and extent of the disease in the patient, route of administration, and the seriousness of the disease or disorder, and should be decided according to the judgment of the practitioner and each patient's circumstances.

Typically, the effective amount of the engineered Ab-drug conjugate is at least about 0.01% of a conjugate by weight of the composition. When intended for oral administration, this amount can be varied to range from about 0.1% to about 80% by weight of the pharmaceutical composition. In one embodiment, oral pharmaceutical compositions can comprise from about 4% to about 50% of the conjugate by weight of the composition. In yet another embodiment, present compositions are prepared so that a parenteral dosage unit contains from about 0.01% to about 2% by weight of the conjugate.

For intravenous administration, the composition can comprise from about 0.01 to about 100 mg of a conjugate per kg of the animal's body weight. In one embodiment, the composition can include from about 1 to about 100 mg of a conjugate per kg of the animal's body weight. In another embodiment, the amount administered will be in the range from about 0.1 to about 25 mg/kg of body weight of the conjugate.

Generally, the dosage of an Ab-conjugate administered to a patient is typically about 0.01 mg/kg to about 2000 mg/kg of the animal's body weight. In one embodiment, the dosage administered to a patient is between about 0.01 mg/kg to about 10 mg/kg of the animal's body weight. In another embodiment, the dosage administered to a patient is between about 0.1 mg/kg and about 250 mg/kg of the animal's body weight. In yet another embodiment, the dosage administered to a patient is between about 0.1 mg/kg and about 20 mg/kg of the animal's body weight. In yet another embodiment the dosage administered is between about 0.1 mg/kg to about 10 mg/kg of the animal's body weight. In yet another embodiment, the dosage administered is between about 1 mg/kg to about 10 mg/kg of the animal's body weight.

The Ab-conjugates can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a conjugate or composition. In certain embodiments, more than one conjugate or composition is administered to a patient.

The term "carrier" as used herein refers to a diluent, adjuvant or excipient, with which a conjugate is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a patient, the Ab-conjugate or compositions and pharmaceutically acceptable carriers are sterile. Water is an exemplary carrier when the conjugate are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The compositions, if desired, can also contain minor amounts of wetting or emulsifying agents, or pH buffering agents.

The compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

Typically, the carriers or vehicles for intravenous administration are sterile isotonic aqueous buffer solutions. Pharmaceutical compositions may also include a solubilizing agent or a local anesthetic such as lignocaine to ease pain at the site of the injection.

Pharmaceutical compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents; coloring agents; and preserving agents, to provide a pharmaceutically palatable preparation. Moreover, where in tablet or pill form, the pharmaceutical compositions can be coated to delay disintegration and absorption in the gastrointestinal tract thereby providing a sustained action over an extended period of time.

Pharmaceutical compositions can also be administered topically, in which case the carrier may be in the form of a solution, emulsion, ointment or gel base. For transdermal administration, the pharmaceutical composition can be in the form of a transdermal patch or an iontophoresis device. Topical formulations can comprise a concentration of an engineered Ab-drug conjugate of from about 0.05% to about 50% w/v (weight per unit volume of composition), in another embodiment, from 0.1% to 10% w/v.

Methods of Preparing Engineered mAb-Drug Conjugates

In another embodiment, a method of preparing a conjugated N-glycosylated IgG Ab or fragment thereof containing one to ten non-native N-glycosylation sites in the heavy chain constant domain is provided, the method comprising:

(a) transforming a yeast or filamentous fungus host cell genetically engineered to produce N-glycans comprising terminal galactose residues of the structure $Gal_{(1-4)}GlcNAc_{(1-4)}Man_3GlcNAc_2$) or the structure $Gal_{(1-2)}GlcNAc_{(1-2)}Man_5GlcNAc_2$, with a nucleic acid encoding an IgG heavy chain contain domain, wherein the IgG heavy chain constant domain comprises one to ten amino acid mutations, and wherein the amino acid mutations generate at least one non-native N-glycosylation site in the IgG heavy chain constant domain;

(b) culturing the transformed host cell under conditions that allow the expression of IgG heavy chain constant domain comprising terminal galactose residues;

(c) contacting the expressed IgG heavy chain constant domain with a reagent that oxidizes the terminal galactose residues; and (d) conjugating a drug to the oxidized moiety of the terminal galactose residues.

The yeast host cell used in step (a) of the method of preparing a conjugated N-glycosylated IgG Ab or fragment thereof containing one to ten non-native N-glycosylation sites in the heavy chain constant domain is selected from the group consisting of *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia minuta* (*Ogataea minuta*, *Pichia lindneri*), *Pichia* sp., *Saccharomyces cerevisiae*, *Saccharomyces* sp., *Hansenula* polymorphs, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa* and *Yarrowia lipolytica*. In an embodiment, the yeast host cell is *Pichia pastoris*.

Methods for producing yeast host cells and filamentous fungal host cells genetically engineered to produce human-like complex N-glycans containing terminal galactose residues $(Gal_{(1-4)}GlcNAc_{(1-4)}Man_3GlcNAc_2)$, or human-like hybrid N-glycans containing galactose residues $(Gal_{(1-2)}GlcNAc_{(1-2)}Man_5GlcNAc_2)$ are described in the art, e.g., in U.S. Pat. No. 8,815,544; Bobrowicz P, et al., Glycobiology 14: 757-766; Li et al., (2006) Nat. Biotechnol. 24: 210-215; Zha, 2013. In one embodiment, the yeast host cell is a *Pichia pastoris* host cell that has been engineered to produce N-glycans comprising predominantly the $Gal_{(1-4)}GlcNAc_{(1-4)}Man_3GlcNAc_2$ glycoforms. In another embodiment, the yeast host cell is a *Pichia pastoris* host cell that has been engineered to produce N-glycans comprising predominantly the $Gal_{(1-2)}GlcNAc_{(1-2)}Man_5GlcNAc_2$ glycoforms. In another embodiment, the yeast host cell is a *Pichia pastoris* host cell that has been engineered to produce N-glycans comprising predominantly the $Gal_2GlcNAc_2Man_3GlcNAc_2$ glycoforms.

The nucleic acid encoding a heavy chain constant domain, in useful embodiments may comprise the complete heavy chain of the IgG Ab e.g., anti-Her2 IgG1 (SEQ ID NO: 1), wherein the heavy chain constant domain can be modified to effect the substitution of the relevant amino acid residues by site directed mutagenesis as in Example 1. Alternatively, the nucleic acid encoding the heavy chain domain may be prepared by chemical synthesis, wherein oligonucleotides are designed based on the specific amino acid sequence of the antibody mutant.

In an embodiment, the aforementioned nucleic acid comprises a nucleotide sequence encoding an anti-Her2 heavy chain mutant polypeptide comprising an amino acid sequence selected from SEQ ID NOs: 4-29, 31, 32, 33, 34, 35, 36, 37, 38, 39 and 40.

In another embodiment, the aforementioned nucleic acid comprises a nucleotide sequence encoding an anti-mouse PD-1 heavy chain mutant polypeptide comprising an amino acid sequence selected from SEQ ID NOs: 41-45.

In another embodiment, the aforementioned nucleic acid comprises a nucleotide sequence encoding an anti-CS1 heavy chain mutant polypeptide comprising an amino acid sequence selected from SEQ ID NOs: 46-50.

In another embodiment, the aforementioned nucleic acid comprises a nucleotide sequence encoding an anti-CD70 heavy chain mutant polypeptide comprising an amino acid sequence selected from SEQ ID NOs: 51-55.

In another embodiment, the yeast or filamentous host cell is transformed with the complete nucleotide sequences encoding one or both of the heavy and light chain sequences of an IgG Ab, e.g., anti-Her2 IgG1 heavy and light chain sequences (SEQ ID NOs: 1 and 2, respectively) or a fragment thereof. Transformation is effected by inserting the nucleotide sequences encoding the heavy and/or light chains of the antibody into a recombinant vector and operably linked to control sequences required for expression of the heavy and light chain in the transformed host cell. One of skill in the art may make a selection among vectors and expression control sequences well known in the art. In an embodiment, the vector is an expression vector in which the nucleotide sequence encoding the heavy and light chain of the antibodies is operably linked to additional segments required for transcription of the nucleotide sequence. The vector is typically derived from plasmid (see Example 1) or viral DNA. A number of suitable expression vectors for expression in the host cells mentioned herein are commercially available or described in the literature.

In another embodiment of the foregoing method, the IgG Ab or fragment thereof prepared by the aforementioned method comprises one to ten mutations (or pairs of mutations) in the heavy chain constant polypeptide selected from the group consisting of S134N, G161T, G161S, N203T, N203S, V363T, V363S, Q438N, S176N, A118N, S132N, K133N, A162N, T195N, K210T, Y391T, F423T, F423S, Y436T, Y436S, L193N, K392T, K392S, F423T, S176N/G178T, S176N/G178S, Q419N/N421T, Q419N/N421S, S191N/L193T, S191N/L193S, G194N/Q196T, and G194N/Q196S, according to EU numbering.

Following transformation of the yeast or filamentous host cells (step a), the transformed host cells are cultured (step b) in a nutrient medium suitable for production of the engineered Ab or fragment thereof using methods known in the art. For example, the host cells may be cultured by shake flask, small-scale or large-scale fermentation (including continuous, batch, fed-batch, or solid state fermentations) in laboratory or industrial fermenters performed in a suitable medium and under conditions allowing the heavy and light chains to be expressed and isolated. Suitable media are available from commercial suppliers or may be prepared according to published composition. The produced Abs or fragments thereof contain an engineered N-glycosylated heavy chain constant domain comprising an N-glycan comprising terminal galactose residues of the structure $Gal_{(1-4)}GlcNAc_{(1-4)}Man_3GlcNAc_2)$ or the structure $Gal_{(1-2)}GlcNAc_{(1-2)}Man_5GlcNAc_2$.

In an embodiment, the engineered Ab prepared by the foregoing method comprises about 50 to about 100 mole % of N-glycan with terminal galactose residues of the structure $Gal_{(1-4)}GlcNAc_{(1-4)}Man_3GlcNAc_2)$ or the structure $Gal_{(1-2)}GlcNAc_{(1-2)}Man_5GlcNAc_2$. In another embodiment, the engineered antibody prepared by the foregoing method comprises about 80 to about 100 mole % of N-glycan with terminal galactose residues of the structure $Gal_{(1-4)}GlcNAc_{(1-4)}Man_3GlcNAc_2)$ or the structure $Gal_{(1-2)}GlcNAc_{(1-2)}Man_5GlcNAc_2$.

The aforementioned expressed Ab comprising the N-glycosylated heavy chain constant domain may be recovered from the nutrient medium by methods known in the art, e.g., centrifugation, filtration, extraction, evaporation, or precipitation.

The engineered Ab may then be purified by a variety of procedures known in the art including, but not limited to, chromatography (e.g. ion exchange, affinity, hydrophobic, chromatofocusing, and size exclusion), electrophoretic procedures (e.g. preparative isoelectric focusing), differential solubility (e.g. ammonium sulfate precipitation), SDS-PAGE, or extraction. In an embodiment, the engineered Ab is purified by protein A chromatography (See Example 3.

The purified engineered Ab containing the expressed N-glycosylated heavy chain constant domain is then contacted with a reagent that oxidizes the terminal galactose residues of the N-glycan to generate an aldehyde (step c).

In an embodiment, the reagent is the enzyme galactose oxidase (GAL, D-galactose: oxygen 6-oxidoreductase; EC 1.1.3.9, commercially available from Sigma purified from *Dactylium dendroites*; also referred herein as GO) which specifically oxidizes terminal galactose residues at the C-6 position to generate an aldehyde group (see e.g., Cooper et al., 1959). The aldehyde group is a chemically reactive group that can be directly conjugated with a reactive amine group such as an alkoxyamine (also known as aminooxy) present in a derivatized-drug to form a stable oxime bond (Ramya et al., 2013) between the derivatized drug and the engineered N-glycan.

The term "derivatived drug" refers to a drug that contains or is modified to contain a reactive amine.

The term "reactive amine" refers to any nitrogen-containing functional group that can be covalently attached or bonded through a nitrogen atom to an aldehyde functional group by a simple chemical condensation reaction. Examples of other reactive amines include but are not limited to hydrazine, hydrazide, phenylhydrazine, phenylhydrazide, phenoxyamine, semicarbazide and thiosemicarbazide.

With respect to carrying out oxidation of the terminal galactose residues of the engineered N-glycosylated Abs, the Ab is present in aqueous solution at a concentration of about 0.1 to 100 mg/ml, 0.5 to 50 mg/ml, 1.0 to 20 mg/ml, or 0.5 to 20 mg/ml (see e.g., Copper et al., and Rayma et al., 2013). The enzyme GO generally is used at a pH about 5.5 to about 8.0. The influence of pH, substrate concentration, buffers and buffer concentrations on enzyme reaction are reported in Cooper et al., supra.

In another embodiment utilizing GO as the oxidizing reagent, the purified engineered Abs containing the expressed N-glycosylated heavy chain constant domain can be contacted with GO by producing the GO in vivo in the yeast and filamentous fungi host cells that have been genetically engineered to produce N-glycosylated mAbs containing N-glycans comprising terminal galactose residues. For example, a yeast or host cell can also be transformed with a plasmid containing the nucleotide sequence encoding GO (e.g., GO from *Fusarium graminearum*, SEQ ID NO: 57; see Paukner, 2014; Anasontzis, 2014; Deacon, 2004). In another embodiment, the terminal galactose residue of the engineered N-glycan of the Ab can also be oxidized to form aldehyde groups utilizing chemical oxidizing reagents. Examples of chemical oxidizing reagents include, but are not limited to periodic acid, paraperiodic acid, sodium metaperiodate and potassium metaperiodate. Among these, oxygen acids and salts thereof are preferred since secondary or undesirable side reactions are less frequent. For a general discussion, see Jackson, 1944, in Organic Reactions 2, p. 341; Bunton, 1965, Oxidation in Organic Chemistry, Vol. 1 Wiberg, ed., Academic Press, New York, p. 367.

Oxidation of the engineered Abs with these chemical oxidizing reagents can be carried out by known methods. In the oxidation, the engineered Ab is generally present in the form of an aqueous solution at a concentration generally of less than 100 mg/ml, or 1 to 20 mg/ml. When an oxygen acid or salt thereof is used as the oxidizing agent, it is used generally in the form of an aqueous solution, and the concentration is generally 0.001 to 10 mM and preferably 1.0 to 10 mM. The amount of the oxygen acid or salt thereof depends on the kind of antibody, but generally it is used in excess, for example, ten to 100 times as much as the amount of the oxidizable N-glycan. The optimal amount, however, can be determined by routine experimentation.

Following oxidation of the engineered N-glycosylated Ab, the Ab can be conjugated to a drug by reacting the Ab with a drug having a reactive amine group selected from the group consisting of hydrazine, hydrazide, phenylhydrazine, phenylhydazide, alkoxyamine, phenoxyamino, semicarbazide and thiosemicarbazide groups.

In a useful embodiment, the reactive amine group is an alkoxyamine (aminooxy) group. Drugs modified to contain a reactive amino group such as alkoxyamine can be synthesized by methods known in the art (Jayasekara, 2014; Trimaille 2014; Su 2005; Singh 2005) and are also commercially available (e.g., the amino oxy activated C5-linker containing DM1 (chemically synthesized by Concortis Biosystems in San Diego, Calif., see Example 10; aminooxy activated Exendin-4-peptide chemically synthesized by Biopeptek in Malvern, Pa., see Example 9; and aminooxy activated CF633 dye chemically synthesized by Biotium in Hayward, Calif., Example 5).

In an embodiment, a solution of the oxidized engineered Ab at a concentration from about 0.5 to 20 mg/ml is mixed with an amine derivative of a drug (molar ratios of reactive amine group to antibody aldehyde ranging from about 1 to about 10,000) and the solution incubated for from about 1 to 72 hours, preferably in the dark. Suitable temperatures are from 0° to 37° C. and pH may be from about 6 to 8.

The aforementioned method of preparing Ab-drug conjugate can also be used to prepare Ab-drug conjugate, wherein the engineered Ab contains one to two non-native N-glycosylation sites in the heavy chain framework domain as is described above.

In another embodiment, a method of preparing a conjugated N-glycosylated Ab or fragment thereof containing one to ten non-native N-glycosylation sites in the heavy chain constant domain is provided, the method comprising:
(a) transforming a yeast or filamentous fungus host cell genetically engineered to produce N-glycans comprising terminal sialic acid residues (NANA$_{(1-4)}$Gal$_{(1-4)}$GlcNAc$_{(1-4)}$Man$_3$GlcNAc$_2$) with a nucleic acid encoding a heavy chain contain domain, wherein the heavy chain comprises one to ten amino acid mutations, and wherein the one to ten amino acid mutation generates at least one non-native N-glycosylation site in the heavy chain constant domain;
(b) culturing the transformed yeast host cell under conditions that allow the expression of the heavy chain constant domain comprising terminal sialic acid residues,
(c) contacting the expressed heavy chain constant domain with neuraminidase to remove the terminal sialic acid residues to form N-glycosylated heavy chain constant domain comprising terminal galactose residues;
(d) contacting the expressed glycosylated heavy chain constant domain comprising terminal galactose residues of step (c), with a reagent that oxidizes the terminal galactose residues;
(e) conjugating a drug to the oxidized moiety of the terminal galactose residues.

Methods for producing yeast host cells and filamentous fungal host cells genetically engineered to produce human-like complex N-glycans containing terminal sialic acid residues are described e.g. in U.S. Pat. Nos. 8,715,963; 7,863, 020; Nett et al., (2011), Yeast 28(3):237-52 (2011); Hamilton et al., Curr Opin Biotechnol. 18(5):387-92 (2007); Hamilton et al., (2006) Science 313: 1441-1443.

Methods of transforming the yeast strains to produce N-glycans with terminal sialic acid residues, preparing mutated nucleic acids containing the non-native N-glycosylation sites, and culturing steps (steps a-b) are as described above (strains containing N-glycans with terminal galactose residues). With respect to step (c), N-glycans comprising sialic acid residues can be desialyated using the enzyme Acetyl-neuroaminyl hydrolase (neuraminidase, New England Biolabs, Ipswich, Mass.) according to the manufacturer's recommended reaction conditions, to efficiently remove the sialic acid residues leaving predominantly terminal galactose residues. Step (d) of contacting the expressed glycosylated heavy chain constant domain with a reagent, e.g., GO or a chemical reagent, that oxidizes the terminal galactose residues, and step (e) of conjugating a drug to the oxidized moiety of the terminal galactose residues is as described above.

Sequences
(anti-Her2/trastuzumab IgG1 H chain)

SEQ ID NO: 1
EVQLVESGGGLVQPGGSLRLSCAASGFNIKDTYIHWVRQAPGKGLEWVARTYPTNGYT

RYADSVKGRFTISADTSKNTAYLQMNSLRAEDTAVYYCSRWGGDGFYAMDYWGQGT

-continued

LVTVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYS

KLTVDKSRWQQGNVFSCSVMHEALHNHYTQKSLSLSPG (anti-HER2/trastuzumab Kappa L chain)
SEQ ID NO: 2
DIQMTQSPSSLSASVGDRVTITCRASQDVNTAVAWYQQKPGKAPKLLIYSASFLYSGVP

SRFSGSRSGTDFTLTISSLQPEDFATYYCQQHYTTPPTFGQGTKVEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC (pGLY5883 nucleotide sequence)
SEQ ID NO: 3
TCGCGCGTTTCGGTGATGACGGTGAAAACCTCTGACACATGCAGCTCCCGGAGACG

GTCACAGCTTGTCTGTAAGCGGATGCCGGGAGCAGACAAGCCCGTCAGGGCGCGTC

AGCGGGTGTTGGCGGGTGTCGGGGCTGGCTTAACTATGCGGCATCAGAGCAGATTG

TACTGAGAGTGCACCATATGCGGTGTGAAATACCGCACAGATGCGTAAGGAGAAAA

TACCGCATCAGGCGCCATTCGCCATTCAGGCTGCGCAACTGTTGGGAAGGGCGATC

GGTGCGGGCCTCTTCGCTATTACGCCAGCTGGCGAAAGGGGGATGTGCTGCAAGGC

GATTAAGTTGGGTAACGCCAGGGTTTTCCCAGTCACGACGTTGTAAAACGACGGCCA

GTGAATTGAGATCTAACATCCAAAGACGAAAGGTTGAATGAAACCTTTTTGCCATCC

GACATCCACAGGTCCATTCTCACACATAAGTGCCAAACGCAACAGGAGGGGATACA

CTAGCAGCAGACCGTTGCAAACGCAGGACCTCCACTCCTCTTCTCCTCAACACCCAC

TTTTGCCATCGAAAAACCAGCCCAGTTATTGGGCTTGATTGGAGCTCGCTCATTCCA

ATTCCTTCTATTAGGCTACTAACACCATGACTTTATTAGCCTGTCTATCCTGGCCCCC

CTGGCGAGGTTCATGTTTGTTTATTTCCGAATGCAACAAGCTCCGCATTACACCCGA

ACATCACTCCAGATGAGGGCTTTCTGAGTGTGGGGTCAAATAGTTTCATGTTCCCCA

AATGGCCCAAAACTGACAGTTTAAACGCTGTCTTGGAACCTAATATGACAAAAGCG

TGATCTCATCCAAGATGAACTAAGTTTGGTTCGTTGAAATGCTAACGGCCAGTTGGT

CAAAAAGAAACTTCCAAAAGTCGGCATACCGTTTGTCTTGTTTGGTATTGATTGACG

AATGCTCAAAAATAATCTCATTAATGCTTAGCGCAGTCTCTCTATCGCTTCTGAACCC

CGGTGCACCTGTGCCGAAACGCAAATGGGGAAACACCCGCTTTTTGGATGATTATGC

ATTGTCTCCACATTGTATGCTTCCAAGATTCTGGTGGGAATACTGCTGATAGCCTAA

CGTTCATGATCAAAATTTAACTGTTCTAACCCCTACTTGACAGCAATATATAAACAG

AAGGAAGCTGCCCTGTCTTAAACCTTTTTTTTTATCATCATTATTAGCTTACTTTCAT

AATTGCGACTGGTTCCAATTGACAAGCTTTTGATTTTAACGACTTTTAACGACAACTT

GAGAAGATCAAAAAACAACTAATTATTCGAAACGGAATTCGAAACGATGAGATTCC

CATCCATCTTCACTGCTGTTTTGTTCGCTGCTTCTTCTGCTTTGGCTGAGGTTCAGTTG

GTTGAATCTGGAGGAGGATTGGTTCAACCTGGTGGTTCTTTGAGATTGTCCTGTGCT

GCTTCCGGTTTCAACATCAAGGACACTTACATCCACTGGGTTAGACAAGCTCCAGGA

AAGGGATTGGAGTGGGTTGCTAGAATCTACCCAACTAACGGTTACACAAGATACGC

-continued

```
TGACTCCGTTAAGGGAAGATTCACTATCTCTGCTGACACTTCCAAGAACACTGCTTA

CTTGCAGATGAACTCCTTGAGAGCTGAGGATACTGCTGTTTACTACTGTTCCAGATG

GGGTGGTGATGGTTTCTACGCTATGGACTACTGGGGTCAAGGAACTTTGGTTACTGT

TTCCTCCGCTTCTACTAAGGGACCATCTGTTTTCCCATTGGCTCCATCTTCTAAGTCT

ACTTCCGGTGGTACTGCTGCTTTGGGATGTTTGGTTAAAGACTACTTCCCAGAGCCA

GTTACTGTTTCTTGGAACTCCGGTGCTTTGACTTCTGGTGTTCACACTTTCCCAGCTG

TTTTGCAATCTTCCGGTTTGTACTCTTTGTCCTCCGTTGTTACTGTTCCATCCTCTTCC

TTGGGTACTCAGACTTACATCTGTAACGTTAACCACAAGCCATCCAACACTAAGGTT

GACAAGAAGGTTGAGCCAAAGTCCTGTGACAAGACACATACTTGTCCACCATGTCC

AGCTCCAGAATTGTTGGGTGGTCCATCCGTTTTCTTGTTCCCACCAAAGCCAAAGGA

CACTTTGATGATCTCCAGAACTCCAGAGGTTACATGTGTTGTTGTTGACGTTTCTCAC

GAGGACCCAGAGGTTAAGTTCAACTGGTACGTTGACGGTGTTGAAGTTCACAACGCT

AAGACTAAGCCAAGAGAAGAGCAGTACAACTCCACTTACAGAGTTGTTTCCGTTTTG

ACTGTTTTGCACCAGGACTGGTTGAACGGTAAAGAATACAAGTGTAAGGTTTCCAAC

AAGGCTTTGCCAGCTCCAATCGAAAAGACTATCTCCAAGGCTAAGGGTCAACCAAG

AGAGCCACAGGTTTACACTTTGCCACCATCCAGAGAAGAGATGACTAAGAACCAGG

TTTCCTTGACTTGTTTGGTTAAAGGATTCTACCCATCCGACATTGCTGTTGAGTGGGA

ATCTAACGGTCAACCAGAGAACAACTACAAGACTACTCCACCAGTTTTGGATTCTGA

TGGTTCCTTCTTCTTGTACTCCAAGTTGACTGTTGACAAGTCCAGATGGCAACAGGG

TAACGTTTTCTCCTGTTCCGTTATGCATGAGGCTTTGCACAACCACTACACTCAAAAG

TCCTTGTCTTTGTCCCCTGGTTAATGAGGCCGGCCATTTAAATACAGGCCCCTTTTCC

TTTGTCGATATCATGTAATTAGTTATGTCACGCTTACATTCACGCCCTCCTCCCACAT

CCGCTCTAACCGAAAAGGAAGGAGTTAGACAACCTGAAGTCTAGGTCCCTATTTATT

TTTTTTAATAGTTATGTTAGTATTAAGAACGTTATTTATATTTCAAATTTTTCTTTTTT

TTCTGTACAAACGCGTGTACGCATGTAACATTATACTGAAAACCTTGCTTGAGAAGG

TTTTGGGACGCTCGAAGGCTTTAATTTGCAAGCTGGATCTAACATCCAAAGACGAAA

GGTTGAATGAAACCTTTTTGCCATCCGACATCCACAGGTCCATTCTCACACATAAGT

GCCAAACGCAACAGGAGGGGATACACTAGCAGCAGACCGTTGCAAACGCAGGACC

TCCACTCCTCTTCTCCTCAACACCCACTTTTGCCATCGAAAAACCAGCCCAGTTATTG

GGCTTGATTGGAGCTCGCTCATTCCAATTCCTTCTATTAGGCTACTAACACCATGACT

TTATTAGCCTGTCTATCCTGGCCCCCCTGGCGAGGTTCATGTTTGTTTATTTCCGAAT

GCAACAAGCTCCGCATTACACCCGAACATCACTCCAGATGAGGGCTTTCTGAGTGTG

GGGTCAAATAGTTTCATGTTCCCCAAATGGCCCAAAACTGACAGTTTAAACGCTGTC

TTGGAACCTAATATGACAAAAGCGTGATCTCATCCAAGATGAACTAAGTTTGGTTCG

TTGAAATGCTAACGGCCAGTTGGTCAAAAAGAAACTTCCAAAAGTCGGCATACCGT

TTGTCTTGTTTGGTATTGATTGACGAATGCTCAAAAATAATCTCATTAATGCTTAGCG

CAGTCTCTCTATCGCTTCTGAACCCCGGTGCACCTGTGCCGAAACGCAAATGGGGAA

ACACCCGCTTTTTGGATGATTATGCATTGTCTCCACATTGTATGCTTCCAAGATTCTG

GTGGGAATACTGCTGATAGCCTAACGTTCATGATCAAAATTTAACTGTTCTAACCCC

TACTTGACAGCAATATATAAACAGAAGGAAGCTGCCCTGTCTTAAACCTTTTTTTTT

ATCATCATTATTAGCTTACTTTCATAATTGCGACTGGTTCCAATTGACAAGCTTTTGA
```

```
TTTTAACGACTTTTAACGACAACTTGAGAAGATCAAAAAACAACTAATTATTCGAAA

CGGAATTCGAAACGATGAGATTCCCATCCATCTTCACTGCTGTTTTGTTCGCTGCTTC

TTCTGCTTTGGCTGACATCCAAATGACTCAATCCCCATCTTCTTTGTCTGCTTCCGTT

GGTGACAGAGTTACTATCACTTGTAGAGCTTCCCAGGACGTTAATACTGCTGTTGCT

TGGTATCAACAGAAGCCAGGAAAGGCTCCAAAGTTGTTGATCTACTCCGCTTCCTTC

TTGTACTCTGGTGTTCCATCCAGATTCTCTGGTTCCAGATCCGGTACTGACTTCACTT

TGACTATCTCCTCCTTGCAACCAGAAGATTTCGCTACTTACTACTGTCAGCAGCACTA

CACTACTCCACCAACTTTCGGACAGGGTACTAAGGTTGAGATCAAGAGAACTGTTGC

TGCTCCATCCGTTTTCATTTTCCCACCATCCGACGAACAGTTGAAGTCTGGTACAGCT

TCCGTTGTTTGTTTGTTGAACAACTTCTACCCAAGAGAGGCTAAGGTTCAGTGGAAG

GTTGACAACGCTTTGCAATCCGGTAACTCCCAAGAATCCGTTACTGAGCAAGACTCT

AAGGACTCCACTTACTCCTTGTCCTCCACTTTGACTTTGTCCAAGGCTGATTACGAGA

AGCACAAGGTTTACGCTTGTGAGGTTACACATCAGGGTTTGTCCTCCCCAGTTACTA

AGTCCTTCAACAGAGGAGAGTGTTAATAGGGCCGGCCATTTAAATACAGGCCCCTTT

TCCTTTGTCGATATCATGTAATTAGTTATGTCACGCTTACATTCACGCCCTCCTCCCA

CATCCGCTCTAACCGAAAAGGAAGGAGTTAGACAACCTGAAGTCTAGGTCCCTATTT

ATTTTTTTTAATAGTTATGTTAGTATTAAGAACGTTATTTATATTTCAAATTTTTCTTT

TTTTTCTGTACAAACGCGTGTACGCATGTAACATTATACTGAAAACCTTGCTTGAGA

AGGTTTTGGGACGCTCGAAGGCTTTAATTTGCAAGCTGGATCCGCGGCCGCTTACGC

GCCGATCCCCCACACACCATAGCTTCAAAATGTTTCTACTCCTTTTTTACTCTTCCAG

ATTTTCTCGGACTCCGCGCATCGCCGTACCACTTCAAAACACCCAAGCACAGCATAC

TAAATTTCCCCTCTTTCTTCCTCTAGGGTGTCGTTAATTACCCGTACTAAAGGTTTGG

AAAGAAAAAGAGACCGCCTCGTTTCTTTTTCTTCGTCGAAAAAGGCAATAAAAA

TTTTTATCACGTTTCTTTTTCTTGAAAATTTTTTTTTTGATTTTTTTCTCTTTCGATGA

CCTCCCATTGATATTTAAGTTAATAAACGGTCTTCAATTTCTCAAGTTTCAGTTTCAT

TTTTCTTGTTCTATTACAACTTTTTTTACTTCTTGCTCATTAGAAAGAAAGCATAGCA

ATCTAATCTAAGTTTTAATTACAAATTAATTAATGGCCAAGTTGACCAGTGCCGTTC

CGGTGCTCACCGCGCGCGACGTCGCCGGAGCGGTCGAGTTCTGGACCGACCGGCTC

GGGTTCTCCCGGGACTTCGTGGAGGACGACTTCGCCGGTGTGGTCCGGGACGACGTG

ACCCTGTTCATCAGCGCGGTCCAGGACCAGGTGGTGCCGGACAACACCCTGGCCTG

GGTGTGGGTGCGCGGCCTGGACAGAGCTGTACGCCGAGTGGTCGGAGGTCGTGTCCA

CGAACTTCCGGGACGCCTCCGGGCCTGCCATGACCGAGATCGGCGAGCAGCCGTGG

GGGCGGGAGTTCGCCCTGCGCGACCCGGCCGGCAACTGCGTGCACTTCGTGGCCGA

GGAGCAGGACTGATTAATTAACAGGCCCCTTTTCCTTTGTCGATATCATGTAATTAG

TTATGTCACGCTTACATTCACGCCCTCCTCCCACATCCGCTCTAACCGAAAAGGAAG

GAGTTAGACAACCTGAAGTCTAGGTCCCTATTTATTTTTTTTAATAGTTATGTTAGTA

TTAAGAACGTTATTTATATTTCAAATTTTCTTTTTTTTCTGTACAAACGCGTGTACGC

ATGTAACATTATACTGAAAACCTTGCTTGAGAAGGTTTTGGGACGCTCGAAGGCTTT

AATTTGCAAGCTGCGGCCTAAGGCGCGCCAGGCCATAATGGCCAAACGGTTTCTCA

ATTACTATATACTACTAACCATTTACCTGTAGCGTATTTCTTTTCCCTCTTCGCGAAA
```

-continued

```
GCTCAAGGGCATCTTCTTGACTCATGAAAAATATCTGGATTTCTTCTGACAGATCAT
CACCCTTGAGCCCAACTCTCTAGCCTATGAGTGTAAGTGATAGTCATCTTGCAACAG
ATTATTTTGGAACGCAACTAACAAAGCAGATACACCCTTCAGCAGAATCCTTTCTGG
ATATTGTGAAGAATGATCGCCAAAGTCACAGTCCTGAGACAGTTCCTAATCTTTACC
CCATTTACAAGTTCATCCAATCAGACTTCTTAACGCCTCATCTGGCTTATATCAAGCT
TACCAACAGTTCAGAAACTCCCAGTCCAAGTTTCTTGCTTGAAAGTGCGAAGAATGG
TGACACCGTTGACAGGTACACCTTTATGGGACATTCCCCCAGAAAAATAATCAAGAC
TGGGCCTTTAGAGGGTGCTGAAGTTGACCCCTTGGTGCTTCTGGAAAAAGAACTGAA
GGGCACCAGACAAGCGCAACTTCCTGGTATTCCTCGTCTAAGTGGTGGTGCCATAGG
ATACATCTCGTACGATTGTATTAAGTACTTTGAACCAAAAACTGAAAGAAAACTGAA
AGATGTTTTGCAACTTCCGGAAGCAGCTTTGATGTTGTTCGACACGATCGTGGCTTTT
GACAATGTTTATCAAAGATTCCAGGTAATTGGAAACGTTTCTCTATCCGTTGATGAC
TCGGACGAAGCTATTCTTGAGAAATATTATAAGACAAGAGAAGAAGTGGAAAAGAT
CAGTAAAGTGGTATTTGACAATAAAACTGTTCCCTACTATGAACAGAAAGATATTAT
TCAAGGCCAAACGTTCACCTCTAATATTGGTCAGGAAGGGTATGAAAACCATGTTCG
CAAGCTGAAAGAACATATTCTGAAAGGAGACATCTTCCAAGCTGTTCCCTCTCAAAG
GGTAGCCAGGCCGACCTCATTGCACCCTTTCAACATCTATCGTCATTTGAGAACTGT
CAATCCTTCTCCATACATGTTCTATATTGACTATCTAGACTTCCAAGTTGTTGGTGCT
TCACCTGAATTACTAGTTAAATCCGACAACAACAACAAAATCATCACACATCCTATT
GCTGGAACTCTTCCCAGAGGTAAAACTATCGAAGAGGACGACAATTATGCTAAGCA
ATTGAAGTCGTCTTTGAAAGACAGGGCCGAGCACGTCATGCTGGTAGATTTGGCCAG
AAATGATATTAACCGTGTGTGTGAGCCCACCAGTACCACGGTTGATCGTTTATTGAC
TGTGGAGAGATTTTCTCATGTGATGCATCTTGTGTCAGAAGTCAGTGGAACATTGAG
ACCAAACAAGACTCGCTTCGATGCTTTCAGATCCATTTTCCCAGCAGGAACCGTCTC
CGGTGCTCCGAAGGTAAGAGCAATGCAACTCATAGGAGAATTGGAAGGAGAAAAG
AGAGGTGTTTATGCGGGGGCCGTAGGACACTGGTCGTACGATGGAAAATCGATGGA
CACATGTATTGCCTTAAGAACAATGGTCGTCAAGGACGGTGTCGCTTACCTTCAAGC
CGGAGGTGGAATTGTCTACGATTCTGACCCCTATGACGAGTACATCGAAACCATGAA
CAAAATGAGATCCAACAATAACACCATCTTGGAGGCTGAGAAAATCTGGACCGATA
GGTTGGCCAGAGACGAGAATCAAAGTGAATCCGAAGAAAACGATCAATGAACGGA
GGACGTAAGTAGGAATTTATGGTTTGGCCATAATGGCCTAGCTTGGCGTAATCATGG
TCATAGCTGTTTCCTGTGTGAAATTGTTATCCGCTCACAATTCCACACAACATACGA
GCCGGAAGCATAAAGTGTAAAGCCTGGGGTGCCTAATGAGTGAGCTAACTCACATT
AATTGCGTTGCGCTCACTGCCCGCTTTCCAGTCGGGAAACCTGTCGTGCCAGCTGCA
TTAATGAATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGTATCAGC
TCACTCAAAGGCGGTAATACGGTTATCCACAGAATCAGGGGATAACGCAGGAAAGA
ACATGTGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTT
```

-continued

```
TCTCCCTTCGGGAAGCGTGGCGCTTTCTCATAGCTCACGCTGTAGGTATCTCAGTTCG

GTGTAGGTCGTTCGCTCCAAGCTGGGCTGTGTGCACGAACCCCCCGTTCAGCCCGAC

CGCTGCGCCTTATCCGGTAACTATCGTCTTGAGTCCAACCCGGTAAGACACGACTTA

TCGCCACTGGCAGCAGCCACTGGTAACAGGATTAGCAGAGCGAGGTATGTAGGCGG

TGCTACAGAGTTCTTGAAGTGGTGGCCTAACTACGGCTACACTAGAAGGACAGTATT

TGGTATCTGCGCTCTGCTGAAGCCAGTTACCTTCGGAAAAAGAGTTGGTAGCTCTTG

ATCCGGCAAACAAACCACCGCTGGTAGCGGTGGTTTTTTTGTTTGCAAGCAGCAGAT

TACGCGCAGAAAAAAAGGATCTCAAGAAGATCCTTTGATCTTTTCTACGGGGTCTGA

CGCTCAGTGGAACGAAAACTCACGTTAAGGGATTTTGGTCATGAGATTATCAAAAA

GGATCTTCACCTAGATCCTTTTAAATTAAAAATGAAGTTTTAAATCAATCTAAAGTA

TATATGAGTAAACTTGGTCTGACAGTTACCAATGCTTAATCAGTGAGGCACCTATCT

CAGCGATCTGTCTATTTCGTTCATCCATAGTTGCCTGACTCCCCGTCGTGTAGATAAC

TACGATACGGGAGGGCTTACCATCTGGCCCCAGTGCTGCAATGATACCGCGAGACC

CACGCTCACCGGCTCCAGATTTATCAGCAATAAACCAGCCAGCCGGAAGGGCCGAG

CGCAGAAGTGGTCCTGCAACTTTATCCGCCTCCATCCAGTCTATTAATTGTTGCCGG

GAAGCTAGAGTAAGTAGTTCGCCAGTTAATAGTTTGCGCAACGTTGTTGCCATTGCT

ACAGGCATCGTGGTGTCACGCTCGTCGTTTGGTATGGCTTCATTCAGCTCCGGTTCCC

AACGATCAAGGCGAGTTACATGATCCCCCATGTTGTGCAAAAAAGCGGTTAGCTCCT

TCGGTCCTCCGATCGTTGTCAGAAGTAAGTTGGCCGCAGTGTTATCACTCATGGTTA

TGGCAGCACTGCATAATTCTCTTACTGTCATGCCATCCGTAAGATGCTTTTCTGTGAC

TGGTGAGTACTCAACCAAGTCATTCTGAGAATAGTGTATGCGGCGACCGAGTTGCTC

TTGCCCGGCGTCAATACGGGATAATACCGCGCCACATAGCAGAACTTTAAAAGTGCT

CATCATTGGAAAACGTTCTTCGGGGCGAAAACTCTCAAGGATCTTACCGCTGTTGAG

ATCCAGTTCGATGTAACCCACTCGTGCACCCAACTGATCTTCAGCATCTTTTACTTTC

ACCAGCGTTTCTGGGTGAGCAAAAACAGGAAGGCAAAATGCCGCAAAAAAGGGAA

TAAGGGCGACACGGAAATGTTGAATACTCATACTCTTCCTTTTTCAATATTATTGAA

GCATTTATCAGGGTTATTGTCTCATGAGCGGATACATATTTGAATGTATTTAGAAAA

ATAAACAAATAGGGGTTCCGCGCACATTTCCCCGAAAAGTGCCACCTGACGTCTAA

GAAACCATTATTATCATGACATTAACCTATAAAAATAGGCGTATCACGAGGCCCTTT

CGTC
```

(anti-Her2/trastuzumab IgG1 H chain, Q105N (Kabat), pGLY10044)

SEQ ID NO: 4

```
EVQLVESGGGLVQPGGSLRLSCAASGFNIKDTYIHWVRQAPGKGLEWVARIYPTNGYT

RYADSVKGRFTISADTSKNTAYLQMNSLRAEDTAVYYCSRWGGDGFYAMDYWGNGT

LVTVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYS

KLTVDKSRWQQGNVFSCSVMHEALHNHYTQKSLSLSPG
```

(anti-Her2/trastuzumab IgG1 H chain, S134N (EU), pGLY10045)

SEQ ID NO: 5

EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGT
LVTVSSASTKGPSVFPLAPSSKNTSGGTAALGCLVKDYFPEPVTVSWNSGALTSGVHTFP
AVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPG (anti-Her2/trastuzumab IgG1 H chain, G161T (EU), pGLY10046)

SEQ ID NO: 6

EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGT
LVTVSSASTKGPSVFPLAPSSKSTSGGTAALGCLVKDYFPEPVTVSWNSTALTSGVHTFP
AVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPG (anti-Her2/trastuzumab IgG1 H chain, Q175N (EU), pGLY10047)

SEQ ID NO: 7

EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGT
LVTVSSASTKGPSVFPLAPSSKSTSGGTAALGCLVKDYFPEPVTVSWNSGALTSGVHTFP
AVLNSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPG (anti-Her2/trastuzumab IgG1 H chain, N203T (EU), pGLY10048)

SEQ ID NO: 8

EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGT
LVTVSSASTKGPSVFPLAPSSKSTSGGTAALGCLVKDYFPEPVTVSWNSGALTSGVHTFP
AVLQSSGLYSLSSVVTVPSSSLGTQTYICNVTHKPSNTKVDKKVEPKSCDKTHTCPPCPA
PELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQV
YTLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPG (anti-Her2/trastuzumab IgG1 H chain, V363T (EU), pGLY10049)
SEQ ID NO: 9

EVQLVESGGGLVQPGGSLRLSCAASGFNIKDTYIHWVRQAPGKGLEWVARIYPTNGYT

RYADSVKGRFTISADTSKNTAYLQMNSLRAEDTAVYYCSRWGGDGFYAMDYWGQGT

LVTVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQV

YTLPPSREEMTKNQTSLTCLVKGFYPSDIAVEWESNGQPENNYKTTPPVLDSDGSFFLYS

KLTVDKSRWQQGNVFSCSVMHEALHNHYTQKSLSLSPG (anti-Her2/trastuzumab IgG1 H chain, Q386T (EU), pGLY10050)
SEQ ID NO: 10

EVQLVESGGGLVQPGGSLRLSCAASGFNIKDTYIHWVRQAPGKGLEWVARIYPTNGYT

RYADSVKGRFTISADTSKNTAYLQMNSLRAEDTAVYYCSRWGGDGFYAMDYWGQGT

LVTVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQV

YTLPPSREEMTKNQVSLTCLVKGFYPSDIAVEWESNGTPENNYKTTPPVLDSDGSFFLYS

KLTVDKSRWQQGNVFSCSVMHEALHNHYTQKSLSLSPG (anti-Her2/trastuzumab IgG1 H chain, Q438N (EU), pGLY10051)
SEQ ID NO: 11

EVQLVESGGGLVQPGGSLRLSCAASGFNIKDTYIHWVRQAPGKGLEWVARIYPTNGYT

RYADSVKGRFTISADTSKNTAYLQMNSLRAEDTAVYYCSRWGGDGFYAMDYWGQGT

LVTVSSASTKGPSVFPLAPSSKSTSGGTAALGCLVKDYFPEPVTVSWNSGALTSGVHTFP

AVLQSSGLYSLSSVVTVPSSSLGTQTYICNVNHKPSNTKVDKKVEPKSCDKTHTCPPCPA

PELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYS

KLTVDKSRWQQGNVFSCSVMHEALHNHYTNKSLSLSPG (anti-Her2/trastuzumab IgG1 H chain, S113N (Kabat), pGLY14120)
SEQ ID NO: 12

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSNASTKGPSVFPLAPSSKSTSGGTAALGCLVKDYFPEPV

TVSWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, A118N (EU),
pGLY14121)
SEQ ID NO: 13
MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSNSTKGPSVFPLAPSSKSTSGGTAALGCLVKDYFPEPV

TVSWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, S132N (EU),
pGLY14122)
SEQ ID NO: 14
MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSNKSTSGGTAALGCLVKDYFPEPV

TVSWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, K133N (EU),
pGLY14123)
SEQ ID NO: 15
MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSNSTSGGTAALGCLVKDYFPEPV

TVSWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, A162N (EU),
pGLY14124)
SEQ ID NO: 16
MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGNLTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG

-continued (anti-Her2/trastuzumab IgG1 H chain, T195N (EU),
pGLY14125)

SEQ ID NO: 17

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQSSGLYSLSSVVTVPSSSLGNQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, K210T (EU),
pGLY14126)

SEQ ID NO: 18

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPSNTTVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, Y391T (EU),
pGLY14127)

SEQ ID NO: 19

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NTKTTPPVLDSDGSFFLYSKLTVDKSRWQQGNVFSCSVMHEALHNHYTQKSLSLSPG (anti-Her2/trastuzumab IgG1 H chain, F423T (EU),
pGLY14128)

SEQ ID NO: 20

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVTSCSVMHEALHNHYTQKSLSLSPG (anti-Her2/trastuzumab IgG1 H chain, Y436T (EU), pGLY14129)

SEQ ID NO: 21

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHTTQKSLSLSPG (anti-Her2/trastuzumab IgG1 H chain, L193N (EU), pGLY14130)

SEQ ID NO: 22

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQSSGLYSLSSVVTVPSSSNGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, Q419N, N421T (EU), pGLY14131)

SEQ ID NO: 23

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQNGTVFSCSVMHEALHNHYTQKSLSLSPG (anti-Her2/trastuzumab IgG1 H chain, S176N, G178T (EU), pGLY14132)

SEQ ID NO: 24

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQNSTLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, S191N, L193T
(EU), pGLY14133)

SEQ ID NO: 25

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQSSGLYSLSSVVTVPSNSTGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, G194N, Q196T (EU),
pGLY14134)

SEQ ID NO: 26

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKSTSGGTAALGCLVKDYFPEPV

TVSWNSGALTSGVHTFPAVLQSSGLYSLSSVVTVPSSSLNTTTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, G161T, S134N (EU),
pGLY14135)

SEQ ID NO: 27

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKNTSGGTAALGCLVKDYFPEPV

TVSWNSTALTSGVHTFPAVLQSSGLYSLSSVVTVPSSSLGTQTYICNVNHKPSNTKVDK

KVEPKSCDKTHTCPPCPAPELLGGPSVFLFPPKPKDTLMISRTPEVTCVVVDVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (anti-Her2/trastuzumab IgG1 H chain, G161S, S134N (EU),
pGLY14136)

SEQ ID NO: 28

MRFPSIFTAVLFAASSALAEVQLVESGGGLVQPGGSLRLSCAASGFNIKDTYIHWVRQAP

GKGLEWVARIYPTNGYTRYADSVKGRFTISADTSKNTAYLQMNSLRAEDTAVYYCSRW

GGDGFYAMDYWGQGTLVTVSSASTKGPSVFPLAPSSKNTSGGTAALGCLVKDYFPEPV

TVSWNSSALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPG

-continued (null-Her2 IgG1 H chain, F243A, F264A (EU), pGLY11576)
SEQ ID NO: 29
EVQLVESGGGLVQPGGSLRLSCAASGFNIKDTYIHWVRQAPGKGLEWVAEIYPTNGYTR

YADSVKGRFTISADTSKNTAYLQMNSLRAEDTAVYYCSRWGGDGFGAMDYWGQGTL

VTVSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPPCPAP

ELLGGPSVFLAPPKPKDTLMISRTPEVTCVVADVSHEDPEVKFNWYVDGVEVHNAKTK

PREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYS

KLTVDKSRWQQGNVFSCSVMHEALHNHYTQKSLSLSPG (null-Her2 L chain, pGLY11576)
SEQ ID NO: 30
DIQMTQSPSSLSASVGDRVTITCRASQDVNTAVAWYQQKPGKAPKLLIYSASFLYSGVP

SRFSGSGSGTDFTLTISSLQPEDFATYYCQQHYTTPPTFGQGTKVEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC (null-Her2 IgG1 H chain, S134N (EU), pGLY14137)
SEQ ID NO: 31
MRFPSIFTAVLFAASSALAEVQLVESGGGLVQPGGSLRLSCAASGFNIKDTYIHWVRQAP

GKGLEWVAEIYPTNGYTRYADSVKGRFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSGALTSGVHTFPAVLQSSGLYSLSSVVTVPSSSLGTQTYICNVNHKPSNTKVDK

KVEPKSCDKTHTCPPCPAPELLGGPSVFLAPPKPKDTLMISRTPEVTCVVADVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (null-Her2 IgG1 H chain, G161T (EU), pGLY14138)
SEQ ID NO: 32
MRFPSIFTAVLFAASSALAEVQLVESGGGLVQPGGSLRLSCAASGFNIKDTYIHWVRQAP

GKGLEWVAEIYPTNGYTRYADSVKGRFTISADTSKNTAYLQMNSLRAEDTAVYYCSRW

GGDGFGAMDYWGQGTLVTVSSASTKGPSVFPLAPSSKSTSGGTAALGCLVKDYFPEPV

TVSWNSTALTSGVHTFPAVLQSSGLYSLSSVVTVPSSSLGTQTYICNVNHKPSNTKVDK

KVEPKSCDKTHTCPPCPAPELLGGPSVFLAPPKPKDTLMISRTPEVTCVVADVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (null-Her2 IgG1 H chain, S134N, G161T (EU), pGLY14139)
SEQ ID NO: 33
MRFPSIFTAVLFAASSALAEVQLVESGGGLVQPGGSLRLSCAASGFNIKDTYIHWVRQAP

GKGLEWVAEIYPTNGYTRYADSVKGRFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSTALTSGVHTFPAVLQSSGLYSLSSVVTVPSSSLGTQTYICNVNHKPSNTKVDK

KVEPKSCDKTHTCPPCPAPELLGGPSVFLAPPKPKDTLMISRTPEVTCVVADVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (null-Her2 IgG1 H chain, S134N, G161T, N203T (EU),
pGLY14172)

SEQ ID NO: 34

MRFPSIFTAVLFAASSALAEVQLVESGGGLVQPGGSLRLSCAASGFNIKDTYIHWVRQAP

GKGLEWVAEIYPTNGYTRYADSVKGRFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSTALTSGVHTFPAVLQSSGLYSLSSVVTVPSSSLGTQTYICNVTHKPSNTKVDKK

VEPKSCDKTHTCPPCPAPELLGGPSVFLAPPKPKDTLMISRTPEVTCVVADVSHEDPEVK

FNWYVDGVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPG (null-Her2 IgG1 H chain, K30T, Y56T (Kabat), S134N (EU),
G161T (EU), pGLY14173)

SEQ ID NO: 35

MRFPSIFTAVLFAASSALAEVQLVESGGGLVQPGGSLRLSCAASGFNITDTYIHWVRQAP

GKGLEWVAEIYPTNGTTRYADSVKGRFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSTALTSGVHTFPAVLQSSGLYSLSSVVTVPSSSLGTQTYICNVNHKPSNTKVDK

KVEPKSCDKTHTCPPCPAPELLGGPSVFLAPPKPKDTLMISRTPEVTCVVADVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (null-Her2 IgG1 H chain, K30T (Kabat), K64N/R66T
(Kabat), S134N (EU), G161T (EU), pGLY14174)

SEQ ID NO: 36

MRFPSIFTAVLFAASSALAEVQLVESGGGLVQPGGSLRLSCAASGFNITDTYIHWVRQAP

GKGLEWVAEIYPTNGYTRYADSVNGTFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSTALTSGVHTFPAVLQSSGLYSLSSVVTVPSSSLGTQTYICNVNHKPSNTKVDK

KVEPKSCDKTHTCPPCPAPELLGGPSVFLAPPKPKDTLMISRTPEVTCVVADVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQKSLSLSPG (null-Her2 IgG1 H chain, Y56T, K64N/R66T (Kabat),
S134N(EU), G161T (EU), N203T (EU), pGLY14175)

SEQ ID NO: 37

MRFPSIFTAVLFAASSALAEVQLVESGGGLVQPGGSLRLSCAASGFNIKDTYIHWVRQAP

GKGLEWVAEIYPTNGTTRYADSVNGTFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSTALTSGVHTFPAVLQSSGLYSLSSVVTVPSSSLGTQTYICNVTHKPSNTKVDKK

VEPKSCDKTHTCPPCPAPELLGGPSVFLAPPKPKDTLMISRTPEVTCVVADVSHEDPEVK

FNWYVDGVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPG

-continued (null-Her2 IgG1 H chain, Y56T (Kabat), S134N (EU),
G161T (EU), S176N/G178T (EU), N203T (EU), pGLY14176)

SEQ ID NO: 38

MRFPSIFTAVLFAASSALAEVQLVESGGGLVQPGGSLRLSCAASGFNIKDTYIHWVRQAP

GKGLEWVAEIYPTNGTTRYADSVKGRFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSTALTSGVHTFPAVLQNSTLYSLSSVVTVPSSSLGTQTYICNVTHKPSNTKVDKK

VEPKSCDKTHTCPPCPAPELLGGPSVFLAPPKPKDTLMISRTPEVTCVVADVSHEDPEVK

FNWYVDGVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPG (null-Her2 IgG1 H chain, K30T (Kabat), Y56T (Kabat),
K64N/R66T (Kabat), S134N (EU), G161T (EU), N203T (EU),
pGLY14177)

SEQ ID NO: 39

MRFPSIFTAVLFAASSALAEVQLVESGGGLVQPGGSLRLSCAASGFNITDTYIHWVRQAP

GKGLEWVAEIYPTNGTTRYADSVNGTFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSTALTSGVHTFPAVLQSSGLYSLSSVVTVPSSSLGTQTYICNVTHKPSNTKVDKK

VEPKSCDKTHTCPPCPAPELLGGPSVFLAPPKPKDTLMISRTPEVTCVVADVSHEDPEVK

FNWYVDGVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPG (null-Her2 IgG1 H chain, K30T, Y56T, K64N/R66T (Kabat),
S134N, G161T, S176N/G178T, N203T, V363T, K392T, F423T
(EU), pGLY14178)

SEQ ID NO: 40

MRFPSIFTAVLFAASSALAEVQLVESGGGLVQPGGSLRLSCAASGFNITDTYIHWVRQAP

GKGLEWVAEIYPTNGTTRYADSVNGTFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSTALTSGVHTFPAVLQNSTLYSLSSVVTVPSSSLGTQTYICNVTHKPSNTKVDKK

VEPKSCDKTHTCPPCPAPELLGGPSVFLAPPKPKDTLMISRTPEVTCVVADVSHEDPEVK

FNWYVDGVEVHNAKTKPREEQYNSTYRVVSVLTVLHQDWLNGKEYKCKVSNKALPA

PIEKTISKAKGQPREPQVYTLPPSREEMTKNQTSLTCLVKGFYPSDIAVEWESNGQPENN

YTTTPPVLDSDGSFFLYSKLTVDKSRWQQGNVTSCSVMHEALHNHYTQKSLSLSPG (null-Her2 IgG1 H chain, K30T (Kabat), Y56T (Kabat),
K64N/R66T (Kabat), S134N (EU), G161T (EU), L193N (EU),
N203T (EU), V363T (EU), K392T (EU), F423T (EU),
pGLY14179)

SEQ ID NO: 41

MRFPSIFTAVLFAASSALAEVQLVESGGGLVQPGGSLRLSCAASGFNITDTYIHWVRQAP

GKGLEWVAEIYPTNGTTRYADSVNGTFTISADTSKNTAYLQMNSLRAEDTAVYYCSRW

GGDGFGAMDYWGQGTLVTVSSASTKGPSVFPLAPSSKNTSGGTAALGCLVKDYFPEPV

TVSWNSTALTSGVHTFPAVLQSSGLYSLSSVVTVPSSSNGTQTYICNVTHKPSNTKVDK

KVEPKSCDKTHTCPPCPAPELLGGPSVFLAPPKPKDTLMISRTPEVTCVVADVSHEDPEV

KFNWYVDGVEVHNAKTKPREEQYNSTYRVVSVLTVLHQDWLNGKEYKCKVSNKALP

APIEKTISKAKGQPREPQVYTLPPSREEMTKNQTSLTCLVKGFYPSDIAVEWESNGQPEN

NYTTTPPVLDSDGSFFLYSKLTVDKSRWQQGNVTSCSVMHEALHNHYTQKSLSLSPG (anti-mouse PD1 chimeric IgG1 H chain, pGLY13649)
SEQ ID NO: 42

EVQLVESGGGLVQPGGSLKLSCAASGFTFSNSGLAWVRQAPEKGLEWVATITYNGTST

YYRDSVKGRFTISRDNAKNTLYLQMSSLRSEDTATYYCARWVPGSGNFDYWGQGTLV

TVSSASTKGPSVFPLAPSSKSTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSDGSFFLYSKLT

VDKSRWQQGNVFSCSVMHEALHNHYTQKSLSLSPG (anti-mouse PD1 mouse L chain, pGLY13649)
SEQ ID NO: 43

DIVLTQSPASLAVSLGQRATISCRASQSVTISRYTLMHWYQQKPGQPPKLLIYRASNLAS

GIPARFSGSGSGTDFTLNIHPVEEDDAATYYCQQSRESPWTFGGGTKLEIKRADAAPTVS

IFPPSSEQLTSGGASVVCFLNNFYPKDINVKWKIDGSERQNGVLNSWTDQDSKDSTYSM

SSTLTLTKDEYERHNSYTCEATHKTSTSPIVKSFNRNEC (anti-mouse PD1 chimeric IgG1 H chain, S134N (EU), pGLY14163)
SEQ ID NO: 44

EVQLVESGGGLVQPGGSLKLSCAASGFTFSNSGLAWVRQAPEKGLEWVATITYNGTST

YYRDSVKGRFTISRDNAKNTLYLQMSSLRSEDTATYYCARWVPGSGNFDYWGQGTLV

TVSSASTKGPSVFPLAPSSKNTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDSDGSFFLYSK

LTVDKSRWQQGNVFSCSVMHEALHNHYTQKSLSLSPG (anti-mouse PD1 chimeric IgG1 H chain, G161T (EU), pGLY14164)
SEQ ID NO: 45

EVQLVESGGGLVQPGGSLKLSCAASGFTFSNSGLAWVRQAPEKGLEWVATITYNGTST

YYRDSVKGRFTISRDNAKNTLYLQMSSLRSEDTATYYCARWVPGSGNFDYWGQGTLV

TVSSASTKGPSVFPLAPSSKNTSGGTAALGCLVKDYFPEPVTVSWNSTALTSGVHTFPAV

LQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSDGSFFLYSKLT

VDKSRWQQGNVFSCSVMHEALHNHYTQKSLSLSPG (anti-mouse PD1 chimeric IgG1 H chain, S134N, G161T (EU), pGLY14165)
SEQ ID NO: 46

EVQLVESGGGLVQPGGSLKLSCAASGFTFSNSGLAWVRQAPEKGLEWVATITYNGTST

YYRDSVKGRFTISRDNAKNTLYLQMSSLRSEDTATYYCARWVPGSGNFDYWGQGTLV

TVSSASTKGPSVFPLAPSSKNTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDSDGSFFLYSK

LTVDKSRWQQGNVFSCSVMHEALHNHYTQKSLSLSPG (anti-CS1 IgG1 H chain, pGLY8040)
SEQ ID NO: 47

EVQLVESGGGLVQPGGSLRLSCAASGFDFSRYWMSWVRQAPGKGLEWIGEINPDSSTIN

YAPSLKDKFIISRDNAKNSLYLQMNSLRAEDTAVYYCARPDGNYWYFDVWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGSFFLYSKLTV

DKSRWQQGNVFSCSVMHEALHNHYTQKSLSLSPG (anti-CS1 L chain, pGLY8040)
SEQ ID NO: 48

DIQMTQSPSSLSASVGDRVTITCKASQDVGIAVAWYQQKPGKVPKLLIYWASTRHTGVP

DRFSGSGSGTDFTLTISSLQPEDVATYYCQQYSSYPYTFGQGTKVEIKRTVAAPSVFIFPP

SDEQLKSGTASVVCLLNNFYPREAKVQWKVDNALQSGNSQESVTEQDSKDSTYSLSST

LTLSKADYEKHKVYACEVTHQGLSSPVTKSFNRGEC (anti-CS1 IgG1 H chain, S134N (EU), pGLY14157)
SEQ ID NO: 49

EVQLVESGGGLVQPGGSLRLSCAASGFDFSRYWMSWVRQAPGKGLEWIGEINPDSSTIN

YAPSLKDKFIISRDNAKNSLYLQMNSLRAEDTAVYYCARPDGNYWYFDVWGQGTLVT

VSSASTKGPSVFPLAPSSKNTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSDGSFFLYSKLT

VDKSRWQQGNVFSCSVMHEALHNHYTQKSLSLSPG (anti-CS1 IgG1 H chain, G161T (EU), pGLY14158)
SEQ ID NO: 50

EVQLVESGGGLVQPGGSLRLSCAASGFDFSRYWMSWVRQAPGKGLEWIGEINPDSSTIN

YAPSLKDKFIISRDNAKNSLYLQMNSLRAEDTAVYYCARPDGNYWYFDVWGQGTLVT

VSSASTKGPSVFPLAPSSKSTSGGTAALGCLVKDYFPEPVTVSWNSTALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGSFFLYSKLTV

DKSRWQQGNVFSCSVMHEALHNHYTQKSLSLSPG (anti-CS1 IgG1 H chain, S134N, G161T (EU), pGLY14159)
SEQ ID NO: 51

EVQLVESGGGLVQPGGSLRLSCAASGFDFSRYWMSWVRQAPGKGLEWIGEINPDSSTIN

YAPSLKDKFIISRDNAKNSLYLQMNSLRAEDTAVYYCARPDGNYWYFDVWGQGTLVT

VSSASTKGPSVFPLAPSSKNTSGGTAALGCLVKDYFPEPVTVSWNSTALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPRE

```
EQYNSTYRVVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGSFFLYSKLTV

DKSRWQQGNVFSCSVMHEALHNHYTQKSLSLSPG (anti-CD70 IgG1 H chain, pGLY14148)
                                                  SEQ ID NO: 52
QVQLVESGGGVVQPGRSLRLSCAASGFTFSSYIMHWVRQAPGKGLEWVAVISYDGRNK

YYADSVKGRFTISRDNSKNTLYLQMNSLRAEDTAVYYCARDTDGYDFDYWGQGTLVT

VSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGSFFLYSKLTV

DKSRWQQGNVFSCSVMHEALHNHYTQKSLSLSPG (anti-CD70 L chain, pGLY14148)
                                                  SEQ ID NO: 53
EIVLTQSPATLSLSPGERATLSCRASQSVSSYLAWYQQKPGQAPRLLIYDASNRATGIPA

RFSGSGSGTDFTLTISSLEPEDFAVYYCQQRTNWPLTFGGGTKVEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC (anti-CD70 IgG1 H chain, S134N (EU), pGLY14149)
                                                  SEQ ID NO: 54
QVQLVESGGGVVQPGRSLRLSCAASGFTFSSYIMHWVRQAPGKGLEWVAVISYDGRNK

YYADSVKGRFTISRDNSKNTLYLQMNSLRAEDTAVYYCARDTDGYDFDYWGQGTLVT

VSSASTKGPSVFPLAPSSKNTSGGTAALGCLVKDYFPEPVTVSWNSGALTSGVHTFPAV

LQSSGLYSLSSVVTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSDGSFFLYSKLT

VDKSRWQQGNVFSCSVMHEALHNHYTQKSLSLSPG (anti-CD70 IgG1 H chain, G161T (EU), pGLY14150)
                                                  SEQ ID NO: 55
QVQLVESGGGVVQPGRSLRLSCAASGFTFSSYIMHWVRQAPGKGLEWVAVISYDGRNK

YYADSVKGRFTISRDNSKNTLYLQMNSLRAEDTAVYYCARDTDGYDFDYWGQGTLVT

VSSASTKGPSVFPLAPSSKSTSGGTAALGCLVKDYFPEPVTVSWNSTALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGSFFLYSKLTV

DKSRWQQGNVFSCSVMHEALHNHYTQKSLSLSPG (anti-CD70 IgG1 H chain, S134N, G161T (EU), pGLY14151)
                                                  SEQ ID NO: 56
QVQLVESGGGVVQPGRSLRLSCAASGFTFSSYIMHWVRQAPGKGLEWVAVISYDGRNK

YYADSVKGRFTISRDNSKNTLYLQMNSLRAEDTAVYYCARDTDGYDFDYWGQGTLVT

VSSASTKGPSVFPLAPSSKNTSGGTAALGCLVKDYFPEPVTVSWNSTALTSGVHTFPAVL

QSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPRE
```

-continued

EQYNSTYRVVSVLTVLHQDWLNGKEYKCKVSNKALPAPIEKTISKAKGQPREPQVYTLP

PSRDELTKNQVSLTCLVKGFYPSDIAVEWESNGQPENNYKTTPPVLDSDGSFFLYSKLTV

DKSRWQQGNVFSCSVMHEALHNHYTQKSLSLSPG (Protein sequence of Galactose Oxidase from *Fusarium graminearum* Genbank: P0CS93)

SEQ ID NO: 57

MKHLLTLALCFSSINAVAVTVPHKAVGTGIPEGSLQFLSLRASAPIGSAISRNNWAVTCD

SAQSGNECNKAIDGNKDTFWHTFYGANGDPKPPHTYTIDMKTTQNVNGLSMLPRQDG

NQNGWIGRHEVYLSSDGTNWGSPVASGSWFADSTTKYSNFETRPARYVRLVAITEANG

QPWTSIAEINVFQASSYTAPQPGLGRWGPTIDLPIVPAAAAIEPTSGRVLMWSSYRNDAF

GGSPGGITLTSSWDPSTGIVSDRTVTVTKHDMFCPGISMDGNGQIVVTGGNDAKKTSLY

DSSSDSWIPGPDMQVARGYQSSATMSDGRVFTIGGSWSGGVFEKNGEVYSPSSKTWTSL

PNAKVNPMLTADKQGLYRSDNHAWLFGWKKGSVFQAGPSTAMNWYYTSGSGDVKSA

GKRQSNRGVAPDAMCGNAVMYDAVKGKILTFGGSPDYQDSDATTNAHIITLGEPGTSP

NTVFASNGLYFARTFHTSVVLPDGSTFITGGQRRGIPFEDSTPVFTPEIYVPEQDTFYKQN

PNSIVRVYHSISLLLPDGRVFNGGGGLCGDCTTNHFDAQIFTPNYLYNSNGNLATRPKIT

RTSTQSVKVGGRITISTDSSISKASLIRYGTATHTVNTDQRRIPLTLTNNGGNSYSFQVPSD

SGVALPGYWMLFVMNSAGVPSVASTIRVTQ (Gene sequence of Galactose Oxidase from *Fusarium graminearum*)

SEQ ID NO: 58

ATGGCCGATCAGCAAACGGTCCTTAGTGTATCCGTACCTGGATATATAAGACTGGAA

GATATCAGTTGTTCTTCATCTGCCAGTATCACCTTCATTATCTATTCAAGTCACTCTC

TCAACTTATTCTTGCCTCTCTCTATGTCAATATGAAACACTTTTTATCACTCGCTCTTT

GCTTCAGCAGCATCAATGCTGTTGCTGTCACCGTCCCTCACAAGTCCGGAGGAACTG

GAAGTCCTGAAGGGAGTCTTCAGTTCCTGAGTCTTCGGGCCTCAGCACCTATCGGAA

GCGCTATTTCTCGCAACAACTGGGCCGTCACTTGCGACAGTGCACAGTCGGGAAATG

AATGCAACAAGGCCATCGATGGCAACAAGGATACCTTTTGGCACACATTCTATGGG

GCCAATGGAGATCCAAAGCCCCCTCACACATACACGATTGACATGAAGACAACTCA

GAATGTCAACGGCTTGTCTATGTTGCCTCGACAGGATGGTAACCAAAACGGCTGGAT

CGGTCGCCATGAGGTTTATCTAAGCTCAGATGGCACAAACTGGGGCAGCCCTGTTGC

GTCAGGTAGTTGGTTTGCCGACTCTACTACAAAATACTCCAACTTTGAAACTCGCCC

TGCTCGCTATGTTCGTCTTGTCGCTGTCACTGAAGCGAATGGCCAGCCTTGGACTAG

CATTGCAGAGATCAACGTCTTCCAAGCTAGTTCTTACACAGCCCCTCAGCCTGGCCT

TGGCCGCTGGGGTCCGACTATTGACTTGCCGATTGTTCCTGCGGCTGCAGCAATTGA

GCCGACATCGGGACGAGTCCTTATGTGGTCTTCGTATCGCAATGATGCATTTGGAGG

ATCCCCTGGTGGTATCACTTTGACGTCTTCGTGGGATCCATCCACTGGCATTGTTTCC

GACCGCACTGTGACAGTCACCAAGCATGATATGTTCTGCCCTGGTATCTCCATGGAT

GGTAACGGTCAGATCGTAGTCACAGGTGGCAACGACGCCAAGAAGACCAGTTTGTA

TGATTCATCTAGCGATAGCTGGATCCCGGGACCTGACATGCAAGTGGCTCGTGGGTA

TCAGTCATCAGCTACCATGTCAGACGGTCGTGTTTTTACCATTGGAGGCTCCTGGAG

CGGTGGCGTATTTGAGAAGAATGGCGAAGTCTATAGCCCATCTTCAAAGACATGGA

CGTCCCTACCCAATGCCAAGGTCAACCCAATGTTGACGGCTGACAAGCAAGGATTG

-continued

```
TACCGTTCAGACAACCACGCGTGGCTCTTTGGATGGAAGAAGGGTTCGGTGTTCCAA

GCGGGACCTAGTACAGCCATGAACTGGTACTATACCAGTGGAAGTGGCGATGTGAA

GTCAGCCGGAAAACGCCAGTCTAACCGTGGTGTAGCCCCTGATGCCATGTGCGGAA

ACGCTGTCATGTACGACGCCGTTAAAGGAAAGATCCTGACCTTTGGCGGCTCCCAG

ACTATCAAGACTCTGACGCCACAACCAACGCCCACATCATCACCCTCGGTGAACCCG

GAACATCTCCCAACACTGTCTTTGCTAGCAATGGCTTGTACTTTGCTCGAACGTTCCA

CACCTCTGTTGTTCTTCCAGACGGAAGCACGTTCATTACAGGAGGCCAACGACGTGG

AATTCCGTTCGAGGATTCAACCCCGGTATTTACACCTGAGATCTACGTCCCTGAACA

AGACACTTTCTACAAGCAGAACCCCAACTCCATTGTTCGCGTCTACCACAGCATTTC

CCTTTTGTTACCTGATGGCAGGGTATTTAACGGTGGTGGTGGTCTTTGTGGCGATTGT

ACCACGAATCATTTCGACGCGCAAATCTTTACGCCAAACTATCTTTACAATAGCAAC

GGCAATCTCGCGACACGTCCCAAGATTACCAGAACCTCTACACAGAGCGTCAAGGT

CGGTGGCAGGATCACAATCTCGACGGACTCTTCGATTACAAAGGCGTCGTTGATTCG

CTATGGTACAGCGACACACACGGTTAATACTGACCAGCGTCGCATTCCCCTGACTCT

GACAAACAATGGAGGAAATAGCTATTCTTTCCAAGTTCCTAGCGACTCTGGTGTTGC

TTTGCCTGGCTACTGGATGTTGTTCGTGATGAACTCGGCCGGTGTTCCTAGTGTGGCT

TCGACGATTCGCGTTACTCAGTGA
```

REFERENCES

Alley S C, Okeley N M, Senter P D. Antibody-drug conjugates: targeted drug delivery for cancer. Curr Opin Chem Biol. 2010 August; 14(4):529-37. doi: 10.1016/j.cbpa.2010.06.170. Epub 2010 Jul. 17. Review. PubMed PMID: 20643572.

Axup J Y, Bajjuri K M, Ritland M, Hutchins B M, Kim C H, Kazane S A, Halder R, Forsyth J S, Santidrian A F, Stafin K, Lu Y, Tran H, Seller A J, Biroc S L, Szydlik A, Pinkstaff J K, Tian F, Sinha S C, Felding-Habermann B, Smider V V, Schultz P G. Synthesis of site-specific antibody-drug conjugates using unnatural amino acids. Proc Natl Acad Sci USA. 2012 Oct. 2; 109(40):16101-6. doi: 10.1073/pnas.1211023109. Epub 2012 Sep. 17. PubMed PMID: 22988081; PubMed Central PMCID: PMC3479532.

Barnard G C, Kull A R, Sharkey N S, Shaikh S S, Rittenhour A M, Burnina I, Jiang Y, Li F, Lynaugh H, Mitchell T, Nett J H, Nylen A, Potgieter T I, Prinz B, Rios S E, Zha D, Sethuraman N, Stadheim T A, Bobrowicz P. High-throughput screening and selection of yeast cell lines expressing monoclonal antibodies. J Ind Microbiol Biotechnol. 2010 September; 37(9):961-71.

Burnina I, Hoyt E, Lynaugh H, Li H, Gong B. A cost-effective plate-based sample preparation for antibody N-glycan analysis. J Chromatogr A. 2013 Sep. 13; 1307: 201-6. doi: 10.1016/j.chroma.2013.07.104. Epub 2013 Aug. 2. PubMed PMID: 23932029.

Burris H A. Developments in the use of antibody-drug conjugates. Am Soc Clin Oncol Educ Book. 2013. doi: 10.1200/EdBook A M.2013.33.e99. PubMed PMID: 23714468.

Butler M, Meneses-Acosta A. Recent advances in technology supporting biopharmaceutical production from mammalian cells. Appl Microbiol Biotechnol. 2012 November; 96(4):885-94. doi: 10.1007/s00253-012-4451-z. Epub 2012 Oct. 5. Review. PubMed PMID: 23053101.

Choi B K, Bobrowicz P, Davidson R C, Hamilton S R, Kung D H, Li H, Miele R G, Nett J H, Wildt S, Gerngross T U. Use of combinatorial genetic libraries to humanize N-linked glycosylation in the yeast Pichia pastoris. Proc Natl Acad Sci USA. 2003 Apr. 29; 100(9):5022-7. Epub 2003 Apr. 17. PubMed PMID: 12702754; PubMed Central PMCID: PMC154291.

Choi B K, Actor J K, Rios S, d'Anjou M, Stadheim T A, Warburton S, Giaccone E, Cukan M, Li H, Kull A, Sharkey N, Gollnick P, Kocieba M, Artym J, Zimecki M, Kruzel M L, Wildt S. Recombinant human lactoferrin expressed in glycoengineered Pichia pastoris: effect of terminal N-acetylneuraminic acid on in vitro secondary humoral immune response. Glycoconj J. 2008 August; 25(6):581-93. doi: 10.1007/s10719-008-9123-y. Epub 2008 Mar. 26. PubMed PMID: 18365311; PubMed Central PMCID.

Cooper J A D, Smith W, Bacila M and heitor M. Galactose Oxidase from Polyporus circinatus, Fr. J. Biol. Chem. 1959 Mar. 1; 234: 445-448.

Cregg J M, Cereghino J L, Shi J, Higgins D R. Recombinant protein expression in Pichia pastoris. Mol Biotechnol. 2000 September; 16(1):23-52. PubMed PMID: 11098467.

Crisalli P, Kool E T. Water-soluble organocatalysts for hydrazone and oxime formation. J Org Chem. 2013 Feb. 1; 78(3):1184-9. doi: 10.1021/jo302746p. Epub 2013 Jan. 15. PubMed PMID: 23289546; PubMed Central PMCID: PMC3562402.

Lynaugh H, Li H, Gong B. Rapid Fc glycosylation analysis of Fc fusions with IdeS and liquid chromatography mass spectrometry. MAbs. 2013 September-October; 5(5):641-5. doi: 10.4161/mabs.25302. Epub 2013 Jun. 20. PubMed PMID: 23839239.

Flygare J A, Pillow T H, Aristoff P. Antibody-drug conjugates for the treatment of cancer. Chem Biol Drug Des.

2013 January; 81(1):113-21. doi: 10.1111/cbdd.12085. Review. PubMed PMID: 23253133.

Gomathinayagam S, Hoyt E, Thompson A M, Brown E, Karaveg K, Hamilton S R, Li H. High-throughput multimodal strong anion exchange purification and N-glycan characterization of endogenous glycoprotein expressed in glycoengineered *Pichia pastoris*. Methods Mol Biol. 2012; 899:315-23. doi: 10.1007/978-1-61779-921-1_20. PubMed PMID: 22735962.

Hamilton S R, Davidson R C, Sethuraman N, Nett J H, Jiang Y, Rios S, Bobrowicz P, Stadheim T A, Li H, Choi B K, Hopkins D, Wischnewski H, Roser J, Mitchell T, Strawbridge R R, Hoopes J, Wildt S, Gerngross T U. Humanization of yeast to produce complex terminally sialylated glycoproteins. Science. 2006 September 8; 313(5792):1441-3. PubMed PMID: 16960007.

Hopkins D, Gomathinayagam S, Rittenhour A M, Du M, Hoyt E, Karaveg K, Mitchell T, Nett J H, Sharkey N J, Stadheim T A, Li H, Hamilton S R. Elimination of β-mannose glycan structures in *Pichia pastoris*. Glycobiology. 2011 December; 21(12):1616-26. doi: 10.1093/glycob/cwr108. Epub 2011 Aug. 12.

Hossler P, Khattak S F, Li Z J. Optimal and consistent protein glycosylation in mammalian cell culture. Glycobiology. 2009 September; 19(9):936-49. doi: 10.1093/glycob/cwp079. Epub 2009 Jun. 3. Review. PubMed PMID: 19494347.

Jackson D, Atkinson J, Guevara C I, Zhang C, Kery V, Moon S J, Virata C, Yang P, Lowe C, Pinkstaff J, Cho H, Knudsen N, Manibusan A, Tian F, Sun Y, Lu Y, Sellers A, Jia X C, Joseph I, Anand B, Morrison K, Pereira D S, Stover D. In vitro and in vivo evaluation of cysteine and site specific conjugated herceptin antibody-drug conjugates. PLoS One. 2014 Jan. 14; 9(1):e83865. doi: 10.1371/journal.pone.0083865. eCollection 2014. PubMed PMID: 24454709; PubMed Central PMCID: PMC3891645.

Jayasekara P S, Jacobson K A, Rapid synthesis of alkoxyamine hydrochloride derivatives from alkyl bromide and N,N'-di-tert-butoxycarbonylhydroxylamine. Synth. Commun. 2014, Aug. 1, 2014, 44(16): 2344-2347.

Jiang Y, Li F, Zha D, Potgieter T I, Mitchell T, Moore R, Cukan M, Houston-Cummings N R, Nylen A, Drummond J E, McKelvey T W, d'Anjou M, Stadheim T A, Sethuraman N, Li H. Purification process development of a recombinant monoclonal antibody expressed in glycoengineered *Pichia pastoris*. Protein Expr Purif. 2011 March; 76(1):7-14. doi: 10.1016/j.pep.2010.11.004. Epub 2010 Nov. 11. PubMed PMID: 21074617.

Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. Site-specific conjugation of a cytotoxic drug to an antibody improves the therapeutic index. Nat Biotechnol. 2008 August; 26(8):925-32. doi: 10.1038/nbt.1480. Epub 2008 Jul. 20. PubMed PMID: 18641636.

Junutula J R, Flagella K M, Graham R A, Parsons K L, Ha E, Raab H, Bhakta S, Nguyen T, Dugger D L, Li G, Mai E, Lewis Phillips G D, Hiraragi H, Fuji R N, Tibbitts J, Vandlen R, Spencer S D, Scheller R H, Polakis P, Sliwkowski M X. Engineered thio-trastuzumab-DM1 conjugate with an improved therapeutic index to target human epidermal growth factor receptor 2-positive breast cancer. Clin Cancer Res. 2010 Oct. 1; 16(19):4769-78. doi: 10.1158/1078-0432.CCR-10-0987. Epub 2010 Aug. 30. PubMed PMID: 20805300.

Kaneko Y, Nimmerjahn F, Ravetch J V. Anti-inflammatory activity of immunoglobulin G resulting from Fc sialylation. Science. 2006 Aug. 4; 313(5787):670-3. PubMed PMID: 16888140.

Li H, Sethuraman N, Stadheim T A, Zha D, Prinz B, Ballew N, Bobrowicz P, Choi B K, Cook W J, Cukan M, Houston-Cummings N R, Davidson R, Gong B, Hamilton S R, Hoopes J P, Jiang Y, Kim N, Mansfield R, Nett J H, Rios S, Strawbridge R, Wildt S, Gerngross T U. Optimization of humanized IgGs in glycoengineered *Pichia pastoris*. Nat Biotechnol. 2006 February; 24(2):210-5. Epub 2006 Jan. 22. PubMed PMID: 16429149.

Liu H F, Ma J, Winter C, Bayer R. Recovery and purification process development for monoclonal antibody production. MAbs. 2010 September-October; 2(5):480-99. Epub 2010 Sep. 1. Review. PubMed PMID: 20647768; PubMed Central PMCID: PMC2958570.

Mullard A. Maturing antibody-drug conjugate pipeline hits 30. Nat Rev Drug Discov. 2013 May; 12(5):329-32. doi: 10.1038/nrd4009. Erratum in: Nat Rev Drug Discov. 2013 June; 12(6):483.

Nett J H, Gomathinayagam S, Hamilton S R, Gong B, Davidson R C, Du M, Hopkins D, Mitchell T, Mallem M R, Nylen A, Shaikh S S, Sharkey N, Barnard G C, Copeland V, Liu L, Evers R, Li Y, Gray P M, Lingham R B, Visco D, Forrest G, DeMartino J, Linden T, Potgieter T I, Wildt S, Stadheim T A, d'Anjou M, Li H, Sethuraman N. Optimization of erythropoietin production with controlled glycosylation-PEGylated erythropoietin produced in glycoengineered *Pichia pastoris*. J Biotechnol. 2012 January; 157(1):198-206. doi: 10.1016/j.jbiotec.2011.11.002. Epub 2011 Nov. 9. PubMed PMID: 22100268.

Nitschke L. CD22 and Siglec-G: B-cell inhibitory receptors with distinct functions. Immunol Rev. 2009 July; 230(1): 128-43. doi: 10.1111/j.1600-065X.2009.00801.x. Review. PubMed PMID: 19594633.

Omasa T, Onitsuka M, Kim W D. Cell engineering and cultivation of chinese hamster ovary (CHO) cells. Curr Pharm Biotechnol. 2010 April; 11(3):233-40. Review. PubMed PMID: 20210750.

Panowski S, Bhakta S, Raab H, Polakis P, Junutula J R. Site-specific antibody drug conjugates for cancer therapy. MAbs. 2014 January-February; 6(1):34-45. doi: 10.4161/mabs.27022. PubMed PMID: 24423619; PubMed Central PMCID: PMC3929453.

Potgieter T I, Cukan M, Drummond J E, Houston-Cummings N R, Jiang Y, Li F, Lynaugh H, Mallem M, McKelvey T W, Mitchell T, Nylen A, Rittenhour A, Stadheim T A, Zha D, d'Anjou M. Production of monoclonal antibodies by glycoengineered *Pichia pastoris*. J Biotechnol. 2009 Feb. 23; 139(4):318-25. doi: 10.1016/j.jbiotec.2008.12.015. Epub 2008 Dec. 27. PubMed PMID: 19162096.

Prime S, Dearnley J, Ventom A M, Parekh R B, Edge C J. Oligosaccharide sequencing based on exo- and endoglycosidase digestion and liquid chromatographic analysis of the products. J Chromatogr A. 1996 Jan. 12; 720(1-2): 263-74. Review. PubMed PMID: 8601195.

Ramya T N, Weerapana E, Cravatt B F, Paulson J C. Glycoproteomics enabled by tagging sialic acid- or galactose-terminated glycans. Glycobiology. 2013 February; 23(2):211-21. Epub 2012 Oct. 15. PubMed PMID: 23070960.

Restelli V, Wang M D, Huzel N, Ethier M, Perreault H, Butler M. The effect of dissolved oxygen on the production and the glycosylation profile of recombinant human erythropoietin produced from CHO cells. Biotechnol Bioeng. 2006 Jun. 20; 94(3):481-94.

Ricart A D, Tolcher A W. Technology insight: cytotoxic drug immunoconjugates for cancer therapy. Nat Clin Pract Oncol. 2007 April; 4(4):245-55. Review. PubMed PMID: 17392715.

Rita Costa A, Elisa Rodrigues M, Henriques M, Azeredo J, Oliveira R. Guidelines to cell engineering for monoclonal antibody production. Eur J Pharm Biopharm. 2010 February; 74(2):127-38. doi: 10.1016/j.ejpb.2009.10.002. Epub 2009 Oct. 22. Review. PubMed PMID: 19853660.

Schirrmann T, Al-Halabi L, Dithel S, Hust M. Production systems for recombinant antibodies. Front Biosci. 2008 May 1; 13:4576-94. Review. PubMed PMID: 18508530.

Schrama D, Reisfeld R A, Becker J C. Antibody targeted drugs as cancer therapeutics. Nat Rev Drug Discov. 2006 February; 5(2):147-59. Review. PubMed PMID: 16424916.

Sethuraman N, Stadheim T A. Challenges in therapeutic glycoprotein production. Curr Opin Biotechnol. 2006 August; 17(4):341-6. Epub 2006 Jul. 7. Review. PubMed PMID: 16828275.

Singh Y, Renauder O, Defranco E, Dumy P. Preparation of a multitopic glycopeptide-oligonucleotice conjugate. Org. Lett. 2005 Mar. 31; 7(7): 1359-62.

Su S, Acquilano De, Arumagasamy J, Beeler A B, Eastwood El, Giguere J R, Lan P, Lei X, Min G K, Yeager A R, Zhou Y, Panek J S, Snyder J K, Schaus S E, Porco J A Jr. Convergent synthesis of a complex oxime library using chemical domain shuffling. Org. Lett. 2005 Jun. 23; 7(13):2751-4.

Tian F, Lu Y, Manibusan A, Sellers A, Tran H, Sun Y, Phuong T, Barnett R, Hehli B, Song F, DeGuzman M J, Ensari S, Pinkstaff J K, Sullivan L M, Biroc S L, Cho H, Schultz P G, DiJoseph J, Dougher M, Ma D, Dushin R, Leal M, Tchistiakova L, Feyfant E, Gerber H P, Sapra P. A general approach to site-specific antibody drug conjugates. Proc Natl Acad Sci USA. 2014 Feb. 4; 111(5): 1766-71. doi: 10.1073/pnas.1321237111. Epub 2014 Jan. 17. PubMed PMID: 24443552; PubMed Central PMCID: PMC3918752.

Trimalille T, Autissier L, Rakotonirina M D, Guillaneuf Y, Villard C, Bertin D, Gigmes D, Mabrouk K. Peptide ligation from alkoxyamine based radical addition. Chem. Commun (Camb). 2014 Mar. 14; 50(21): 2744-7

Tsubata T. Role of inhibitory BCR co-receptors in immunity. Infect Disord Drug Targets. 2012 June; 12(3):181-90. Review. PubMed PMID: 22394175.

Verma S, Miles D, Gianni L, Krop I E, Welslau M, Baselga J, Pegram M, Oh D Y, Diéras V, Guardino E, Fang L, Lu M W, Olsen S, Blackwell K; EMILIA Study Group. Trastuzumab emtansine for HER2-positive advanced breast cancer. N Engl J Med. 2012 Nov. 8; 367(19):1783-91. doi: 10.1056/NEJMoa1209124. Epub 2012 Oct. 1. Erratum in: N Engl J Med. 2013 Jun. 20; 368(25):2442. PubMed PMID: 23020162.

Walsh G. Biopharmaceutical benchmarks 2014. Nat Biotechnol. 2014 October; 32(10):992-1000. doi: 10.1038/nbt.3040. PubMed PMID: 25299917.

Wang, R E, Liu, T, Wang, Y, Cao, Y, Du, J, Luo, X, Deshmukh, V, Kim, C H, Lawson, B R, Tremblay, M S, Young, T S, Kazane, S A, Wang, F and Schultz, P G. JACS. January 2015 (web, communication),"An Immunosuppressive Antibody-Drug Conjugate".

Zhang N, Liu L, Dumitru C D, Cummings N R, Cukan M, Jiang Y, Li Y, Li F, Mitchell T, Mallem M R, Ou Y, Patel R N, Vo K, Wang H, Burnina I, Choi B K, Huber H E, Stadheim T A, Zha D. Glycoengineered *Pichia* produced anti-HER2 is comparable to trastuzumab in preclinical study. MAbs. 2011 May-June; 3(3):289-98. Epub 2011 May 1. PubMed PMID: 21487242; PubMed Central PMCID: PMC3149709.

Zha D. Glycoengineered *Pichia*-based expression of monoclonal antibodies. Methods Mol Biol. 2013; 988:31-43. doi: 10.1007/978-1-62703-327-5_3. PubMed PMID: 23475712.

Zhou H, Liu Z G, Sun Z W, Huang Y, Yu W Y. Generation of stable cell lines by site-specific integration of transgenes into engineered Chinese hamster ovary strains using an FLP-FRT system. J Biotechnol. 2010 May 17; 147(2):122-9. doi: 10.1016/j.jbiotec.2010.03.020. Epub 2010 Apr. 3. PubMed PMID: 20371256.

Zimmerman E S, Heibeck T H, Gill A, Li X, Murray C J, Madlansacay M R, Tran C, Uter N T, Yin G, Rivers P J, Yam A Y, Wang W D, Steiner A R, Bajad S U, Penta K, Yang W, Hallam T J, Thanos C D, Sato A K. Production of site-specific antibody-drug conjugates using optimized non-natural amino acids in a cell-free expression system. Bioconjug Chem. 2014 Feb. 19; 25(2):351-61. doi: 10.1021/bc400490z. Epub 2014 Jan. 29. PubMed PMID: 24437342.

EXAMPLES

Figure 3:
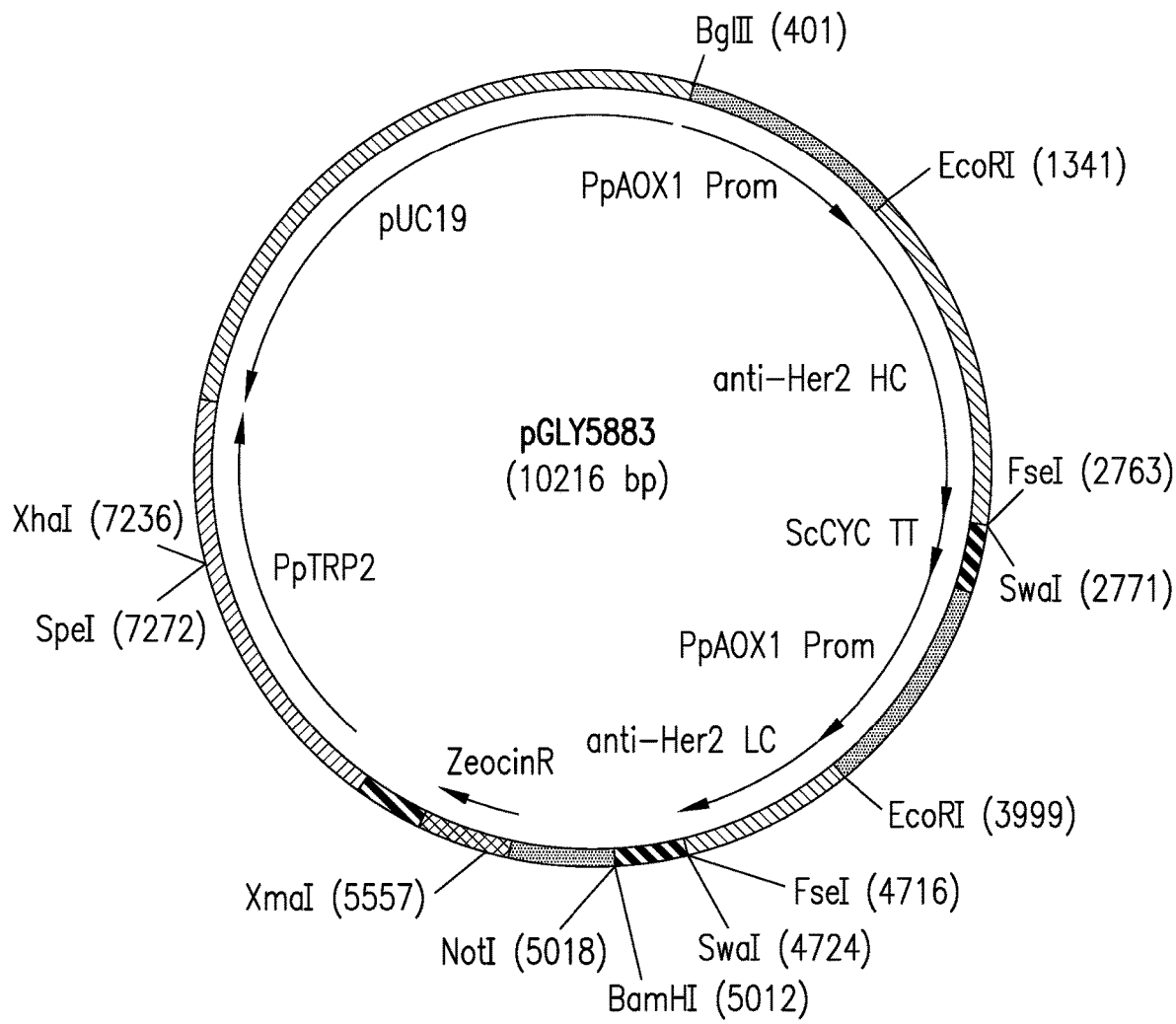
FIG. 3: Restriction map of plasmid pGLY5883. The *E. coli/P. pastoris* shuttle vector is depicted circularly as it is maintained in *E. coli*. The plasmid contains the pUC19 Ori and AmpR region for *E. coli* maintenance as well as the Sh ble gene encoding Zeocin resistance (ZeoR) and the *P. pastoris* TRP2 gene, used as an integration site. The genes encoding the trastuzumab anti-Her2 H (heavy) chain and L (light) chain are contained as separate cassettes, each with the *P. pastoris* AOX1 promoter and *S. cerevisiae* CYC1 transcriptional terminator.

Example 1: Expression of Anti-Her2 with Non-Native N-Glycan-Incorporating Site-Directed Alterations The anti-HER2 (trastuzumab) IgG1 H chain and L chain sequences (Seq ID NO: 1 and 2, respectively) were incorporated into a single $Zeo^R$-marked, TRP2-integrating *Pichia pastoris* roll-in expression plasmid, each as part of separate AOX1-driven expression cassettes containing the *Saccharomyces cerevisiae* alpha factor pre signal sequence (Seq ID NO: 3) to generate plasmid pGLY5883 (FIG. 3; SEQ ID NO: 4). Site-directed mutations were then designed based on desirable locations within the H chain. These locations were chosen as sites that would: 1) be within or near loop or where a side chain was solvent exposed to not disrupt an Ig-fold, 2) not be near critical sites related to mAb function (e.g. Ag-binding, FcRN binding, FcγR-binding), and 3) be converted to an N-glycan sequon with a minimum of primary sequence modification. Initially 8 sites were chosen to test whether non-native N-glycosylation sites can be efficiently incorporated into an immunoglobulin with a high degree of N-glycan occupancy without disrupting the normal folding or function of the parent antibody. These 8 sites are indicated in Table 1.

Plasmids pGLY10044-10051, constructed by Genewiz (South Plainfield, N.J.), are derived from plasmid pGLY5883 and differ only by the indicated non-native N-glycosylation site introducing mutations in the anti-HER2 H chain cassette (Table 1) resulting in SEQ ID NO: 4-11.

TABLE 1

| Plasmid | Heavy chain protein Seq ID | Sequence change (EU) | Sequence change (anti-HER2) | Sequence change (Kabat) | Secreted and folded mAb? | N-glycan site is Occupied? | Conjugated with Fluorophore? |
|---|---|---|---|---|---|---|---|
| pGLY10044 | Seq. ID NO: 4 | N/A | Q112N | Q105N | Yes | Yes | No |
| pGLY10045 | Seq. ID NO: 5 | S134N | S137N | S130N | Yes | Yes | Yes |
| pGLY10046 | Seq. ID NO: 6 | G161T | G164T | G158T | Yes | Yes | Yes |
| pGLY10047 | Seq. ID NO: 7 | Q175N | Q178N | Q179N | No | N/A | N/A |
| pGLY10048 | Seq. ID NO: 8 | N203T | N206T | N211T | Yes | Yes | Yes |
| pGLY10049 | Seq. ID NO: 9 | V363T | V366T | V386T | Yes | Yes | Yes |
| pGLY10050 | Seq. ID NO: 10 | Q386T | Q389T | Q414T | Yes | No | N/A |
| pGLY10051 | Seq. ID NO: 11 | Q438N | Q441N | Q469N | Yes | Yes | Yes |

Figure 4A:
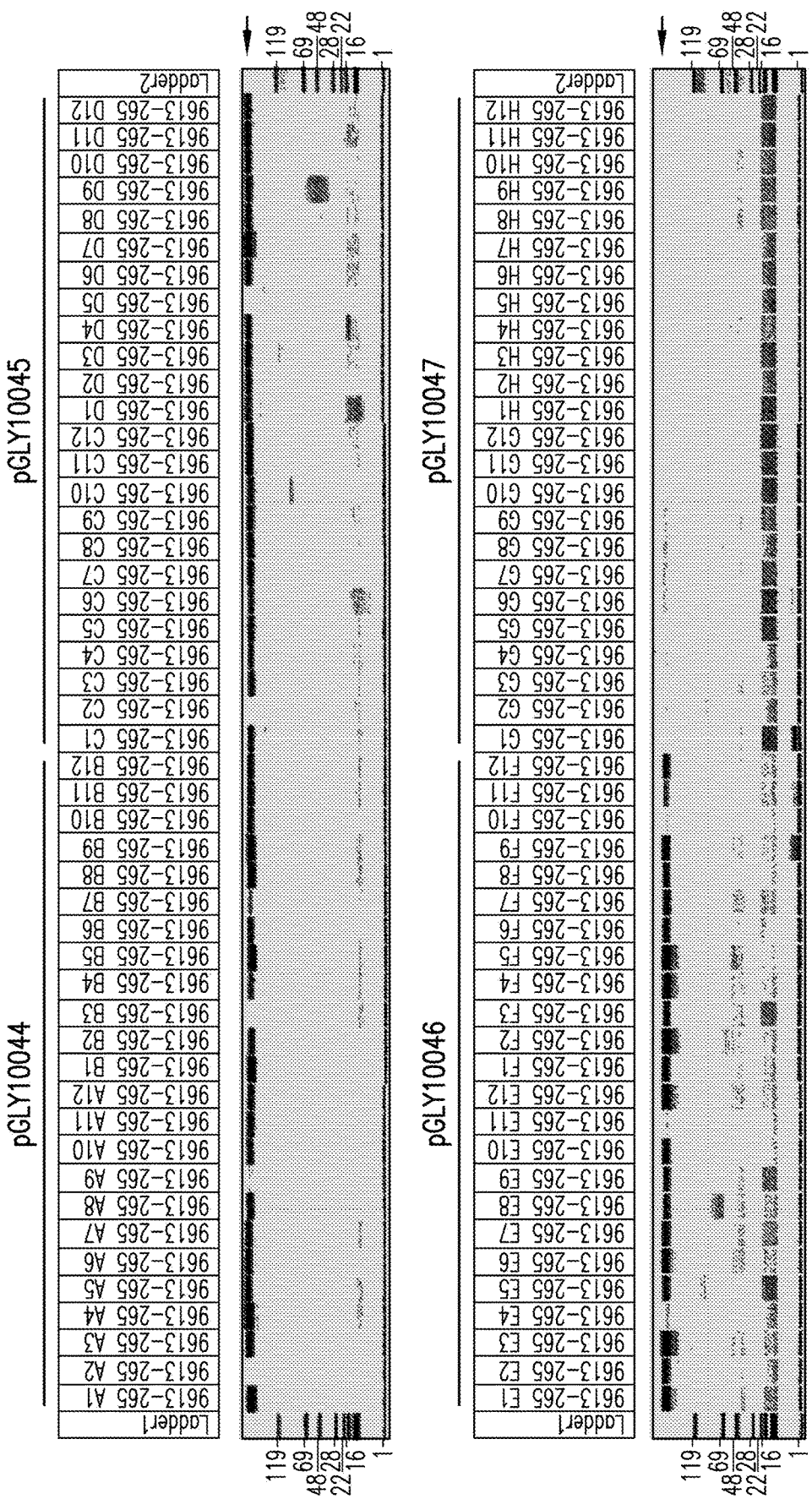
FIG. 4 (A-B): Capillary electrophoretic analysis of N-glycan modified antibodies. Gel animation image depicting protein bands following separation by capillary electrophoresis of glycan-engineered versions of the trastuzumab anti-Her2 antibody under denatured non-reduced conditions. Antibodies are described in Table 1 and were expressed in GS5.0 (FIG. 2) glycoengineered *Pichia*, then resulting clones cultivated in 96 deep well plates, and culture supernatant protein A purified. Arrows indicate the presence of an antibody tetramer band. Sizes are indicated by the markers at the far left and right.
Figure 4B:
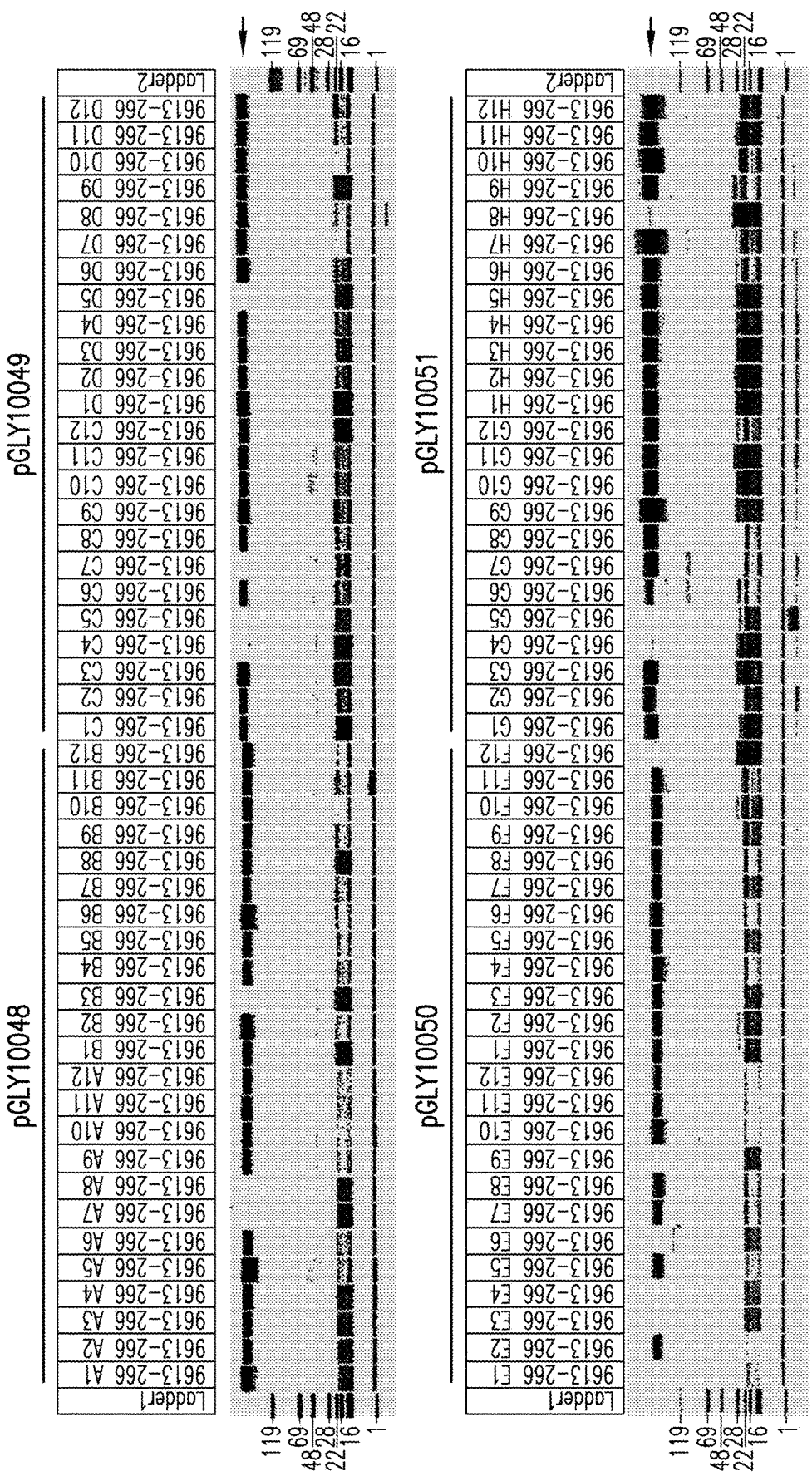

Each of these plasmids was transformed into strain YGLY30329, a glycoengineered strain of P. pastoris that has been genetically engineered to produce N-glycans of the human complex type with terminal galactose acid residues (FIG. 1, GS5.0; see also, e.g., Bobrowicz, 2004). Transformations were performed as previously described (Cregg et al, 2000) and clones were selected on YSD (1% yeast extract, 2% soytone, 2% dextrose) agar plates containing 100 µg/ml Zeocin (Life Technologies, Carlsbad, Calif.). Clones were then cultivated in 96 deep well plates (DWP), in BMGY liquid medium, and induced in BMMY containing methanol as a sole carbon source, as previously described (Barnard et al, 2010). Cultures were centrifuged at 2500×g for 10 minutes in a Beckman swinging bucket centrifuge and supernatants were subjected to protein A purification (Jiang et al, 2011). The protein A-purified samples were subjected to capillary electrophoresis (CE) using a Caliper GXII (Perkin Elmer, Waltham, Mass.) using the standard HT Protein Express 200 method as detailed previously (Gomathinayagam, 2012). Upon CE analysis, seven of the eight constructs yielded bands consistent with heavy and light chain under reducing conditions and a band consistent with a uniform, well assembled antibody under non-reducing conditions when visualized using the Caliper LabChip GX software version 4.1 (FIG. 4). The clones transformed with plasmid pGLY10047 (Q175N) did not produce any antibody presumably because the additional N-glycosylation site disrupted antibody folding and prevented proper assembly. Thus, even though the engineered sites were carefully chosen to be exposed and not affect antibody folding, there is an empirical aspect to the N-glycan site engineering that was not predicted.

Example 2: Microreactor Cultivation of N-Glycan Site Engineered Anti-Her2 Antibody-Producing Clones Representative clones from the seven constructs that yielded fully folded antibody were cultivated in an Applikon (Foster City, Calif.) micro24 5 ml mini-fermenter apparatus. Seed cultures were prepared by inoculating strains from YSD plates to a Whatman 24-well Uniplate (10 ml, natural polypropylene) containing 3.5 ml of 4% BMGY medium (Invitrogen, Carlsbad, Calif.) buffered to pH 6.0 with potassium phosphate buffer. The seed cultures were grown 65-72 hours in a temperature controlled shaker at 24° C. and 650 rpm agitation. 1.0 ml of the 24 well plate grown seed culture and 4.0 ml of 4% BMGY medium was then used to inoculate each well of a Micro24 plate (Type:REG2). 30 ml of Antifoam 204 (1:25 dilution, Sigma Aldrich) was added to each well. The Micro24 was operated in Microaerobicl mode and the fermentations were controlled at 200% dissolved oxygen, pH at 6.5, temperature at 24° C. and agitation at 800 rpm. The induction phase was initiated upon observance of a dissolved oxygen (DO) spike after the growth phase by adding bolus shots of methanol feed solution (100% [w/w] methanol, 5 mg/l biotin and 12.5 ml/l PTM2 salts), 50 µl in the morning and 125 µl in the afternoon. After approximately 72 hours of methanol induction, the cell-free culture supernatant was harvested by centrifugation at 2500×g in a Beckman swinging bucket centrifuge and subjected to protein A purification by standard methods (Jiang, 2011).

Figure 5A:
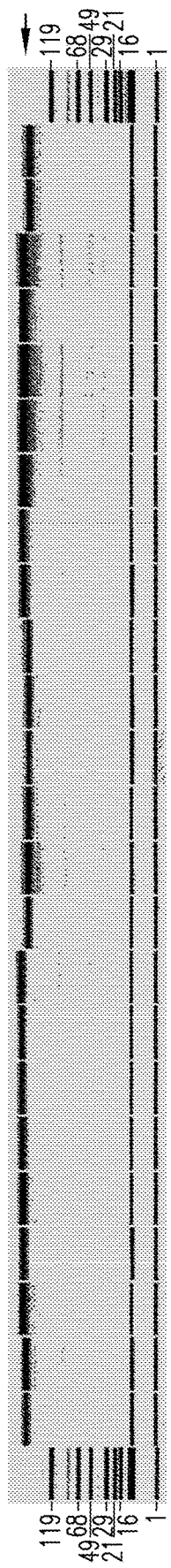
FIG. 5 (A-D): Capillary electrophoresis analysis of N-glycan modified antibodies cultivated in micro24. Clones expressing indicated plasmids were cultivated in micro24 5 ml fermenter vessels. Following protein A purification, purified protein was analyzed by Caliper GXII under denatured non-reducing conditions and reducing conditions. Arrows indicate the presence of an antibody tetramer band in the non-reduced samples and the antibody H chain monomer in the reduced samples. C, control samples, are samples from cultivation of strain YGLY13979, expressing the wild type trastuzumab antibody sequence. Sizes are indicated by the markers at the far left and right.
Figure 5B:
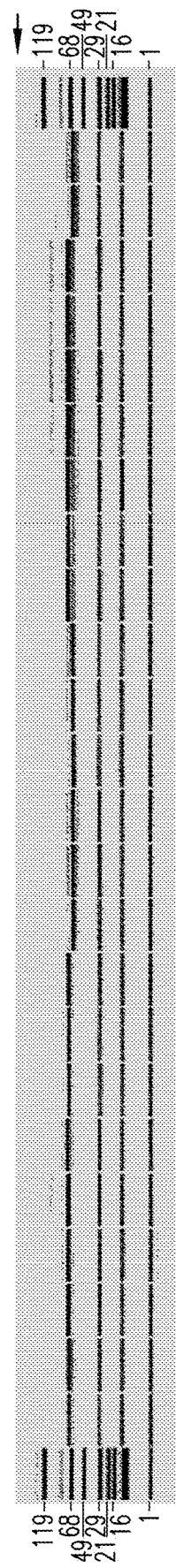
Figure 6A:
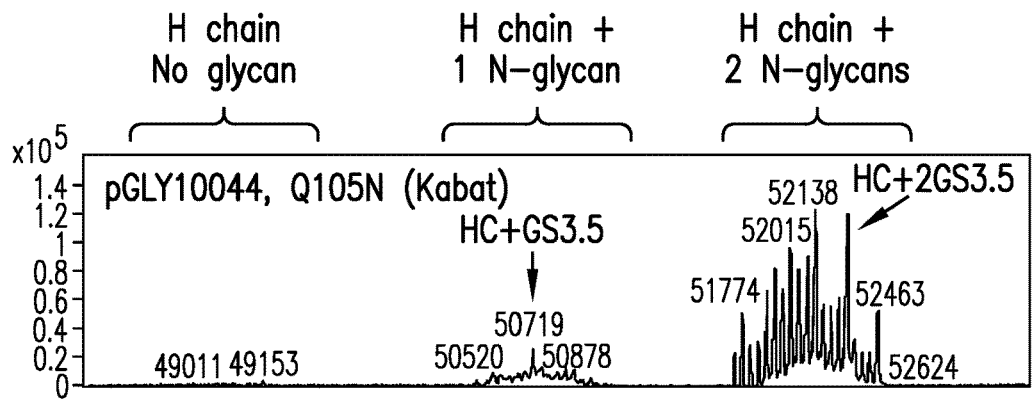
FIG. 6 (A-G): Q-ToF Mass spectrometry analysis of N-glycan modified antibodies. Deconvoluted mass spectra of reduced antibodies isolated from the strains indicated after cultivation in micro24 5 ml fermenters. The expected mass range for H chain with 0, 1, and 2 N-glycans is indicated. Where actual masses agree closely with a predicted size for a modified glycosylated antibody, the structure is indicated for the peak representing expected modified protein. GS, glycan structure (see FIG. 2).
Figure 6B:
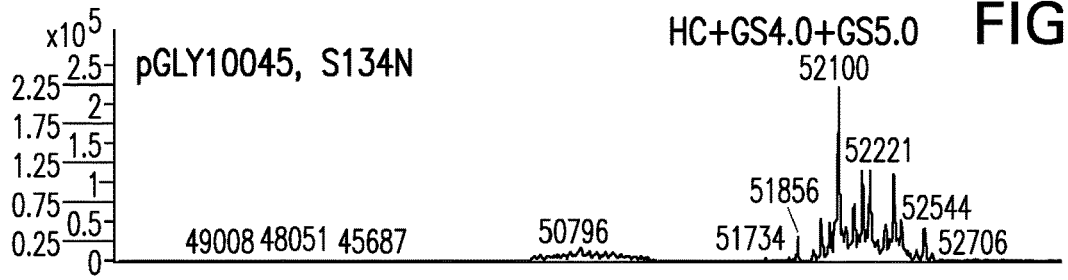
Figure 6C:
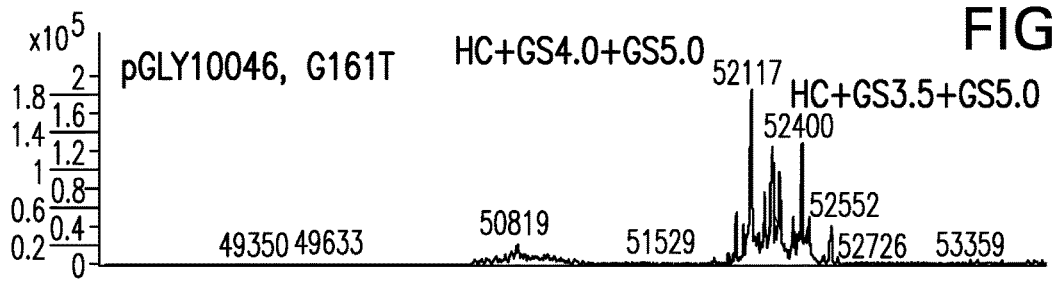
Figure 6D:
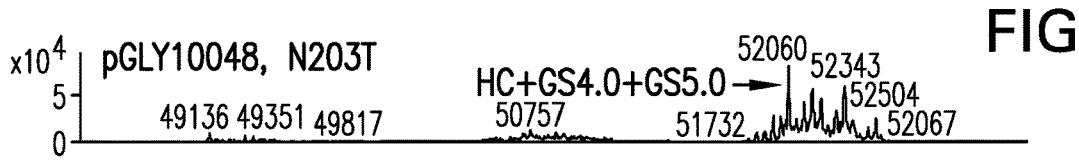
Figure 6E:
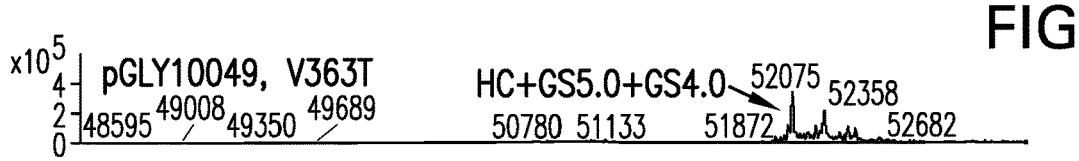
Figure 6F:
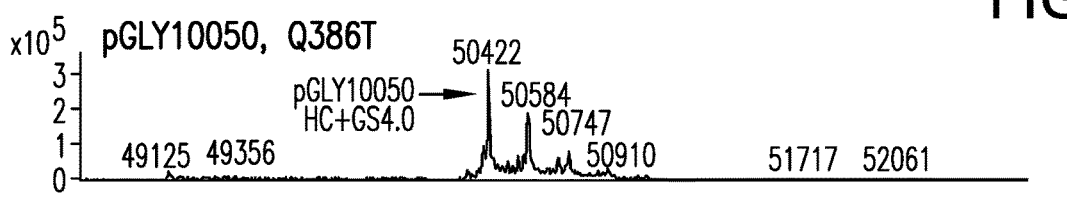
Figure 6G:
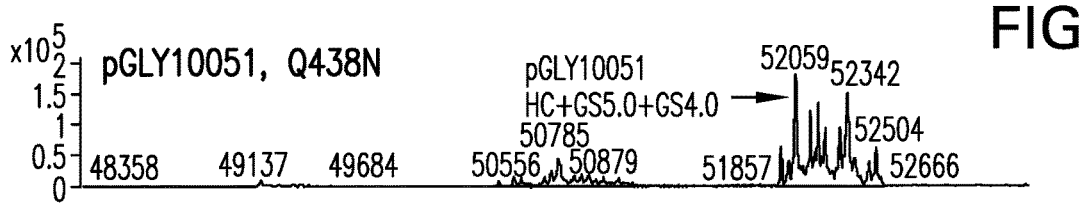

Antibody was quantified by reverse phase HPLC (Barnard et al, 2010) and also analyzed by capillary electrophoresis as described above, in this case both under non-reduced and reduced conditions. In all cases upon analysis using the Caliper LabChip GX software version 4.1, the selected clones produced protein consistent with well-assembled antibody, and consisting of a single heavy and light chain band in the reducing condition (FIG. 5).

The protein was further subjected to Quadrapole Time-of-Flight Liquid chromatography/Mass spectrometry (Q-ToF mass spectrometry or Q-ToF LCMS or Q-ToF MS) analysis under reduced conditions as described previously (Lynaugh et al, 2013). Briefly, 5 µl (1 mg/ml) was injected in an Agilent Q-TOF 6520 mass spectrometer. The dual ESI ion source was set as follows: gas temp at 350° C.; drying gas at 13 L/min; nebulizer at 45 psig; fragmentor at 150 V; skimmer at 65 V; Oct1 RF VPP at 750 V; Vcap at 3500 V. Data were analyzed using MassHunter software. Of the seven constructs that were tested, six resulted in proteins where the second engineered N-glycan site was occupied with a glycan in addition to the canonical N-297 site (FIG. 6). The only exception is in panel 5F where only a single N-glycan is added, the Fc N-297 glycan. Therefore it was concluded that the engineered N-glycan site in pGLY10050 (resulting from the Q386T mutation) is not efficiently occupied. The remaining samples resulted in profiles consistent with a majority of the protein being occupied with two N-glycans per H chain (4 N-glycans per mAb), one at N-297 and another at each of the respective engineered sites.

Therefore, based on this evidence, it is not possible to simply select a site and introduce an Asn-turn sequence through mutagenesis that will lead to a well-folded protein and be efficiently N-glycan occupied.

Example 3: Bioreactor Expression and Purification of Non-Native N-Glycosylation Site Engineered Anti-HER2 Antibody Representative clones from the six constructs that yielded fully folded antibody with a well-occupied non-native N-glycosylation site (See Table 1) were cultured in 1 L Fedbatch Pro fermenters (DASGIP Biotools, Shrewsbury, Mass.) using a glycerol fedbatch and methanol induction similarly to what has been described previously (Hopkins, 2011), with the notable difference of using a dissolved oxygen (DO) limited fed-batch induction paradigm. Briefly, inocula derived from yeast patches (isolated from a single colony) on agar plates were cultivated in 0.5 L baffled seed flasks in 0.1 L of 4% BSGY (without maltitol, table 2). Seed flasks were grown at 180 rpm and 24° C. (Innova 44, New Brunswick Scientific) for 48 hours. Bioreactor vessels were charged with 0.6 L of 0.2 µm filtered 4% BSGY media (plus 4 drops/L Sigma 204 antifoam, Table 2) and autoclaved at 121° C. for 45 minutes.

TABLE 2

| Media/Reagent | Composition |
|---|---|
| 4% BSGY medium: | 40 g/L glycerol, 20 g/L soytone, 10 g/L yeast extract, 11.9 g/L KH2PO4, 2.3 g/L K2HPO4, 50 g/L maltitol, 13.4 g/L YNB with ammonium sulfate without amino acids, 8 mg/L Biotin. |
| PTM2 salts: | 0.6 g/L CuSO4—5H2O, 80 mg/L NaI, 1.8 g/L MnSO—4H2O, 20 mg/L H3BO4, 6.5 g/L FeSO4—7H2O, 2.0 g/L ZnCl2, 0.5 g/L CoCl2—6H2O, 0.2 g/L Na2MoO4—2H2O, 0.2 g/L biotin, 5 mL/L H2SO4 (85%) |

After sterilization and cooling, the aeration, agitation, and temperatures were set to 0.7 vvm, 600 rpm, and 24° C. respectively. The pH was adjusted to and controlled at 6.5 using 15% ammonium hydroxide. Inoculation of a prepared bioreactor occurred aseptically with 60 mL from a seed flask. Agitation was ramped to maintain 20% DO saturation. After the initial glycerol charge was consumed, denoted by a sharp increase in the DO, a 50% w/w glycerol solution containing 5 mg/L biotin and 32.3 mg/L PMTi4 was triggered to feed at 7.7 g/L-h for 8 hours. During the glycerol fed-batch phase 0.42 mL of PTM2 salts (Table 2) was injected manually. After completion of the glycerol fed-batch phase, the agitation rate was locked at 600 rpm and a bolus addition of 6.0 g of methanol containing 5 mg/L biotin and 12.5 mL/L PTM2 salts was added. During methanol induction phase the DO remains near 0% until the methanol bolus is entirely consumed. Each time the DO increases to >30% another 6.0 g bolus of the methanol feed solution is added to prolong the induction time. After methanol adaptation, it takes on average 9-10 hours to consume the 1% methanol boluses. Injections of 0.25 mL of 2.1 mg/mL PMTi4 (in methanol) were added each 24 hours of induction time. After 80-90 hours of methanol induction, the cell-free culture supernatant was harvested by centrifugation (Sorvall Evolution RC, Thermo Scientific) at 8500 rpm for 40 minutes and then subjected to small scale protein A purification by standard methods (Jiang, 2011).

Antibody was quantified by reverse phase HPLC and calculated on a per liter basis (Barnard et al, 2010). Fermentation titers indicated that the N-glycan sites that were occupied and tolerated by the mAb structure based on small scale expression resulted in no significant alteration in mAb titer at 1 L fermentation scale (Table 3).

TABLE 3

| Ferm. # | 1 L Ferm. Sample ID | Strain name | Sequence change (EU) | mAb liter (mg/L) HPLC | mAb titer (mg/L) Bradford |
|---|---|---|---|---|---|
| 1 | D133201 | YGLY35490 | N203T | 332 | ND |
| 2 | D133202* | YGLY35491 | N203T | 499 | 440 |
| 3 | D133203* | YGLY35492 | V363T | 569 | 446 |
| 4 | D133204 | YGLY35493 | V363T | 279 | ND |
| 5 | D133205 | YGLY35494 | V363T | 275 | ND |
| 6 | D133206 | YGLY35495 | Q438N | 488 | ND |
| 7 | D133207 | YGLY35496 | Q438N | 269 | ND |
| 8 | D133208* | YGLY35497 | Q438N | 705 | 569 |
| 9 | D133401 | YGLY35516 | Q109N# | 443 | ND |
| 10 | D133402 | YGLY35517 | Q109N# | 512 | ND |
| 11 | D133403 | YGLY35518 | S134N | 276 | ND |
| 12 | D133404* | YGLY35519 | S134N | 299 | 253 |
| 13 | D133405 | YGLY35520 | G161T | 646 | ND |
| 14 | D133406* | YGLY35521 | G161T | 384 | 305 |
| 15 | D133407 | YGLY35522 | N203T | 445 | ND |
| 16 | D133408 | YGLY35523 | N203T | 393 | ND |
| C | Anti-HER2 | multiple | None | 509 +/− 54 | ND |

Figure 7:
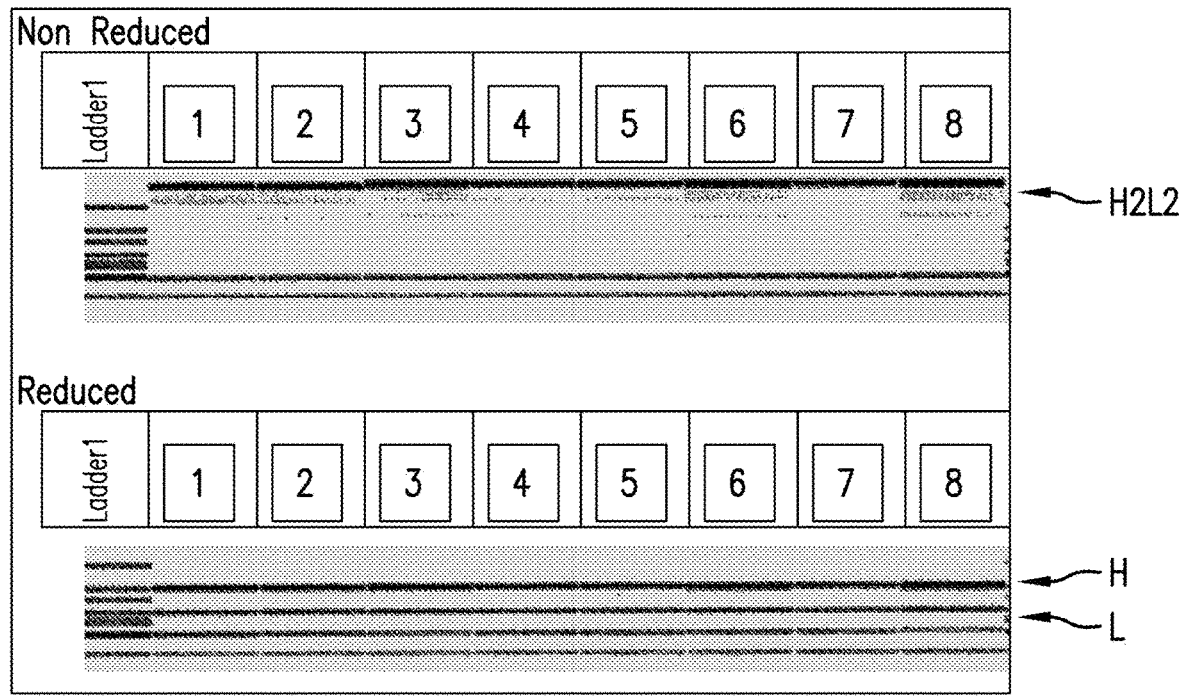
FIG. 7: Capillary electrophoretic analysis of N-glycan modified antibodies cultivated in Dasgip 1 L fermenters. Clones expressing the plasmids indicated in Table 3 were cultivated in Dasgip (Shrewsbury, Mass.) 1 L fermenter vessels. Following protein A purification, purified protein was analyzed by Caliper GXII under denatured non-reducing and reducing conditions. Arrows indicate the presence of an antibody tetramer band in the non-reduced samples and the antibody H and L chain monomers in the reduced samples. Sizes are indicated by the markers at the far left.
Figure 7:
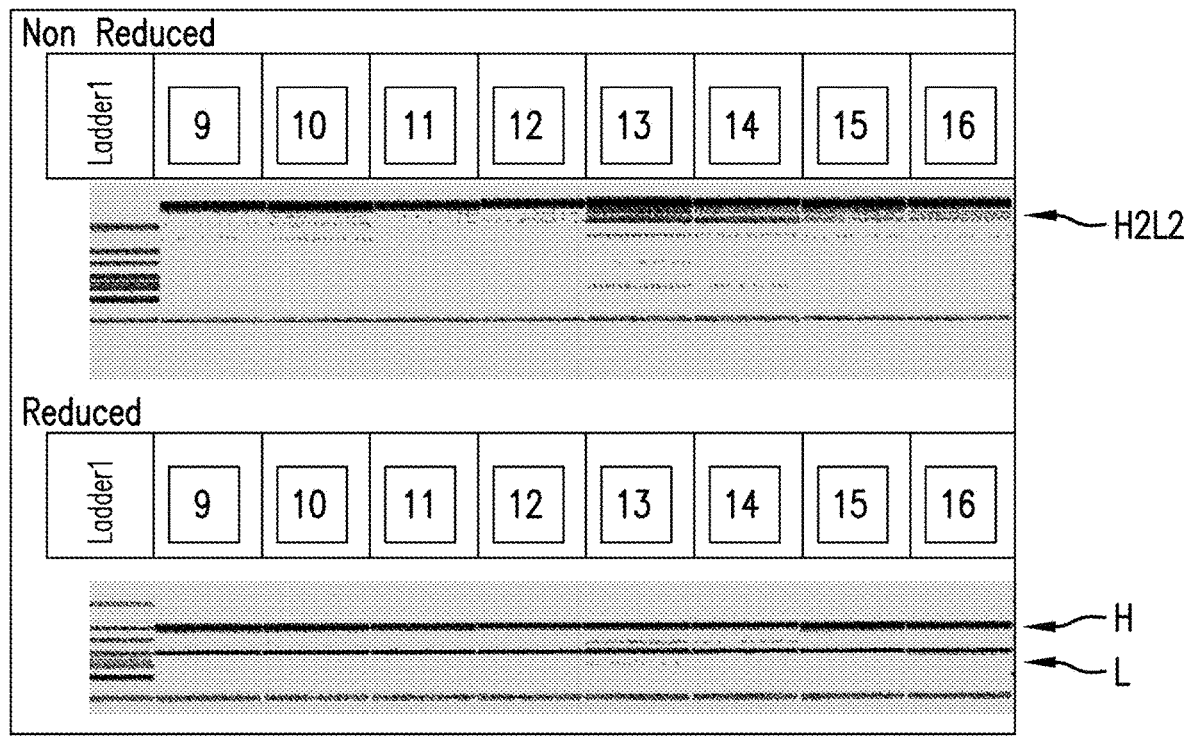
Figure 8A:
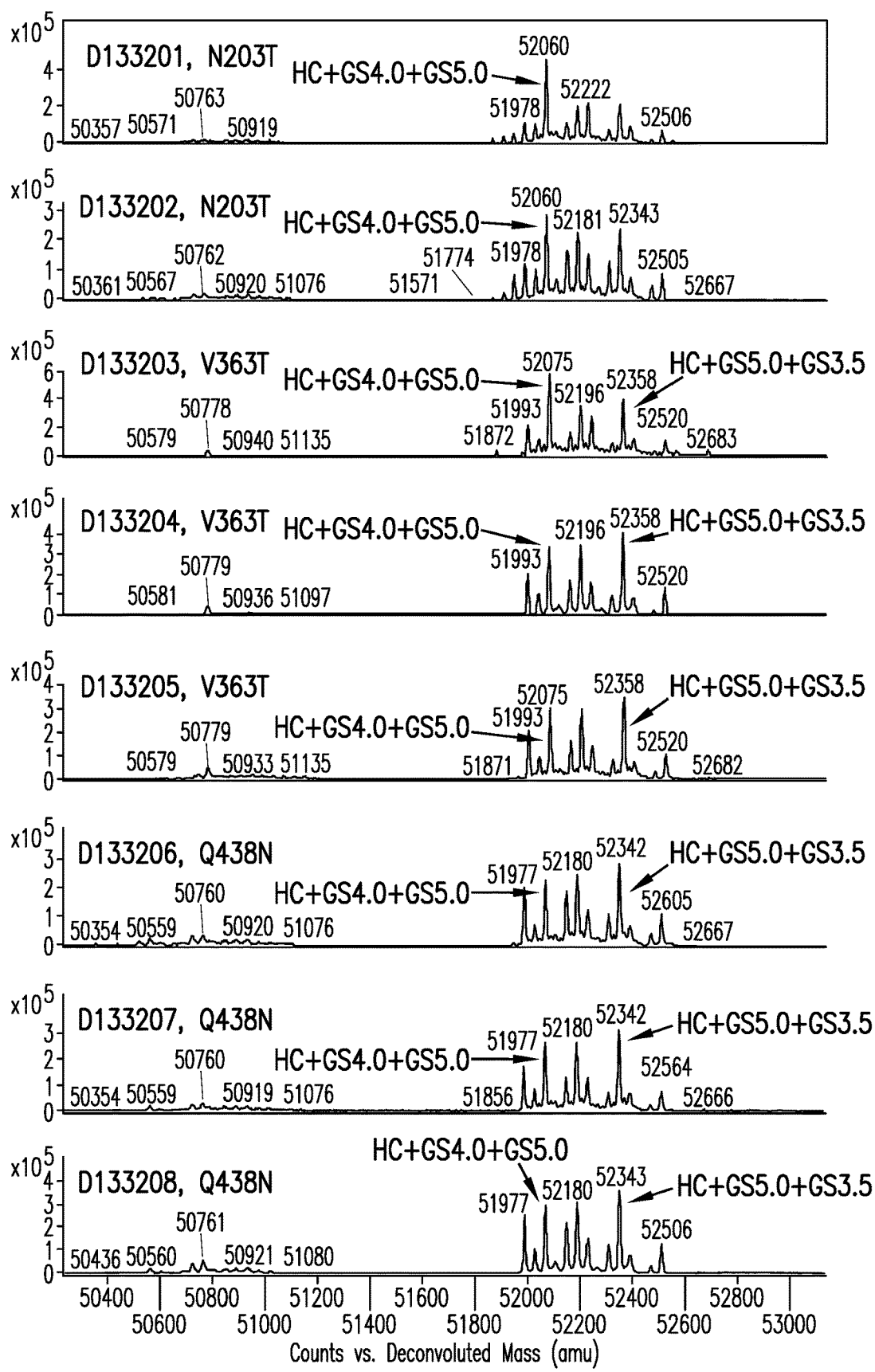
FIG. 8 (A-C): Q-ToF Mass spectrometry analysis of N-glycan engineered antibodies cultivated in Dasgip 1 L fermenters. Deconvoluted mass spectra of reduced antibodies isolated and purified by small scale high throughput protein A from strains cultivated in Dasgip 1 L fermenters. The strain cultivated in each fermenter and associated plasmid/antibody information is indicated in Table 3. The expected mass range for H chain with 0, 1, and 2 N-glycans is indicated. Where actual masses agree closely with a predicted size for a modified glycosylated antibody, the structure is indicated for the peak representing expected modified protein. A, samples D133201-08; B, samples D133401-04; C, samples D133405-08. GS, glycan structure (see FIG. 2).
Figure 8B:
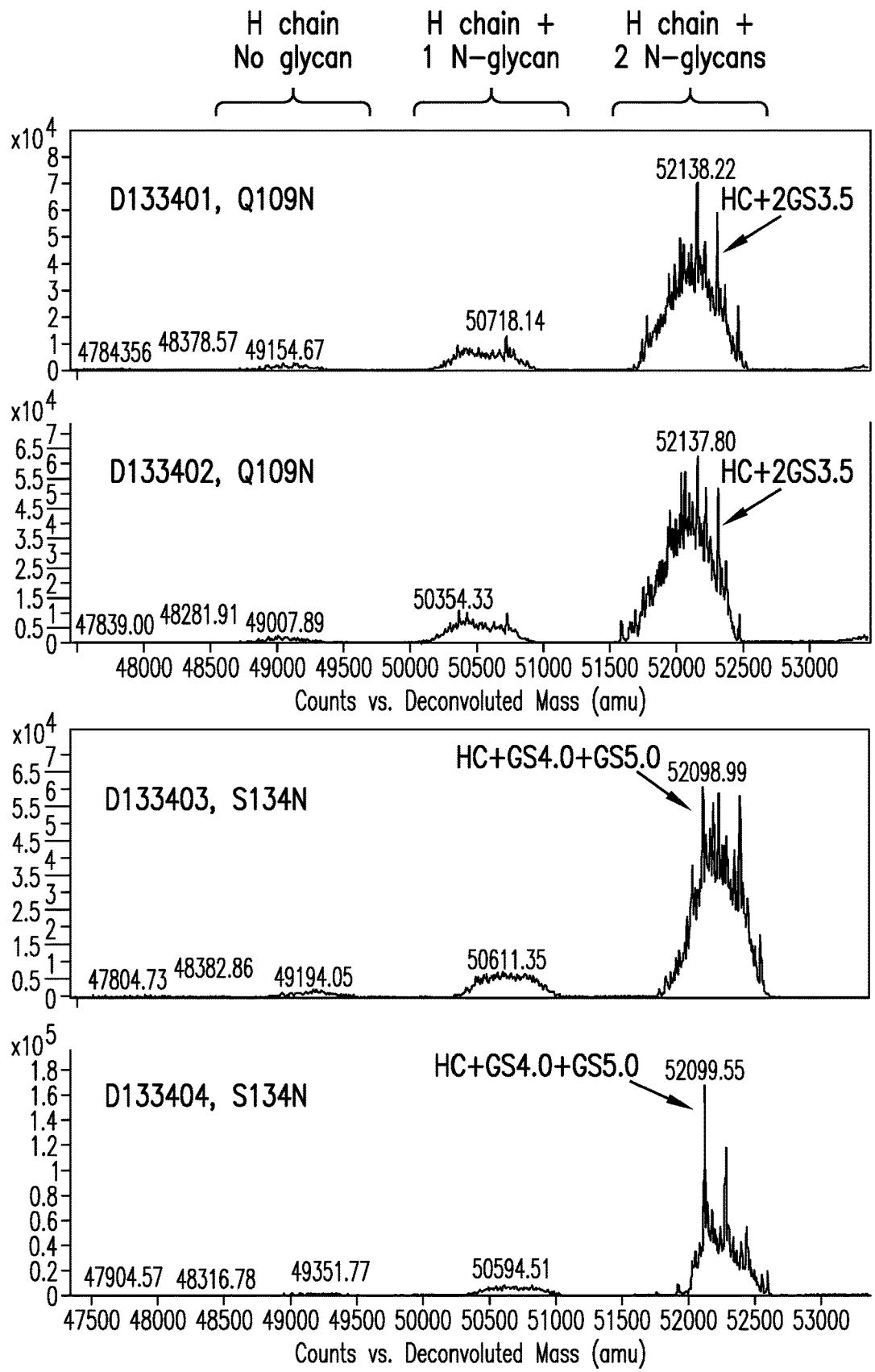
Figure 8C:
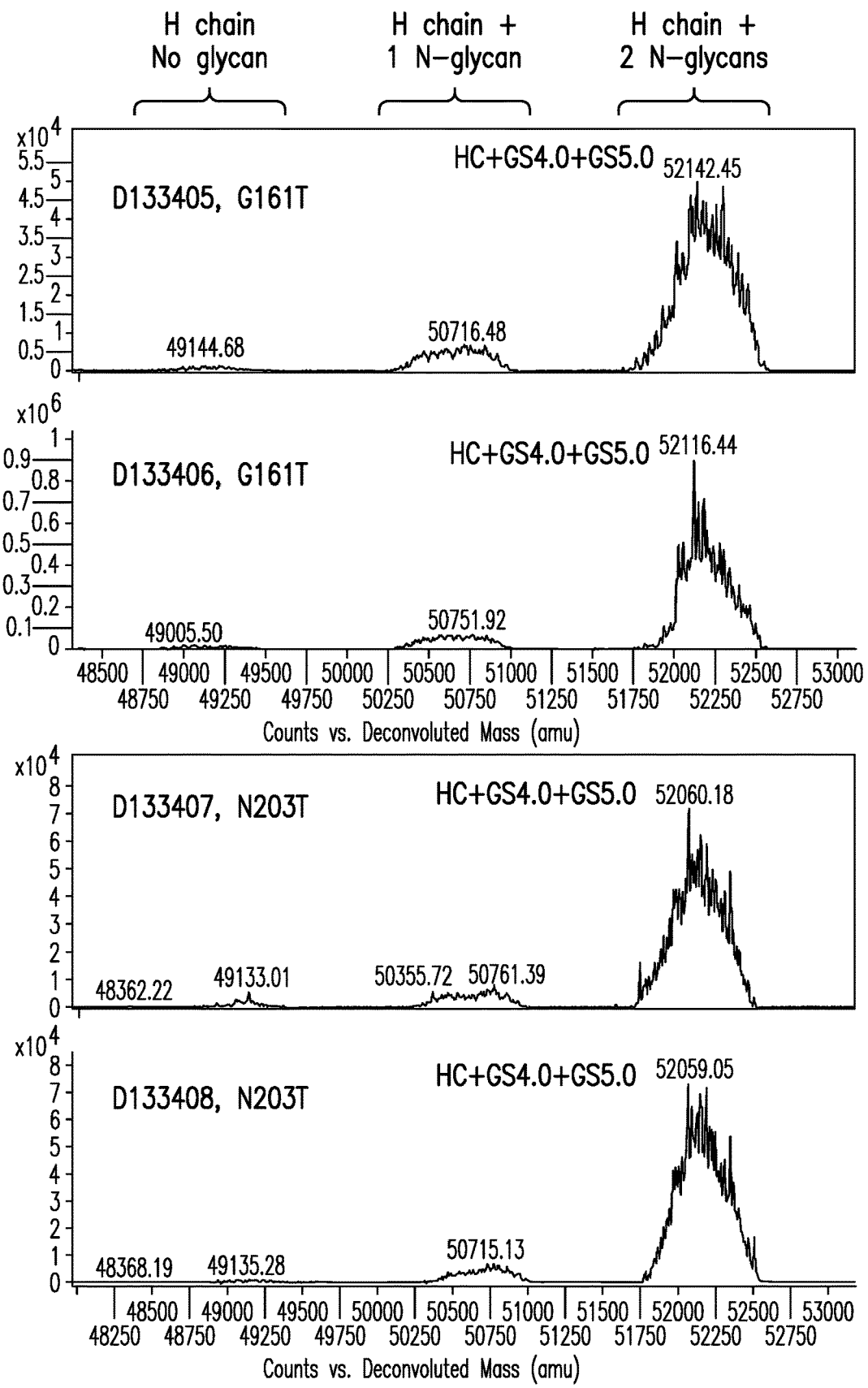
Figure 9A:
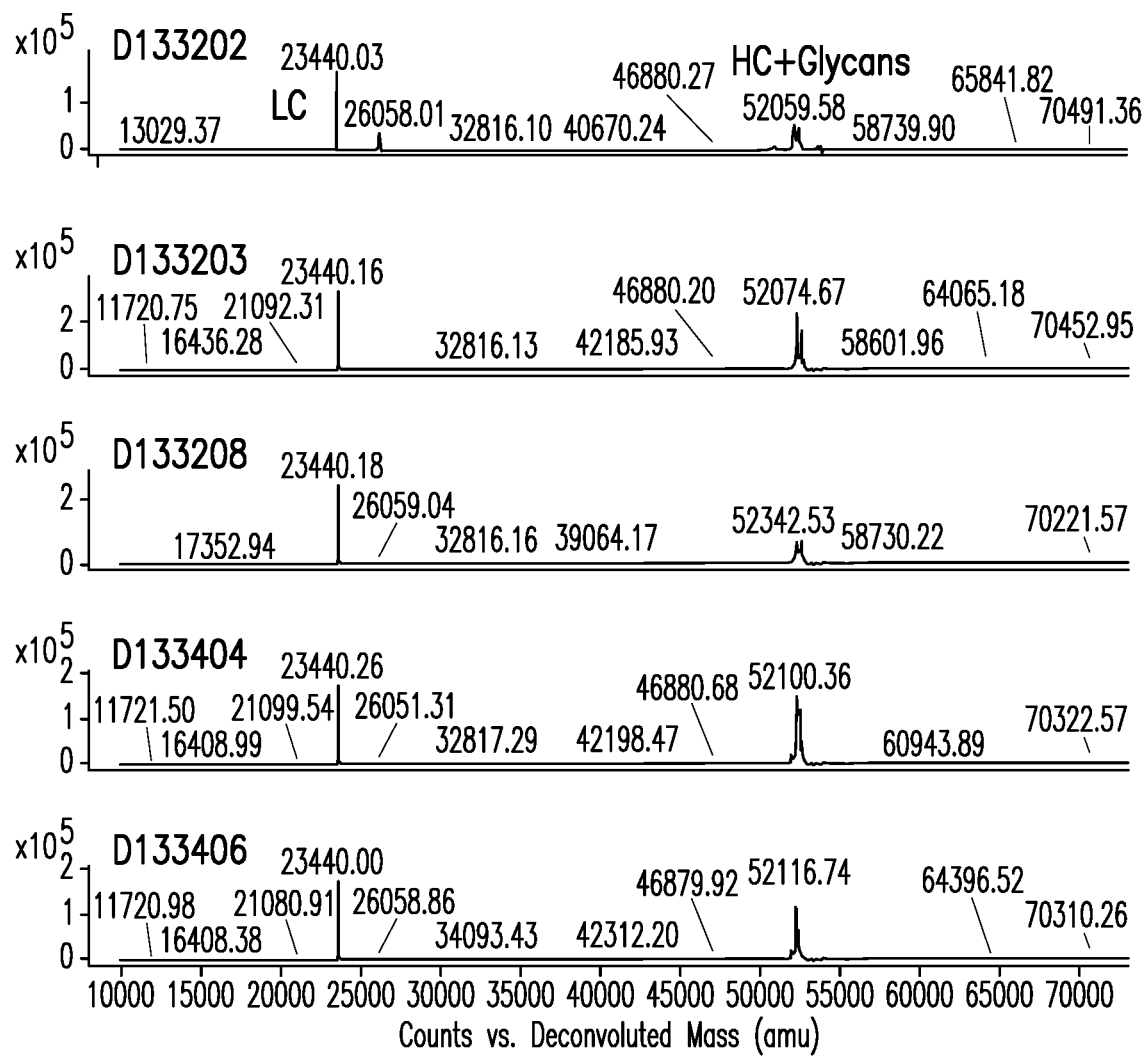
FIG. 9 (A-B): Mass spectrometry analysis of highly purified N-glycan engineered antibodies cultivated in Dasgip 1 L fermenters. Deconvoluted mass spectra are shown for reduced antibodies isolated and purified by larger scale protein A purification (Zha, 2013) from 1 L fermentation samples D133202, D133203, D133208, D133404, and D133406 (see Table 3). A) Mass spectra are gated to include expected L and H chain masses. The expected mass ranges for L chain (LC) and glycosylated H chain (HC+glycans) are indicated. B) Mass spectra gated to zoom in on H chain expected mass. Where actual masses agree closely with a predicted size for a modified glycosylated antibody, the structure is indicated for the peak representing expected modified protein. GS, glycan structure (see FIG. 2).
Figure 9B:
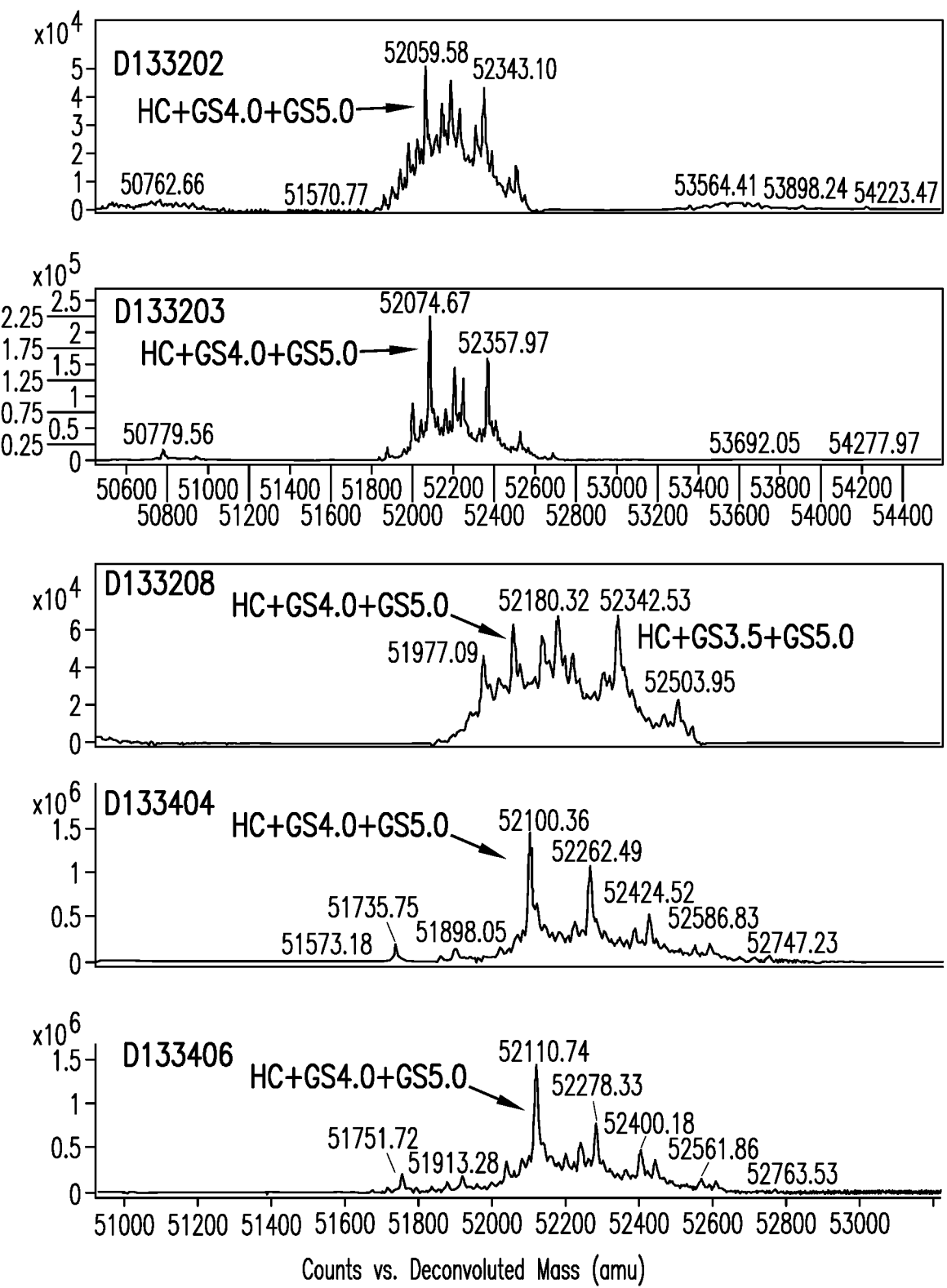
Figure 10:
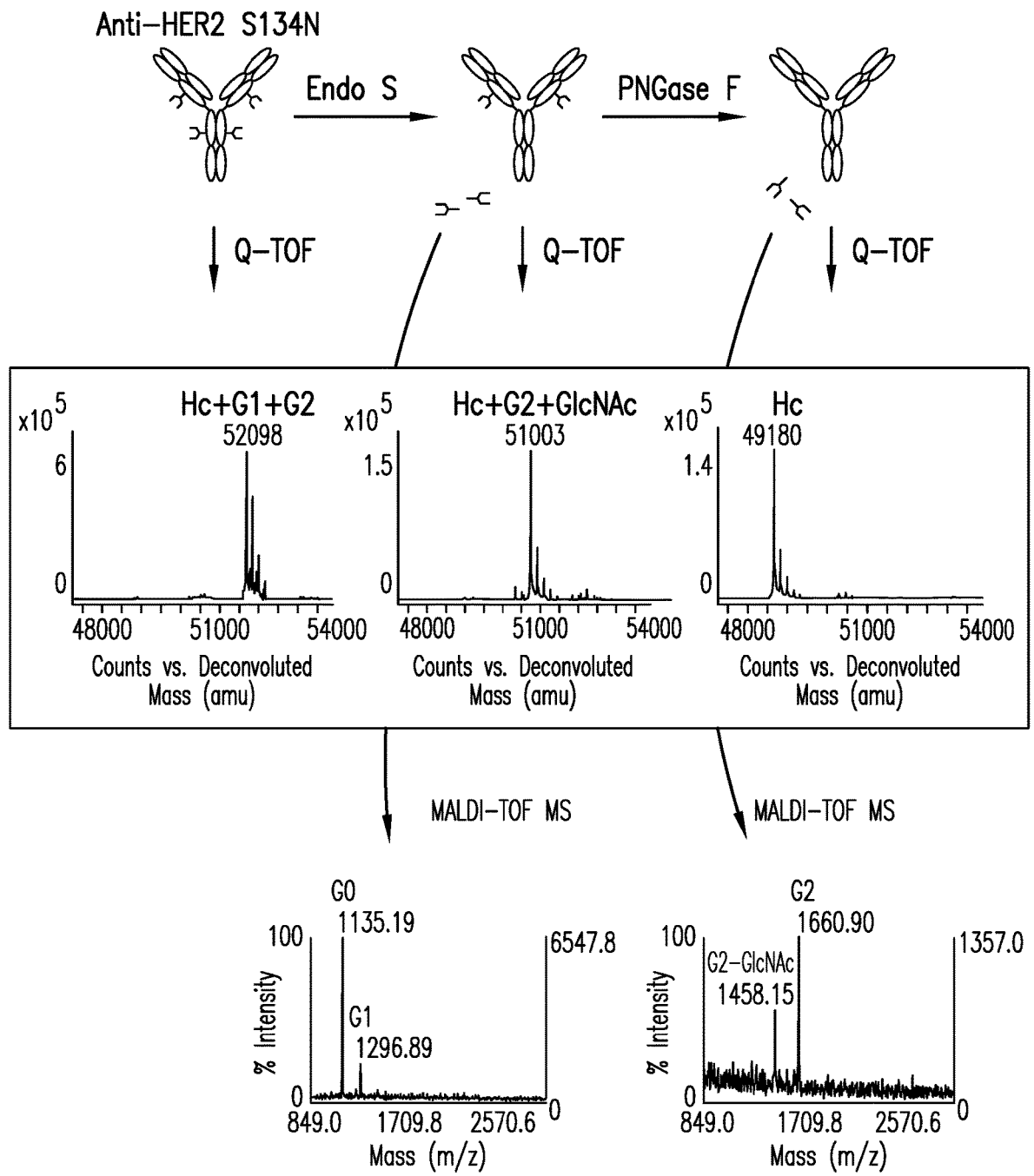
FIG. 10: Glycosidase digestion and analysis of N-glycan modified antibodies. Purified antibody from batch D133404 (trastuzumab, S134N) was analyzed directly by Q-ToF MS, as previously shown, then subjected to EndoS glycosidase digestion to remove the N-297 glycan. The released N-glycans were analyzed by MALDI-ToF MS and the remaining intact protein analyzed by Q-ToF MS and deconvoluted. Finally, the Endo S digested protein was further subjected to PNGase F glycosidase digestion and N-glycans and protein were again separately analyzed by MALDI-TOF MS and Q-ToF, respectively.
Figure 11A:
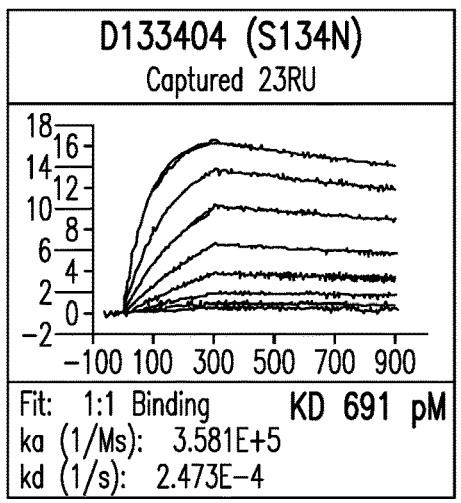
FIG. 11 (A-F): Analysis of binding of glycan modified anti-Her2 antibodies to Her2 antigen. Protein A purified N-glycan modified antibodies analyzed for binding to Her2 protein using surface plasmon resonance. Anti-human Fc antibody was immobilized and used to capture purified glycoengineered *Pichia*-produced mutant trastuzumab variants (A) S134N, (B) G161T, (C) N203T, and (D) V363T as well as (E) commercial Herceptin (trastuzumab) and (F) S134N conjugated with DM1 cytotoxin.
Figure 11B:
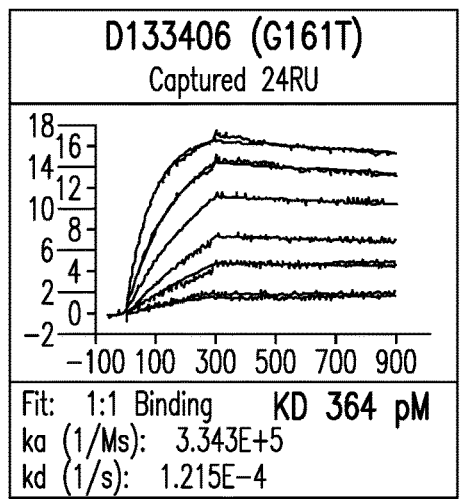
Figure 11C:
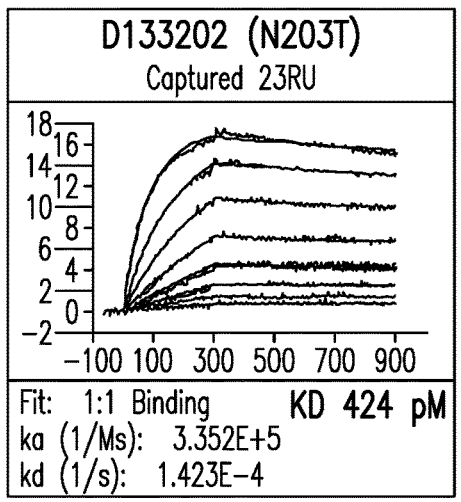
Figure 11D:
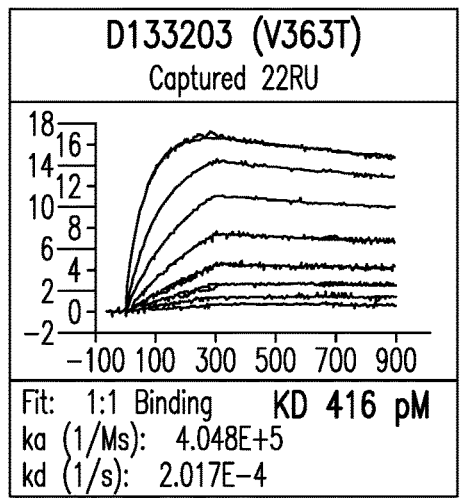
Figure 11E:
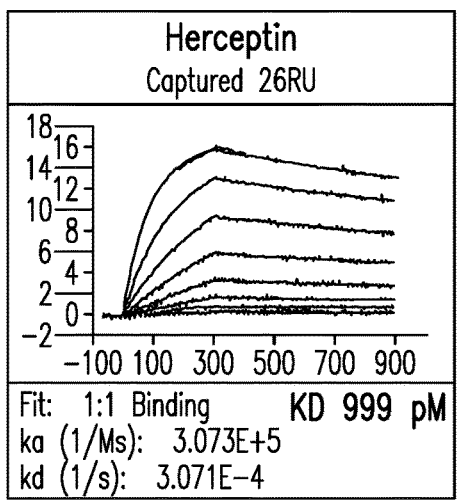
Figure 11F:
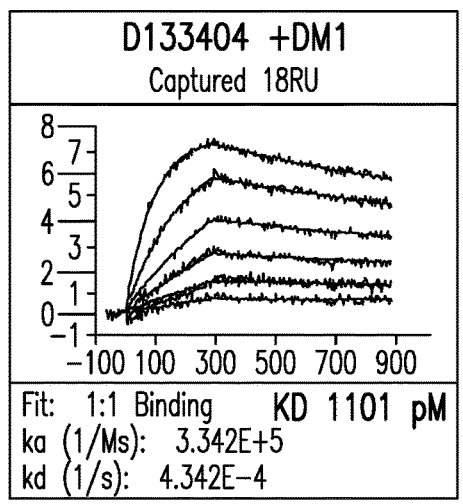

The purified antibody was further subjected to capillary electrophoresis and Q-ToF mass spectrometry analysis as outlined above. As with smaller scale cultivation, the selected clones produced protein consistent with well-assembled antibody, and consisting of a single heavy and light chain band in the reducing condition (FIG. 7). Based on reduced Q-Tof, the clones selected also yielded a majority of antibody with N-glycans fully occupied at two sites, the N-297 canonical site and the respective engineered non-native N-glycosylation site (FIG. 8A-8C). Some of the additional sites resulted in better N-glycan uniformity than others. For instance, the Q109N site resulted in poor conversion to complex forms with the resulting N-glycans primarily of the hybrid type whereas S134N resulted in predominantly complex terminally galactosylated N-glycans, with the assumption of a mixture of GS4.0, GS4.5 and GS5.0 at the Fc N-297 site based on previous mAb N-glycan analysis (FIG. 8B). Larger aliquots (500 ml) of fermentation supernatant were purified by protein A chromatography for one each of the five best mutations (Samples D133202, D133203, D133208, D133404, and D133406, Table 3). The quantification of purified protein as measured by Bradford assay agreed well with the HPLC measurements from supernatant (Table 3). Purified protein was analyzed by Q-ToF and revealed masses that correspond to the expected L chain mass and several clustered masses that corresponded to the expected H chain mass (FIG. 9A). Upon zooming to the H chain mass region on the trace, the predominant H chain mass in each case corresponded to the predicted anti-Her2 H chain with 2 N-glycans one comprised of a GS4.0 glycoform and the other of a GS5.0 glycform (FIG. 9B). Previous analysis of antibodies in the same host strain yielded N-297 canonical Fc N-glycans consisting of primarily GS4.0 with a minority of GS4.5 and GS5.0 glycoforms (Zhang et al, 2011). It was therefore concluded that the additional N-linked site was occupied with predominantly GS5.0 N-glycans. In support of this, sample D133404 was digested with Endoglycosidase S (EndoS, Genovis, Cambridge, Mass.) and subsequently digested with Peptide-N-glycosidase F (PNGase, New England Biolabs, Ipswich, Mass.). The EndoS enzyme will remove the N-297 canonical glycan, cleaving between the core GlcNAc residues, and leave any other mAb glycans intact. N-glycan analysis by MALDI-TOF MS of the EndoS released N-glycans revealed the expected predominant GS4.0 mass (less one GlcNAc which is the core GlcNAc not removed); while Q-ToF analysis of the reduced H chain showed a mass consistent with the H chain containing G2 and GlcNAc (FIG. 10). Moreover, PNGase digestion of the EndoS digested sample and MALDI-TOF MS of the released N-glycans revealed G2 and G2-GlcNAc (the EndoS enzyme, still active in the mixture, can remove a GlcNAc from the released G2 glycan; FIG. 10). Finally, Q-ToF analysis of the EndoS and PNGase digested mAb yielded an expected mass consistent with the deglycosylated H chain (FIG. 10). Taken together these data demonstrate that the additional N-glycosylation site (at N134 in sample D133404) is occupied with a predominant GS5.0 N-glycan while the canonical N-297 glycan is occupied with the expected mixture of predominantly GS4.0 plus a minority of GS4.5 and GS5.0.

Example 4: Antigen Binding of Anti-Her2 Modified Abs with Non-Native N-Glycosylation Sites To determine whether incorporation of non-canonical N-glycans into the anti-Her2 mAb sequence impacts binding of the antibody to the Her2 protein, the affinity of purified N-glycan modified mAbs was measured by surface plasmon resonance using a Biacore T-100 instrument (GE Healthcare, Little Chalfont, UK). First, a Series S CM5 Chip (GE Healthcare) was immobilized via amine coupling kit (GE Healthcare) to >10000 RU with an anti-human Fc capture antibody kit (GE Healthcare). Purified anti-Her2 antibody protein samples from batches D133202, D133203, D133404, and D133406 along with the commercial (CHO-produced trastuzumab) anti-Her2 were were captured to 30RU on the active flowcells and no antibody was captured on the reference flowcell. Serially diluted human Her2 ectodomain (Biotang, Lexington, Mass.), ranging in concentration from 50 nM to 0.39 nM, was injected for 5 minutes over all flowcells and dissociation was monitored for 10 minutes. Binding data was double referenced by subtracting the reference flowcell signal and a 0 nM Her2 injection. All of the reagents were prepared in 1×HBS-EP+ (GE Healthcare, pH7.4) running buffer and the binding measurements were performed on a Biacore T100 at 25° C. All data was fit with 1:1 Binding Model in Biacore T100 Evaluation Software (v2.0.4). Analysis of the binding curves, maximum binding capacity, and affinity, based on a 1:1 binding fit revealed no significant differences between commercial anti-Her2, trastuzumab (FIG. 11, Panel E), and any of the N-glycan modified, glycoengineered *Pichia*-produced Abs (FIG. 11, Panels A-D)

Figure 12:
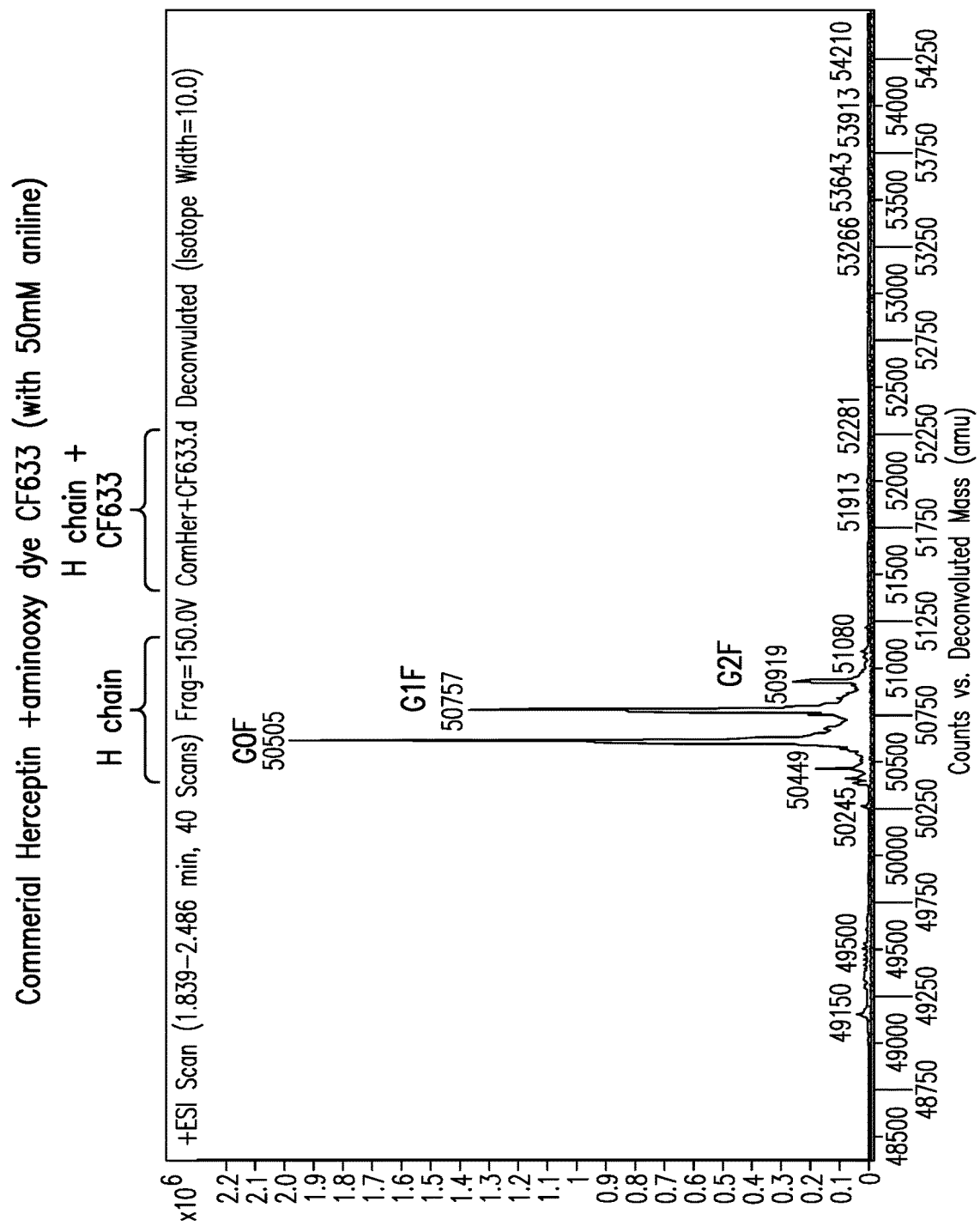
FIG. 12: Conjugation of a fluorescent dye to native N-glycans on commercial trastuzumab by galactose oxidase treatment. Commercial trastuzumab was subjected to galactose oxidase enzyme treatment for 48 h in the presence of aminooxy CF633 fluorophore and 50 mM aniline and the resulting protein was reduced and analyzed by Q-ToF MS. The deconvoluted mass spectrum is shown with the mass range expected for unconjugated (H chain) and conjugated (H chain+CF633) indicated. Peaks corresponding to the expected mass of trastuzumab glycan-containing heavy chain variants are labeled with the canonical glycan structures.
Figure 13:
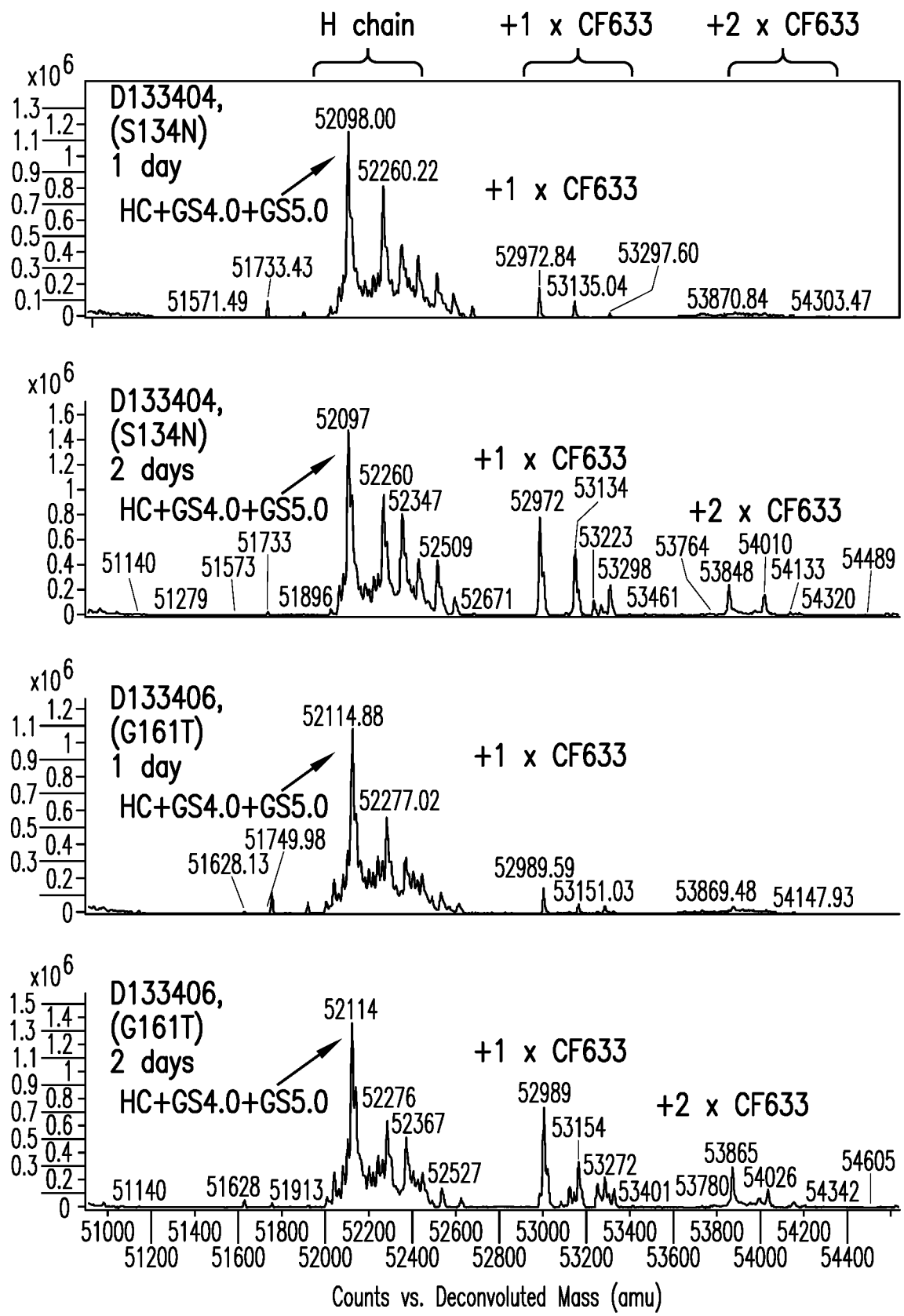
FIG. 13: Glycan-mediated conjugation of a fluorescent dye glycan-engineered antibodies using galactose oxidase. *Pichia*-produced glycan-engineered versions of trastuzumab were subjected to galactose oxidase enzyme treatment in the presence of aminooxy CF633 fluorophore and the resulting protein was reduced and analyzed by Q-ToF MS. The deconvoluted mass spectra are shown with the mass range expected for unconjugated (HC), singly conjugated (+1× CF633), and doubly conjugated (+2×CF633) antibody indicated. The predominant peak corresponding to the expected mass of the glycosylated mutated trastuzumab heavy chain is labeled (HC+GS4.0+GS5.0) with glycan structures referenced in FIG. 2.

Example 5: Conjugation of an Activated Fluorophore to Enzymatically Oxidized Terminal Galactose of N-Glycans Next, we asked whether N-glycans at non-native N-glycosylation sites on mAbs would be appropriate substrates and locales for chemical conjugation. Galactose oxidase (d-galactose:oxygen 6-oxidoreductase GO; EC 1.1.3.9) from *Fusarium graminarium*, aka *Dactylium dendroides* (Fg GO) is a glycan-modifying enzyme previously shown to oxidize terminal β-1,4-galactose residues in the context of a protein (Cooper et al, 1959). The result of this enzymatic galactose oxidation is a chemically reactive aldehyde group that is receptive to direct conjugation with an alkoxyamine substrate to form a stable oxime bond (Ramya et al, 2013). However, attempts to oxidize and efficiently conjugate to the asialylated complex Fc N-297 glycan of a standard IgG, which typically contains a small but significant amount of terminal β-1,4-linked galactose (20-40% on one arm, 1-10% on both arms), have been unsuccessful to date; a finding that was recapitulated here with commercial trastuzumab (FIG. 12). Given that the location of this canonical IgG glycan is known to be buried between and closely tethered to the Ig folds of the Fc $C_H2$ domain, it is likely that steric hindrance prevents either enzyme modification or addition of a conjugate to this N-glycan site. As shown, when mAbs with non-native N-glycosylation sites are produced in a GFI5.0 glycoengineered yeast strain (FIG. 2) the additional non-native N-glycosylation sites are composed predominantly of biantennary terminal β-1,4-linked galactose (FIG. 9). Therefore, we interrogated whether it is possible to enzymatically oxidase and chemically conjugate an activated fluorophore to an antibody via these engineered terminal galactose sugars. In a one-pot reaction method, 200 µg of the purified anti-HER2 antibodies containing extra N-glycans (Table 1) was incubated with 0.45 units of Fg GO (Sigma, St. Louis, Mo.), 800 units of catalase and an aminooxy activated CF633 dye (Biotium, Hayward, Calif.) to a final concentration of 100 µM in 50 mM sodium phosphate buffer at pH 7 and 25° C. in dark conditions for 24 and 48 hours. For the mAb variants that were most efficiently conjugated, the S134N and G161T mutant anti-HER2 proteins, significant transfer of up to two fluorophore moieties were observed per reduced H chain as determined by Q-ToF, with two per H chain being the expected maximum number of available sites given a theoretical 100% biantennary galactose structure and 100% N-glycan occupancy and no conjugation at the Fc N-297 glycan (FIG. 13).

Figure 14:
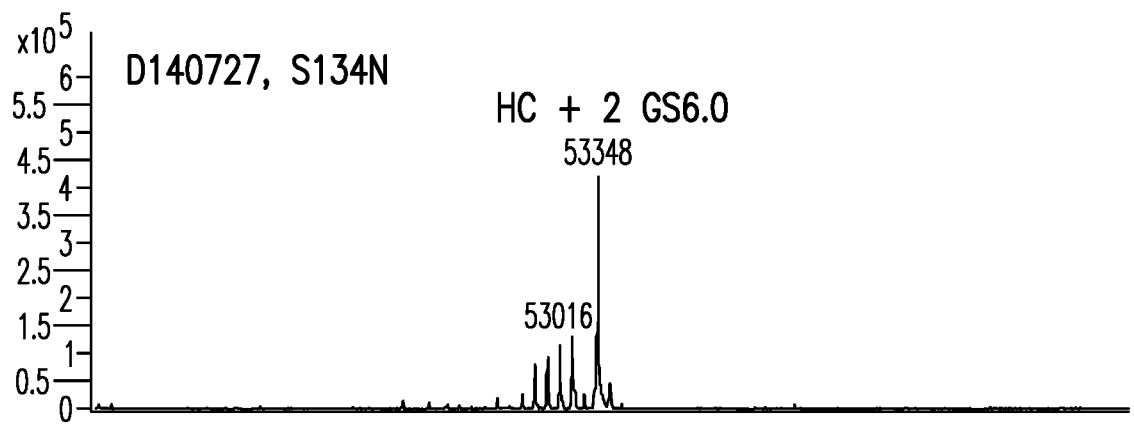
FIG. 14: Q-ToF Mass spectrometry analysis of sialylated N-glycan engineered antibodies. Deconvoluted mass spectra are shown for reduced glycan engineered trastuzumab antibodies isolated and purified by small scale high throughput protein A expressed in GS6.0 glycoengineered *Pichia* strains cultivated in Dasgip 1 L fermenters with batch numbers shown. The predominant peaks corresponding to the expected masses of the glycosylated mutated trastuzumab heavy chain is labeled (HC+2 GS6.0) with glycan structures referenced in FIG. 2.
Figure 14:
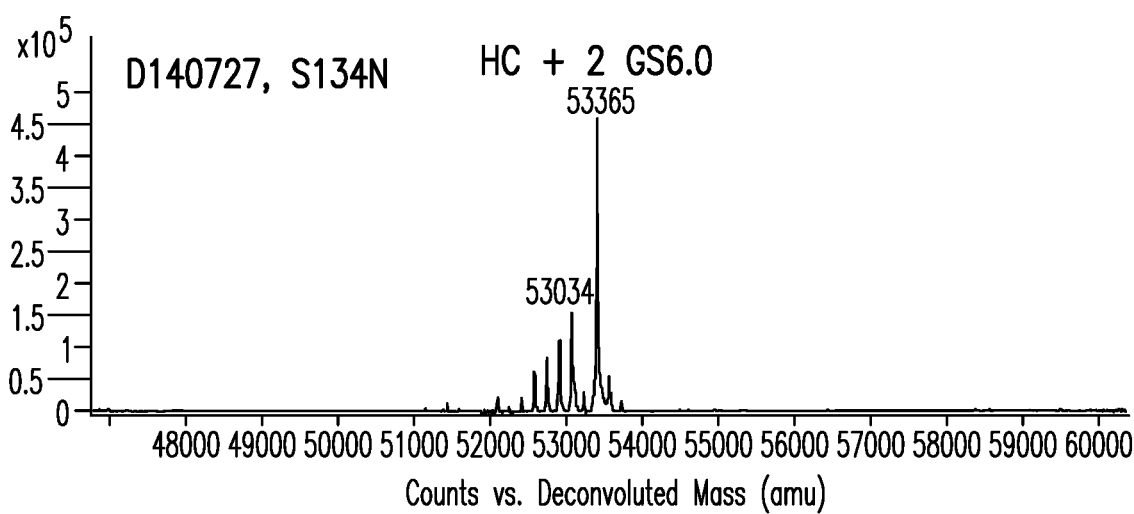

Example 6: Desialylation and Conjugation of mAbs Containing Sialylated N-Glycans For non-native N-glycosylation site containing mAbs produced in GFI6.0 glycoengineered strains (FIG. 2) the N-glycans will be predominantly sialylated and thus resistant to galactose oxidase (which requires a terminal galactose sugar). Therefore, to generate a substrate for enzymatic/chemical conjugation in such a strain, plasmids expressing modified anti-Her2 mAbs containing non-native N-glycosylation sites (pGLY14137 and pGLY14138) were transformed into GFI6.0 strain YGLY36472 and clones were selected on 100 mg/ml zeocin plates. The resulting clones were cultivated in micro24 5 mL bioreactors as described earlier (see Example 2). Selected clones were then cultivated in 1 L Dasgip bioreactors as described (Example 3). The harvested supernatants were purified by protein A chromatography also as referenced (Jiang, 2011). The resulting protein was analyzed by Q-ToF under reducing conditions, which resulted in masses consistent with the intact H chain of the modified anti-Her2 mAb with the expected sialylated N-glycan profile (FIG. 14). The purified protein was subsequently desialylated using Acetyl-neuraminyl hydrolase (neuraminidase, New England Biolabs, Ipswich, Mass.) according to the manufacturer's recommended reaction conditions. The resulting protein was analyzed by Q-ToF under reducing conditions and N-glycans were removed enzymatically by PNGase digestion (New England Biolabs, Ipswich, Mass.) and analyzed quantitatively by HPLC (Burnina, 2012). The results indicated that as expected the sialic acid residues were efficiently removed by the Neuraminidase enzyme leaving predominantly terminal galactose residues (Prime, 1996), which have been shown here and previously to be efficient substrates for the GO enzyme to support oxime ligation.

Example 7: Optimization of Combined Enzymatic/Chemical Conjugation Step

Figure 15:
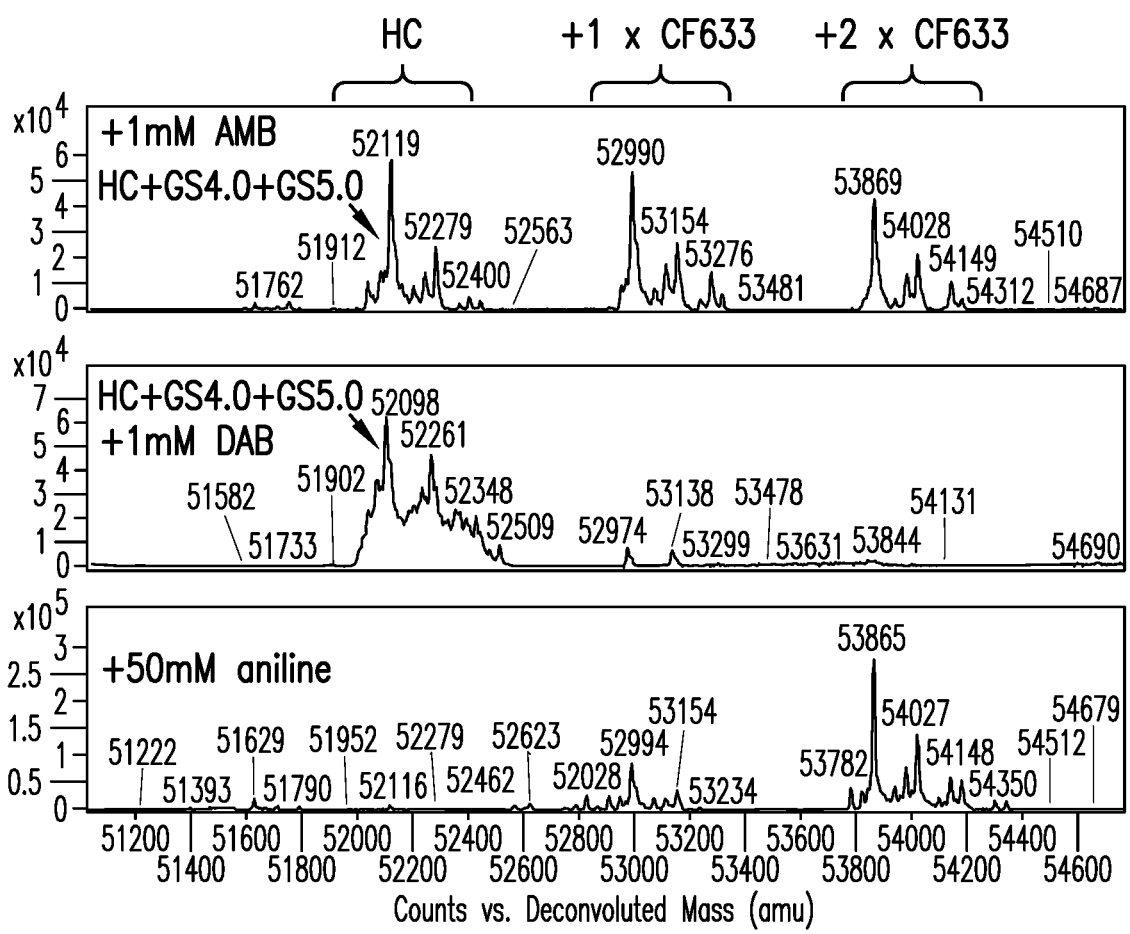
FIG. 15: Glycan-mediated conjugation of a fluorophore to glycan-engineered antibodies with galactose oxidase in the presence of reaction catalysts. *Pichia*-produced glycan-engineered versions of trastuzumab were conjugated with an aminooxy activated CF633 fluorophore using galactose oxidase in the presence of reaction catalysts 2-Amino-5-methoxybenzoic acid (AMB), 3,5-diaminobenzoic acid (DAB), and aniline. The resulting conjugated protein was reduced and analyzed by Q-ToF MS and deconvoluted mass spectra are shown with the mass range expected for unconjugated (HC), singly conjugated (+1×CF633), and doubly conjugated (+2×CF633) antibody indicated. The predominant peak corresponding to the expected mass of the glycosylated mutated trastuzumab heavy chain is labeled (HC+GS4.0+GS5.0) with glycan structures referenced in FIG. 2.

Conjugation reactions were next carried out with chemical catalysts for the two most receptive acceptor position anti-Her2 muteins (S134N and G161T). Initially, three different catalysts were used: 2-Amino-5-methoxybenzoic acid (AMB), 3,5-diaminobenzoic acid (DAB), and aniline (Crisalli 2013). Both aniline and AMB improved the conjugation efficiency, whereas addition of DAB did not result in increased conjugation. The conjugation reaction was improved most by the presence of 50 mM Aniline which, after 72 h resulted in >90% of the available terminal galactose residues having a fluorophore (FIG. 15). Also, temperature and pH optimization can be applied to the initial reaction to reduce the amount of aniline or time required for complete conjugation (not shown).

Figure 16:
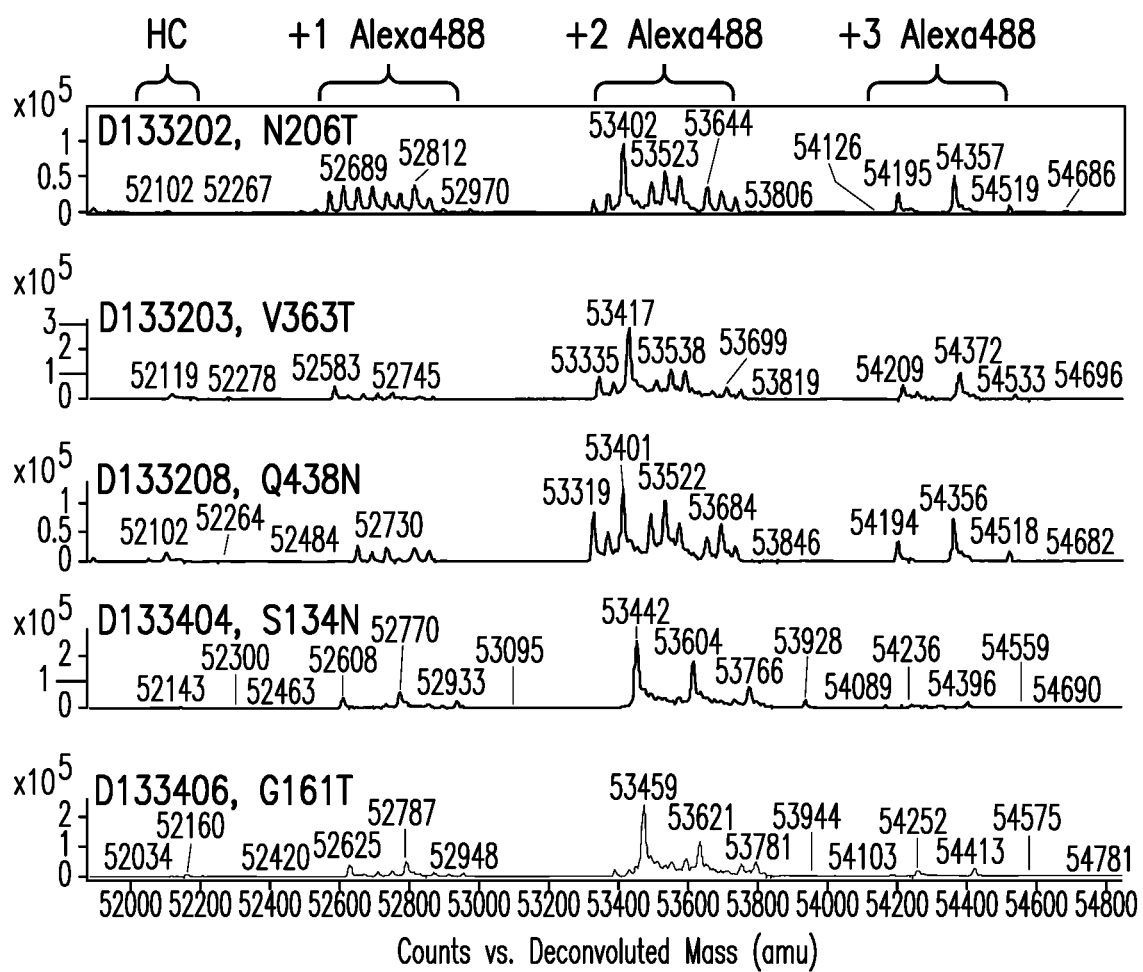
FIG. 16: Glycan-mediated conjugation of a fluorescent dye at multiple different sites on glycan-engineered antibodies. Multiple *Pichia*-produced glycan-engineered versions of trastuzumab (Sample IDs and mutations as described in Table 2) were conjugated with an aminooxy activated CF633 fluorophore in the presence of aniline as a reaction catalyst. The resulting conjugated protein was reduced and analyzed by Q-ToF MS and deconvoluted mass spectra are shown with the mass range expected for unconjugated (HC), singly conjugated (+1 Alexa488), and doubly conjugated (+2 Alexa488) antibody indicated as well as triply conjugated (+3 Alexa488).

Using these optimized conditions, conjugation reactions were carried out for each of the five purified modified mAbs containing non-native N-glycosylation sites (N206T, V363T, Q438N, S134N, and G161T). The glycan modified antibodies were conjugated with alkoxyamine-modified Alexafluor488 fluorophore (Alexa488, Invitrogen, Claremont, Calif.). Conjugation proceeded highly efficiently for 4 of the 5 with a significant proportion of singly conjugated H chain remaining for the N203T variant. However, even for this protein the plurality of resulting mAb contained two conjugated fluorophores (FIG. 16). For the other four glycan-modified mAbs, the predominant species (>80%) following optimized conjugation was H chain containing two fluorophores, where in each case the maximum number of available sites is two, considering one extra N-glycan per H chain, each containing a predominantly biantennary N-glycan with terminal galactose (FIG. 16). The heterogeneity of peaks observed in the Q-ToF arise from the expected N-glycan profile at the Fc N-297 site, which typically contains a mixture of GS4.0, GS4.5 and GS5.0 structures with a small amount of hybrid and mannose forms (Zha, 2013).

The minor conjugation of a $3^{rd}$ site observed for three of the glycan modified mAbs (N206T, V363T, and Q438N), can be interpreted based on mass to be conjugation of the N-297 glycan on hybrid galactosylated (GS3.5, FIG. 1) structures. These three protein samples contained a larger degree of such hybrid structures than the S134N and G161T sample preparations. While previous data showed that conjugation was not possible to complex N-glycans at the N-297 site, this result indicates that conjugation can be directed to the N-297 site if the N-glycan is a hybrid structure. This important finding demonstrates that for a mAb produced with exclusively hybrid N-glycoforms at the N-297 site (an outcome that is possible using glycoengineered yeast strain GFI3.5, FIG. 2), conjugation could be performed at this site with a single available site per N-glycan. However, confirming previous results, no conjugation to complex N-glycan structures is observed at the N-297 site, which allows for discrete control over conjugation position if glycosylation microheterogeneity is controlled.

Taken together, these data demonstrate that nearly quantitative oxime conjugation can be achieved at certain non-native N-glycosylation sites of glycan modified mAbs following enzymatic oxidation of galactose residues to a reactive aldehyde form. Moreover, even under conditions that promote highly efficient conjugation to the desired site, no non-specific oxidation or conjugation is observed. Finally under these conditions, complex N-glycans at the N-297 of the Fc (a modest fraction of which are galactosylated GS4.5 and GS5.0) are not oxidized by the GalOx enzyme, thereby maintaining site-specificity of the conjugation reaction irrespective of the presence of a complex glycan at the canonical N-297 site. Thus, importantly, this glycan-based conjugation is completely compatible with full effector function-enabled antibodies.

Example 8: Scale-Up and Bioanalytical Characterization of Glyco-Conjugated Abs

Figure 17:
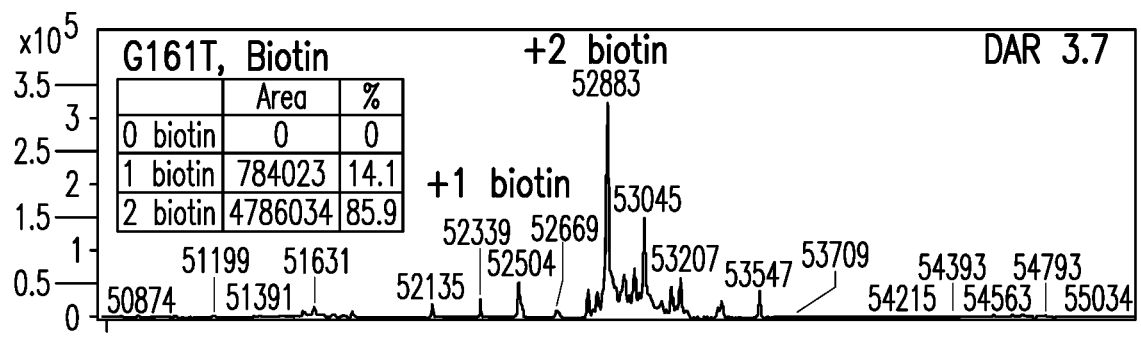
FIG. 17: Scale-up and quantification of conjugation to glycan-engineered antibodies. *Pichia*-produced glycan-engineered versions of trastuzumab were conjugated with an alkoxyamine activated Biotin and an alkoxyamine activated fluorophore (Alexa488) in the presence of aniline then reduced and the resulting reaction products analyzed by Q-ToF MS. The peak areas were then calculated and ratioed to determine the average number of conjugates per whole mAb (Drug-antibody-ratio, DAR).
Figure 17:
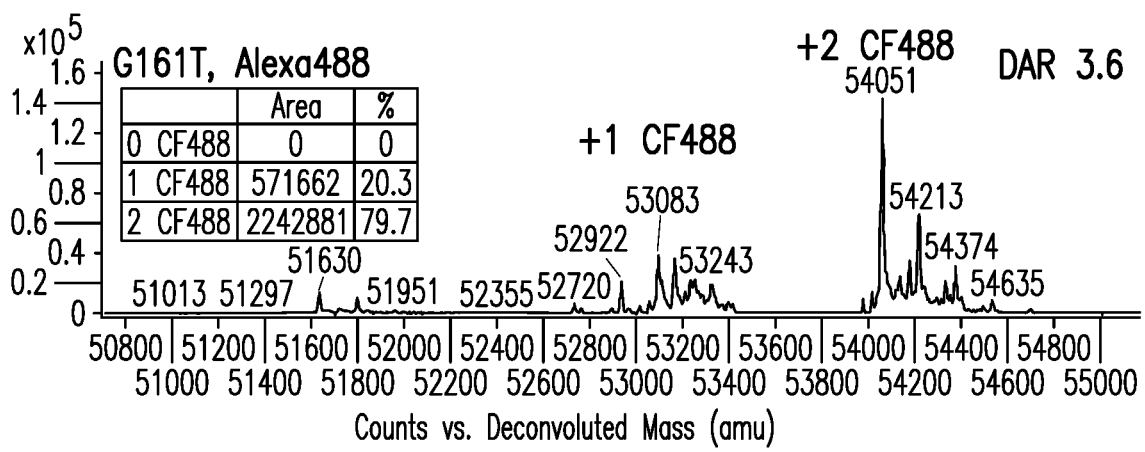
Figure 17:
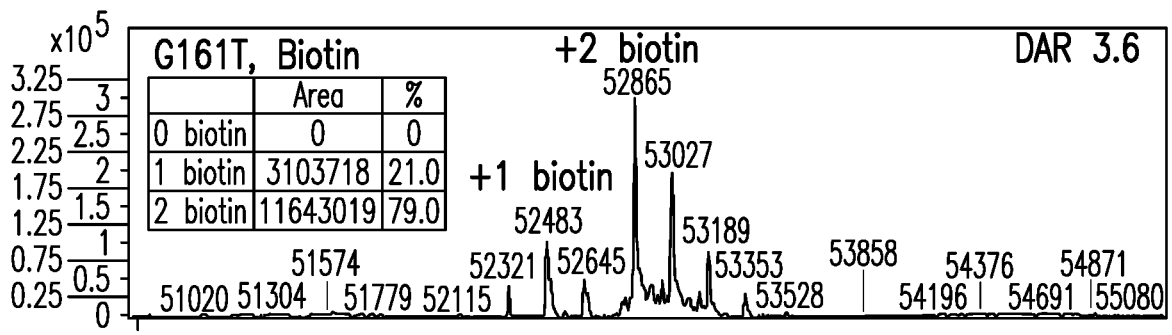
Figure 17:
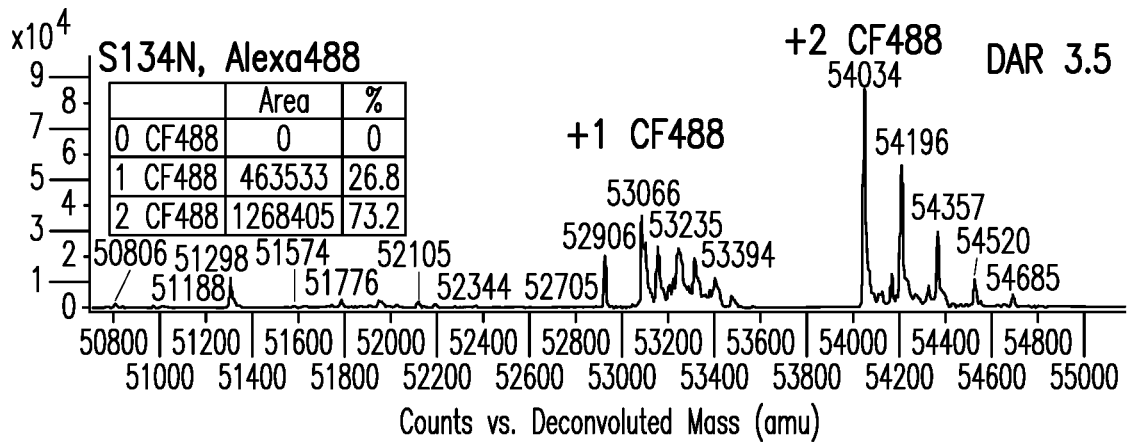
Figure 18A:
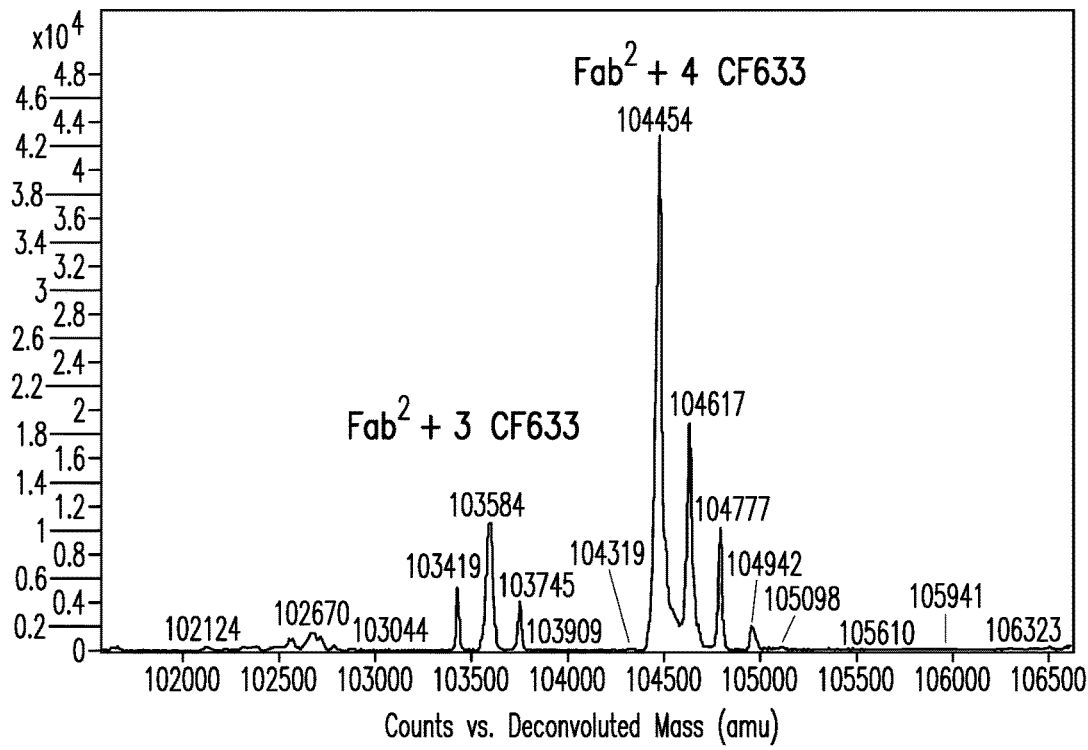
FIG. 18 (A-B): IdeS digestion and mass spectrometry analysis of a conjugated, glycan-engineered antibody. Glycan-engineered (G161T) trastuzumab that was produced in glycoengineered *Pichia* and conjugated with CF633 fluorescent dye was digested with IdeS enzyme to separate the F(ab')$_2$ and Fc domains and the resulting protein analyzed by Q-ToF MS. Expected mass ranges for glycosylated, conjugated Fab fragments A, (F(ab')$_2$+3 CF633 and F(ab')$_2$+4 CF633) and glycosylated unconjugated B, (Fc+GS4.0) as well as conjugated Fc fragments (Fc+GS3.5+CF633) are identified.
Figure 18B:
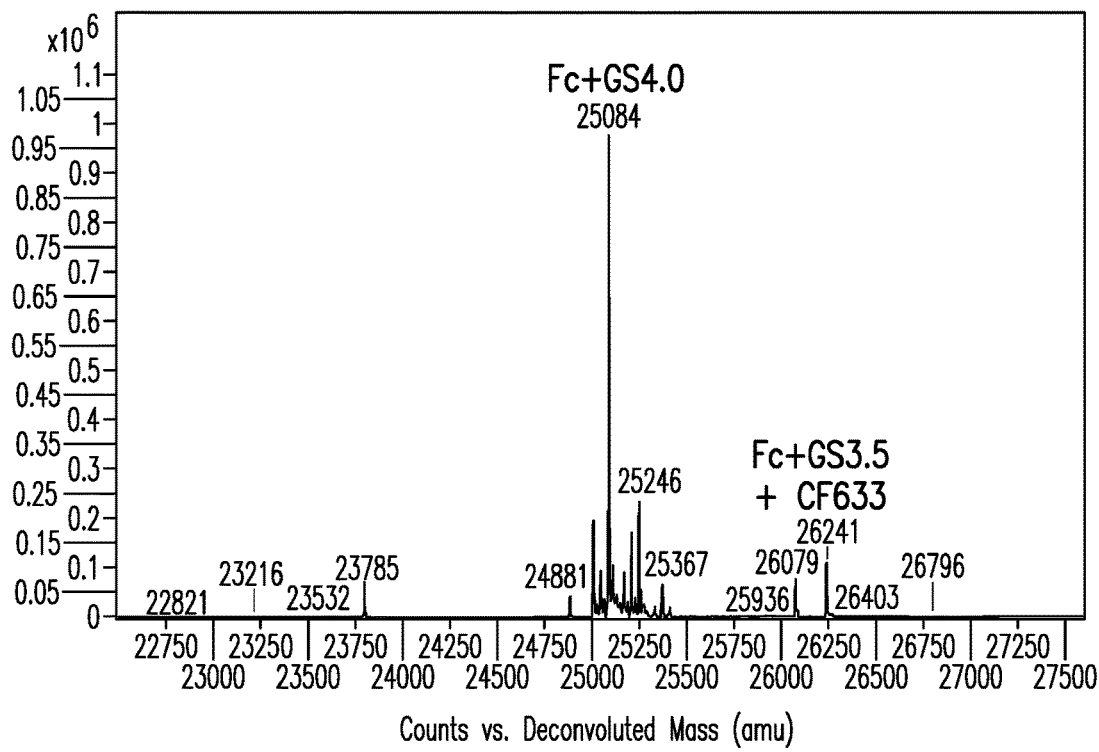

The conjugation reaction described in Example 5 (modified by addition of aniline as described in Example 7) was scaled to larger volume using the S134N and G161T modified anti-Her2 mAb sequences. Alkoxyamine-modified Alexa488 and alkoxyamine modified biotin were used as conjugation substrates (100 mM for each) and conjugation reactions were carried out at 25° C. for 72 h. The reaction products were subjected to Q-ToF MS with the results shown in FIG. 17. In each case the DAR was calculated based on the relative abundance of the peaks assigned to the bi-conjugated, mono-conjugated, and unconjugated antibody (FIG. 17).

The Alexa488 conjugated G161T glycan modified anti-Her2 antibody was also subjected to IdeS (Fabricator, NEB, Ipswich, Mass.) digestion and Q-ToF MS to confirm the location of the conjugated dye. The IdeS digestion was carried out according to the manufacturer's instructions. Upon digestion and MS analysis, it was observed that the two non-native N-glycosylation sites residing on the F(ab')$_2$ were modified with 3-4 Alexa 488 moieties while the Fc-fragment was nearly completely unmodified.

Figure 19:
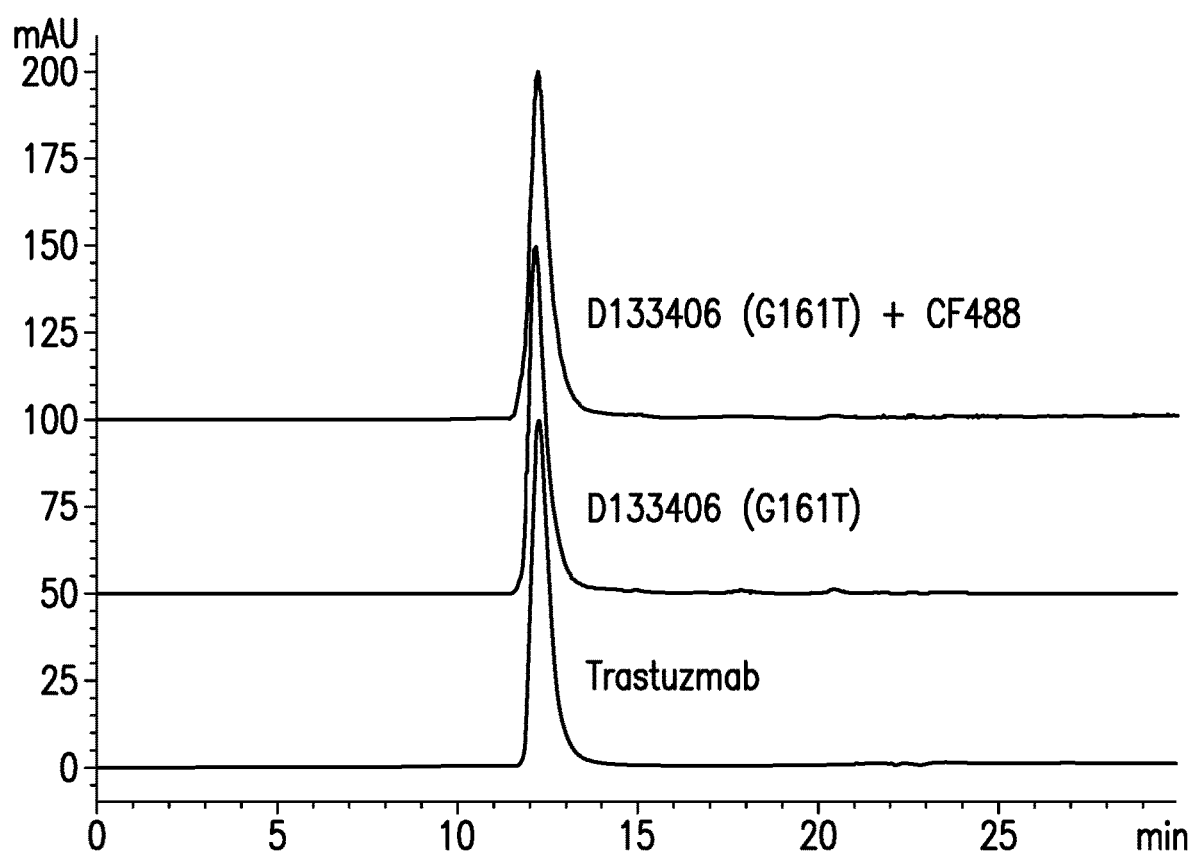
FIG. 19: Size Exclusion Chromatography of a glycan-engineered and conjugated antibody. Glycan-engineered (G161T) trastuzumab that was produced in glycoengineered *Pichia* and then conjugated with CF633 fluorescent dye was analyzed by native size exclusion chromatography prior to and after conjugation compared to the commercially available trastuzumab as a control.

The same Alexa488 conjugated G161T glycan modified anti-Her2 antibody (FIG. 19) was subjected to size exclusion chromatography (SEC) along with the parental unconjugated G161T anti-Her2 mAb (FIG. 9B, D133406) and commercial anti-Her2 (Trastuzumab). SEC was performed as previously described (Potgieter et al, 2009). Retention times and peak analysis indicates that the glycan modified anti-Her2 produced in glycoengineered *Pichia* and the Alexa488 conjugated version retain a minimal propensity for aggregation and in general have a comparable initial stability compared to the commercial control. Thus, the addition of a non-native N-glycosylation sites or conjugation to the glycan does not increase propensity for aggregation or mis-folding of the antibody.

Figure 20:
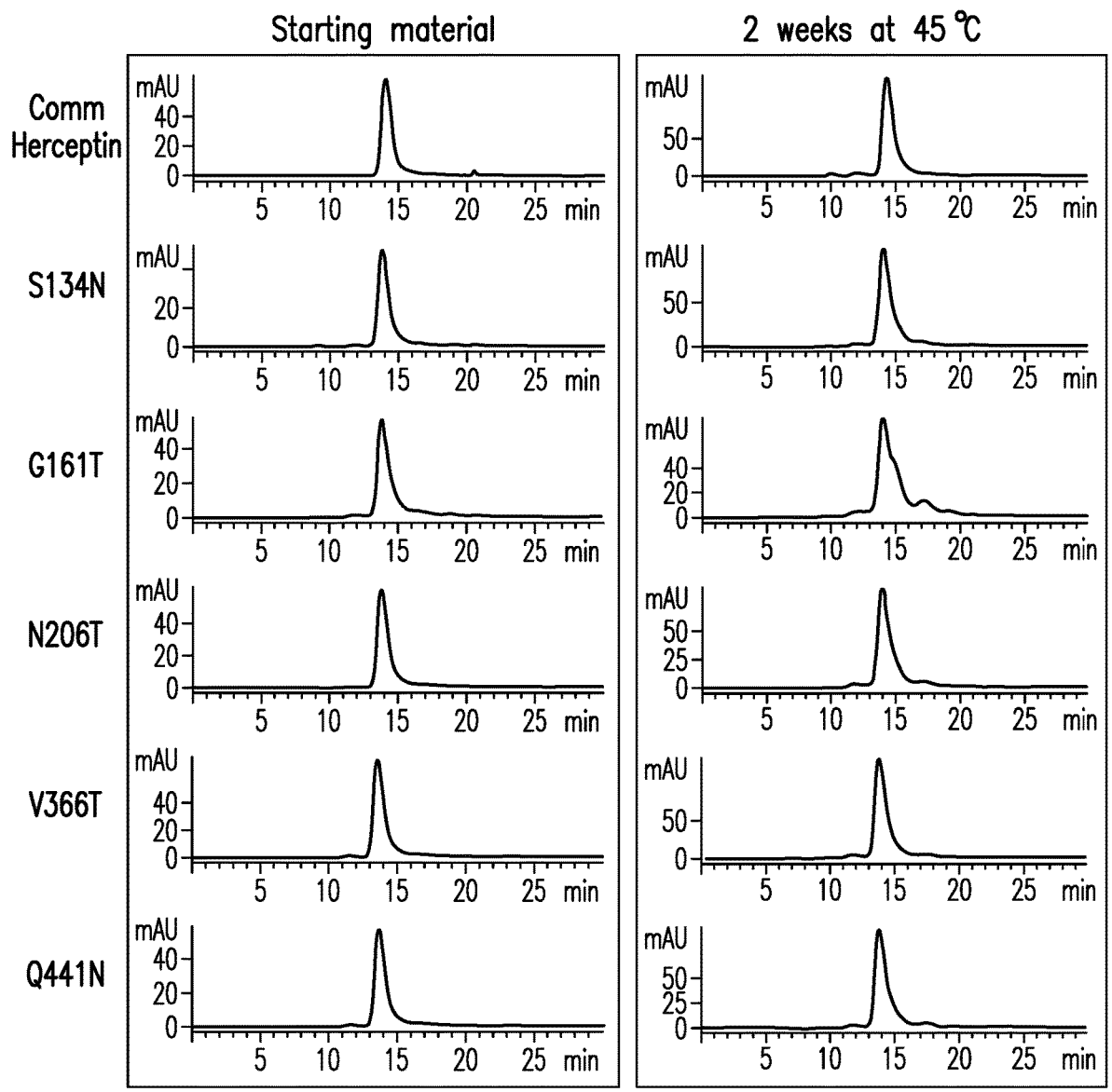
FIG. 20: Temperature stability of glycan-conjugated antibodies. Glycan-engineered trastuzumab variants produced in glycoengineered *Pichia* were analyzed by native size exclusion chromatography compared commercially available trastuzumab as a control prior to and after a two week incubation at 45° C. in 100 mM sodium phosphate pH 7.0.

In order to further probe stability, the glycan-modified antibodies were incubated at 45° C. for 2 weeks in 100 mM sodium phosphate pH 7.0 at a concentration of 5 mg/ml and then subjected to SEC. All samples retained intactness and resisted aggregation except for the G161T modified antibody, which degraded slightly more rapidly at 45° C. than the commercial control or other glycan-modified mAbs (FIG. 20).

Example 9: Covalent Attachment of an Aminooxy Activated GLP-1 Receptor Agonistic Peptide to an Ab Via Glyco-Conjugation An aminooxy chemically activated Exendin-4 peptide modified at the gamma amine of the C-terminal Lysine (FIG. 21) was constructed by Biopeptek (Malvern, Pa.). This peptide was conjugated to the purified S134N and G161T modified anti-Her2 Abs using the one-pot combined enzymatic/chemical conjugation procedure illustrated in Examples 5 (with a 100 µM final concentration of peptide and 50 mM aniline). The conjugated peptide was analyzed by Q-ToF MS and shown to be intact and conjugated to a DAR of 3.3 out of a theoretical maximum of 4 potential sites (FIG. 21). The glyco-ADC exendin-4 conjugate was evaluated for its ability to bind and activate the GLP-1 receptor (GLP-1R) using a recombinant Chinese Hamster Ovary (CHO) cell-based assay. A recombinant CHO stable cell line was generated by expression of the serpentine G protein coupled receptor GLP-1R, which induces intracellular cAMP production by native CHO Adenylyl Cyclase via G protein activation. To evaluate glyco-ADC exendin-4 activity, CHO GLP-1R cells were exposed to either glyco-ADC exendin-4 conjugate or native GLP-1 as a control at a range of concentrations. Resulting changes in cAMP levels were determined using the HitHunter cAMP XS+ system (DiscoveRx Corporation, Fremont, Calif.) on a Tecan infinite 200Pro reader. Results were compiled and plotted and EC50 values were calculated using Graphpad Prism 5 software. The glyco-ADC exendin-4 conjugate was active with EC50 values ranging from 2-5 fold lower than native GLP-1 peptide (FIG. 21). These data indicate that an active peptide can be conjugated to antibodies at non-native N-glycosylation sites via galactose oxidase and oxime ligation.

Figure 22A:
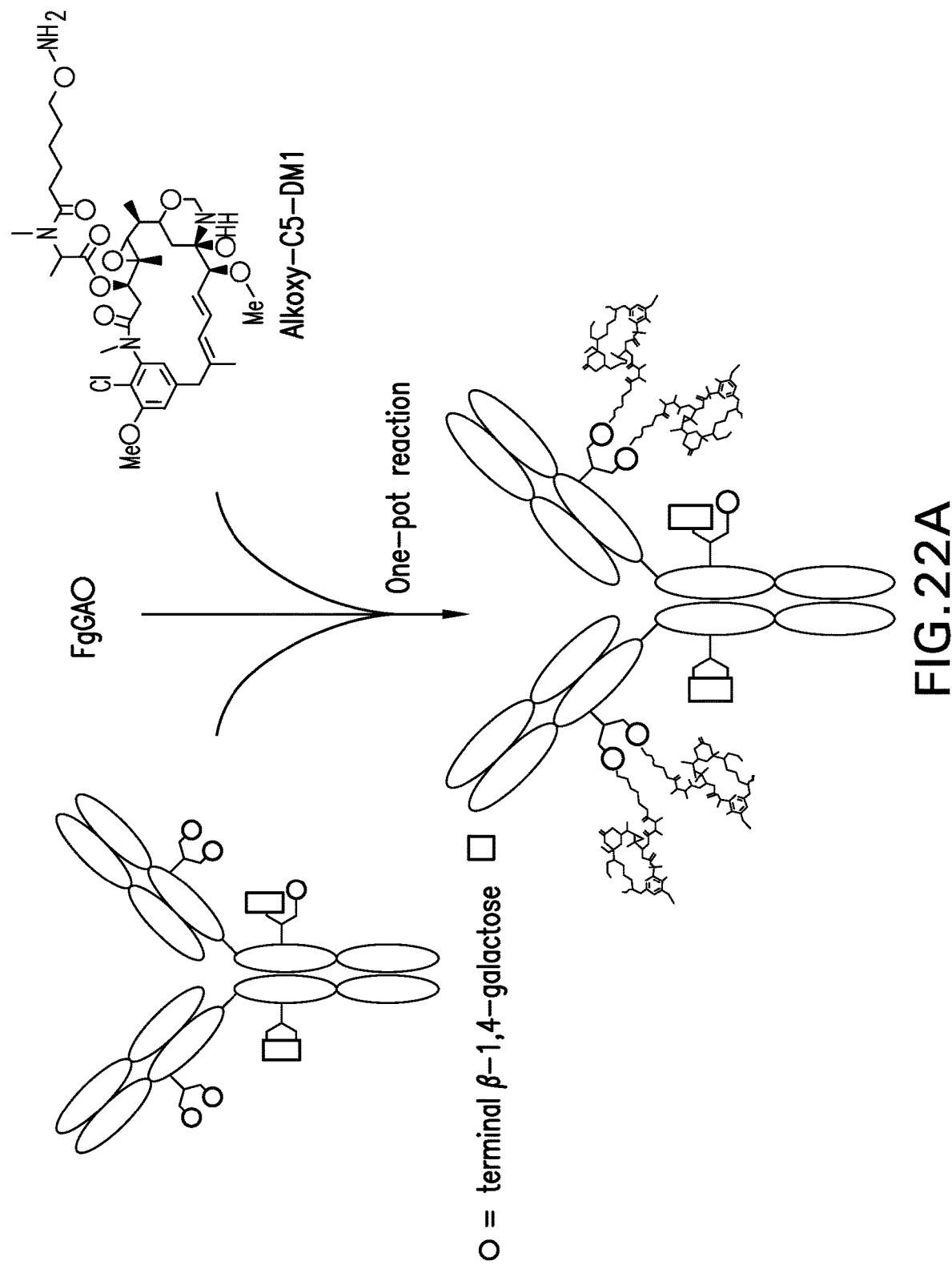
FIG. 22 (A-B): Conjugation of a modified DM1 cytotoxin to a glycan-engineered antibody. A, Illustration of the conjugation reaction of alkoxy-labeled, C5-linked, Mertansine (DM1) to the galactose residues of the Fab glycans on a glycan-engineered anti-Her2 antibody in one-pot with FgGalOx. B, Deconvoluted Q-ToF mass spectrum of reduced antibody (H chain) after conjugation with DM1 for two different glycan-engineered anti-Her2 antibodies.
Figure 22B:
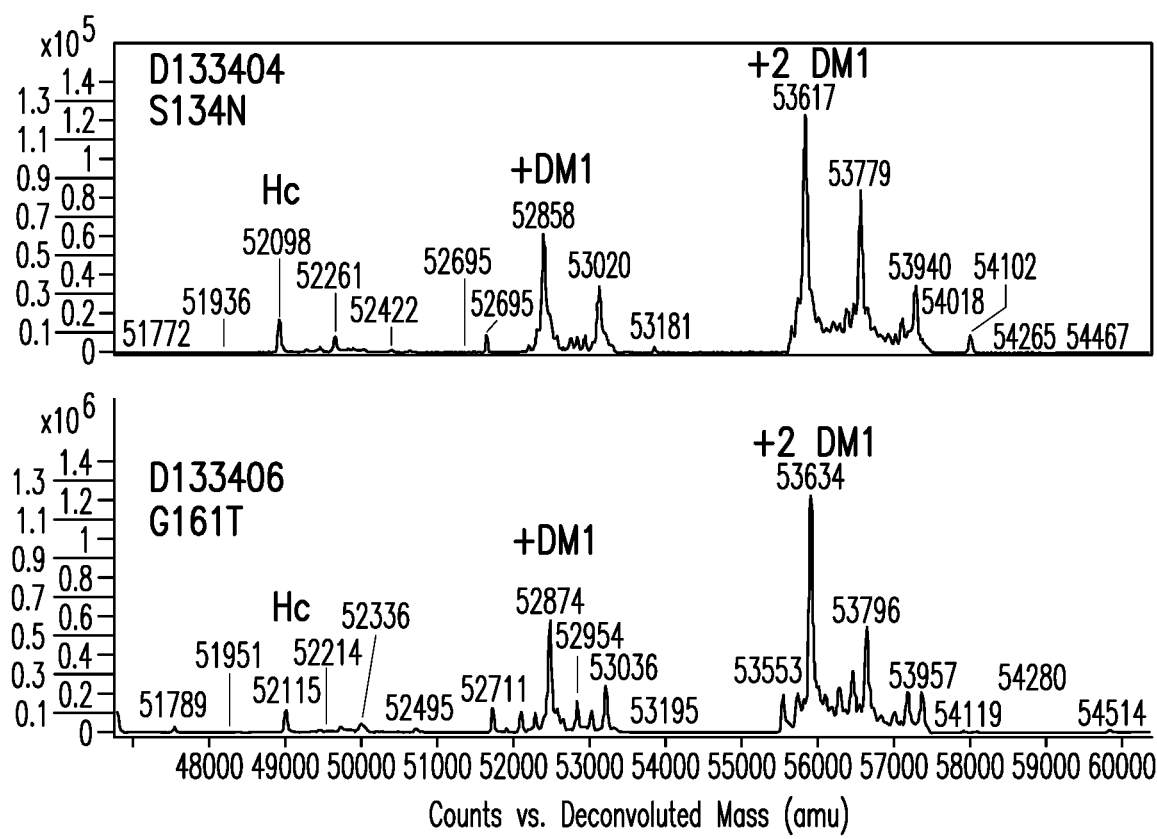
Figure 23A:
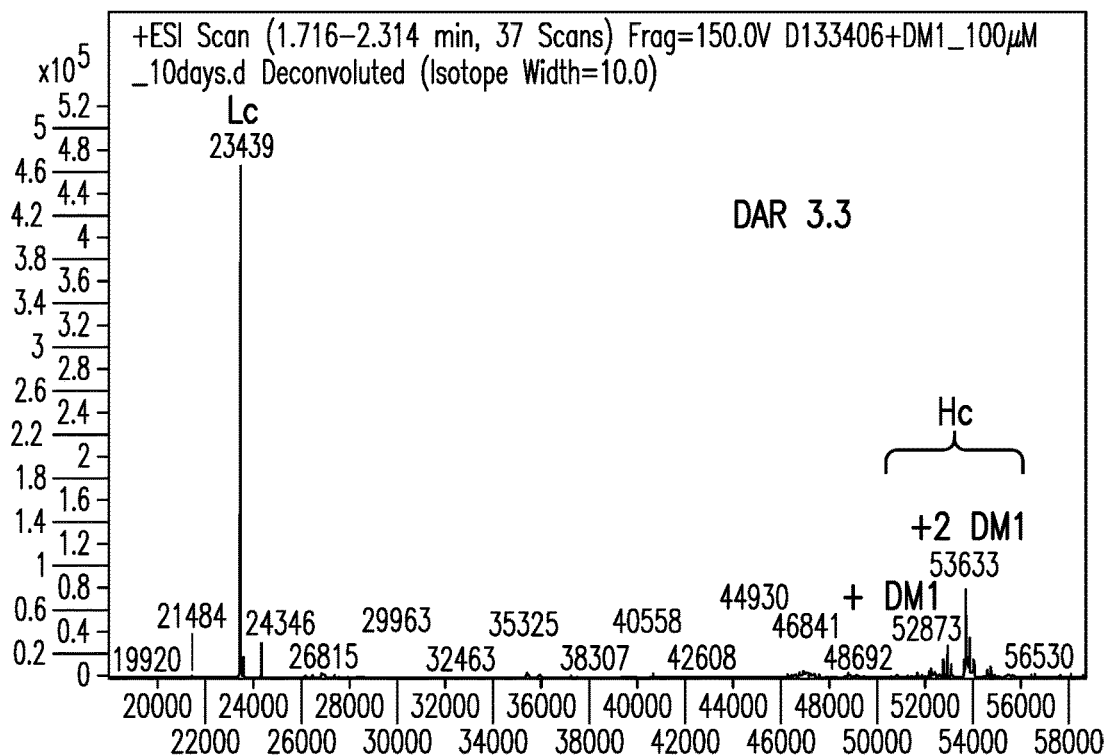
FIG. 23 (A-B): Q-ToF Mass spectrometry analysis of DM1-conjugated antibodies. A, Deconvoluted Q-ToF mass spectrum of reduced DM1-conjugated anti-Her2 G161T glycan-engineered antibody, gated to include predicted heavy (Hc) and light (Lc) chain masses, with conjugation efficiency calculated (DAR) based on integrated peak areas. B, Deconvoluted Q-ToF mass spectrum of reduced DM1-conjugated anti-Her2 (ado-trastuzumab emtansine) antibody, gated to include predicted H and L chain masses.
Figure 23B:
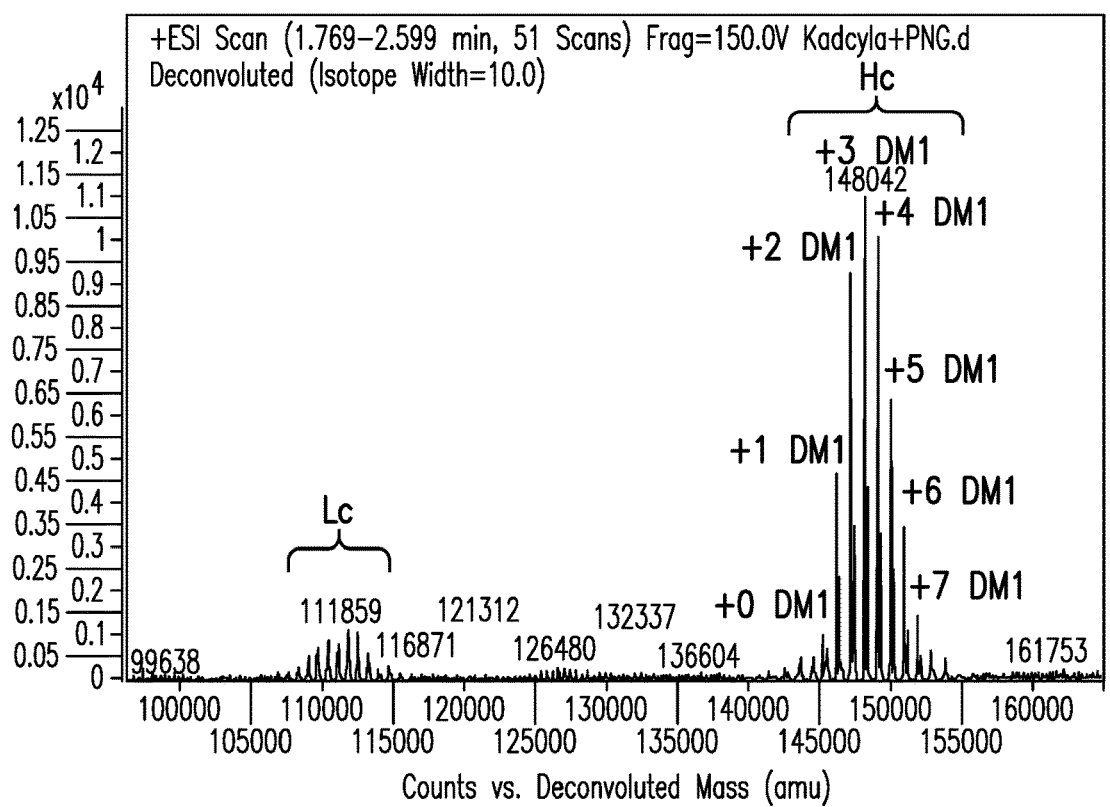

Example 10: Conjugation of a Cytotoxic Agent to an Antibody at Non-Native N-Glycosylation Sites An aminooxy activated C5-linker containing DM1 (alkoxy-O5-DM1, FIG. 22A) chemically synthesized by Concortis Biosystems (San Diego, Calif.), was conjugated to the S134N and G161T anti-Her2 mAbs using the protocol described in example 5 (with 100 µM DM1 and 50 mM aniline) to generate oxime ligated C5-DM1 conjugated mAbs. The C5-DM1 conjugated mAbs were subjected to Q-ToF MS under reducing conditions and the G161T MS trace is shown as an example (FIG. 22B). For both S134N and G161T C5-DM1 conjugated Abs, masses were observed that are consistent with addition of a single and two C5-DM1 molecules as well as a very small fraction of unconjugated H chain. This is in contrast to the heterogeneity observed in commercial ado-trastuzumab emtansine, which contains from 0-8 DM1 molecules dispersed throughout the H and L chains as evidenced by Q-ToF MS (FIG. 23). This diversity has been demonstrated in other studies to contribute to lower serum stability (PK) and activity (PD) compared to similar but more homogeneous ADCs based on the same mAb scaffold, resulting in better efficacy for the more homogeneous molecule, even with a lower DAR (Jackson, 2014; Tian, 2014; Axup, 2012).

Example 11: Generation of Additional Non-Native N-Glycosylation Site-Modified Antibodies for Site-Specific Glyco-Conjugation With the knowledge that combined enzymatic/chemical conjugation can occur efficiently at selected engineered N-glycan sequons a further set of native N-glycosylation sites were constructed by introducing site-directed mutants into an IgG to determine whether these new structurally selected sites would be suitable substrates for 1) efficient addition of N-glycans and 2) conjugation of cargo. A list of mutations that were constructed and the associated sequence references is found in Table 4.

TABLE 4

| Plasmid name | Mutation (EU numbering) | Mutation (Herceptin numbering) | Mutation (Kabat numbering) | H chain Sequence |
|---|---|---|---|---|
| pGLY14120 | N/A | S120N | S113N | SEQ ID NO: 12 |
| pGLY14121 | A118N | A121N | A114N | SEQ ID NO: 13 |
| pGLY14122 | S132N | S135N | S128M | SEQ ID NO: 14 |
| pGLY14123 | K133N | K136N | K129N | SEQ ID NO: 15 |
| pGLY14124 | A162N | A165N | A165N | SEQ ID NO: 16 |
| pGLY14125 | T195N | T198N | T200N | SEQ ID NO: 17 |
| pGLY14126 | K210T | K213T | K218T | SEQ ID NO: 18 |
| pGLY14127 | Y391T | Y394T | Y419T | SEQ ID NO: 19 |
| pGLY14128 | F423T | F426T | F454T | SEQ ID NO: 20 |
| pGLY14129 | Y436T | Y439T | Y467T | SEQ ID NO: 21 |
| pGLY14130 | L193N | L196N | L198N | SEQ ID NO: 22 |
| pGLY14131 | Q419N/N421T | Q422N/N424T | Q450N/N452T | SEQ ID NO: 23 |
| pGLY14132 | S176N/G178T | S179N/G181T | S180N/G183T | SEQ ID NO: 24 |
| pGLY14133 | S191N/L193T | S194N/L196T | S196N/L198T | SEQ ID NO: 25 |
| pGLY14134 | G194N/Q196T | G197N/Q199T | G199N/Q203T | SEQ ID NO: 26 |

Figure 24A:
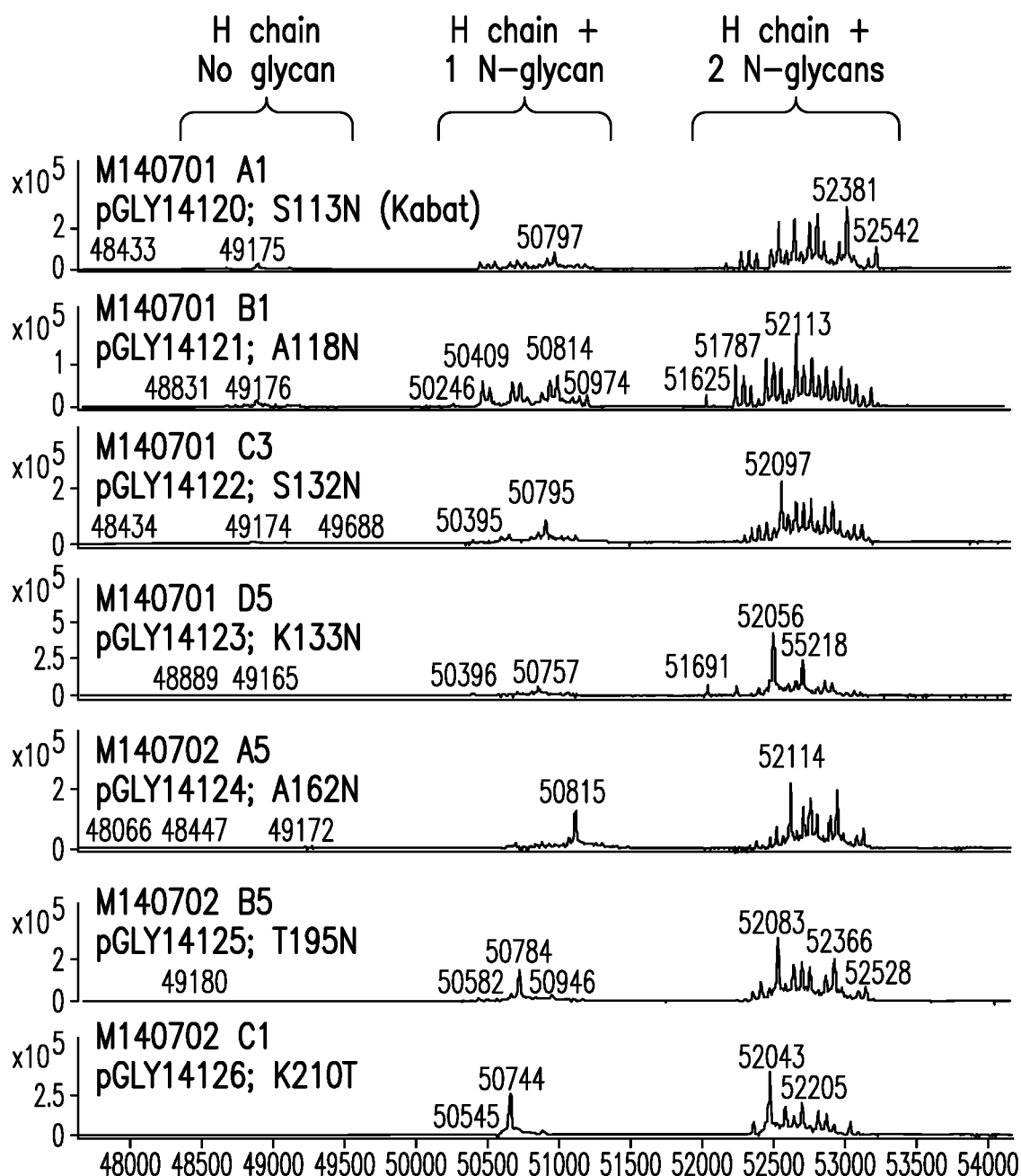
FIG. 24 (A-B): Q-ToF Mass spectrometry analysis of glycan-engineered antibodies isolated from microfermenter cultivation. Deconvoluted Q-ToF mass spectra of reduced antibodies for A) one set of 7 glycan-engineered anti-Her2 antibodies with $F_{ab}$ and $C_H 1$-localized muteins, and B) an additional set of 7 diverse glycan-engineered anti-Her2 antibodies including CH3-located and double mutant sequences. All spectra are gated to include predicted heavy (H) chain masses. Unglycosylated, singly glycosylated (+1 N-glycan) and doubly glycosylated (+2 N-glycans) predicted masses are identified, while specific masses differ slightly depending on the mutational change(s) made to incorporate the respective N-glycan sequon. Sequence-related information for each mutation is found in Table 4.
Figure 24B:
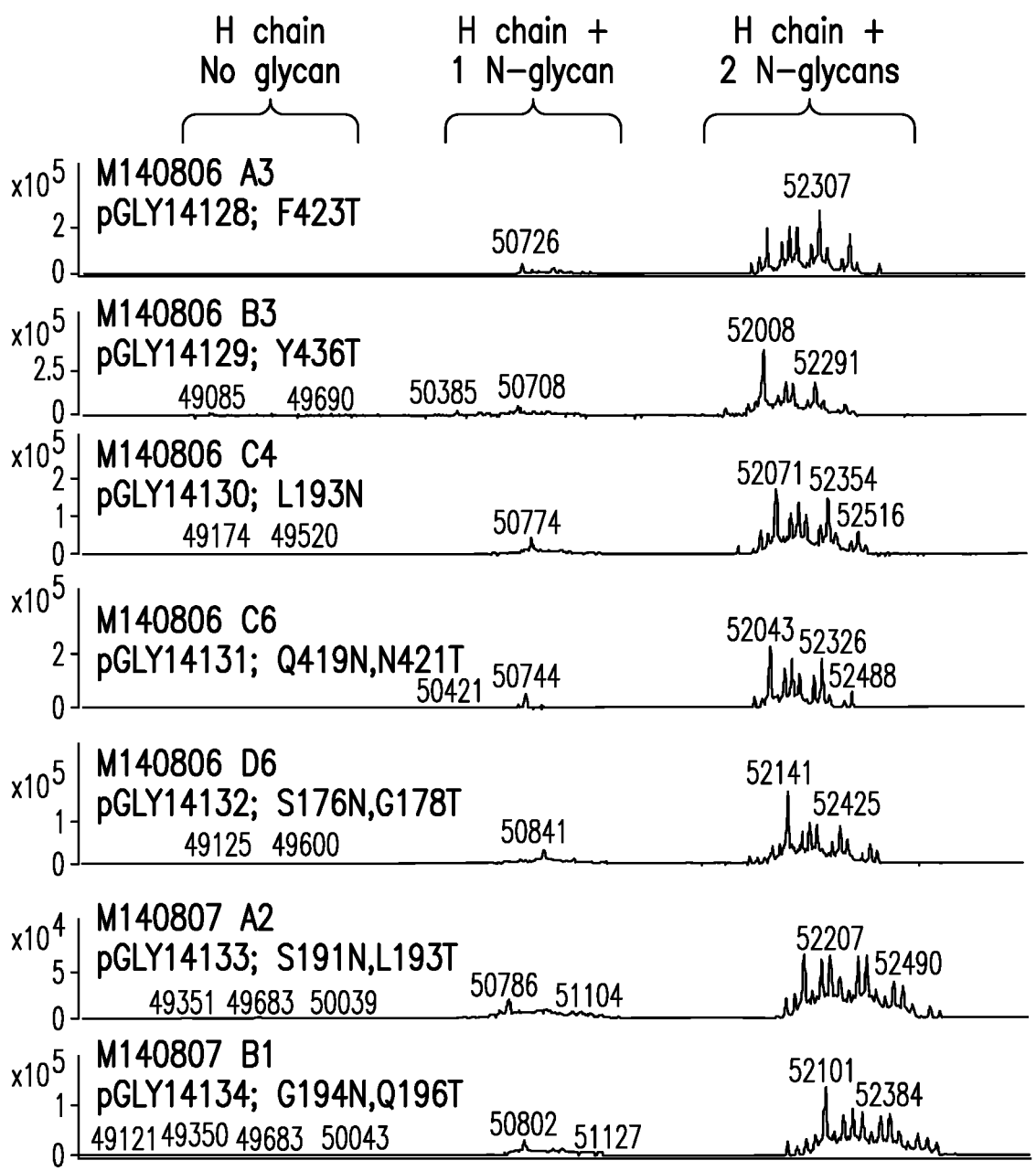

Notably, at some sites more than a single mutation was required to generate an efficient predicted NXS/T (where X is not Pro) sequon. Mutations were introduced into the anti-Her2 IgG1 mAb sequence in plasmid pGLY5883 (FIG. 3), generating plasmids pGLY14120-pGLY14134, containing the AOX1 promoter and Zeocin resistance cassette. The new anti-HER2 N-glycan mutein expressing plasmids were transformed into glycoengineered *Pichia* strain YGLY30329 by electroporation and clones were selected on medium containing 100 µg/mL and 300 µg/mL Zeocin. Isolated clones were screened for expression by 96 well plate cultivation as described (Example 1 and Barnard, 2010). Clones demonstrated to express mAb were then cultivated in microreactors as described (Example 2). The supernatant was harvested and the produced antibody from these clones was purified by protein A (Jiang et al, 2011). The purified protein was analyzed by Q-ToF MS and the results are shown in FIGS. 24A and 24B. In each case the L chain is the same and was observed as expected (data not shown). The MS traces are zoomed to show the region where the expected H chain masses would reside. The expected mass range for a naked H chain, a H chain with a single N-glycan, and a H chain with two N-glycans is indicated (masses vary slightly due to the mutations introduced). For all Abs shown the predominant peaks observed correspond to H chains with 2 N-linked glycans (the N-297 glycan plus one other glycan at a different location in each case) with the masses varying slightly due to amino acid changes for the introduced mutations and glycan microheterogeneity (FIGS. 24A and 24B). Thus, based on knowledge gained in the first round on mutagenesis, mutations can be selected to add glycans at locations where the glycan will be transferred efficiently and the protein folded and secreted.

Example 12: Generation of Abs with Multiple Non-Native N-Glycosylation Sites

Figure 25A:
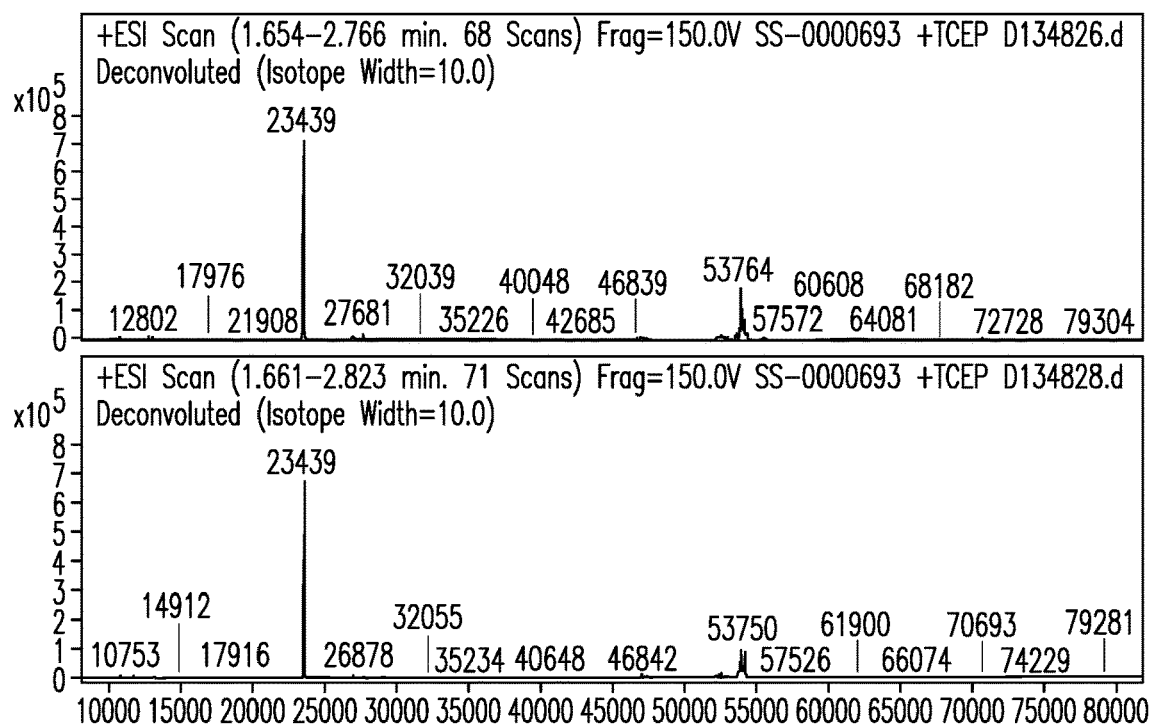
FIG. 25 (A-B): Q-ToF Mass spectrometry analysis of glycan-engineered antibodies with two additional N-glycan sites. Deconvoluted Q-ToF mass spectra of reduced antibodies that have been glycan-engineered to incorporate two non-native N-glycosylation sites, in each case located on the $C_H 1$ domain of the heavy chain. The spectra are gated to include: A) predicted light and heavy chain masses, and B) zoomed to observe the predicted H chain masses.
Figure 25B:
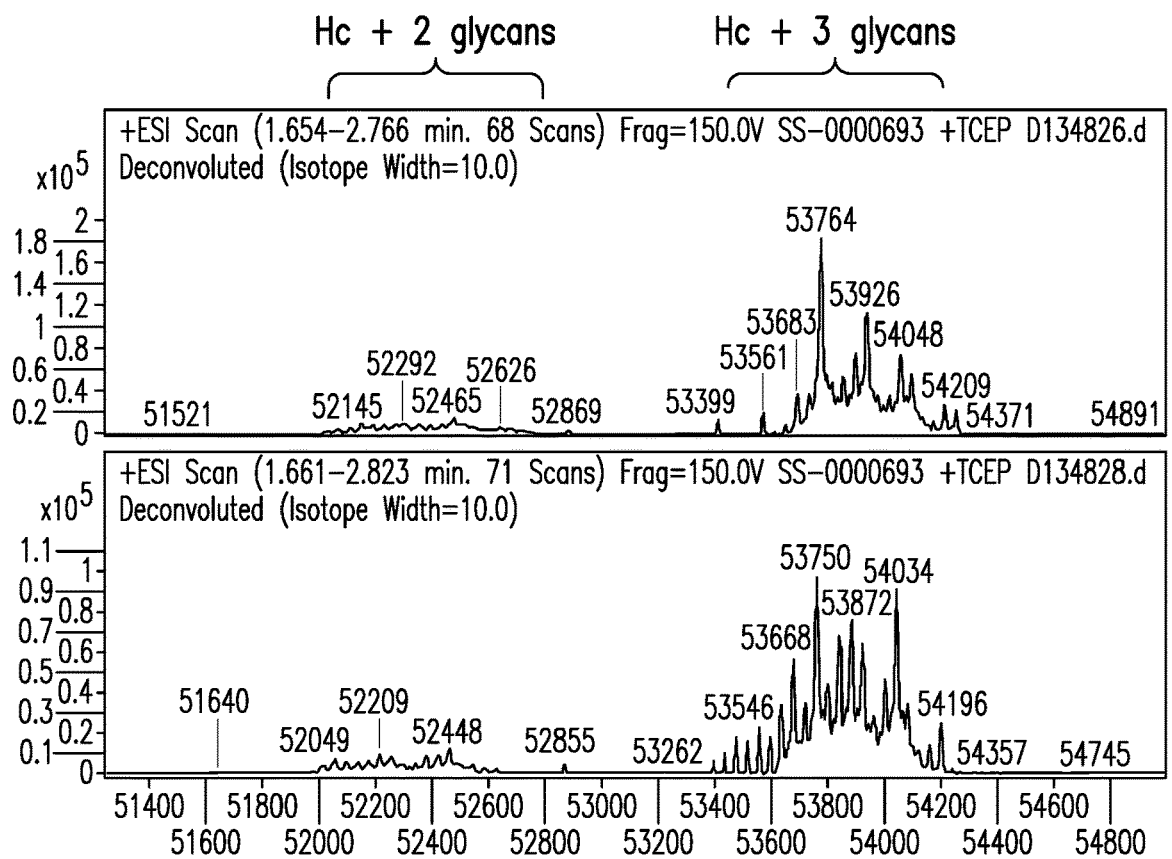

The S134N and G161T mutations provide two efficient N-glycan sites for conjugation (N134 and N159). We next sought to determine if these sites could be combined on the same antibody scaffold to generate an ADC with a DAR:8 at specific sites of conjugation. The S134N mutated anti-Her2 antibody was mutated to incorporate G161T or G161S mutations. The resulting plasmids (pGLY14135 and pGLY14136) were transformed into strain YGLY30329 as described in Example 2. Two resulting clones of each were cultivated in Dasgip 1 L fermenters as described in Example 3. The fermentation supernatant was purified by protein A chromatography and the resulting protein subjected to Q-ToF analysis. Both the S134N/G161T and S134N/G161S double mutein containing mAbs were efficiently glycosylated at 3 sites on each reduced H chain (N134, N159, and N297) with minimal residual singly or doubly glycosylated protein (FIG. 25).

Given that Abs can be produced accommodating two N-glycan sites and the glycoengineered yeast system can modify these sites efficiently to terminal galactose (Illustrated in FIGS. 26A and 26B), we sought to determine how many N-glycans could be added to a structure, for example, to maximize DAR. To accomplish this, a series of sites were chosen to combine that would each be in disparate loops of the same antibody sequence. Between four and ten extra N-glycan sites were introduced by site directed mutagenesis (Illustrated in FIG. 26C) into an engineered version of the anti-Her2 (trastuzumab) sequence, deemed null-HER2, that has been mutated to eliminate Her2 antigen binding by mutation of two residues in the variable region (one each in the VH and VL, See SEQ ID 29 and 30, respectively).

Figure 27:
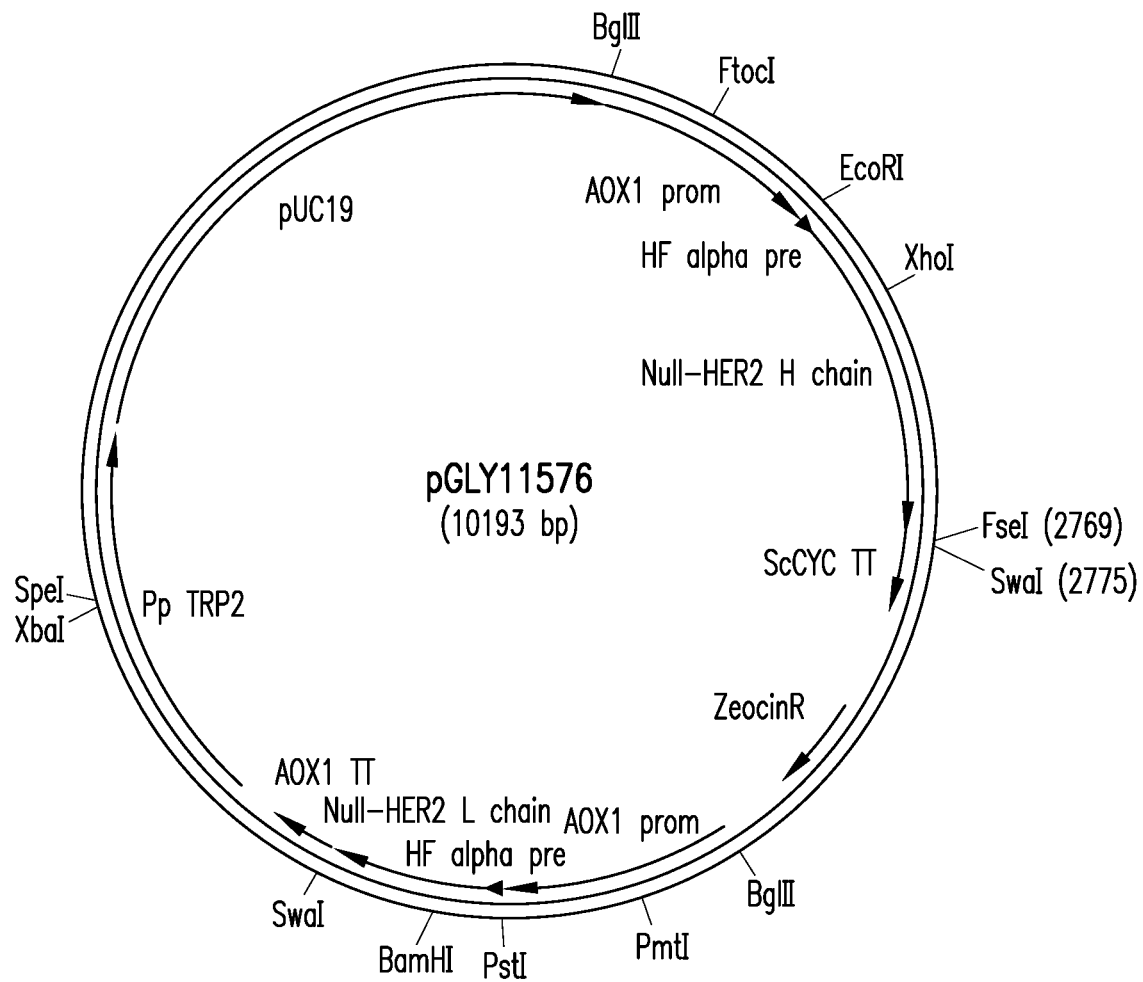
FIG. 27: Restriction map of plasmid pGLY11576. The *E. coli/P. pastoris* shuttle vector is depicted circularly as it is maintained in *E. coli*. The plasmid contains the pUC19 Ori and AmpR region for *E. coli* maintenance as well as the Sh ble gene encoding Zeocin resistance (ZeoR) and the *P. pastoris* TRP2 gene, used as an integration site. The genes encoding the modified trastuzumab-based "null-Her2" H chain and L chain that have been modified to no longer bind the Her2 receptor are contained as separate cassettes. Each antibody gene cassette is flanked with the *P. pastoris* AOX1 promoter and a transcriptional terminator, that from *S. cerevisiae* CYC1 for the H chain and that from *P. pastoris* AOX1 for the L chain.

Plasmids pGLY14172-14179, constructed by Genewiz (South Plainfield, N.J.), contain the null-Her2 H and L chain sequences as derived from pGLY11576 (FIG. 27), and are each modified only by introduction of the mutations as illustrated in Table 5.

Figure 2:
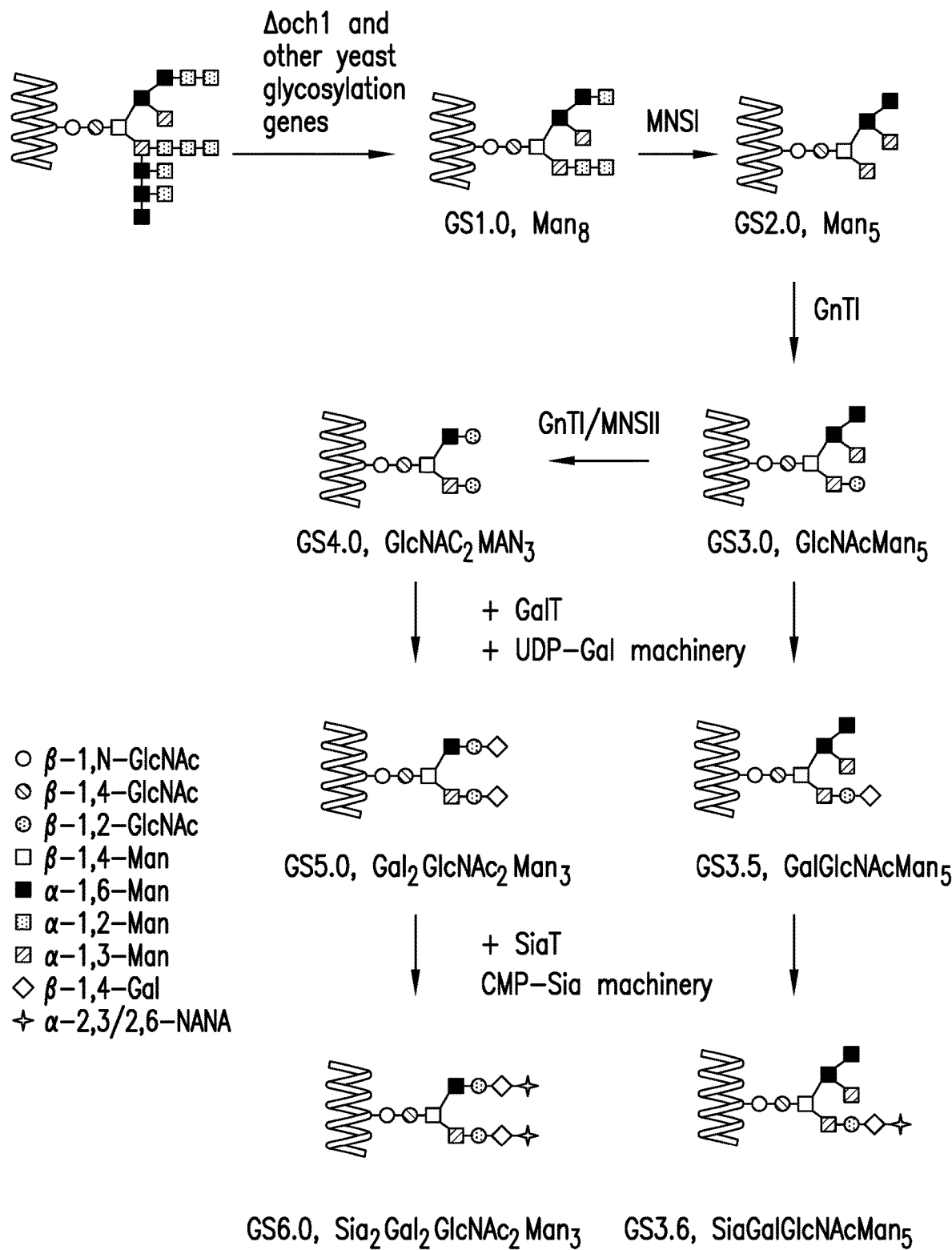
FIG. 2. A flow diagram of an example of the basic molecular genetic steps of yeast N-glycan engineering. OCH1 is knocked out and, depending on the yeast species, other yeast N-glycan machinery encoding genes are also knocked out. Mannosidases and glycosyl transferases responsible for the successive steps in human N-glycan biosynthesis are introduced, wherein each intermediate step can be isolated via a strain producing that particular glycan structure (GS). Man, mannose; GlcNAc, N-acetyl glucosamine; Gal, galactose; MnT, mannosyltransferase; MNS, mannosidase; GnT, GlcNAc transferase; GalT, galactosyl transferase; UDP, Uridine diphosphate; CMP, Cytidine monophosphate.
Figure 26A:
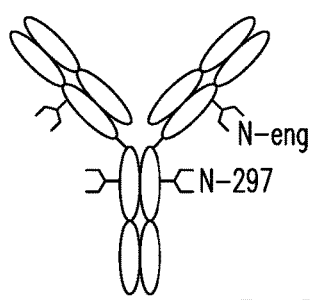
FIG. 26 (A-F): Glycan-engineered antibodies with three or more additional N-glycan sites. A, Illustration depicting the single position glycan-engineered antibody (shown here in the $C_H1$ region), which may or may not also contain the $C_H2$ Fc-297 N-glycan and B, single position glyco-conjugation, leading to a distinct DAR of 2 or 4 depending the N-glycan chosen (or 6 or 8 if multiantennary N-glycans are employed). C, Illustration showing a multi-position glycan-engineered antibody. D, Capillary electrophoresis profile showing several non-reduced multi-position glycan engineered antibodies compared to the one position-modified and control (anti-Her2 Trasutuzmab sequence) antibodies. E, MALDI-TOF MS of released N-glycans from multi-position glycan-engineered antibody modified with ten additional N-glycan sites and expressed in a GS5.0 glycoform strain (see FIG. 2). F, Illustration showing conjugation to the exposed galactose residues of a multi-position glycan-engineered mAb to achieve higher DAR (Drug to Ab Ratio).
Figure 26B:
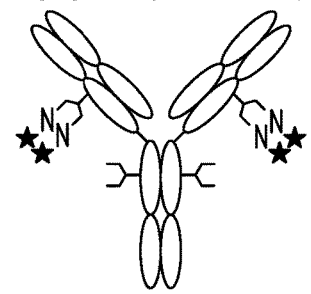
Figure 26C:
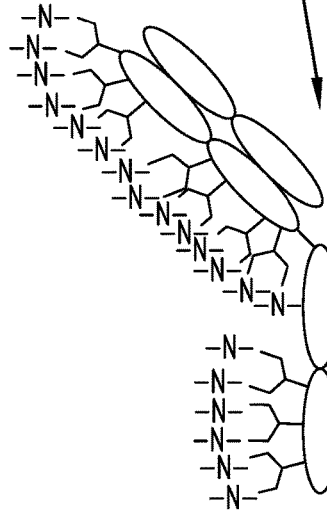
Figure 26F:
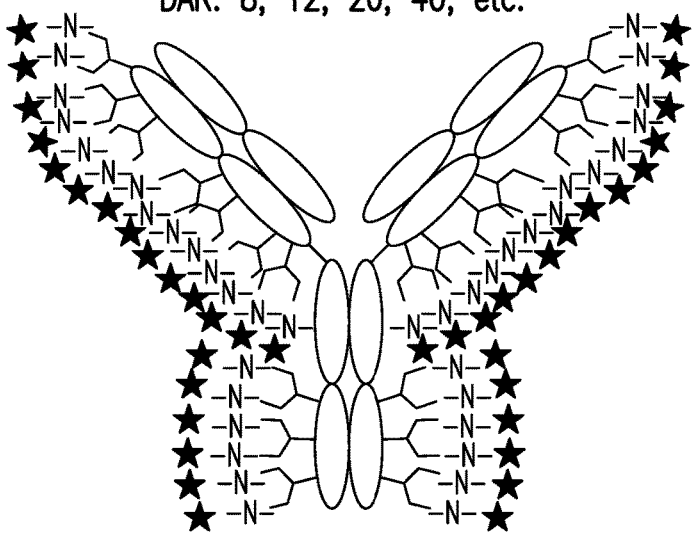
Figure 26D:
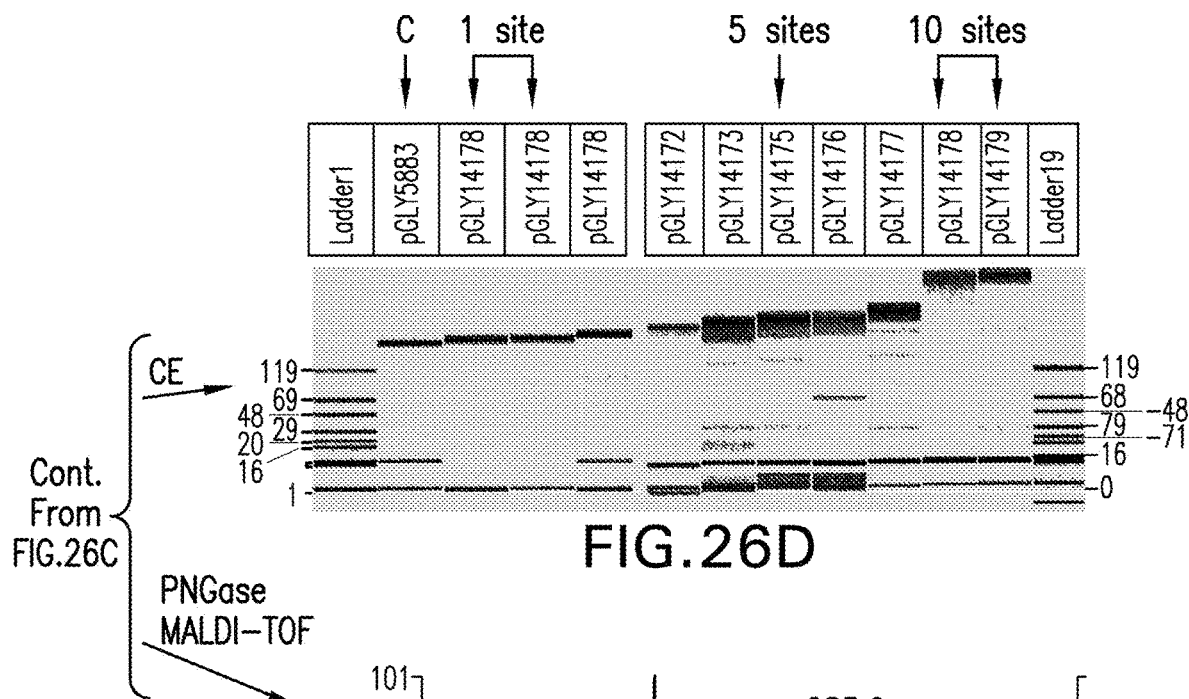
Figure 26E:
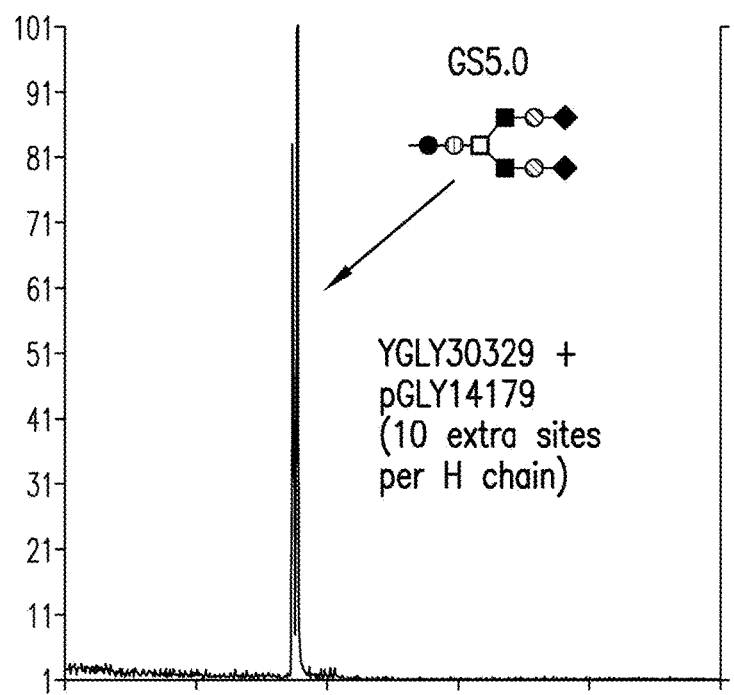

Each of these plasmids was transformed into strain YGLY30329 and clones were selected and screened for secretion of antibody in 96 DWP format as described in Example 1. Following this, several positive clones were cultivated in 5 ml micro24 reactors and the supernatants were harvested by centrifugation and purified by protein A chromatography as described in example 2 above. The purified samples were subjected to capillary electrophoresis (CE) on a Labchip GXII instrument (Caliper Life Sciences, Hopkinton, Mass.) using the standard HT Protein Express 200 method as described (Gomathinayagam, 2012). From this analysis it was possible to conclude that most of the additional N-glycosylation sites were indeed occupied due to the shifts in migration. To illustrate this, a single representative purified non-reduced CE sample from each of the plasmids was displayed using the Labchip GXII visualization software version 4.1 (FIG. 26D). Moreover, these samples were subjected to enzymatic N-glycan removal by PNGase digestion and MALDI-TOF MS of the free N-glycans as previously described (Choi, 2003). Most of the clones revealed a predominant mass at 1660 or 1676 (Na or K adducts), identified to be the biantennary terminally galactosylated human complex N-glycan $Gal_2GlcNAc_2Man_3GlcNAc_2$ (FIG. 2, GS5.0). A representative sample from a clone resulting from introduction of pGLY14179 into YGLY30329 is shown in FIG. 26E. The mAb expressed in this strain contains a total of 22 N-glycosylation sites (11 per H chain). It can also been observed in these non-reducing samples that mAb assembly is of high integrity with mostly a single species observed in each case. Poorly assembled mAb would often result in poor resolution in CE under non-reducing conditions.

Figure 28A:
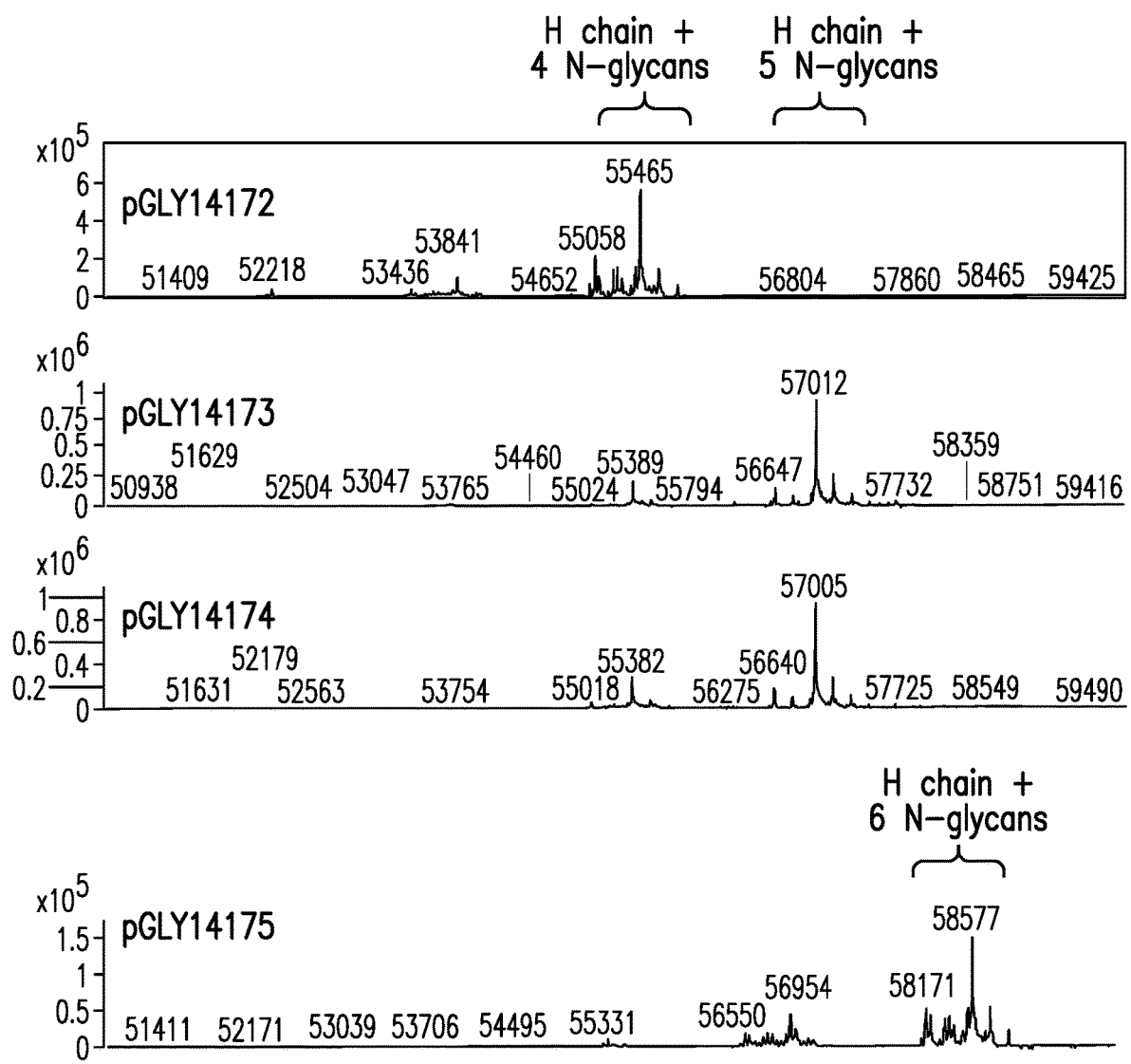
FIG. 28 (A-B): Q-ToF Mass spectrometry analysis of glycan-engineered antibodies with more than two additional N-glycan sites. Deconvoluted Q-ToF mass spectra of reduced antibodies that have been glycan-engineered to incorporate from three to ten non-native N-glycosylation sites resulting from transformation of plasmids: A, pGLY14172-14175 or B, pGLY14176, 14177, and 14179 (see Table 5) into a GS5.0 glycoengineered *Pichia* strain (see FIG. 2). The resulting spectra are gated to include the predicted H chain masses.
Figure 28B:
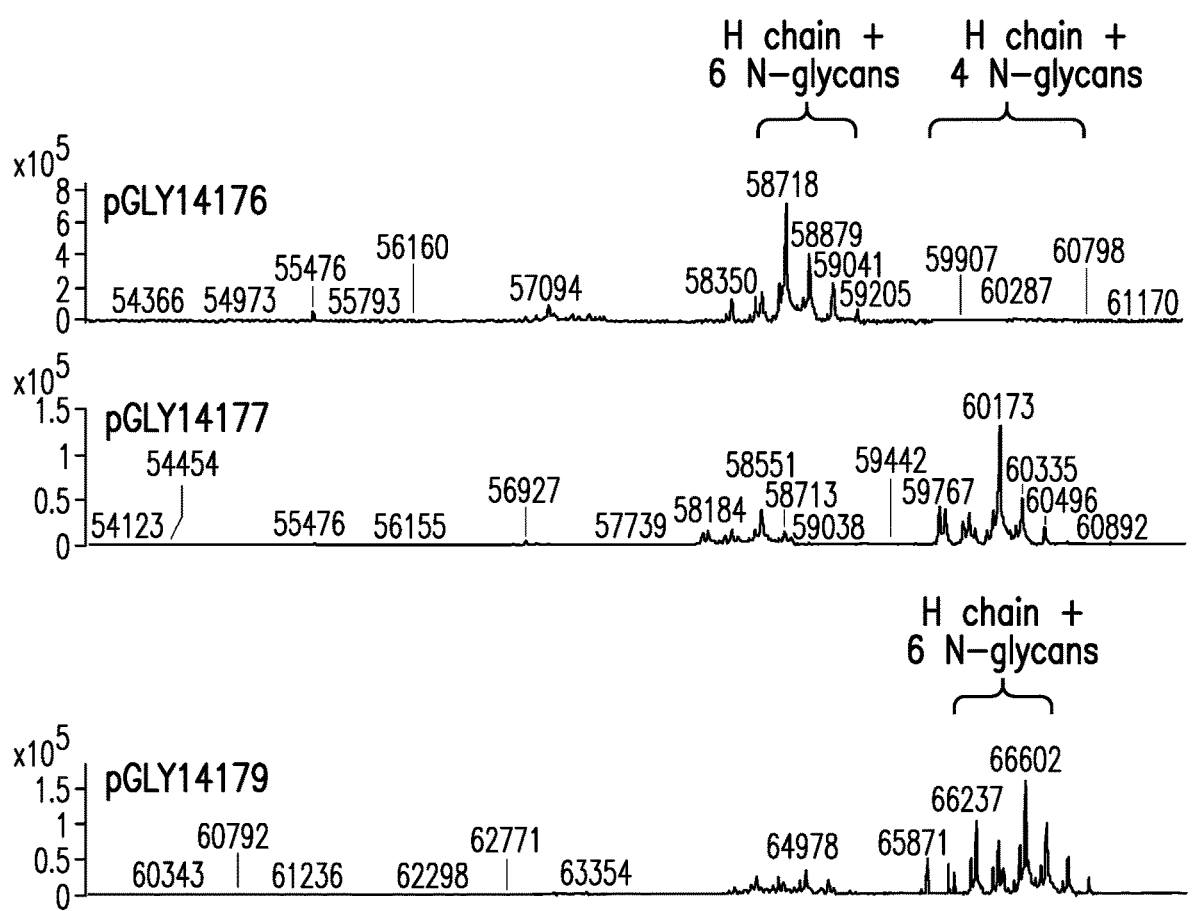

Several clones from strain YGLY30329 expressing plasmids pGLY14172-14179 were cultivated in Dasgip 1 L fermenters as described in Example 3 above. Following around 80-90 h of methanol induction, supernatants were harvested by centrifugation and purified by standard protein A chromatography (Example 3 above and Jiang, 2011). The purified Abs from these strains were then subjected to Q-ToF MS under reducing conditions (see example 2 above). The results, illustrated in FIGS. 28A and 28B, reveal again that the non-native N-glycosylation sites are occupied in each of the newly constructed antibody sequences. Here, with precise mass identification, it can be determined that in each

TABLE 5

| Plasmid name | Mutation (EU numbering) | Mutation (Herceptin numbering) | Mutation (Kabat numbering) | H chain Sequence |
|---|---|---|---|---|
| pGLY14172 | S134N, G161T, N203T | S137, G164T, N206T | S130N, G158T, N211T | SEQ ID NO: 34 |
| pGLY14173 | N/A, N/A, S134N, G161T | K30T, Y57T, S137N, G164T | K30T, Y56T, S137N, G164T | SEQ ID NO: 35 |
| pGLY14174 | N/A, N/A, S134N, G161T | K30T, K65N/R67T, S137N, G164T | K30T, K64N/R66T, S130N, G158T | SEQ ID NO: 36 |
| pGLY14175 | N/A, N/A, S134N, G161T, N203T | Y57T, K65N/R67T, S137N, G164T, N206T | Y56T, K64N/R66T, S130N, G158T, N211T | SEQ ID NO: 37 |
| pGLY14176 | N/A, S134N, G161T, S176N/G178T, N203T | Y57T, S137N, G164T, S179N/G181T, N206T | Y56T, S130N, G158T, S180N/G183T, N211T | SEQ ID NO: 38 |
| pGLY14177 | N/A, N/A, N/A, S134N, G161T, N203T | K30T, Y57T, K65N/R67T, S137N, G164T, N206T | K30T, Y56T, K64N/R66T, S130N, G158T, N211T | SEQ ID NO: 39 |
| PGLY14178 | N/A, N/A, N/A S134N, G161T, S176N/G178T, N203T, V363T, K392T, F423T | K30T, Y57T, K65N/R67T, S137N, G164T, S179N/G181T, N206T, V366T, K395T, F246T | K30T, Y56T, K64N/R66T, S130N, G158T, S180N/G183T, N211T, V386T, K420T, F454T | SEQ ID NO: 40 |
| pGLY14179 | N/A, N/A, N/A, S134N, G161T, L193N, N203T, V363T, K392T, F423T | K30T, Y57T, K65N/R67T, S137N, G164T, L196T, N206T, V366T, K395T, F426T | K30T, Y56T, K64N/R66T, S130N, G158T, L198N, N211T, V386T, K420T, F454T | SEQ ID NO: 41 | case at least the majority of the antibody contains the number of N-glycans as engineered. In most cases there is very little evidence of reduced occupancy at any of the sites. Moreover, it can also be observed that in most cases a single peak is predominantly visible, corresponding to a mass of the H chain plus the corresponding number of N-glycans with the GS5.0 structure (FIG. 2). Importantly, this indicates that the Abs in each case are able to be occupied with a specified number of N-glycans at preselected sites, properly assembled in the ER, and fully glycan matured in the Golgi with high integrity, all of which is required for the desired substrate for efficient conjugation.

Example 13: Highly Sialylated mAbs

In addition to generating highly glycan-modified Abs with terminal galactose for conjugation purposes, it could be desirable to produce antibodies with a high degree of sialylation in the same manner. Such Abs could be used for conjugation by chemical modification of the sialic acid residues (Ramya, 2013).

Figure 29A:
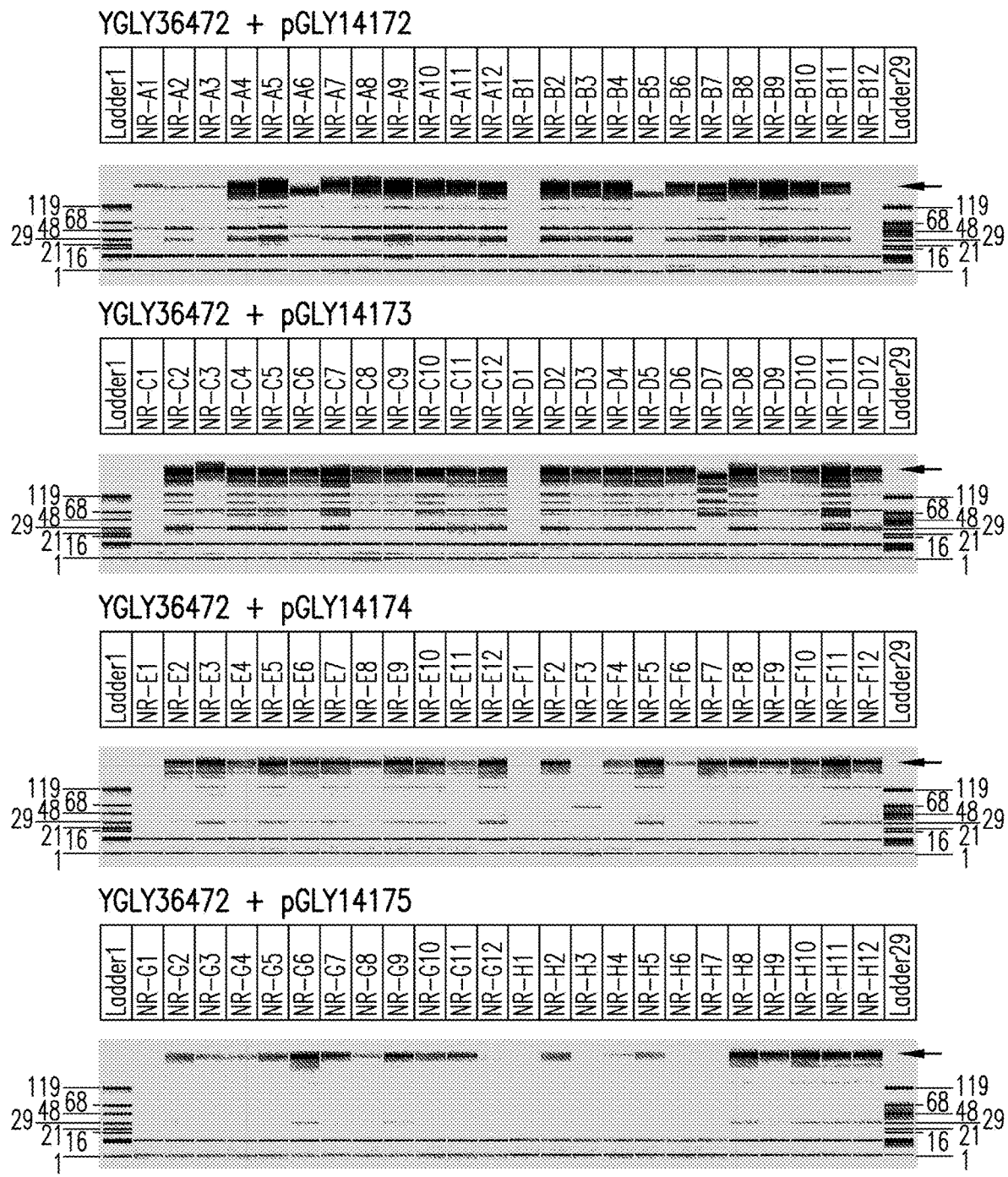
FIG. 29 (A-B): Capillary electrophoresis analysis of sialylated N-glycan modified antibodies containing three to ten additional N-glycans. The plasmids indicated in Table 5 were transformed into GS6.0 (see FIG. 2) glycoengineered strain YGLY36472 and Zeocin resistant clones were cultivated in 96 deep well plates. Protein A purified protein was analyzed by capillary electrophoresis under denatured, non-reducing conditions. Arrows indicate the presence of an antibody tetramer band in the non-reduced samples and the antibody H and L chain monomers in the reduced samples. Sizes are indicated by the markers at the far left.
Figure 29B:
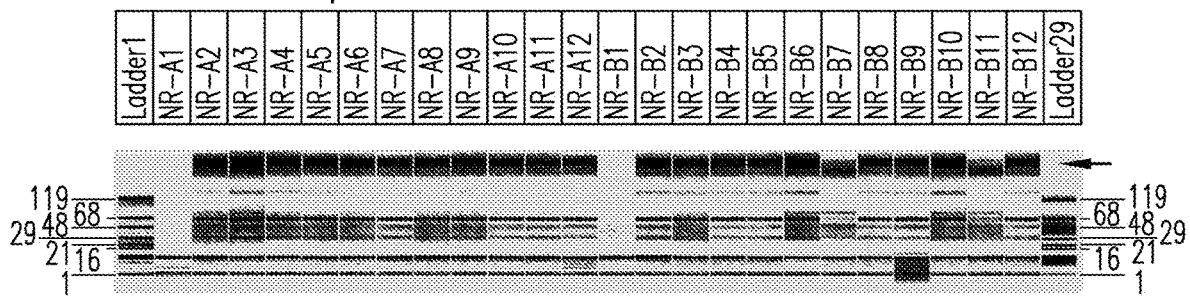
Figure 29B:
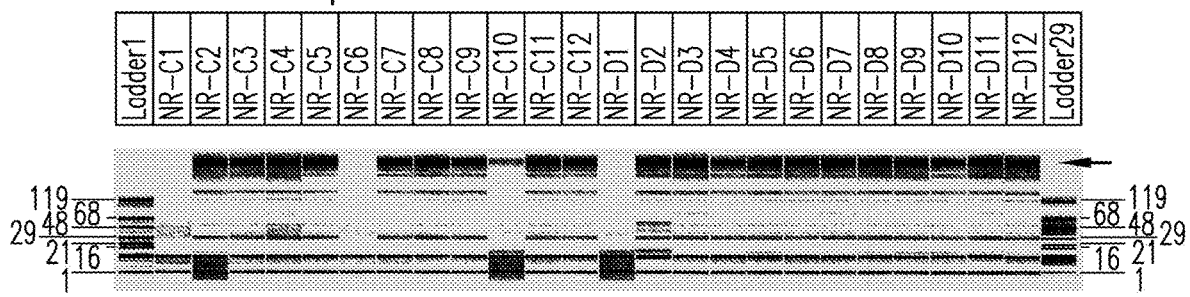
Figure 29B:
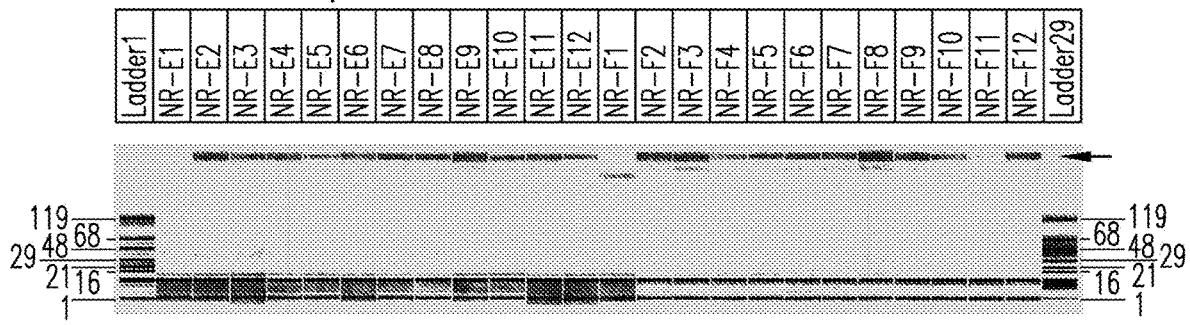
Figure 29B:
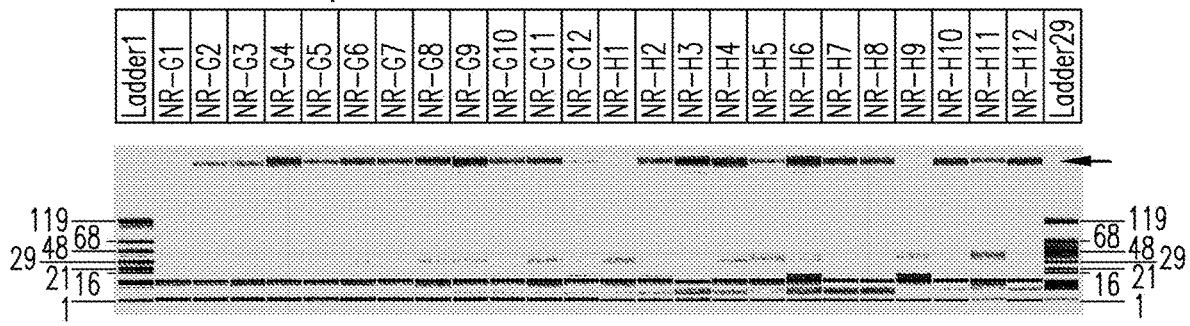
Figure 30:
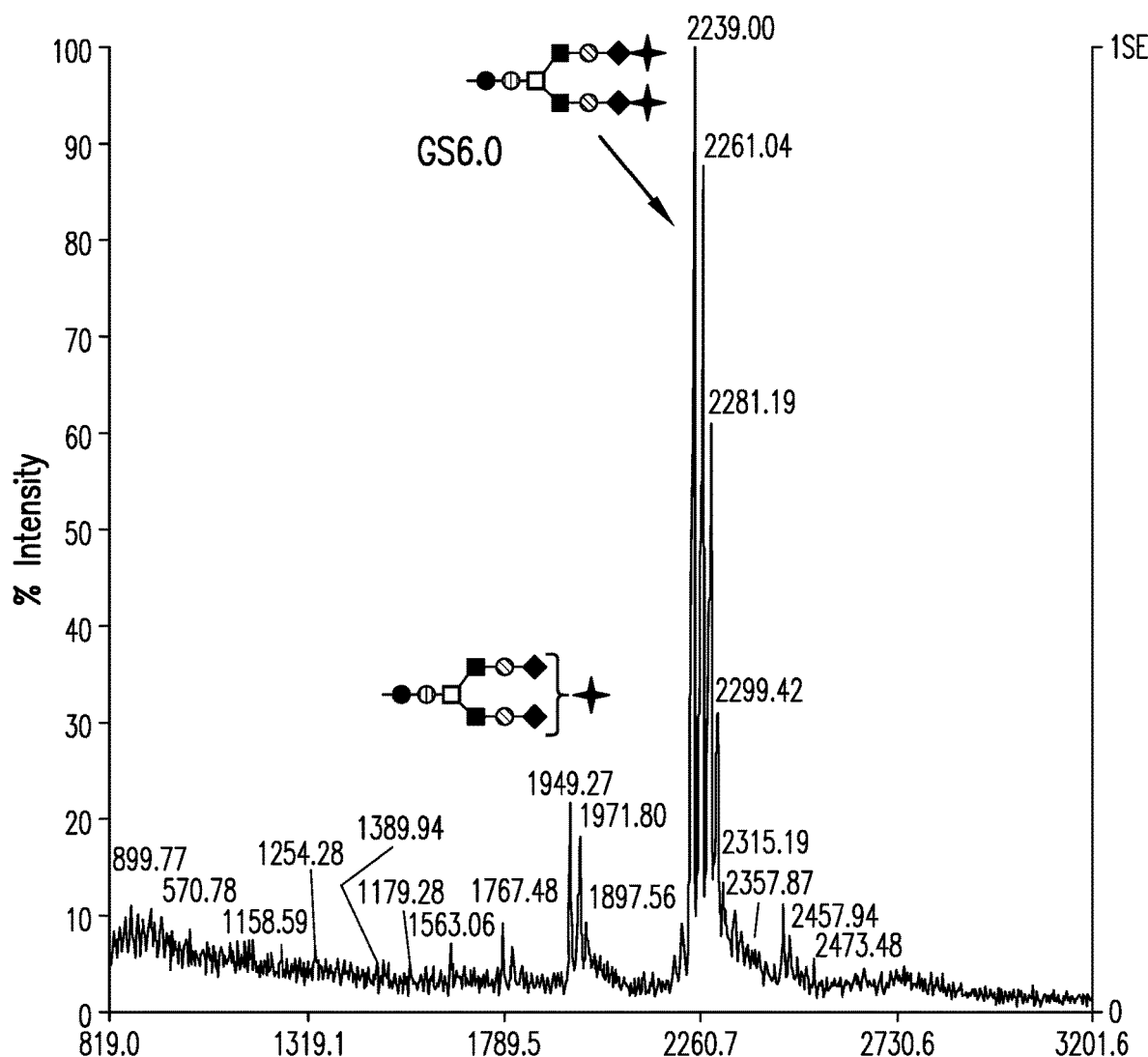
FIG. 30: MALDI-TOF MS of released N-glycans from a multi-position glycan-engineered antibody. A MALDI-TOF mass spectrum in negative ion mode of released N-glycans from an antibody protein A purified from a clone of plasmid pGLY14179 expressed in GS6.0 strain YGLY36472 (see FIG. 2 and Table 5), following cultivation of the clone in a 1 L fermenter. The spectrum is gated to include masses consistent with N-glycans and the masses representative of predicted GS6.0 and a singly sialylated version are identified.
Figure 31A:
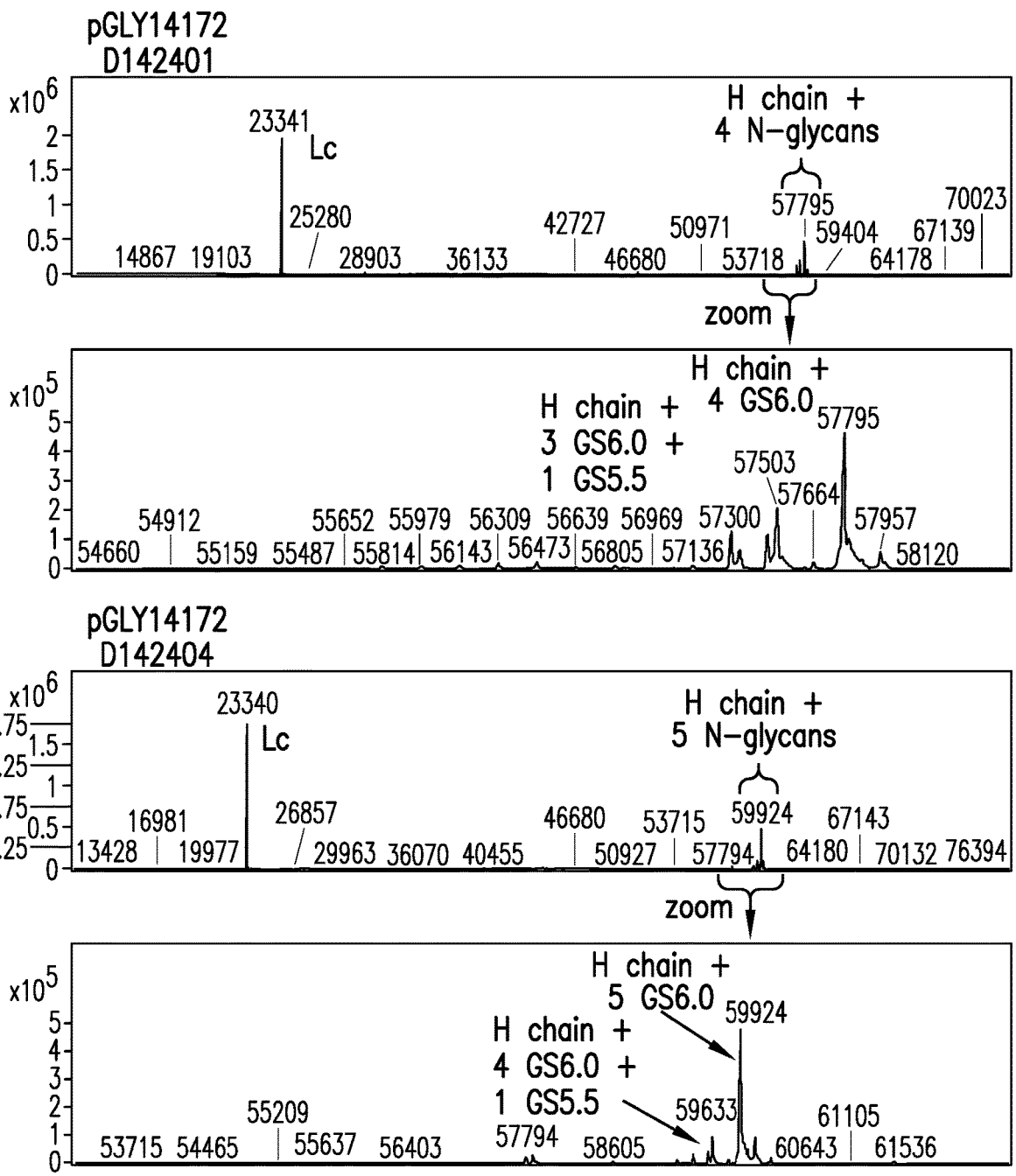
FIG. 31 (A-D): Q-ToF Mass spectrometry analysis of glycan-engineered antibodies with more than two additional N-glycan sites expressed with GS6.0 N-glycans. Deconvoluted Q-ToF mass spectra of reduced antibodies that have been glycan-engineered to incorporate from three to ten non-native N-glycosylation sites resulting from transformation of plasmids: A, pGLY14172 and 14173; B, pGLY14174 and 14175; C, pGLY14176 and 14177; or D, pGLY14178 and 14179 (see Table 5) into a GS6.0 glycoengineered *Pichia* strain (see FIG. 2), and following 1 L fermentation and protein A purification. The resulting spectra are paired and gated to include first both the predicted L and H chain masses and then zoomed to include only the predicted H chain masses. Where individual peaks closely match predicted masses, these glycosylated species are identified.
Figure 31B:
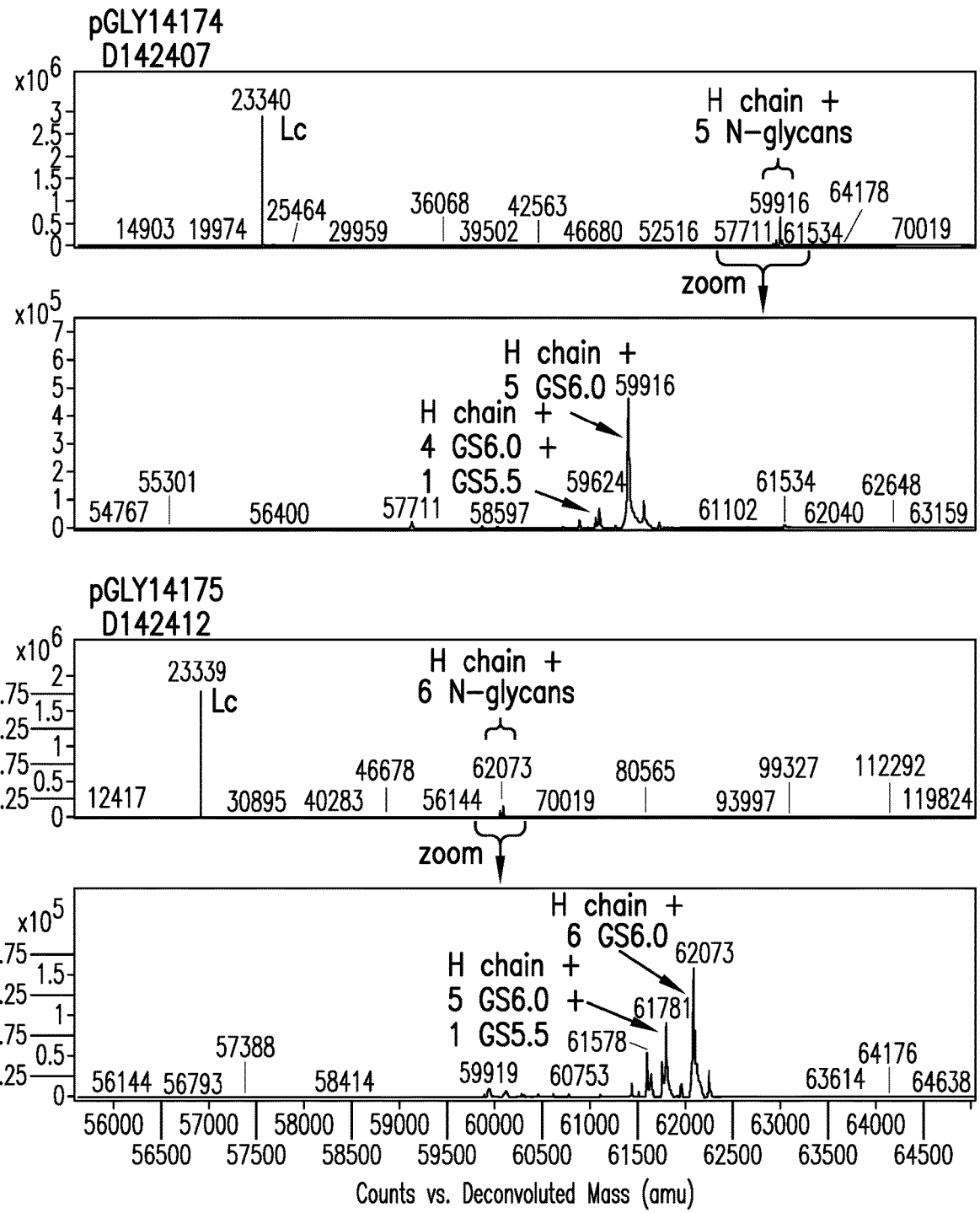
Figure 31C:
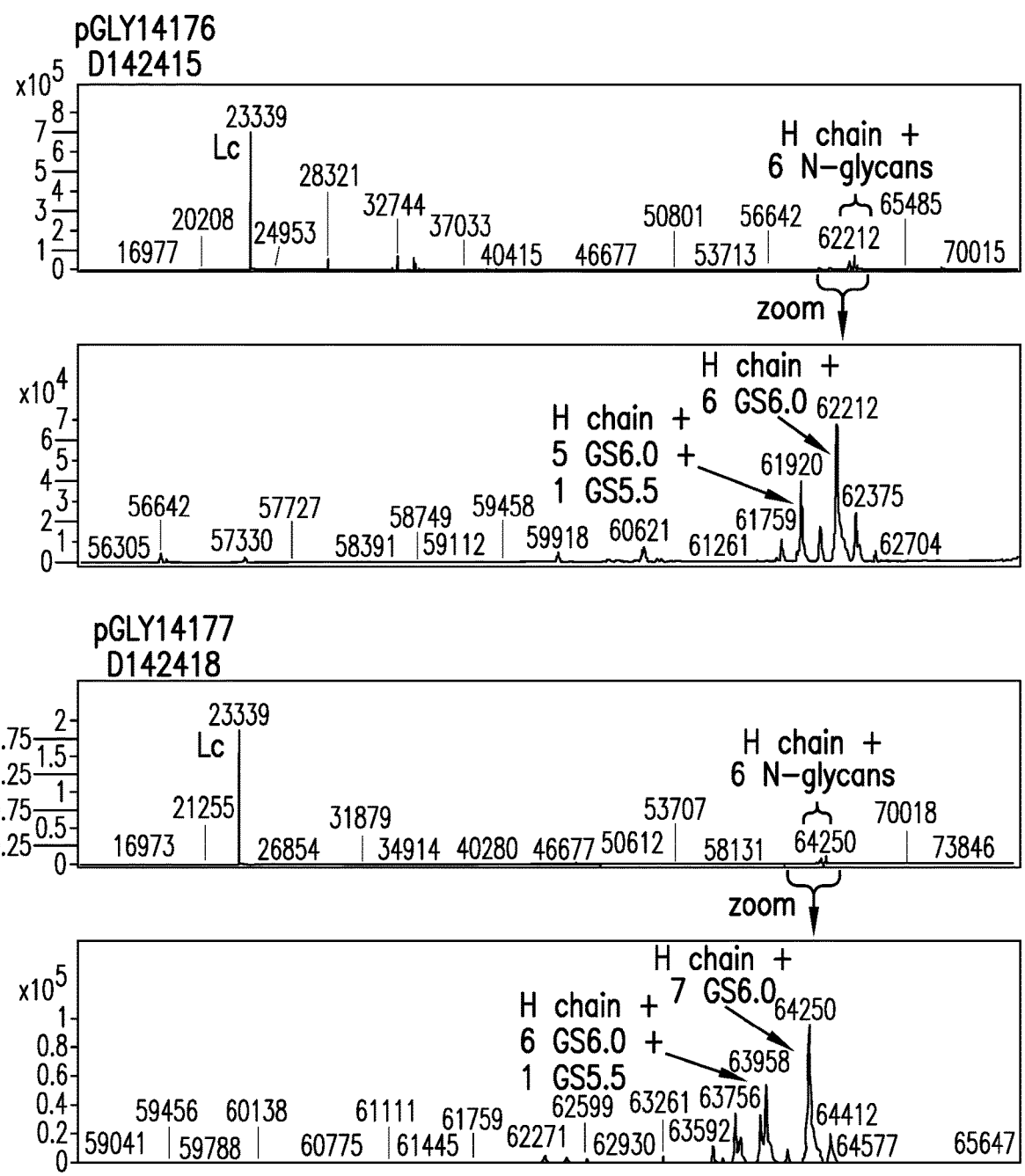
Figure 31D:
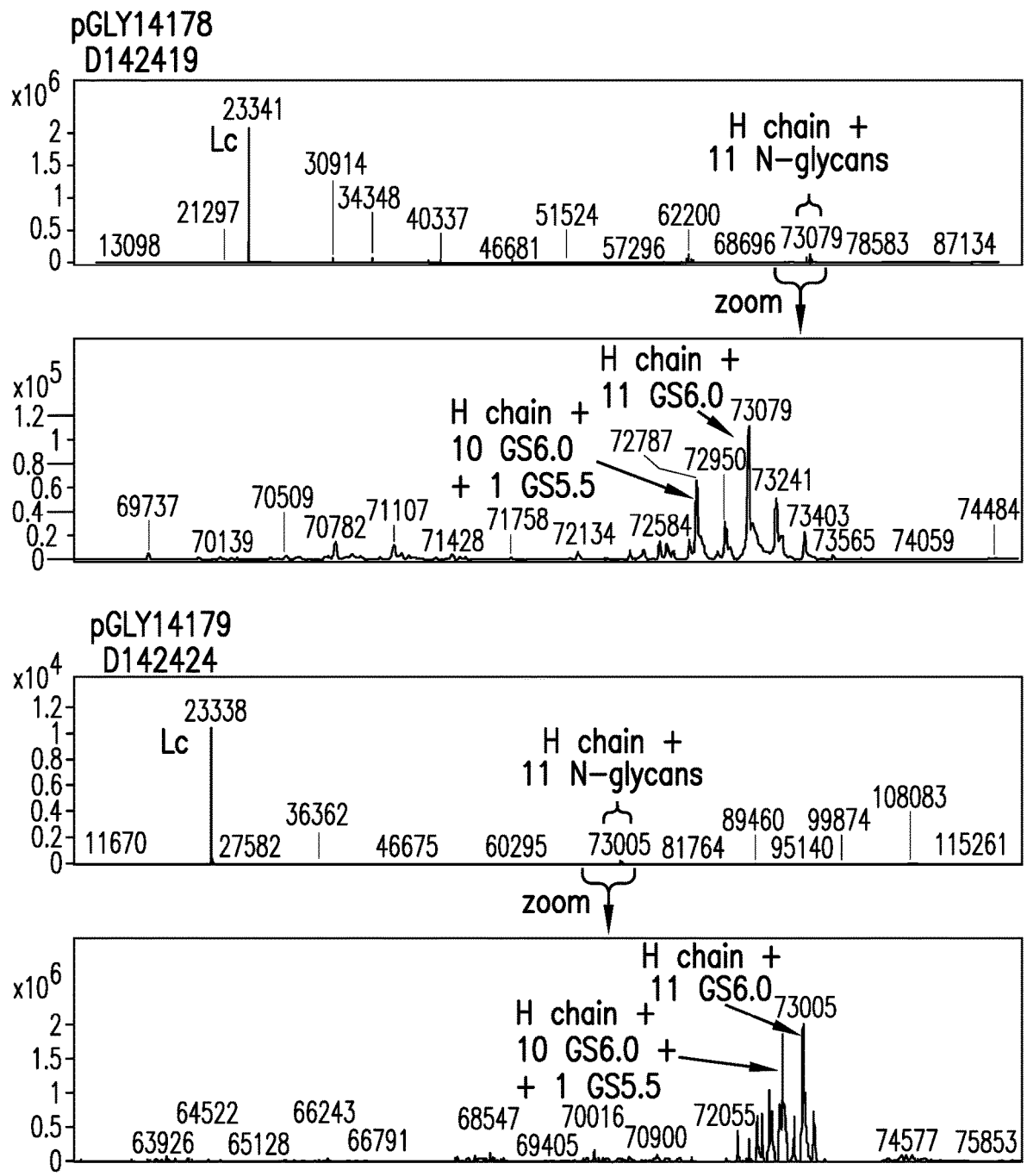

To generate mAbs with a high degree of sialylation, the plasmids illustrated in Example 12 (see table 5) were transformed into Glycoengineered *Pichia* strain YGLY36472 capable of modifying secreted proteins with the biantennary sialylated human N-glycan (see, e.g., Hamilton, 2006; FIG. 2, GS6.0). Clones were selected and screened for secretion of antibody in 96 DWP format as described in Example 1. Supernatants from these 96 DWP cultures were harvested by centrifugation at 2500×g in a Beckman swinging bucket centrifuge and purified by protein A chromatography as described previously (Barnard, 2010). The purified samples were subjected to non-reducing CE analysis on a Labchip GXII instrument (Caliper Life Sciences, Hopkinton, Mass.) using the standard HT Protein Express 200 method as described (Gomathinayagam, 2012). As illustrated in FIGS. 29A and 29B using the Labchip GX gel image software version 4.1, it can be concluded that most of the additional N-glycosylation sites were indeed occupied due to the shifts in migration. Moreover, it can also be observed in these non-reduced samples that the assembly, while somewhat clone- and plasmid-dependent is very robust overall with generally a single predominant band in each lane as illustrated by (FIGS. 29A and B). Moreover, when the N-glycans from these Abs were released and analyzed by MALDI-TOF as described (Choi, 2003). The predominant N-glycan observed in most clones was consistent with $NANA_2Gal_2GlcNAc_2Man_3GlcNAc_2$ (FIG. 2, GS6.0) based on mass with the $2^{nd}$ most predominant species being $NANAGal_2GlcNAc_2Man_3GlcNAc_2$. A representative MALDI-TOF MS trace from a clone resulting from introducing plasmid pGLY14179 into strain YGLY36472 is depicted in FIG. 30. Moreover, the purified intact Abs from these strains were subjected to Q-ToF MS under reducing conditions (see example 2 above). The results, illustrated in FIGS. 31A, 31B, 31C, and 31D, reveal that the non-native N-glycosylation sites are occupied in each of the constructed antibody sequences in GS6.0 strains similar to in GS5.0 strains. Here, with precise mass identification, it can be determined that in each case at vast the majority of the antibody contains the number of N-glycans as engineered. In most cases there is very little evidence of reduced occupancy at any of the sites. Moreover, it can also be observed that in most cases a single peak is predominantly visible, corresponding to a mass of the H chain plus the corresponding number of N-glycans with the GS6.0 structure (FIG. 2), indicating that antibodies modified with non-native N-glycosylation sites can be expressed efficiently in GS6.0 strains and are suitable for conjugation by the methods described herein.

Example 14: Generation of Additional Abs with Non-Native N-Glycosylation Sites

Figure 32:
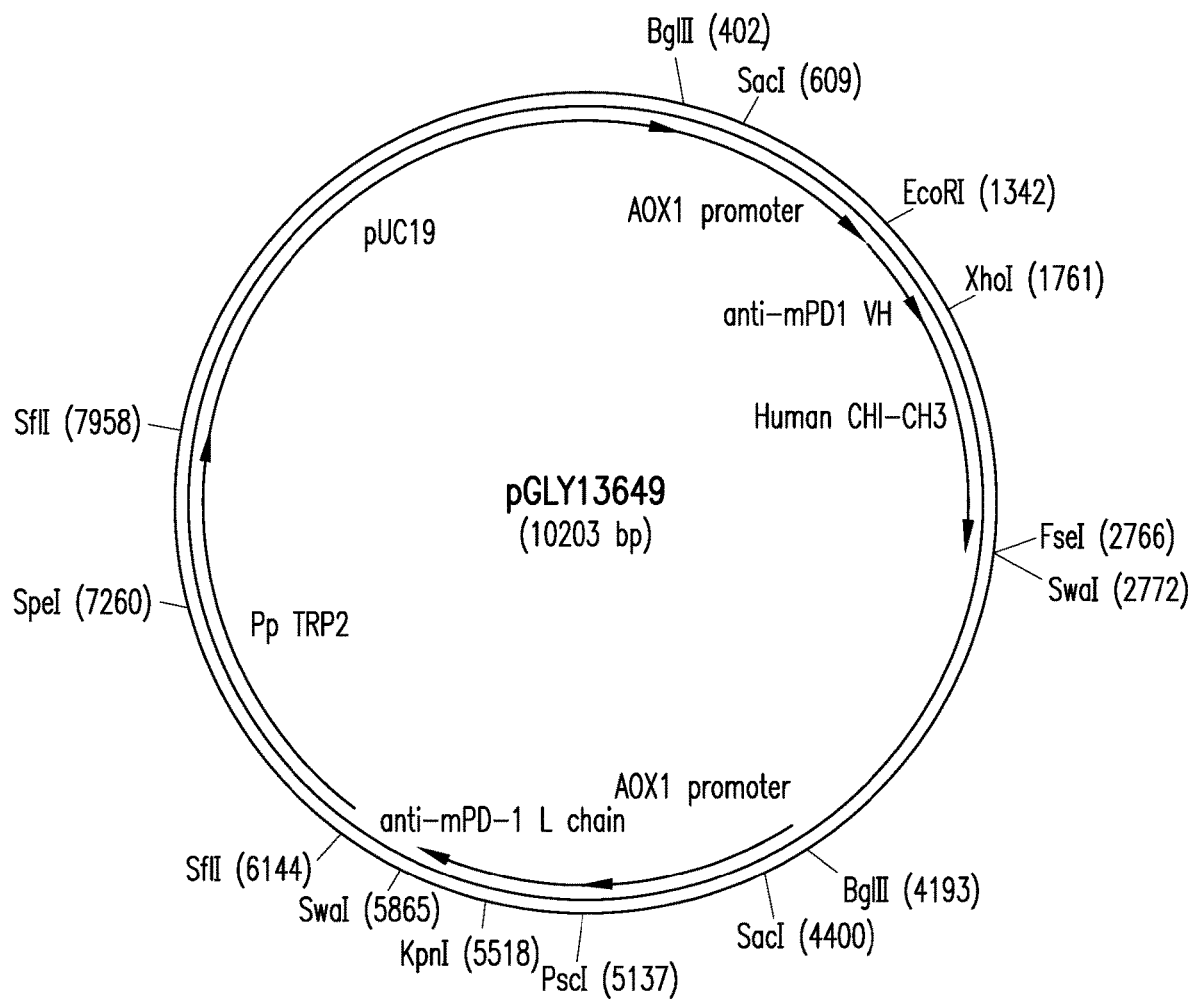
FIG. 32: Restriction map of plasmid pGLY13649. The *E. coli/P. pastoris* shuttle vector is depicted circularly as it is maintained in *E. coli*. The plasmid contains the pUC19 Ori and AmpR region for *E. coli* maintenance as well as the Sh ble gene encoding Zeocin resistance (not marked) and the *P. pastoris* TRP2 gene, used as an integration site. The genes encoding an anti-murine PD1 antibody H chain and L chain are contained as separate cassettes, each initiated with the *P. pastoris* AOX1 promoter.
Figure 33:
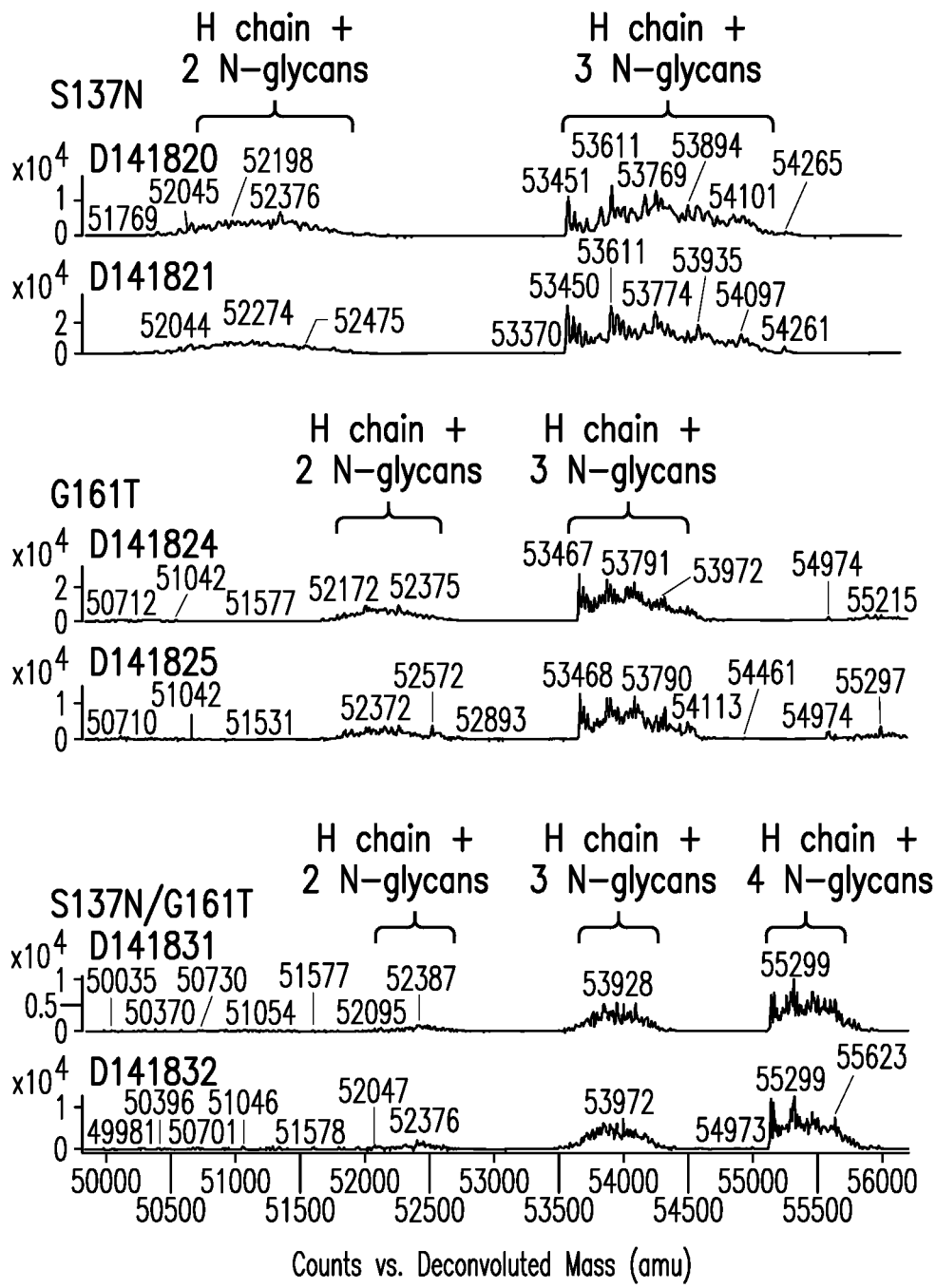
FIG. 33: Q-ToF Mass spectrometry analysis of an N-glycan engineered anti-PD1 antibody. Deconvoluted mass spectra of reduced glycan-engineered anti-murine PD1 antibodies modified to incorporate one or two non-native N-glycosylation sites, then isolated and purified by protein A from clones cultivated in 1 L fermenters. The incorporated mutations (EU numbering) are noted for each modified antibody and the expected mass range for H chain with two, three, and four N-glycans is indicated (the anti-murine mAb clone contains a H chain CDR N-glycan in addition to the Fc-297 N-glycan in the native sequence).

To assure that the efficient modification of the anti-HER2 antibody with non-canonical N-glycans is not restricted to the anti-HER2 sequence we modified additional mAb sequences with different antigen-binding Fab regions. A pair (H and L) of variable domain sequences directed against the murine Programmed Cell Death 1 (PD-1) ligand was constructed as a human IgG1 chimera (Seq ID 42 and 43). This chimeric mAb sequence was further modified to incorporate the S134N (EU, Seq ID 44) or G161T (EU, Seq ID 45) mutations, which each add one additional N-glycan to the CH1 domain or the combined S137N/G161T mutations (EU, Seq ID 46), which adds two additional N-glycans per H chain. The original anti-mPD-1 H chain sequence (pGLY13649, FIG. 32) was modified using site-directed mutagenesis by Genewiz (South Plainfield, N.J.) to generate plasmids pGLY14163 (S134N), pGLY14164 (G161T), and pGLY14165 (S134N/G161T). These plasmids were transformed into strain YGLY30329 and clones were selected and screened for mAb secretion as described in Examples 1 and 2 above. Clones deemed to be expressing antibody were then cultivated in 1 L Dasgip fermenters as described in Example 3 above. The fermentation supernatant was purified by protein A chromatography and the resulting protein subjected to Q-ToF analysis. Each of the S134N, and G161T single mutein mAbs was efficiently glycosylated at 3 sites on each reduced H chain, the canonical N-297 site, a variable chain site that was part of the anti-PD-1 CDR sequence, and the non-native N-glycosylation (either N134 or N159) site with a majority of GS5.0 biantennary terminally galactosylated N-glycans at both the CDR N-glycan and at the non-native site and a mixture of GS4.0, GS4.5 and GS5.0 N-glycans at the N-297 site (FIG. 33). Similarly, the S134N/G161T double mutein containing mAbs were efficiently glycosylated at 4 sites on each reduced H chain (FIG. 33).

Figure 34:
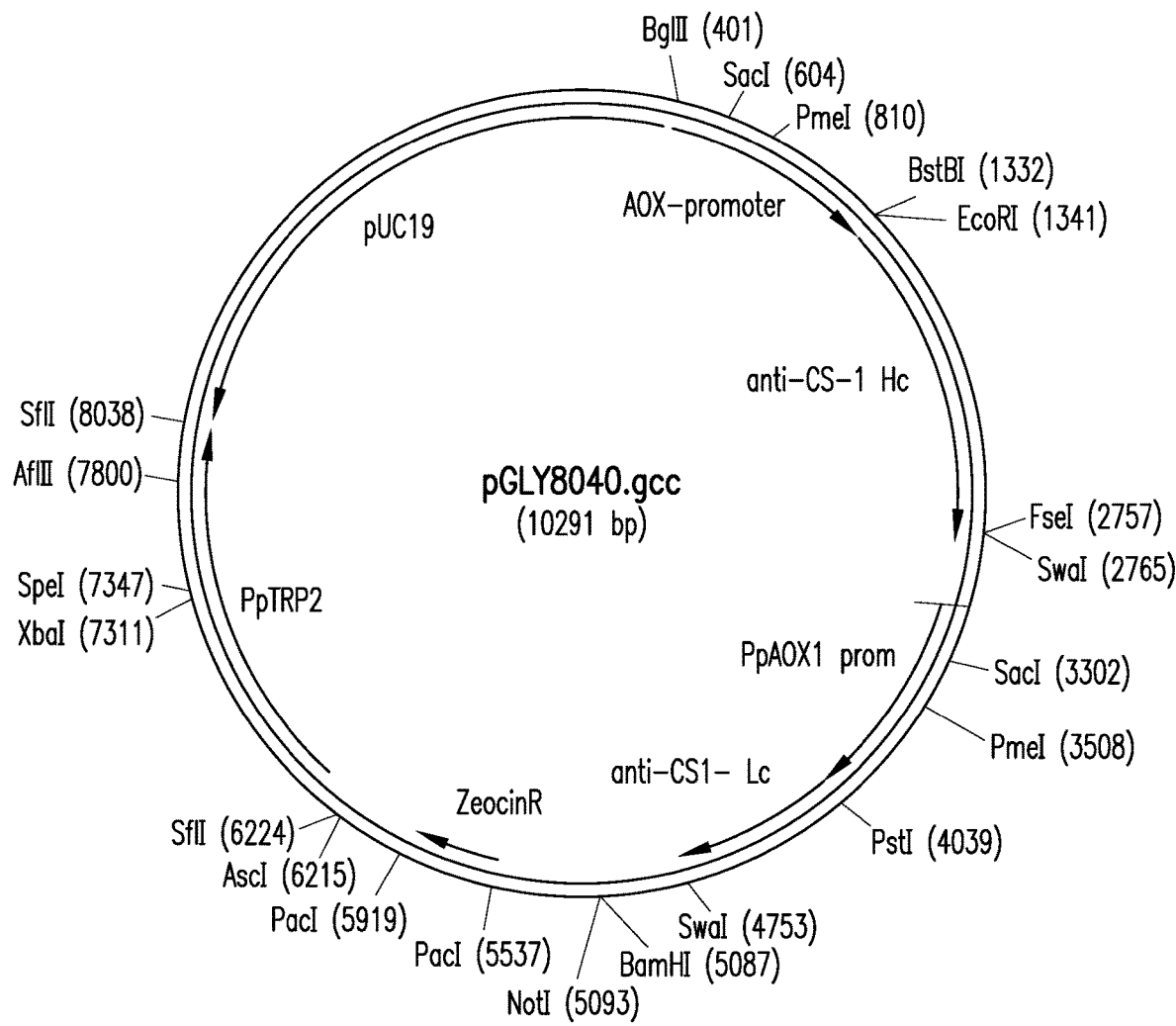
FIG. 34: Restriction map of plasmid pGLY8040. The *E. coli/P. pastoris* shuttle vector is depicted circularly as it is maintained in *E. coli*. The plasmid contains the pUC19 Ori and AmpR region for *E. coli* maintenance as well as the Sh ble gene encoding Zeocin resistance (not marked) and the *P. pastoris* TRP2 gene, used as an integration site. The genes encoding an anti-CS1 antibody H chain and L chain are contained as separate cassettes, each flanked with the *P. pastoris* AOX1 promoter and a transcriptional terminator (not marked).
Figure 35:
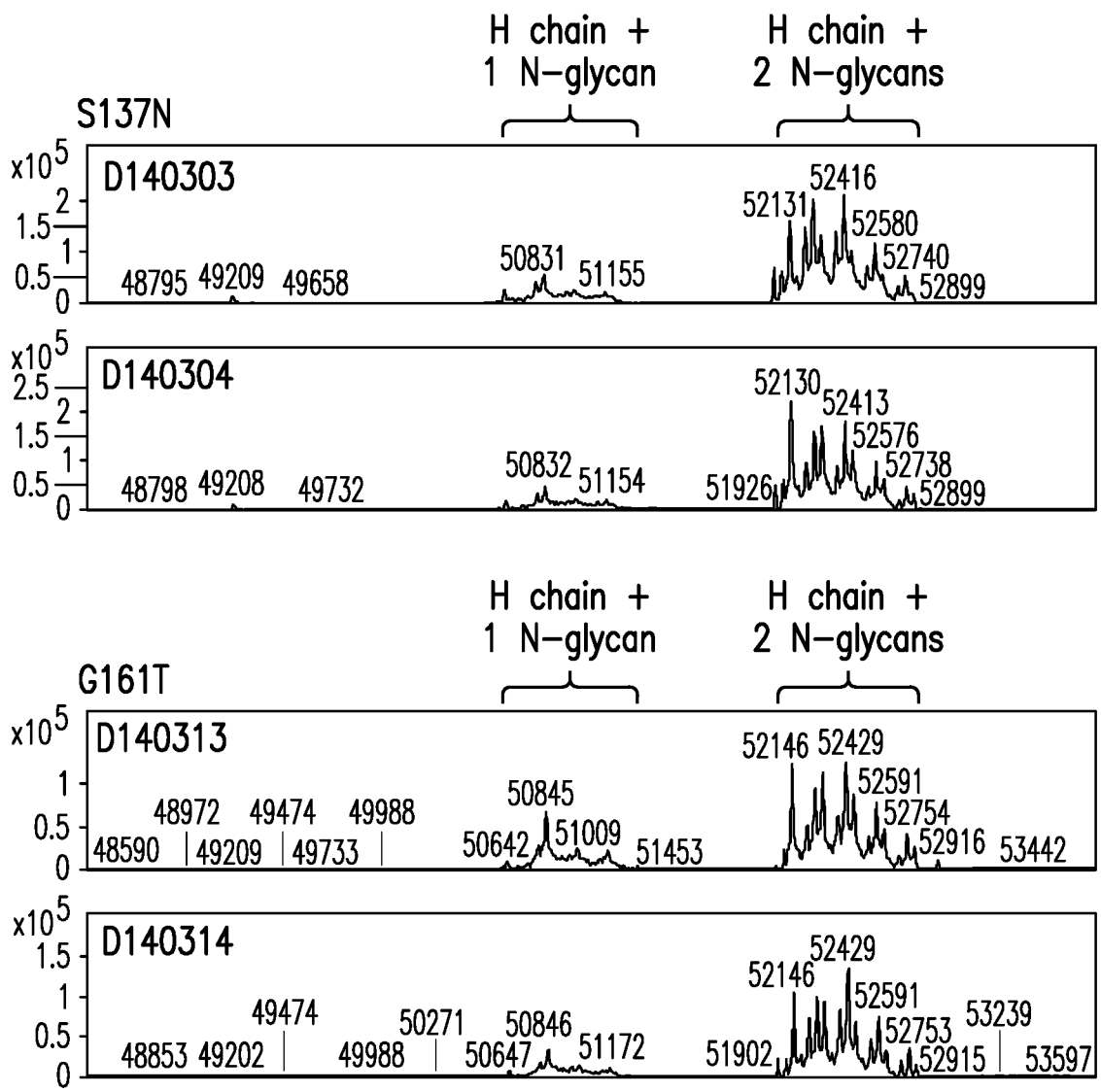
FIG. 35: Q-ToF Mass spectrometry analysis of an N-glycan engineered anti-CS1 antibody. Deconvoluted mass spectra of reduced glycan-engineered anti-murine PD1 antibodies modified to incorporate two separate non-native N-glycosylation sites, then isolated and purified by protein A from clones cultivated in 1 L fermenters. The incorporated mutations (EU numbering) are noted for each modified antibody and the expected mass range for H chain with one or two N-glycans is indicated.

In addition to the anti-mPD-1 Ab sequence, an anti-CS1 Ab sequence H chain and L chain (Zha 2013, Seq ID 47 and Seq ID 48, respectively) was modified to incorporate the same sets of mutations, S134N (EU, Seq ID 49), G161T (EU, Seq ID 50), and the double mutant S134N/G161T (EU, Seq ID 51). The original anti-CS-1 H chain sequence (pGLY8040, FIG. 34) was modified using site-directed mutagenesis by Genewiz (South Plainfield, N.J.) to generate plasmids pGLY14157 (S134N), pGLY14158 (G161T), and pGLY14159 (S134N/G161T). These plasmids were transformed into strain YGLY30329 and clones were selected and screened for mAb secretion as described in Examples 1 and 2 above. Clones deemed to be expressing antibody were then cultivated in 1 L Dasgip fermenters as described in Example 3 above. The fermentation supernatant was purified by protein A chromatography and the resulting protein subjected to Q-ToF analysis. Each of the S134N, and G161T single mutein mAbs was efficiently glycosylated at 2 sites on each reduced H chain, the canonical N-297 site, and the non-canonical (either N134 or N159) site with a majority of GS5.0 biantennary terminally galactosylated N-glycans at the non-canonical site and a mixture of GS4.0, GS4.5 and GS5.0 N-glycans at the N-297 site (FIG. 35). Similarly, the S134N/G161T double mutein containing mAbs were efficiently glycosylated at 3 sites on each reduced H chain (FIG. 35).

Figure 36:
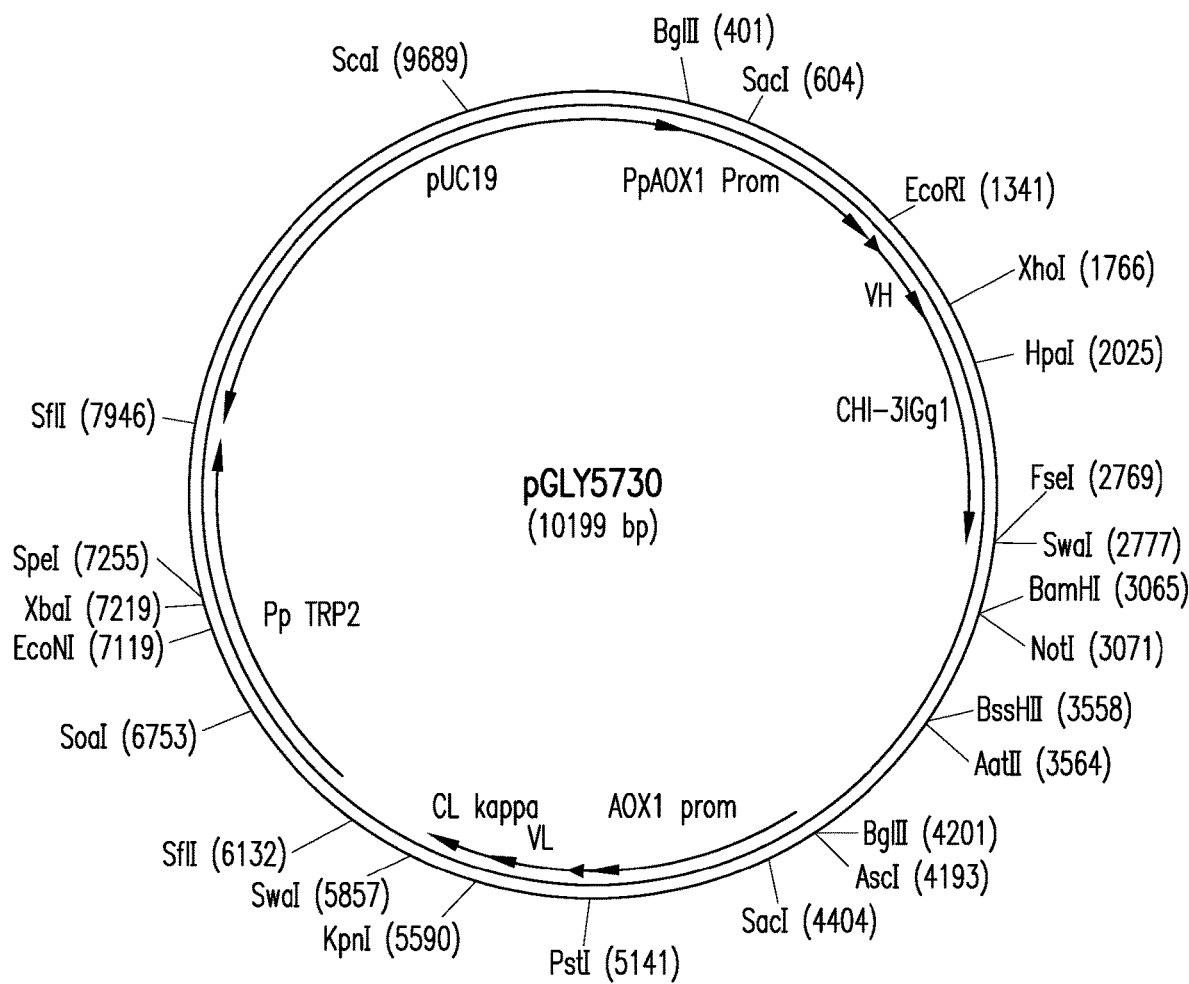
FIG. 36: Restriction map of plasmid pGLY5730. The *E. coli/P. pastoris* shuttle vector is depicted circularly as it is maintained in *E. coli*. The plasmid contains the pUC19 Ori and AmpR region for *E. coli* maintenance as well as the Sh ble gene encoding Zeocin resistance (not marked) and the *P. pastoris* TRP2 gene, used as an integration site. The genes encoding an antibody H chain and L chain (with the D2E7 anti-TNFα variable regions from commercial antibody adalimumab) are contained as separate cassettes, each flanked with the *P. pastoris* AOX1 promoter and a transcriptional terminator (not marked).
Figure 37:
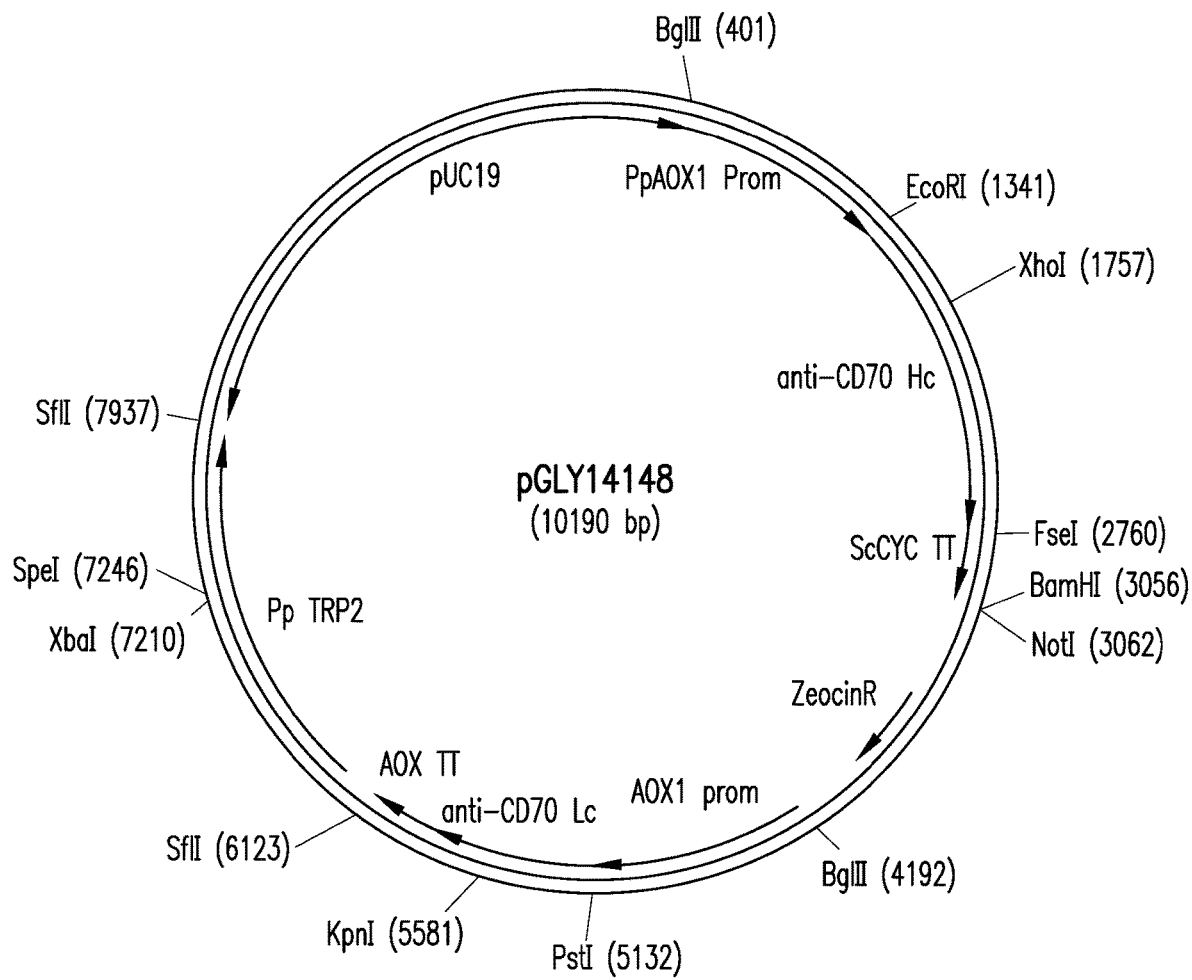
FIG. 37: Restriction map of plasmid pGLY14148. The *E. coli/P. pastoris* shuttle vector is depicted circularly as it is maintained in *E. coli*. The plasmid contains the pUC19 Ori and AmpR region for *E. coli* maintenance as well as the Sh ble gene encoding Zeocin resistance (ZeocinR) and the *P. pastoris* TRP2 gene, used as an integration site. The genes encoding an anti-CD70 antibody H chain and L chain are contained as separate cassettes, each flanked with the *P. pastoris* AOX1 promoter and a transcriptional terminator (TT).
Figure 38:
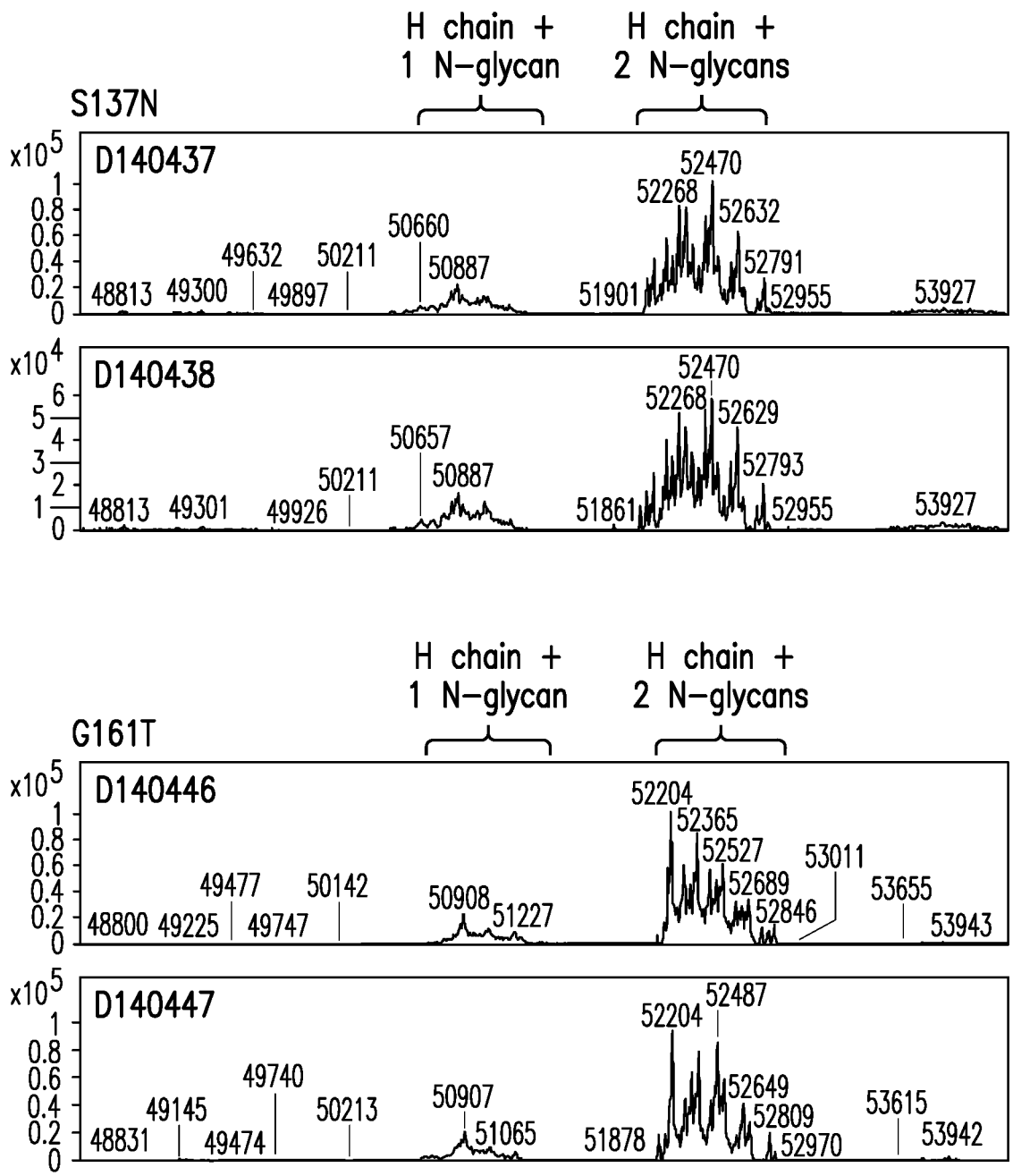
FIG. 38: Q-ToF Mass spectrometry analysis of an N-glycan engineered anti-CD70 antibody. Deconvoluted mass spectra of reduced glycan-engineered anti-CD70 antibodies modified to incorporate two separate non-native N-glycosylation sites, then isolated and purified by protein A from clones cultivated in 1 L fermenters. The incorporated mutations (EU numbering) are noted for each modified antibody and the expected mass range for H chain with one or two N-glycans is indicated.

Finally, a previously published anti-CD70 antibody sequence (Coccia, USapp 2010/0150950 A1) was modified to incorporate the same sets of mutations, S134N (EU), G161T (EU), and the double mutant (S134N/G161T). The anti-CD70 VH and VL sequences (Seq ID 52 and 53, respectively) were synthesized and constructed by Genewiz (South Plainfield, N.J.) in a human IgG1 framework by cloning into plasmid pGLY5730 (FIG. 36) to generate a *P. pastoris* IgG1 anti-CD70 expression plasmid named pGLY14148. This plasmid was then further modified to incorporate three sets of N-glycan site-generating muteins to generate plasmids pGLY14149 (S134N, Seq ID 54), pGLY14150 (G161T, Seq ID 55), and pGLY14151 (S134N/G161T, Seq ID 56). These plasmids were transformed into strain YGLY30329 and clones were selected and screened for mAb secretion as described in Examples 1 and 2 above. Clones deemed to be expressing antibody were then cultivated in 1 L Dasgip fermenters as described in Example 3 above. The fermentation supernatant was purified by protein A chromatography and the resulting protein subjected to Q-ToF analysis. Each of the S134N, and G161T single mutein mAbs was efficiently glycosylated at 2 sites on each reduced H chain, the canonical N-297 site, and the non-canonical (either N134 or N159) site with a majority of GS5.0 biantennary terminally galactosylated N-glycans at the non-canonical site and a mixture of GS4.0, GS4.5 and GS5.0 N-glycans at the N-297 site (FIG. 37). Similarly, the S134N/G161T double mutein containing mAbs were efficiently glycosylated at 3 sites on each reduced H chain (FIG. 37).

We claim:

1. An engineered IgG antibody or heavy chain constant domain fragment comprising
an S134N mutation in the heavy chain constant domain, which forms a non-native N-glycosylation site having the amino acid sequence NTS over positions 134-136 of the heavy chain constant domain, said non-native N-glycosylation site having an N-glycan attached to the N at position 134, wherein the N-glycan has a Gal$_2$GlcNAc$_2$Man$_3$GlcNAc$_2$ glycoform in which the terminal galactose residues have been oxidized to a C-6 aldehyde group, which is conjugated to a reactive amine group of a derivatized drug by an oxime bond, and wherein the amino acid positions of the heavy chain constant domain are according to Eu numbering.

2. The engineered antibody or heavy chain constant domain fragment of claim 1, wherein the antibody or heavy chain constant domain fragment further comprises a G161T mutation, which forms a second non-native N-glycosylation site in the heavy chain constant domain having the amino acid sequence NST over positions 159-161 of the heavy chain constant domain, said second non-native N-glycosylation site having an N-glycan attached to the N at position 159, wherein the N-glycan has a Gal$_2$GlcNAc$_2$Man$_3$GlcNAc$_2$ glycoform in which the terminal galactose residues have been oxidized to have a C-6 aldehyde group, which is conjugated to a reactive amine group of a derivatized drug by an oxime bond, and wherein the amino acid positions of the heavy chain constant domain are according to Eu numbering.

3. The engineered IgG antibody or constant domain fragment of claim 1, wherein the IgG antibody is selected from the group consisting of anti-Her2, anti-Her2/neu, anti-glycoprotein IIb/IIIa, anti-TNF-α, anti-CD52, anti-CD25, anti-BAFF, anti-Vascular endothelial growth factor, anti-CD30, anti-IL-1β, anti-epidermal growth factor receptor, anti-RANK Ligand, anti-Complement C5, anti-CD11a, anti-CD33, anti-CD20, anti-CTLA-4, anti-T cell CD3 Receptor, anti-α-4 (α4) integrin, anti-Immunoglobulin E, anti-RSV F protein, anti-epidermal growth factor receptor, anti-VEGF-A, anti-ErbB2, anti-IL-12/IL-23, anti-integrin α4β7, anti-CD274, anti-3-amyloid, anti-4-1BB, anti-SAC, anti-5T4, anti-ACVR2B, anti-adenocarcinomaantigen, anti-AGS-22M6, anti-α-fetoprotein, anti-angiopoietin 2, anti-angiopoietin 3, anti-anthrax toxin, anti-AOC3, anti-B7-H3, anti-*Bacillus anthracia*, anti-β amyloid, anti-B-lymphoma cell, anti-C242 antigen, anti-05, anti-CA-125, anti-carbonic anhydrase 9, anti-cardiac myosin, anti-CCL11, anti-CCR4, anti-CCR5, anti-CD11/CD18, anti-CD125, anti-CD140a, anti-CD147, anti-CD15, anti-CD152, anti-CD154, anti-CD19, anti-CD2, anti-CD200, anti-CD22, anti-CD221, anti-CD23, anti-CD27, anti-CD28, anti-CD3, anti-CD3 epsilon, anti-CD30, anti-CD37, anti-CD38, anti-CD4, anti-CD40, anti-CD41, anti-CD44, anti-CD5, anti-CD51, anti-CD52, anti-CD56, anti-CD6, anti-CD70, anti-CD74, anti-CD79B, anti-CD80, anti-CEA, anti-CFD, anti-ch4D5, anti-CLDN18.2, anti-*C. difficile*, anti-clumping factor A, anti-CSF2, anti-cytomegalovirus, anti-CMV gp B, anti-DLL4, anti-DR5, anti-*E. coli* shiga toxin type-1 or 2, anti-EGFL7, anti-endotoxin, anti-EpCAM, anti-EpCAM/CD3, anti-episialin, anti-ERBB3, anti-*Escherichia coli*, anti-F protein, anti-FAP, anti-fibrin II, anti-β chain, anti-fibronectin extra domain-B, anti-folate receptor 1, anti-Frizzled receptor, anti-GD2 ganglioside, anti-GD3 ganglioside, anti-GMCSF receptor α-chain, anti-GPNMB, anti-Influenza, anti-Influenza hemagglutinin, anti-hepatitis B, anti-surface antigen, anti-HER1, anti-HER3, anti-HGF, anti-HHGFR, anti-HIV-1, anti-HLA-DR, anti-HNGF, anti-Hsp90, anti-human scatter factor receptor kinase, anti-human TNF, anti-human β-amyloid, anti-CD54, anti-IFN-α, anti-IFN-γ, anti-IgE Fc region, anti-IGF-1 receptor, anti-IGF-I, anti-IgG4, anti-IGHE, anti-IL-13, anti-IL-17, anti-IL-17A, anti-IL-10, anti-IL-22, anti-IL-23, anti-IL-4, anti-IL-5, anti-IL-6, anti-IL-6 receptor, anti-IL9, anti-ILGF2, anti-insulin-like growth factor I receptor anti-integrin α4, anti-integrin α5β1, anti-integrin α7β7, anti-integrin αIIbβ3, anti-integrin αvβ3, anti-interferon receptor, anti-interferon α/β receptor, anti-interferon γ-induced protein, anti-ITGA2, anti-KIR2D, anti-Lewis-Y antigen, anti-lipoteichoic acid, anti-LOXL2, anti-L-selectin (CD62L), anti-LTA, anti-MCP-1, anti-mesothelin, anti-MS4A1, anti-MUC1, anti-mucin CanAg, anti-myostatin, anti-NARP-1, anti-NCA-90, anti-NGF, anti-N-glycolylneuraminic acid, anti-NOGO-A, anti-Notch receptor, anti-NRP1, anti-*Oryctolagus cuniculus*, anti-OX-40, anti-oxLDL, anti-PCSK9, anti-PD-1, anti-PDCD1, anti-PDGF-R α, anti-phosphate-sodium co-transporter, anti-phosphatidylserine, anti-prostatic carcinoma cells, anti-*Pseudomonas aeruginosa*, anti-rabies virus, anti-rabies virus glycoprotein, anti-respiratory syncytial virus, anti-RHD, anti-Rhesus factor, anti-RON, anti-RTN4, anti-sclerostin, anti-SDC1, anti-selectin P, anti-SLAMF7, anti-SOST, anti-sphingosine-1-phosphate, anti-TAG-72, anti-T-cell receptor, anti-TEM1, anti-tenascin C, anti-TFPI, anti-TGFβ1, anti-TGFβ2, anti-TGF-β, anti-TRAIL-R1, anti-TRAIL-R2, anti-tumor antigen CTAA16.88, anti-TWEAK receptor, anti-TYRP1, anti-VEGF-A, anti-VEGFR-1, anti-VEGFR2, anti-vimentin, anti-VWF, anti-IL-1, anti-IL-2, anti-IL-5, anti-IL-8, anti-IL-12, anti-IL-15, anti-IL-18, anti-IL-20, anti-IL-21, anti-IL-23R, anti-IL-25, anti-IL-27, anti-IL-33, anti-CD14, anti-CD18, anti-CD64, anti-CD200, anti-CD200R, anti-TSLP, anti-TSLPR, anti-PDL1, anti-VLA-4, anti-E-selectin, anti-Fact II, anti-ICAM-3, anti-β2-integrin, anti-CBL, anti-LCAT, anti-CR3, anti-MDL-1, anti-GITR, anti-CGRP, anti-TRKA, anti-IGF1R, and anti-GTC.

4. The engineered IgG antibody or constant domain fragment of claim 1, wherein the IgG antibody is selected from the group consisting of abciximab, adalimumab, certolizumab pegol, golimumab, infliximab, alemtuzumab, basiliximab, belimumab, bevacizumab, brentuximab vedotin, canakinumab, cetuximab, daclizumab, denosumab, eculizumab, efalizumab, gemtuzumab, ibritumomab tiuxetan, ipilimumab, muromonab-cd3, natalizumab, ofatumumab, omalizumab, palivizumab, panitumumab, ranibizumab, rituximab, tocilizumab, atlizumab, tositumomab, trastuzumab, ustekinumab, and vedolizumab.

\* \* \* \* \*

SEQUENCE LISTING

<160> NUMBER OF SEQ ID NOS: 58

<210> SEQ ID NO 1
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 2
<211> LENGTH: 214
<212> TYPE: PRT
<213> ORGANISM: Artificial Sequence
<220> FEATURE:
<223> OTHER INFORMATION: immunoglobulin chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200             205

Phe Asn Arg Gly Glu Cys
    210

<210> SEQ ID NO 3
<211> LENGTH: 10216
<212> TYPE: DNA
<213> ORGANISM: Artificial Sequence
<220> FEATURE:
<223> OTHER INFORMATION: immunoglobulin chain

<400> SEQUENCE: 3

| | | | | | | |
|---|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcagggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | gagatctaac | atccaaagac | 420 |
| gaaaggttga | atgaaacctt | tttgccatcc | gacatccaca | ggtccattct | cacacataag | 480 |
| tgccaaacgc | aacaggaggg | gatacactag | cagcagaccg | ttgcaaacgc | aggacctcca | 540 |
| ctcctcttct | cctcaacacc | cacttttgcc | atcgaaaaac | cagcccagtt | attgggcttg | 600 |
| attggagctc | gctcattcca | attccttcta | ttaggctact | aacaccatga | ctttattagc | 660 |
| ctgtctatcc | tggccccccct | ggcgaggttc | atgtttgttt | atttccgaat | gcaacaagct | 720 |
| ccgcattaca | cccgaacatc | actccagatg | agggctttct | gagtgtgggg | tcaaatagtt | 780 |
| tcatgttccc | caaatggccc | aaaactgaca | gtttaaacgc | tgtcttggaa | cctaatatga | 840 |
| caaaagcgtg | atctcatcca | agatgaacta | agtttggttc | gttgaaatgc | taacggccag | 900 |
| ttggtcaaaa | agaaacttcc | aaaagtcggc | ataccgtttg | tcttgtttgg | tattgattga | 960 |
| cgaatgctca | aaaataatct | cattaatgct | tagcgcagtc | tctctatcgc | ttctgaaccc | 1020 |
| cggtgcacct | gtgccgaaac | gcaaatgggg | aaacacccgc | ttttttggatg | attatgcatt | 1080 |
| gtctccacat | tgtatgcttc | caagattctg | gtgggaatac | tgctgatagc | ctaacgttca | 1140 |
| tgatcaaaat | ttaactgttc | taaccctac | ttgacagcaa | tatataaaca | gaaggaagct | 1200 |
| gccctgtctt | aaacctttt | ttttatcatc | attattagct | tactttcata | attgcgactg | 1260 |
| gttccaattg | acaagctttt | gattttaacg | acttttaacg | acaacttgag | aagatcaaaa | 1320 |
| aacaactaat | tattcgaaac | ggaattcgaa | acgatgagat | tcccatccat | cttcactgct | 1380 |
| gttttgttcg | ctgcttcttc | tgctttggct | gaggttcagt | ggttgaatc | tggaggagga | 1440 |
| ttggttcaac | ctggtggttc | tttgagattg | tcctgtgctg | cttccggttt | caacatcaag | 1500 |
| gacacttaca | tccactgggt | tagacaagct | ccaggaaagg | gattggagtg | ggttgctaga | 1560 |
| atctacccaa | ctaacggtta | cacaagatac | gctgactccg | ttaagggaag | attcactatc | 1620 |
| tctgctgaca | cttccaagaa | cactgcttac | ttgcagatga | actccttgag | agctgaggat | 1680 |
| actgctgttt | actactgttc | cagatggggt | ggtgatggtt | tctacgctat | ggactactgg | 1740 |

```
ggtcaaggaa ctttggttac tgtttcctcc gcttctacta agggaccatc tgttttccca    1800
ttggctccat cttctaagtc tacttccggt ggtactgctg ctttgggatg tttggttaaa    1860
gactacttcc cagagccagt tactgtttct tggaactccg gtgctttgac ttctggtgtt    1920
cacactttcc cagctgtttt gcaatcttcc ggtttgtact ctttgtcctc cgttgttact    1980
gttccatcct cttccttggg tactcagact tacatctgta acgttaacca caagccatcc    2040
aacactaagg ttgacaagaa ggttgagcca aagtcctgtg acaagacaca tacttgtcca    2100
ccatgtccag ctccagaatt gttgggtggt ccatccgttt tcttgttccc accaaagcca    2160
aaggacactt tgatgatctc cagaactcca gaggttacat gtgttgttgt tgacgtttct    2220
cacgaggacc cagaggttaa gttcaactgg tacgttgacg gtgttgaagt tcacaacgct    2280
aagactaagc caagagaaga gcagtacaac tccacttaca gagttgtttc cgttttgact    2340
gttttgcacc aggactggtt gaacggtaaa gaatacaagt gtaaggtttc caacaaggct    2400
ttgccagctc caatcgaaaa gactatctcc aaggctaagg tcaaccaag agagccacag    2460 gtttacactt tgccaccatc cagagaagag atgactaaga accaggtttc cttgacttgt    2520
ttggttaaag gattctaccc atccgacatt gctgttgagt gggaatctaa cggtcaacca    2580
gagaacaact acaagactac tccaccagtt ttggattctg atggttcctt cttcttgtac    2640
tccaagttga ctgttgacaa gtccagatgg caacaggta acgttttctc ctgttccgtt    2700
atgcatgagg ctttgcacaa ccactacact caaaagtcct tgtctttgtc ccctggttaa    2760
tgaggccggc catttaaata caggcccctt ttcctttgtc gatatcatgt aattagttat    2820
gtcacgctta cattcacgcc ctcctcccac atccgctcta accgaaaagg aaggagttag    2880
acaacctgaa gtctaggtcc ctatttattt tttttaatag ttatgttagt attaagaacg    2940
ttatttatat ttcaaatttt tcttttttt ctgtacaaac gcgtgtacgc atgtaacatt    3000
atactgaaaa ccttgcttga aaggttttg ggacgctcga aggctttaat ttgcaagctg    3060
gatctaacat ccaaagacga aaggttgaat gaaacctttt tgccatccga catccacagg    3120
tccattctca cacataagtg ccaaacgcaa caggagggga tacactagca gcagaccgtt    3180
gcaaacgcag gacctccact cctcttctcc tcaacaccca cttttgccat cgaaaaacca    3240
gcccagttat tgggcttgat tggagctcgc tcattccaat tccttctatt aggctactaa    3300
caccatgact ttattagcct gtctatcctg gccccctgg cgaggttcat gtttgtttat    3360
ttccgaatgc aacaagctcc gcattacacc cgaacatcac tccagatgag ggctttctga    3420
gtgtggggtc aaatagtttc atgttcccca aatggcccaa aactgacagt ttaaacgctg    3480
tcttggaacc taatatgaca aaagcgtgat ctcatccaag atgaactaag tttggttcgt    3540
tgaaatgcta acggccagtt ggtcaaaaag aaacttccaa aagtcggcat accgtttgtc    3600
ttgtttggta ttgattgacg aatgctcaaa ataatctca ttaatgctta gcgcagtctc    3660
tctatcgctt ctgaaccccg gtgcacctgt gccgaaacgc aaatgggaa cacccgctt    3720 tttggatgat tatgcattgt ctccacattg tatgcttcca agattctggt gggaatactg    3780
ctgatagcct aacgttcatg atcaaaattt aactgttcta accccctactt gacagcaata    3840 tataaacaga aggaagctgc cctgtcttaa acctttttt ttatcatcat tattagctta    3900
ctttcataat tgcgactggt tccaattgac aagcttttga ttttaacgac ttttaacgac    3960
aacttgagaa gatcaaaaaa caactaatta ttcgaaacgg aattcgaaac gatgagattc    4020
ccatccatct tcactgctgt tttgttcgct gcttcttctg ctttggctga catccaaatg    4080
```

```
actcaatccc catcttcttt gtctgcttcc gttggtgaca gagttactat cacttgtaga    4140
gcttcccagg acgttaatac tgctgttgct tggtatcaac agaagccagg aaaggctcca    4200
aagttgttga tctactccgc ttccttcttg tactctggtg ttccatccag attctctggt    4260
tccagatccg gtactgactt cactttgact atctcctcct tgcaaccaga agatttcgct    4320
acttactact gtcagcagca ctacactact ccaccaactt tcggacaggg tactaaggtt    4380
gagatcaaga gaactgttgc tgctccatcc gttttcattt tcccaccatc cgacgaacag    4440
ttgaagtctg gtacagcttc cgttgtttgt tgttgaaca acttctaccc aagagaggct    4500
aaggttcagt ggaaggttga caacgctttg caatccggta actcccaaga atccgttact    4560
gagcaagact ctaaggactc cacttactcc ttgtcctcca ctttgacttt gtccaaggct    4620
gattacgaga agcacaaggt ttacgcttgt gaggttacac atcagggttt gtcctcccca    4680
gttactaagt ccttcaacag aggagagtgt taatagggcc ggccatttaa atacaggccc    4740
cttttccttt gtcgatatca tgtaattagt tatgtcacgc ttacattcac gccctcctcc    4800
cacatccgct ctaaccgaaa aggaaggagt tagacaacct gaagtctagg tccctattta    4860
ttttttttaa tagttatgtt agtattaaga acgttattta tatttcaaat ttttcttttt    4920
tttctgtaca aacgcgtgta cgcatgtaac attatactga aaaccttgct tgagaaggtt    4980
ttgggacgct cgaaggcttt aatttgcaag ctggatccgc ggccgcttac gcgccgatcc    5040
cccacacacc atagcttcaa aatgtttcta ctccttttt actcttccag attttctcgg    5100
actccgcgca tcgccgtacc acttcaaaac acccaagcac agcatactaa atttcccctc    5160
tttcttcctc tagggtgtcg ttaattaccc gtactaaagg tttggaaaag aaaaaagaga    5220
ccgcctcgtt tcttttttctt cgtcgaaaaa ggcaataaaa attttatca cgtttctttt    5280
tcttgaaaat ttttttttt gattttttc tctttcgatg acctcccatt gatatttaag    5340
ttaataaacg gtcttcaatt tctcaagttt cagtttcatt tttcttgttc tattacaact    5400
ttttttactt cttgctcatt agaaagaaag catagcaatc taatctaagt tttaattaca    5460
aattaattaa tggccaagtt gaccagtgcc gttccggtgc tcaccgcgcg cgacgtcgcc    5520
ggagcggtcg agttctggac cgaccggctc gggttctccc gggacttcgt ggaggacgac    5580
ttcgccggtg tggtccggga cgacgtgacc ctgttcatca gcgcggtcca ggaccaggtg    5640
gtgccggaca cacccctggc ctgggtgtgg gtgcgcggcc tggacgagct gtacgccgag    5700
tggtcggagg tcgtgtccac gaacttccgg gacgcctccg gcctgccat gaccgagatc    5760
ggcgagcagc cgtgggggcg ggagttcgcc ctgcgcgacc cggccggcaa ctgcgtgcac    5820
ttcgtggccg aggagcagga ctgattaatt aacaggcccc ttttcctttg tcgatatcat    5880
gtaattagtt atgtcacgct tacattcacg ccctcctccc acatccgctc taaccgaaaa    5940
ggaaggagtt agacaacctg aagtctaggt ccctatttat ttttttaat agttatgtta    6000
gtattaagaa cgttatttat atttcaaatt ttctttttt ttctgtacaa acgcgtgtac    6060
gcatgtaaca ttatactgaa aaccttgctt gagaaggttt tgggacgctc gaaggcttta    6120
atttgcaagc tgcggcctaa ggcgcgccag gccataatgg ccaaacggtt tctcaattac    6180
tatatactac taaccattta cctgtagcgt atttcttttc cctcttcgcg aaagctcaag    6240
ggcatcttct tgactcatga aaaatatctg gatttcttct gacagatcat cacccttgag    6300
cccaactctc tagcctatga gtgtaagtga tagtcatctt gcaacagatt attttggaac    6360
gcaactaaca aagcagatac acccttcagc agaatccttt ctggatattg tgaagaatga    6420
tcgccaaagt cacagtcctg agacagttcc taatctttac cccatttaca agttcatcca    6480
```

```
atcagacttc ttaacgcctc atctggctta tatcaagctt accaacagtt cagaaactcc    6540
cagtccaagt ttcttgcttg aaagtgcgaa gaatggtgac accgttgaca ggtacacctt    6600
tatgggacat tcccccagaa aaataatcaa gactgggcct ttagagggtg ctgaagttga    6660
ccccttggtg cttctggaaa aagaactgaa gggcaccaga caagcgcaac ttcctggtat    6720
tcctcgtcta agtggtggtg ccataggata catctcgtac gattgtatta agtactttga    6780
accaaaaact gaaagaaaac tgaaagatgt tttgcaactt ccggaagcag ctttgatgtt    6840
gttcgacacg atcgtggctt ttgacaatgt ttatcaaaga ttccaggtaa ttggaaacgt    6900
ttctctatcc gttgatgact cggacgaagc tattcttgag aaatattata agacaagaga    6960
agaagtggaa aagatcagta aagtggtatt tgacaataaa actgttccct actatgaaca    7020
gaaagatatt attcaaggcc aaacgttcac ctctaatatt ggtcaggaag ggtatgaaaa    7080
ccatgttcgc aagctgaaag aacatattct gaaaggagac atcttccaag ctgttccctc    7140
tcaaagggta gccaggccga cctcattgca ccctttcaac atctatcgtc atttgagaac    7200
tgtcaatcct tctccataca tgttctatat tgactatcta gacttccaag ttgttggtgc    7260
ttcacctgaa ttactagtta aatccgacaa caacaacaaa atcatcacac atcctattgc    7320
tggaactctt cccagaggta aaactatcga agaggacgac aattatgcta agcaattgaa    7380
gtcgtctttg aaagacaggg ccgagcacgt catgctggta gatttggcca gaaatgatat    7440
taaccgtgtg tgtgagccca ccagtaccac ggttgatcgt ttattgactg tggagagatt    7500
ttctcatgtg atgcatcttg tgtcagaagt cagtggaaca ttgagaccaa acaagactcg    7560
cttcgatgct ttcagatcca tttttcccagc aggaaccgtc tccggtgctc cgaaggtaag    7620
agcaatgcaa ctcataggag aattggaagg agaaaagaga ggtgtttatg cgggggccgt    7680
aggacactgg tcgtacgatg gaaaatcgat ggacacatgt attgccttaa gaacaatggt    7740
cgtcaaggac ggtgtcgctt accttcaagc cggaggtgga attgtctacg attctgaccc    7800
ctatgacgag tacatcgaaa ccatgaacaa aatgagatcc aacaataaca ccatcttgga    7860
ggctgagaaa atctggaccg ataggttggc cagagacgag aatcaaagtg aatccgaaga    7920
aaacgatcaa tgaacggagg acgtaagtag gaatttatgg tttggccata atggcctagc    7980
ttggcgtaat catggtcata gctgtttcct gtgtgaaatt gttatccgct cacaattcca    8040
cacaacatac gagccggaag cataaagtgt aaagcctggg gtgcctaatg agtgagctaa    8100
ctcacattaa ttgcgttgcg ctcactgccc gctttccagt cgggaaacct gtcgtgccag    8160
ctgcattaat gaatcggcca acgcgcgggg agaggcggtt tgcgtattgg cgctcttcc    8220
gcttcctcgc tcactgactc gctgcgctcg gtcgttcggc tgcggcgagc ggtatcagct    8280
cactcaaagg cggtaatacg gttatccaca gaatcagggg ataacgcagg aaagaacatg    8340
tgagcaaaag gccagcaaaa ggccaggaac cgtaaaaagg ccgcgttgct ggcgtttttc    8400
cataggctcc gcccccctga cgagcatcac aaaaatcgac gctcaagtca gaggtggcga    8460
aacccgacag gactataaag ataccaggcg tttccccctg gaagctccct cgtgcgctct    8520
cctgttccga ccctgccgct taccggatac ctgtccgcct ttctcccttc gggaagcgtg    8580
gcgctttctc atagctcacg ctgtaggtat ctcagttcgg tgtaggtcgt tcgctccaag    8640
ctgggctgtg tgcacgaacc ccccgttcag cccgaccgct gcgccttatc cggtaactat    8700
cgtcttgagt ccaacccggt aagacacgac ttatcgccac tggcagcagc cactggtaac    8760
aggattagca gagcgaggta tgtaggcggt gctacagagt tcttgaagtg gtggcctaac    8820
```

-continued

```
tacggctaca ctagaaggac agtatttggt atctgcgctc tgctgaagcc agttaccttc   8880
ggaaaaagag ttggtagctc ttgatccggc aaacaaacca ccgctggtag cggtggtttt   8940
tttgtttgca agcagcagat tacgcgcaga aaaaaggat ctcaagaaga tcctttgatc    9000
ttttctacgg ggtctgacgc tcagtggaac gaaaactcac gttaagggat tttggtcatg   9060
agattatcaa aaaggatctt cacctagatc cttttaaatt aaaaatgaag ttttaaatca   9120
atctaaagta tatatgagta aacttggtct gacagttacc aatgcttaat cagtgaggca   9180
cctatctcag cgatctgtct atttcgttca tccatagttg cctgactccc cgtcgtgtag   9240
ataactacga tacgggaggg cttaccatct ggccccagtg ctgcaatgat accgcgagac   9300
ccacgctcac cggctccaga tttatcagca ataaaccagc cagccggaag ggccgagcgc   9360
agaagtggtc ctgcaacttt atccgcctcc atccagtcta ttaattgttg ccgggaagct   9420
agagtaagta gttcgccagt taatagtttg cgcaacgttg ttgccattgc tacaggcatc   9480
gtggtgtcac gctcgtcgtt tggtatggct tcattcagct ccggttccca acgatcaagg   9540
cgagttacat gatcccccat gttgtgcaaa aaagcggtta gctccttcgg tcctccgatc   9600
gttgtcagaa gtaagttggc cgcagtgtta tcactcatgg ttatggcagc actgcataat   9660
tctcttactg tcatgccatc cgtaagatgc ttttctgtga ctggtgagta ctcaaccaag   9720
tcattctgag aatagtgtat gcggcgaccg agttgctctt gcccggcgtc aatacgggat   9780
aataccgcgc cacatagcag aactttaaaa gtgctcatca ttggaaaacg ttcttcgggg   9840
cgaaaactct caaggatctt accgctgttg agatccagtt cgatgtaacc cactcgtgca   9900
cccaactgat cttcagcatc ttttactttc accagcgttt ctgggtgagc aaaaacagga   9960
aggcaaaatg ccgcaaaaaa gggaataagg gcgacacgga aatgttgaat actcatactc  10020
ttcctttttc aatattattg aagcatttat cagggttatt gtctcatgag cggatacata  10080
tttgaatgta tttagaaaaa taaacaaata ggggttccgc gcacatttcc ccgaaaagtg  10140
ccacctgacg tctaagaaac cattattatc atgacattaa cctataaaaa taggcgtatc  10200
acgaggccct ttcgtc                                                  10216
```

<210> SEQ ID NO 4
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Asn
            100                 105                 110
```

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 5
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
```

```
            20                  25                  30
Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
            50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Asn Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445
```

Gly

<210> SEQ ID NO 6
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Thr Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

```
Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 7
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Asn Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly

<210> SEQ ID NO 8
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 8

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Thr His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 9
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Thr Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly
```

<210> SEQ ID NO 10
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 10

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Thr Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly

<210> SEQ ID NO 11
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 11

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
                20                  25                  30
Tyr Ile His Trp Val Arg Gln Ala Pro Gly Lys Gly Leu Glu Trp Val
                35                  40                  45
Ala Arg Ile Tyr Pro Thr Asn Gly Tyr Thr Arg Tyr Ala Asp Ser Val
50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
                210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
                290                 295                 300
Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Asn Lys Ser Leu Ser Leu Ser Pro
        435                 440                 445

Gly

<210> SEQ ID NO 12
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 12

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Asn Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
```

```
225                 230                 235                 240
Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
        450                 455                 460

Leu Ser Pro Gly
465

<210> SEQ ID NO 13
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 13

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
```

```
            115                 120                 125
Trp Gly Gln Gly Thr Leu Val Thr Val Ser Ser Asn Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly
465

<210> SEQ ID NO 14
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 14

Met Arg Phe Pro Ser Ile Phe Thr Ala Val Leu Phe Ala Ala Ser Ser
```

```
            1               5                  10                 15
         Ala Leu Ala Glu Val Gln Leu Val Glu Ser Gly Gly Gly Leu Val Gln
                         20                  25                 30

Pro Gly Gly Ser Leu Arg Leu Ser Cys Ala Ala Ser Gly Phe Asn Ile
                         35                  40                  45

Lys Asp Thr Tyr Ile His Trp Val Arg Gln Ala Pro Gly Lys Gly Leu
                 50                      55                  60

Glu Trp Val Ala Arg Ile Tyr Pro Thr Asn Gly Tyr Thr Arg Tyr Ala
          65                      70                  75                  80

Asp Ser Val Lys Gly Arg Phe Thr Ile Ser Ala Asp Thr Ser Lys Asn
                             85                  90                  95

Thr Ala Tyr Leu Gln Met Asn Ser Leu Arg Ala Glu Asp Thr Ala Val
                         100                 105                 110

Tyr Tyr Cys Ser Arg Trp Gly Asp Gly Phe Tyr Ala Met Asp Tyr
                         115                 120                 125

Trp Gly Gln Gly Thr Leu Val Thr Val Ser Ser Ala Ser Thr Lys Gly
                         130                 135                 140

Pro Ser Val Phe Pro Leu Ala Pro Ser Asn Lys Ser Thr Ser Gly Gly
         145                 150                 155                 160

Thr Ala Ala Leu Gly Cys Leu Val Lys Asp Tyr Phe Pro Glu Pro Val
                         165                 170                 175

Thr Val Ser Trp Asn Ser Gly Ala Leu Thr Ser Gly Val His Thr Phe
                         180                 185                 190

Pro Ala Val Leu Gln Ser Ser Gly Leu Tyr Ser Leu Ser Ser Val Val
                         195                 200                 205

Thr Val Pro Ser Ser Ser Leu Gly Thr Gln Thr Tyr Ile Cys Asn Val
                 210                     215                 220

Asn His Lys Pro Ser Asn Thr Lys Val Asp Lys Lys Val Glu Pro Lys
         225                 230                 235                 240

Ser Cys Asp Lys Thr His Thr Cys Pro Pro Cys Pro Ala Pro Glu Leu
                         245                 250                 255

Leu Gly Gly Pro Ser Val Phe Leu Phe Pro Pro Lys Pro Lys Asp Thr
                         260                 265                 270

Leu Met Ile Ser Arg Thr Pro Glu Val Thr Cys Val Val Val Asp Val
                         275                 280                 285

Ser His Glu Asp Pro Glu Val Lys Phe Asn Trp Tyr Val Asp Gly Val
                         290                 295                 300

Glu Val His Asn Ala Lys Thr Lys Pro Arg Glu Glu Gln Tyr Asn Ser
         305                 310                 315                 320

Thr Tyr Arg Val Val Ser Val Leu Thr Val Leu His Gln Asp Trp Leu
                         325                 330                 335

Asn Gly Lys Glu Tyr Lys Cys Lys Val Ser Asn Lys Ala Leu Pro Ala
                         340                 345                 350

Pro Ile Glu Lys Thr Ile Ser Lys Ala Lys Gly Gln Pro Arg Glu Pro
                         355                 360                 365

Gln Val Tyr Thr Leu Pro Pro Ser Arg Glu Glu Met Thr Lys Asn Gln
                         370                 375                 380

Val Ser Leu Thr Cys Leu Val Lys Gly Phe Tyr Pro Ser Asp Ile Ala
         385                 390                 395                 400

Val Glu Trp Glu Ser Asn Gly Gln Pro Glu Asn Asn Tyr Lys Thr Thr
                         405                 410                 415

Pro Pro Val Leu Asp Ser Asp Gly Ser Phe Phe Leu Tyr Ser Lys Leu
                         420                 425                 430
```

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly
465

<210> SEQ ID NO 15
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 15

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Asn Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

```
Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 16
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 16

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Asn Leu Thr Ser Gly Val His Thr Phe
            180                 185                 190

Pro Ala Val Leu Gln Ser Ser Gly Leu Tyr Ser Leu Ser Ser Val Val
        195                 200                 205
```

-continued

Thr Val Pro Ser Ser Leu Gly Thr Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly
465

<210> SEQ ID NO 17
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 17

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
                100                 105                 110

Tyr Tyr Cys Ser Arg Trp Gly Gly Asp Gly Phe Tyr Ala Met Asp Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Asn Gln Thr Tyr Ile Cys Asn Val
    210                 215                 220

Asn His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 18
<211> LENGTH: 468
<212> TYPE: PRT
<213> ORGANISM: Artificial Sequence
<220> FEATURE:

<223> OTHER INFORMATION: immunoglobulin chain

<400> SEQUENCE: 18

```
Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Thr Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400
```

-continued

```
Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly
465

<210> SEQ ID NO 19
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 19

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285
```

```
Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly
465

<210> SEQ ID NO 20
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 20

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175
```

```
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
        195                 200                 205
Thr Val Pro Ser Ser Ser Leu Gly Thr Gln Thr Tyr Ile Cys Asn Val
    210                 215                 220
Asn His Lys Pro Ser Asn Thr Lys Val Asp Lys Lys Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
        275                 280                 285
Ser His Glu Asp Pro Glu Val Lys Phe Asn Trp Tyr Val Asp Gly Val
    290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Glu Glu Met Thr Lys Asn Gln
    370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Thr Ser Cys Ser
        435                 440                 445
Val Met His Glu Ala Leu His Asn His Tyr Thr Gln Lys Ser Leu Ser
    450                 455                 460
Leu Ser Pro Gly
465

<210> SEQ ID NO 21
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 21

Met Arg Phe Pro Ser Ile Phe Thr Ala Val Leu Phe Ala Ala Ser Ser
1               5                   10                  15
Ala Leu Ala Glu Val Gln Leu Val Glu Ser Gly Gly Gly Leu Val Gln
            20                  25                  30
Pro Gly Gly Ser Leu Arg Leu Ser Cys Ala Ala Ser Gly Phe Asn Ile
        35                  40                  45
Lys Asp Thr Tyr Ile His Trp Val Arg Gln Ala Pro Gly Lys Gly Leu
    50                  55                  60
```

```
Glu Trp Val Ala Arg Ile Tyr Pro Thr Asn Gly Tyr Thr Arg Tyr Ala
 65                  70                  75                  80

Asp Ser Val Lys Gly Arg Phe Thr Ile Ser Ala Asp Thr Ser Lys Asn
                 85                  90                  95

Thr Ala Tyr Leu Gln Met Asn Ser Leu Arg Ala Glu Asp Thr Ala Val
            100                 105                 110

Tyr Tyr Cys Ser Arg Trp Gly Asp Gly Phe Tyr Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly
465
```

-continued

```
<210> SEQ ID NO 22
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 22
```

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Asn Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln

```
                    370                 375                 380
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                    405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 23
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 23

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
        50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
                100                 105                 110

Tyr Tyr Cys Ser Arg Trp Gly Gly Asp Gly Phe Tyr Ala Met Asp Tyr
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
```

```
                        260                 265                 270
Leu Met Ile Ser Arg Thr Pro Glu Val Thr Cys Val Val Asp Val
                275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
            450                 455                 460

Leu Ser Pro Gly
465

<210> SEQ ID NO 24
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 24

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
```

```
                145                 150                 155                 160
        Thr Ala Ala Leu Gly Cys Leu Val Lys Asp Tyr Phe Pro Glu Pro Val
                            165                 170                 175

Thr Val Ser Trp Asn Ser Gly Ala Leu Thr Ser Gly Val His Thr Phe
                        180                 185                 190

Pro Ala Val Leu Gln Asn Ser Thr Leu Tyr Ser Leu Ser Ser Val Val
                        195                 200                 205

Thr Val Pro Ser Ser Ser Leu Gly Thr Gln Thr Tyr Ile Cys Asn Val
                    210                 215                 220

Asn His Lys Pro Ser Asn Thr Lys Val Asp Lys Lys Val Glu Pro Lys
        225                 230                 235                 240

Ser Cys Asp Lys Thr His Thr Cys Pro Pro Cys Pro Ala Pro Glu Leu
                            245                 250                 255

Leu Gly Gly Pro Ser Val Phe Leu Phe Pro Pro Lys Pro Lys Asp Thr
                        260                 265                 270

Leu Met Ile Ser Arg Thr Pro Glu Val Thr Cys Val Val Val Asp Val
                    275                 280                 285

Ser His Glu Asp Pro Glu Val Lys Phe Asn Trp Tyr Val Asp Gly Val
                290                 295                 300

Glu Val His Asn Ala Lys Thr Lys Pro Arg Glu Glu Gln Tyr Asn Ser
        305                 310                 315                 320

Thr Tyr Arg Val Val Ser Val Leu Thr Val Leu His Gln Asp Trp Leu
                            325                 330                 335

Asn Gly Lys Glu Tyr Lys Cys Lys Val Ser Asn Lys Ala Leu Pro Ala
                        340                 345                 350

Pro Ile Glu Lys Thr Ile Ser Lys Ala Lys Gly Gln Pro Arg Glu Pro
                    355                 360                 365

Gln Val Tyr Thr Leu Pro Pro Ser Arg Glu Glu Met Thr Lys Asn Gln
                370                 375                 380

Val Ser Leu Thr Cys Leu Val Lys Gly Phe Tyr Pro Ser Asp Ile Ala
        385                 390                 395                 400

Val Glu Trp Glu Ser Asn Gly Gln Pro Glu Asn Asn Tyr Lys Thr Thr
                            405                 410                 415

Pro Pro Val Leu Asp Ser Asp Gly Ser Phe Phe Leu Tyr Ser Lys Leu
                        420                 425                 430

Thr Val Asp Lys Ser Arg Trp Gln Gln Gly Asn Val Phe Ser Cys Ser
                    435                 440                 445

Val Met His Glu Ala Leu His Asn His Tyr Thr Gln Lys Ser Leu Ser
        450                 455                 460

Leu Ser Pro Gly
        465

<210> SEQ ID NO 25
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 25

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
```

```
            35                  40                  45
Lys Asp Thr Tyr Ile His Trp Val Arg Gln Ala Pro Gly Lys Gly Leu
 50                  55                  60

Glu Trp Val Ala Arg Ile Tyr Pro Thr Asn Gly Tyr Thr Arg Tyr Ala
 65                  70                  75                  80

Asp Ser Val Lys Gly Arg Phe Thr Ile Ser Ala Asp Thr Ser Lys Asn
                 85                  90                  95

Thr Ala Tyr Leu Gln Met Asn Ser Leu Arg Ala Glu Asp Thr Ala Val
                100                 105                 110

Tyr Tyr Cys Ser Arg Trp Gly Asp Gly Phe Tyr Ala Met Asp Tyr
                115                 120                 125

Trp Gly Gln Gly Thr Leu Val Thr Val Ser Ser Ala Ser Thr Lys Gly
                130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Asn Ser Thr Gly Thr Gln Thr Tyr Ile Cys Asn Val
                210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
                275                 280                 285

Ser His Glu Asp Pro Glu Val Lys Phe Asn Trp Tyr Val Asp Gly Val
                290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Glu Glu Met Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460
```

```
Leu Ser Pro Gly
465

<210> SEQ ID NO 26
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 26

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Asn Thr Thr Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350
```

```
Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 27
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 27

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240
```

```
Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
        260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 28
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 28

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Arg Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125
```

Trp Gly Gln Gly Thr Leu Val Thr Val Ser Ser Ala Ser Thr Lys Gly
            130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Ser Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 29
<211> LENGTH: 449
<212> TYPE: PRT
<213> ORGANISM: Artificial Sequence
<220> FEATURE:
<223> OTHER INFORMATION: immunoglobulin chain

<400> SEQUENCE: 29

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Glu Ile Tyr Pro Thr Asn Gly Tyr Thr Arg Tyr Ala Asp Ser Val
50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Gly Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Ala Pro Pro Lys Pro Lys Asp Thr Leu Met Ile
                245                 250                 255
Ser Arg Thr Pro Glu Val Thr Cys Val Val Ala Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
                435                 440                 445
Gly

<210> SEQ ID NO 30
<211> LENGTH: 214
<212> TYPE: PRT
<213> ORGANISM: Artificial Sequence
<220> FEATURE:
<223> OTHER INFORMATION: immunoglobulin chain

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 31

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
50                  55                  60
```

```
Glu Trp Val Ala Glu Ile Tyr Pro Thr Asn Gly Tyr Thr Arg Tyr Ala
 65                  70                  75                  80

Asp Ser Val Lys Gly Arg Phe Thr Ile Ser Ala Asp Thr Ser Lys Asn
                 85                  90                  95

Thr Ala Tyr Leu Gln Met Asn Ser Leu Arg Ala Glu Asp Thr Ala Val
            100                 105                 110

Tyr Tyr Cys Ser Arg Trp Gly Asp Gly Phe Gly Ala Met Asp Tyr
        115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Ala Pro Pro Lys Pro Lys Asp Thr
            260                 265                 270

Leu Met Ile Ser Arg Thr Pro Glu Val Thr Cys Val Val Ala Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly
465
```

<210> SEQ ID NO 32
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 32

```
Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Glu Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Gly Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Ala Pro Pro Lys Pro Lys Asp Thr
            260                 265                 270

Leu Met Ile Ser Arg Thr Pro Glu Val Thr Cys Val Val Ala Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
```

```
                    370                 375                 380
Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                    405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
450                 455                 460

Leu Ser Pro Gly
465

<210> SEQ ID NO 33
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 33

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
        50                  55                  60

Glu Trp Val Ala Glu Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
                100                 105                 110

Tyr Tyr Cys Ser Arg Trp Gly Gly Asp Gly Phe Gly Ala Met Asp Tyr
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
                180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Ala Pro Pro Lys Pro Lys Asp Thr
```

```
                    260                 265                 270
Leu Met Ile Ser Arg Thr Pro Glu Val Thr Cys Val Val Ala Asp Val
                275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 34
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 34

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
        50                  55                  60

Glu Trp Val Ala Glu Ile Tyr Pro Thr Asn Gly Tyr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Gly Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Asn Thr Ser Gly Gly
```

```
            145                 150                 155                 160
    Thr Ala Ala Leu Gly Cys Leu Val Lys Asp Tyr Phe Pro Glu Pro Val
                    165                 170                 175

Thr Val Ser Trp Asn Ser Thr Ala Leu Thr Ser Gly Val His Thr Phe
                180                 185                 190

Pro Ala Val Leu Gln Ser Ser Gly Leu Tyr Ser Leu Ser Ser Val Val
                    195                 200                 205

Thr Val Pro Ser Ser Ser Leu Gly Thr Gln Thr Tyr Ile Cys Asn Val
        210                 215                 220

Thr His Lys Pro Ser Asn Thr Lys Val Asp Lys Lys Val Glu Pro Lys
    225                 230                 235                 240

Ser Cys Asp Lys Thr His Thr Cys Pro Pro Cys Pro Ala Pro Glu Leu
                    245                 250                 255

Leu Gly Gly Pro Ser Val Phe Leu Ala Pro Pro Lys Pro Lys Asp Thr
                    260                 265                 270

Leu Met Ile Ser Arg Thr Pro Glu Val Thr Cys Val Val Ala Asp Val
                275                 280                 285

Ser His Glu Asp Pro Glu Val Lys Phe Asn Trp Tyr Val Asp Gly Val
        290                 295                 300

Glu Val His Asn Ala Lys Thr Lys Pro Arg Glu Glu Gln Tyr Asn Ser
    305                 310                 315                 320

Thr Tyr Arg Val Val Ser Val Leu Thr Val Leu His Gln Asp Trp Leu
                    325                 330                 335

Asn Gly Lys Glu Tyr Lys Cys Lys Val Ser Asn Lys Ala Leu Pro Ala
                    340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Glu Glu Met Thr Lys Asn Gln
        370                 375                 380

Val Ser Leu Thr Cys Leu Val Lys Gly Phe Tyr Pro Ser Asp Ile Ala
    385                 390                 395                 400

Val Glu Trp Glu Ser Asn Gly Gln Pro Glu Asn Asn Tyr Lys Thr Thr
                    405                 410                 415

Pro Pro Val Leu Asp Ser Asp Gly Ser Phe Phe Leu Tyr Ser Lys Leu
                    420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
    450                 455                 460

Leu Ser Pro Gly
    465

<210> SEQ ID NO 35
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 35

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Ile
```

```
            35                  40                  45
Thr Asp Thr Tyr Ile His Trp Val Arg Gln Ala Pro Gly Lys Gly Leu
50                  55                  60

Glu Trp Val Ala Glu Ile Tyr Pro Thr Asn Gly Thr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Asp Gly Phe Gly Ala Met Asp Tyr
        115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
        210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Ala Pro Pro Lys Pro Lys Asp Thr
            260                 265                 270

Leu Met Ile Ser Arg Thr Pro Glu Val Thr Cys Val Val Ala Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460
```

Leu Ser Pro Gly
465

<210> SEQ ID NO 36
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 36

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Thr Asp Thr Tyr Ile His Trp Val Arg Gln Ala Pro Gly Lys Gly Leu
    50                  55                  60

Glu Trp Val Ala Glu Ile Tyr Pro Thr Asn Gly Tyr Thr Arg Tyr Ala
65                  70                  75                  80

Asp Ser Val Asn Gly Thr Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Gly Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Ala Pro Pro Lys Pro Lys Asp Thr
            260                 265                 270

Leu Met Ile Ser Arg Thr Pro Glu Val Thr Cys Val Val Ala Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 37
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 37

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Lys Asp Thr Tyr Ile His Trp Val Arg Gln Ala Pro Gly Lys Gly Leu
    50                  55                  60

Glu Trp Val Ala Glu Ile Tyr Pro Thr Asn Gly Thr Thr Arg Tyr Ala
65                  70                  75                  80

Asp Ser Val Asn Gly Thr Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Gly Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Thr His Lys Pro Ser Asn Thr Lys Val Asp Lys Lys Val Glu Pro Lys
225                 230                 235                 240

```
Ser Cys Asp Lys Thr His Thr Cys Pro Pro Cys Pro Ala Pro Glu Leu
            245                 250                 255

Leu Gly Gly Pro Ser Val Phe Leu Ala Pro Pro Lys Pro Lys Asp Thr
            260                 265                 270

Leu Met Ile Ser Arg Thr Pro Glu Val Thr Cys Val Val Ala Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 38
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 38

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
            50                  55                  60

Glu Trp Val Ala Glu Ile Tyr Pro Thr Asn Gly Thr Thr Arg Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Gly Ala Met Asp Tyr
            115                 120                 125
```

Trp Gly Gln Gly Thr Leu Val Thr Val Ser Ser Ala Ser Thr Lys Gly
            130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
            180                 185                 190

Pro Ala Val Leu Gln Asn Ser Thr Leu Tyr Ser Leu Ser Ser Val Val
        195                 200                 205

Thr Val Pro Ser Ser Leu Gly Thr Gln Thr Tyr Ile Cys Asn Val
210                 215                 220

Thr His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Ala Pro Pro Lys Pro Lys Asp Thr
            260                 265                 270

Leu Met Ile Ser Arg Thr Pro Glu Val Thr Cys Val Val Ala Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
450                 455                 460

Leu Ser Pro Gly
465

<210> SEQ ID NO 39
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 39

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Leu Val Gln
             20                  25                  30

Pro Gly Gly Ser Leu Arg Leu Ser Cys Ala Ala Ser Gly Phe Asn Ile
                 35                  40                  45

Thr Asp Thr Tyr Ile His Trp Val Arg Gln Ala Pro Gly Lys Gly Leu
 50                  55                  60

Glu Trp Val Ala Glu Ile Tyr Pro Thr Asn Gly Thr Thr Arg Tyr Ala
 65                  70                  75                  80

Asp Ser Val Asn Gly Thr Phe Thr Ile Ser Ala Asp Thr Ser Lys Asn
                 85                  90                  95

Thr Ala Tyr Leu Gln Met Asn Ser Leu Arg Ala Glu Asp Thr Ala Val
                100                 105                 110

Tyr Tyr Cys Ser Arg Trp Gly Gly Asp Gly Phe Gly Ala Met Asp Tyr
                115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
                180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
                210                 215                 220

Thr His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Ala Pro Pro Lys Pro Lys Asp Thr
                260                 265                 270

Leu Met Ile Ser Arg Thr Pro Glu Val Thr Cys Val Val Ala Asp Val
                275                 280                 285

Ser His Glu Asp Pro Glu Val Lys Phe Asn Trp Tyr Val Asp Gly Val
                290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
                355                 360                 365

Gln Val Tyr Thr Leu Pro Pro Ser Arg Glu Glu Met Thr Lys Asn Gln
                370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

```
Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
    450                 455                 460

Leu Ser Pro Gly
465

<210> SEQ ID NO 40
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 40

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Thr Asp Thr Tyr Ile His Trp Val Arg Gln Ala Pro Gly Lys Gly Leu
    50                  55                  60

Glu Trp Val Ala Glu Ile Tyr Pro Thr Asn Gly Thr Thr Arg Tyr Ala
65                  70                  75                  80

Asp Ser Val Asn Gly Thr Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Gly Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
            180                 185                 190

Pro Ala Val Leu Gln Asn Ser Thr Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Thr His Lys Pro Ser Asn Thr Lys Val Asp Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Ala Pro Pro Lys Pro Lys Asp Thr
            260                 265                 270

Leu Met Ile Ser Arg Thr Pro Glu Val Thr Cys Val Val Ala Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320
```

```
Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
        340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Thr Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Thr Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Thr Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 41
<211> LENGTH: 468
<212> TYPE: PRT
<213> ORGANISM: Artificial Sequence
<220> FEATURE:
<223> OTHER INFORMATION: immunoglobulin chain

<400> SEQUENCE: 41

Met Arg Phe Pro Ser Ile Phe Thr Ala Val Leu Phe Ala Ala Ser Ser
1               5                   10                  15

Ala Leu Ala Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Ile
        35                  40                  45

Thr Asp Thr Tyr Ile His Trp Val Arg Gln Ala Pro Gly Lys Gly Leu
    50                  55                  60

Glu Trp Val Ala Glu Ile Tyr Pro Thr Asn Gly Thr Thr Arg Tyr Ala
65                  70                  75                  80

Asp Ser Val Asn Gly Thr Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Gly Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Asn Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Thr Ala Leu Thr Ser Gly Val His Thr Phe
            180                 185                 190

Pro Ala Val Leu Gln Ser Ser Gly Leu Tyr Ser Leu Ser Ser Val Val
        195                 200                 205
```

Thr Val Pro Ser Ser Ser Asn Gly Thr Gln Thr Tyr Ile Cys Asn Val
            210                 215                 220

Thr His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Ala Pro Pro Lys Pro Lys Asp Thr
            260                 265                 270

Leu Met Ile Ser Arg Thr Pro Glu Val Thr Cys Val Val Ala Asp Val
        275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
370                 375                 380

Thr Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Thr Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Thr Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 42
<211> LENGTH: 448
<212> TYPE: PRT
<213> ORGANISM: Artificial Sequence
<220> FEATURE:
<223> OTHER INFORMATION: immunoglobulin chain

<400> SEQUENCE: 42

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Ser
            20                  25                  30

Gly Leu Ala Trp Val Arg Gln Ala Pro Glu Lys Gly Leu Glu Trp Val
        35                  40                  45

Ala Thr Ile Thr Tyr Asn Gly Thr Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Thr Tyr Tyr Cys
                85                  90                  95

Ala Arg Trp Val Pro Gly Ser Gly Asn Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 43
<211> LENGTH: 218
<212> TYPE: PRT
<213> ORGANISM: Artificial Sequence
<220> FEATURE:
<223> OTHER INFORMATION: immunoglobulin chain

<400> SEQUENCE: 43

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Thr Ile Ser
                20                  25                  30

Arg Tyr Thr Leu Met His Trp Tyr Gln Gln Lys Pro Gly Gln Pro Pro
            35                  40                  45

Lys Leu Leu Ile Tyr Arg Ala Ser Asn Leu Ala Ser Gly Ile Pro Ala
50                  55                  60

Arg Phe Ser Gly Ser Gly Ser Gly Thr Asp Phe Thr Leu Asn Ile His
65                  70                  75                  80

Pro Val Glu Glu Asp Asp Ala Ala Thr Tyr Tyr Cys Gln Gln Ser Arg
                85                  90                  95

Glu Ser Pro Trp Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
            130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
            195                 200                 205

Ile Val Lys Ser Phe Asn Arg Asn Glu Cys
210                 215

<210> SEQ ID NO 44
<211> LENGTH: 448
<212> TYPE: PRT
<213> ORGANISM: Artificial Sequence
<220> FEATURE:
<223> OTHER INFORMATION: immunoglobulin chain

<400> SEQUENCE: 44

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Ser
                20                  25                  30

Gly Leu Ala Trp Val Arg Gln Ala Pro Glu Lys Gly Leu Glu Trp Val
            35                  40                  45

Ala Thr Ile Thr Tyr Asn Gly Thr Ser Thr Tyr Tyr Arg Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Thr Tyr Tyr Cys
                85                  90                  95

Ala Arg Trp Val Pro Gly Ser Gly Asn Phe Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Asn Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 45
<211> LENGTH: 448
<212> TYPE: PRT
<213> ORGANISM: Artificial Sequence
<220> FEATURE:
<223> OTHER INFORMATION: immunoglobulin chain

<400> SEQUENCE: 45

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Ser
            20                  25                  30

Gly Leu Ala Trp Val Arg Gln Ala Pro Glu Lys Gly Leu Glu Trp Val
        35                  40                  45

Ala Thr Ile Thr Tyr Asn Gly Thr Ser Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80
```

```
Leu Gln Met Ser Ser Leu Arg Ser Glu Asp Thr Ala Thr Tyr Tyr Cys
                85                  90                  95
Ala Arg Trp Val Pro Gly Ser Gly Asn Phe Asp Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Asn Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Thr Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445

<210> SEQ ID NO 46
<211> LENGTH: 448
<212> TYPE: PRT
<213> ORGANISM: Artificial Sequence
<220> FEATURE:
<223> OTHER INFORMATION: immunoglobulin chain

<400> SEQUENCE: 46
```

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn Ser
            20                  25                  30

Gly Leu Ala Trp Val Arg Gln Ala Pro Glu Lys Gly Leu Glu Trp Val
                35                  40                  45

Ala Thr Ile Thr Tyr Asn Gly Thr Ser Thr Tyr Tyr Arg Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Thr Tyr Tyr Cys
                85                  90                  95

Ala Arg Trp Val Pro Gly Ser Gly Asn Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Asn Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
                420             425             430
Ala Leu His Asn His Tyr Thr Gln Lys Ser Leu Ser Leu Ser Pro Gly
            435             440             445
```

<210> SEQ ID NO 47
<211> LENGTH: 448
<212> TYPE: PRT
<213> ORGANISM: Artificial Sequence
<220> FEATURE:
<223> OTHER INFORMATION: immunoglobulin chain

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
                    340                 345                 350
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
                435                 440                 445

<210> SEQ ID NO 48
<211> LENGTH: 214
<212> TYPE: PRT
<213> ORGANISM: Artificial Sequence
<220> FEATURE:
<223> OTHER INFORMATION: immunoglobulin chain

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 49
<211> LENGTH: 448
<212> TYPE: PRT
<213> ORGANISM: Artificial Sequence
<220> FEATURE:
<223> OTHER INFORMATION: immunoglobulin chain
```

<400> SEQUENCE: 49

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Asn Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
```

```
                405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 50
<211> LENGTH: 448
<212> TYPE: PRT
<213> ORGANISM: Artificial Sequence
<220> FEATURE:
<223> OTHER INFORMATION: immunoglobulin chain

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Thr Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

-continued

```
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445

<210> SEQ ID NO 51
<211> LENGTH: 448
<212> TYPE: PRT
<213> ORGANISM: Artificial Sequence
<220> FEATURE:
<223> OTHER INFORMATION: immunoglobulin chain

<400> SEQUENCE: 51

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asp Phe Ser Arg Tyr
            20                  25                  30
Trp Met Ser Trp Val Arg Gln Ala Pro Gly Lys Gly Leu Glu Trp Ile
        35                  40                  45
Gly Glu Ile Asn Pro Asp Ser Ser Thr Ile Asn Tyr Ala Pro Ser Leu
    50                  55                  60
Lys Asp Lys Phe Ile Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
            85                  90                  95
Ala Arg Pro Asp Gly Asn Tyr Trp Tyr Phe Asp Val Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Asn Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Thr Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
```

```
                245                 250                 255
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 52
<211> LENGTH: 447
<212> TYPE: PRT
<213> ORGANISM: Artificial Sequence
<220> FEATURE:
<223> OTHER INFORMATION: immunoglobulin chain

<400> SEQUENCE: 52

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ile Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Gly Tyr Asp Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

165                 170                 175
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 53
<211> LENGTH: 214
<212> TYPE: PRT
<213> ORGANISM: Artificial Sequence
<220> FEATURE:
<223> OTHER INFORMATION: immunoglobulin chain

<400> SEQUENCE: 53

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Thr Asn Trp Pro Leu

```
                     85                  90                  95
Thr Phe Gly Gly Gly Thr Lys Val Glu Ile Lys Arg Thr Val Ala Ala
                    100                 105                 110

Pro Ser Val Phe Ile Phe Pro Pro Ser Asp Glu Gln Leu Lys Ser Gly
                    115                 120                 125

Thr Ala Ser Val Val Cys Leu Leu Asn Asn Phe Tyr Pro Arg Glu Ala
                    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                    180                 185                 190

Ala Cys Glu Val Thr His Gln Gly Leu Ser Ser Pro Val Thr Lys Ser
                    195                 200                 205

Phe Asn Arg Gly Glu Cys
                    210

<210> SEQ ID NO 54
<211> LENGTH: 447
<212> TYPE: PRT
<213> ORGANISM: Artificial Sequence
<220> FEATURE:
<223> OTHER INFORMATION: immunoglobulin chain

<400> SEQUENCE: 54

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ile Met His Trp Val Arg Gln Ala Pro Gly Lys Gly Leu Glu Trp Val
                35                  40                  45

Ala Val Ile Ser Tyr Asp Gly Arg Asn Lys Tyr Tyr Ala Asp Ser Val
                50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asp Gly Tyr Asp Phe Asp Tyr Trp Gly Gln Gly Thr
                    100                 105                 110

Leu Val Thr Val Ser Ser Ala Ser Thr Lys Gly Pro Ser Val Phe Pro
                    115                 120                 125

Leu Ala Pro Ser Ser Lys Asn Thr Ser Gly Gly Thr Ala Ala Leu Gly
                    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                    165                 170                 175

Ser Ser Gly Leu Tyr Ser Leu Ser Ser Val Val Thr Val Pro Ser Ser
                    180                 185                 190

Ser Leu Gly Thr Gln Thr Tyr Ile Cys Asn Val Asn His Lys Pro Ser
                    195                 200                 205

Asn Thr Lys Val Asp Lys Lys Val Glu Pro Lys Ser Cys Asp Lys Thr
                    210                 215                 220

His Thr Cys Pro Pro Cys Pro Ala Pro Glu Leu Leu Gly Gly Pro Ser
```

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
            245                 250                 255

Glu Val Lys Phe Asn Trp Tyr Val Asp Gly Val Glu Val His Asn Ala
        260                 265                 270

Lys Thr Lys Pro Arg Glu Glu Gln Tyr Asn Ser Thr Tyr Arg Val Val
    275                 280                 285

Ser Val Leu Thr Val Leu His Gln Asp Trp Leu Asn Gly Lys Glu Tyr
290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
            325                 330                 335

Pro Pro Ser Arg Asp Glu Leu Thr Lys Asn Gln Val Ser Leu Thr Cys
        340                 345                 350

Leu Val Lys Gly Phe Tyr Pro Ser Asp Ile Ala Val Glu Trp Glu Ser
    355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
            405                 410                 415

Leu His Asn His Tyr Thr Gln Lys Ser Leu Ser Leu Ser Pro Gly
        420                 425                 430

<210> SEQ ID NO 55
<211> LENGTH: 447
<212> TYPE: PRT
<213> ORGANISM: Artificial Sequence
<220> FEATURE:
<223> OTHER INFORMATION: immunoglobulin chain

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ile Met His Trp Val Arg Gln Ala Pro Gly Lys Gly Leu Glu Trp Val
        35                  40                  45

Ala Val Ile Ser Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Thr Asp Gly Tyr Asp Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn

```
                145                 150                 155                 160
        Ser Thr Ala Leu Thr Ser Gly Val His Thr Phe Pro Ala Val Leu Gln
                        165                 170                 175
        Ser Ser Gly Leu Tyr Ser Leu Ser Ser Val Val Thr Val Pro Ser Ser
                        180                 185                 190
        Ser Leu Gly Thr Gln Thr Tyr Ile Cys Asn Val Asn His Lys Pro Ser
                        195                 200                 205
        Asn Thr Lys Val Asp Lys Lys Val Glu Pro Lys Ser Cys Asp Lys Thr
                        210                 215                 220
        His Thr Cys Pro Pro Cys Pro Ala Pro Glu Leu Leu Gly Gly Pro Ser
        225                 230                 235                 240
        Val Phe Leu Phe Pro Pro Lys Pro Lys Asp Thr Leu Met Ile Ser Arg
                        245                 250                 255
        Thr Pro Glu Val Thr Cys Val Val Val Asp Val Ser His Glu Asp Pro
                        260                 265                 270
        Glu Val Lys Phe Asn Trp Tyr Val Asp Gly Val Glu Val His Asn Ala
                        275                 280                 285
        Lys Thr Lys Pro Arg Glu Glu Gln Tyr Asn Ser Thr Tyr Arg Val Val
                        290                 295                 300
        Ser Val Leu Thr Val Leu His Gln Asp Trp Leu Asn Gly Lys Glu Tyr
        305                 310                 315                 320
        Lys Cys Lys Val Ser Asn Lys Ala Leu Pro Ala Pro Ile Glu Lys Thr
                        325                 330                 335
        Ile Ser Lys Ala Lys Gly Gln Pro Arg Glu Pro Gln Val Tyr Thr Leu
                        340                 345                 350
        Pro Pro Ser Arg Asp Glu Leu Thr Lys Asn Gln Val Ser Leu Thr Cys
                        355                 360                 365
        Leu Val Lys Gly Phe Tyr Pro Ser Asp Ile Ala Val Glu Trp Glu Ser
                        370                 375                 380
        Asn Gly Gln Pro Glu Asn Asn Tyr Lys Thr Thr Pro Pro Val Leu Asp
        385                 390                 395                 400
        Ser Asp Gly Ser Phe Phe Leu Tyr Ser Lys Leu Thr Val Asp Lys Ser
                        405                 410                 415
        Arg Trp Gln Gln Gly Asn Val Phe Ser Cys Ser Val Met His Glu Ala
                        420                 425                 430
        Leu His Asn His Tyr Thr Gln Lys Ser Leu Ser Leu Ser Pro Gly
                        435                 440                 445

<210> SEQ ID NO 56
<211> LENGTH: 447
<212> TYPE: PRT
<213> ORGANISM: Artificial Sequence
<220> FEATURE:
<223> OTHER INFORMATION: immunoglobulin chain

<400> SEQUENCE: 56

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ile Met His Trp Val Arg Gln Ala Pro Gly Lys Gly Leu Glu Trp Val
                35                  40                  45

Ala Val Ile Ser Tyr Asp Gly Arg Asn Lys Tyr Tyr Ala Asp Ser Val
                50                  55                  60

Lys Gly Arg Phe Thr Ile Ser Arg Asp Asn Ser Lys Asn Thr Leu Tyr
```

```
            65                  70                  75                  80
Leu Gln Met Asn Ser Leu Arg Ala Glu Asp Thr Ala Val Tyr Tyr Cys
                85                  90                  95

Ala Arg Asp Thr Asp Gly Tyr Asp Phe Asp Tyr Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Asn Thr Ser Gly Gly Thr Ala Ala Leu Gly
                130                 135                 140

Cys Leu Val Lys Asp Tyr Phe Pro Glu Pro Val Thr Val Ser Trp Asn
145                 150                 155                 160

Ser Thr Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 57
<211> LENGTH: 680
<212> TYPE: PRT
<213> ORGANISM: Fusarium graminearum

<400> SEQUENCE: 57
```

```
Met Lys His Leu Leu Thr Leu Ala Leu Cys Phe Ser Ile Asn Ala
1               5                   10                  15

Val Ala Val Thr Val Pro His Lys Ala Val Gly Thr Gly Ile Pro Glu
            20                  25                  30

Gly Ser Leu Gln Phe Leu Ser Leu Arg Ala Ser Ala Pro Ile Gly Ser
        35                  40                  45

Ala Ile Ser Arg Asn Asn Trp Ala Val Thr Cys Asp Ser Ala Gln Ser
50                      55                  60

Gly Asn Glu Cys Asn Lys Ala Ile Asp Gly Asn Lys Asp Thr Phe Trp
65                  70                  75                  80

His Thr Phe Tyr Gly Ala Asn Gly Asp Pro Lys Pro Pro His Thr Tyr
                85                  90                  95

Thr Ile Asp Met Lys Thr Thr Gln Asn Val Asn Gly Leu Ser Met Leu
                100                 105                 110

Pro Arg Gln Asp Gly Asn Gln Asn Gly Trp Ile Gly Arg His Glu Val
            115                 120                 125

Tyr Leu Ser Ser Asp Gly Thr Asn Trp Gly Ser Pro Val Ala Ser Gly
    130                 135                 140

Ser Trp Phe Ala Asp Ser Thr Thr Lys Tyr Ser Asn Phe Glu Thr Arg
145                 150                 155                 160

Pro Ala Arg Tyr Val Arg Leu Val Ala Ile Thr Glu Ala Asn Gly Gln
                165                 170                 175

Pro Trp Thr Ser Ile Ala Glu Ile Asn Val Phe Gln Ala Ser Ser Tyr
            180                 185                 190

Thr Ala Pro Gln Pro Gly Leu Gly Arg Trp Gly Pro Thr Ile Asp Leu
            195                 200                 205

Pro Ile Val Pro Ala Ala Ala Ile Glu Pro Thr Ser Gly Arg Val
    210                 215                 220

Leu Met Trp Ser Ser Tyr Arg Asn Asp Ala Phe Gly Gly Ser Pro Gly
225                 230                 235                 240

Gly Ile Thr Leu Thr Ser Ser Trp Asp Pro Ser Thr Gly Ile Val Ser
                245                 250                 255

Asp Arg Thr Val Thr Val Thr Lys His Asp Met Phe Cys Pro Gly Ile
            260                 265                 270

Ser Met Asp Gly Asn Gly Gln Ile Val Val Thr Gly Gly Asn Asp Ala
    275                 280                 285

Lys Lys Thr Ser Leu Tyr Asp Ser Ser Ser Asp Ser Trp Ile Pro Gly
    290                 295                 300

Pro Asp Met Gln Val Ala Arg Gly Tyr Gln Ser Ser Ala Thr Met Ser
305                 310                 315                 320

Asp Gly Arg Val Phe Thr Ile Gly Gly Ser Trp Ser Gly Gly Val Phe
                325                 330                 335

Glu Lys Asn Gly Glu Val Tyr Ser Pro Ser Ser Lys Thr Trp Thr Ser
            340                 345                 350

Leu Pro Asn Ala Lys Val Asn Pro Met Leu Thr Ala Asp Lys Gln Gly
        355                 360                 365

Leu Tyr Arg Ser Asp Asn His Ala Trp Leu Phe Gly Trp Lys Lys Gly
    370                 375                 380

Ser Val Phe Gln Ala Gly Pro Ser Thr Ala Met Asn Trp Tyr Tyr Thr
385                 390                 395                 400

Ser Gly Ser Gly Asp Val Lys Ser Ala Gly Lys Arg Gln Ser Asn Arg
                405                 410                 415

Gly Val Ala Pro Asp Ala Met Cys Gly Asn Ala Val Met Tyr Asp Ala
```

```
            420                 425                 430
Val Lys Gly Lys Ile Leu Thr Phe Gly Gly Ser Pro Asp Tyr Gln Asp
            435                 440                 445

Ser Asp Ala Thr Thr Asn Ala His Ile Ile Thr Leu Gly Glu Pro Gly
        450                 455                 460

Thr Ser Pro Asn Thr Val Phe Ala Ser Asn Gly Leu Tyr Phe Ala Arg
465                 470                 475                 480

Thr Phe His Thr Ser Val Val Leu Pro Asp Gly Ser Thr Phe Ile Thr
                485                 490                 495

Gly Gly Gln Arg Arg Gly Ile Pro Phe Glu Asp Ser Thr Pro Val Phe
            500                 505                 510

Thr Pro Glu Ile Tyr Val Pro Glu Gln Asp Thr Phe Tyr Lys Gln Asn
        515                 520                 525

Pro Asn Ser Ile Val Arg Val Tyr His Ser Ile Ser Leu Leu Leu Pro
    530                 535                 540

Asp Gly Arg Val Phe Asn Gly Gly Gly Leu Cys Gly Asp Cys Thr
545                 550                 555                 560

Thr Asn His Phe Asp Ala Gln Ile Phe Thr Pro Asn Tyr Leu Tyr Asn
                565                 570                 575

Ser Asn Gly Asn Leu Ala Thr Arg Pro Lys Ile Thr Arg Thr Ser Thr
            580                 585                 590

Gln Ser Val Lys Val Gly Gly Arg Ile Thr Ile Ser Thr Asp Ser Ser
        595                 600                 605

Ile Ser Lys Ala Ser Leu Ile Arg Tyr Gly Thr Ala Thr His Thr Val
    610                 615                 620

Asn Thr Asp Gln Arg Arg Ile Pro Leu Thr Leu Thr Asn Asn Gly Gly
625                 630                 635                 640

Asn Ser Tyr Ser Phe Gln Val Pro Ser Asp Ser Gly Val Ala Leu Pro
                645                 650                 655

Gly Tyr Trp Met Leu Phe Val Met Asn Ser Ala Gly Val Pro Ser Val
            660                 665                 670

Ala Ser Thr Ile Arg Val Thr Gln
        675                 680

<210> SEQ ID NO 58
<211> LENGTH: 2189
<212> TYPE: DNA
<213> ORGANISM: Fusarium graminearum

<400> SEQUENCE: 58
atggccgatc agcaaacggt ccttagtgta tccgtacctg gatatataag actggaagat      60
atcagttgtt cttcatctgc cagtatcacc ttcattatct attcaagtca ctctctcaac     120
ttattcttgc ctctctctat gtcaatatga aacactttt atcactcgct ctttgcttca     180
gcagcatcaa tgctgttgct gtcaccgtcc ctcacaagtc cggaggaact ggaagtcctg     240
aagggagtct tcagttcctg agtcttcggg cctcagcacc tatcggaagc gctatttctc     300
gcaacaactg ggccgtcact tgcgacagtg cacagtcggg aaatgaatgc aacaaggcca     360
tcgatggcaa caaggatacc ttttggcaca cattctatgg ggccaatgga gatccaaagc     420 ccctcacac atacacgatt gacatgaaga caactcagaa tgtcaacggc ttgtctatgt      480
tgcctcgaca ggatggtaac caaaacggct ggatcggtcg ccatgaggtt tatctaagct     540
cagatggcac aaaactgggc agccctgttg cgtcaggtag ttggtttgcc gactctacta     600
caaaatactc caactttgaa actcgccctg ctcgctatgt tcgtcttgtc gctgtcactg     660
```

```
aagcgaatgg ccagccttgg actagcattg cagagatcaa cgtcttccaa gctagttctt    720
acacagcccc tcagcctggc cttggccgct ggggtccgac tattgacttg ccgattgttc    780
ctgcggctgc agcaattgag ccgacatcgg gacgagtcct tatgtggtct tcgtatcgca    840
atgatgcatt tggaggatcc cctggtggta tcactttgac gtcttcgtgg gatccatcca    900
ctggcattgt ttccgaccgc actgtgacag tcaccaagca tgatatgttc tgccctggta    960
tctccatgga tggtaacggt cagatcgtag tcacaggtgg caacgacgcc aagaagacca   1020
gtttgtatga ttcatctagc gatagctgga tcccgggacc tgacatgcaa gtggctcgtg   1080
ggtatcagtc atcagctacc atgtcagacg gtcgtgtttt taccattgga ggctcctgga   1140
gcggtggcgt atttgagaag aatggcgaag tctatagccc atcttcaaag acatggacgt   1200
ccctacccaa tgccaaggtc aacccaatgt tgacggctga caagcaagga ttgtaccgtt   1260
cagacaacca cgcgtggctc tttggatgga agaagggttc ggtgttccaa gcgggaccta   1320
gtacagccat gaactggtac tataccagtg gaagtggcga tgtgaagtca gccggaaaac   1380
gccagtctaa ccgtggtgta gcccctgatg ccatgtgcgg aaacgctgtc atgtacgacg   1440
ccgttaaagg aaagatcctg acctttggcg gctccccaga ctatcaagac tctgacgcca   1500
caaccaacgc ccacatcatc accctcggtg aacccggaac atctcccaac actgtctttg   1560
ctagcaatgg cttgtacttt gctcgaacgt tccacacctc tgttgttctt ccagacggaa   1620
gcacgttcat tacaggaggc caacgacgtg gaattccgtt cgaggattca accccggtat   1680
ttacacctga gatctacgtc cctgaacaag acactttcta caagcagaac cccaactcca   1740
ttgttcgcgt ctaccacagc atttcccttt tgttacctga tggcagggta tttaacggtg   1800
gtggtggtct ttgtggcgat tgtaccacga atcatttcga cgcgcaaatc tttacgccaa   1860
actatcttta caatagcaac ggcaatctcg cgacacgtcc caagattacc agaacctcta   1920
cacagagcgt caaggtcggt ggcaggatca caatctcgac ggactcttcg attacaaagg   1980
cgtcgttgat tcgctatggt acagcgacac acacggttaa tactgaccag cgtcgcattc   2040
ccctgactct gacaaacaat ggaggaaata gctattcttt ccaagttcct agcgactctg   2100
gtgttgcttt gcctggctac tggatgttgt tcgtgatgaa ctcggccggt gttcctagtg   2160
tggcttcgac gattcgcgtt actcagtga                                     2189
```